(12) United States Patent
Aicher et al.

(10) Patent No.: US 7,981,918 B2
(45) Date of Patent: Jul. 19, 2011

(54) CYCLOHEXYLPYRAZOLE-LACTAM DERIVATIVES AS INHIBITORS OF 11-BETA-HYDROXYSTEROID DEHYDROGENASE 1

(75) Inventors: Thomas Daniel Aicher, Superior, CO (US); Peter Biagio Anzeveno, Zionsville, IN (US); Renhua Li, Fishers, IN (US); Alexei Pavlovych Krasutsky, Zionsville, IN (US); Thomas Edward Mabry, Indianapolis, IN (US); Ashraf Saeed, Westfield, IN (US); Nancy June Snyder, Lizton, IN (US); Hongqi Tian, Longmont, CO (US); Owen Brendan Wallace, Westfield, IN (US); Leonard Larry Winneroski, Greenwood, IN (US); Yanping Xu, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 33 days.

(21) Appl. No.: 12/297,375

(22) PCT Filed: Apr. 5, 2007

(86) PCT No.: PCT/US2007/066069
§ 371 (c)(1),
(2), (4) Date: Oct. 16, 2008

(87) PCT Pub. No.: WO2007/124254
PCT Pub. Date: Nov. 1, 2007

(65) Prior Publication Data
US 2009/0111800 A1      Apr. 30, 2009

Related U.S. Application Data

(60) Provisional application No. 60/745,320, filed on Apr. 21, 2006.

(51) Int. Cl.
*A61K 31/416* (2006.01)
*C07D 231/56* (2006.01)
(52) U.S. Cl. .................... 514/406; 548/360.1
(58) Field of Classification Search .............. 514/406; 548/360.1
See application file for complete search history.

(56) References Cited

U.S. PATENT DOCUMENTS

| | | |
|---|---|---|
| 2008/0207691 A1 | 8/2008 | Aicher et al. |
| 2008/0214621 A1 | 9/2008 | Aicher et al. |
| 2008/0275043 A1 | 11/2008 | Aicher et al. |
| 2009/0275613 A1 | 1/2009 | Li et al. |
| 2009/0069326 A1 | 3/2009 | Allen et al. |
| 2009/0088428 A1 | 4/2009 | Saeed et al. |
| 2009/0088430 A1 | 4/2009 | Wallace et al. |
| 2009/0099180 A1 | 4/2009 | Mabry et al. |
| 2009/0099182 A1 | 4/2009 | Li et al. |
| 2009/0111809 A1 | 4/2009 | Bush |
| 2009/0156571 A1 | 6/2009 | Aicher et al. |
| 2009/0239911 A1 | 9/2009 | Wallace et al. |
| 2009/0264650 A1 | 10/2009 | Toshiro et al. |

FOREIGN PATENT DOCUMENTS

| | | |
|---|---|---|
| EP | 1864971 | 12/2007 |
| WO | WO 2004/056744 | 7/2004 |
| WO | WO 2005/108360 | 11/2005 |
| WO | WO 2005/108361 | 11/2005 |
| WO | WO 2006/040329 | 4/2006 |
| WO | WO 2006/049952 | 5/2006 |
| WO | WO 2006/053024 | 5/2006 |
| WO | WO 2006/068991 | 6/2006 |
| WO | WO 2006/068992 | 6/2006 |
| WO | WO 2006/104280 | 10/2006 |
| WO | WO 2007/084314 | 7/2007 |
| WO | WO 2007/012688 | 11/2007 |
| WO | WO 2007/124329 | 11/2007 |
| WO | WO 2007/124337 | 11/2007 |
| WO | WO 2007/127693 | 11/2007 |
| WO | WO 2007/127704 | 11/2007 |
| WO | WO 2007/127726 | 11/2007 |
| WO | WO 2007/127763 | 11/2007 |
| WO | WO 2007/127765 | 11/2007 |
| WO | WO 2007/127901 | 11/2007 |
| WO | WO 2008/157752 | 12/2008 |

OTHER PUBLICATIONS

Morissette et al. Advanced Drug Delivery Reviews 2004, 56, 275-300.*

(Continued)

*Primary Examiner* — Rebecca L Anderson
*Assistant Examiner* — Samantha L Shterengarts
(74) *Attorney, Agent, or Firm* — Dan L. Wood

(57) ABSTRACT

The present invention discloses novel compounds of Formula (I): having 11β-HSD type 1 antagonist activity, as well as methods for preparing such compounds. In another embodiment, the invention discloses pharmaceutical compositions comprising compounds of Formula (I), as well as methods of using the compounds and compositions to treat diabetes, hyperglycemia, obesity, hypertension, hyperlipidemia, metabolic syndrome, and other conditions associated with 11β-HSD type 1 activity.

(I)

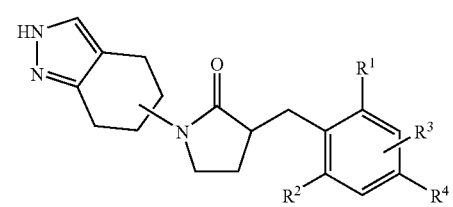

20 Claims, No Drawings

OTHER PUBLICATIONS

Vippagunta et al., abstract, Vippagunta, Sudha R. "Crystalline Solids." Advanced Drug Delivery Reviews 48(2001): 3-26.* A. Maureen Rouhi, The Right Stuff: From research and development to the clinic, getting drug crystals right is full of pitfalls, Chem. & Eng. News, 81(8), Feb. 24, 2003, 32-35.*

Brittain, H.G. (Polymorphism in Pharmaceutical Solids—Drugs and the Pharmaceutical Sciences, V. 95; New York Marcel Dekker, Inc., 1999), p. 236.*

Yeh et al.: Discovery of orally active butyrolactam 11 β-HSD1 inhibitors, Bioorganic & Medicinal Chemistry Letters, Nov. 1, 2006, 16(21), pp. 5555-5560.

Schuster, Daniela et al.: The Discovery of New 11β-Hydroxysteroid Dehydrogenase Type 1 Inhibitors by Common Feature Pharmacophore Modeling and Virtual Screening, J. Medicinal Chemistry, 2006, 49, pp. 3454-3466.

Konno et al.: Electrolytic Partial Fluorination of Organic Compounds. 6. Highly Regioselective Eletrochemical Monofluorination of Aliphatic Nitrogen-Containing Heterocycles, Tetrahedron Letters, 1992, vol. 33, No. 46, pp. 7017-7020.

* cited by examiner

CYCLOHEXYLPYRAZOLE-LACTAM DERIVATIVES AS INHIBITORS OF 11-BETA-HYDROXYSTEROID DEHYDROGENASE 1

This is the national phase application, under 35 USC 371, for PCT/US2007/066069, filed Apr. 5, 2007, which claims the benefit, under 35 USC 119(e), of U.S. provisional application Ser. No. 60/745,320, filed Apr. 21, 2006.

This invention relates to compounds that are inhibitors of 11-β-hydroxysteroid dehydrogenase type 1 ("11-β-HSD1"), and to pharmaceutical compositions thereof, and the uses of these compounds and compositions in the treatment of the human or animal body, and to novel intermediates useful in preparation of the inhibitors. The present compounds show potent and selective inhibition of 11-β-HSD1, and as such are useful in the treatment of disorders responsive to the modulation of 11-β-HSD1, such as diabetes, metabolic syndrome, cognitive disorders, and the like.

Glucocorticoids acting in the liver, adipose tissue, and muscle, are important regulators of glucose, lipid, and protein metabolism. Chronic glucocorticoid excess is associated with insulin resistance, visceral obesity, hypertension, and dyslipidemia, which also represent the classical hallmarks of metabolic syndrome. 11-β-HSD1 catalyses the conversion of inactive cortisone to active cortisol, and has been implicated in the development of metabolic syndrome. Evidence in rodents and humans links 11-β-HSD1 to metabolic syndrome. Evidence suggests that a drug which specifically inhibits 11-β-HSD1 in type 2 diabetic patients will lower blood glucose by reducing hepatic gluconeogenesis, reduce central obesity, improve atherogenic lipoprotein phenotypes, lower blood pressure, and reduce insulin resistance. Insulin effects in muscle will be enhanced, and insulin secretion from the beta cells of the islet may also be increased. Evidence from animal and human studies also indicates that an excess of glucocorticoids impair cognitive function. Recent results indicate that inactivation of 11-β-HSD1 enhances memory function in both men and mice. The 11-β-HSD inhibitor carbenoxolone was shown to improve cognitive function in healthy elderly men and type 2 diabetics, and inactivation of the 11-β-HSD1 gene prevented aging-induced impairment in mice. Selective inhibition of 11-β-HSD1 with a pharmaceutical agent has recently been shown to improve memory retention in mice.

A number of publications have appeared in recent years reporting agents that inhibit 11-β-HSD1. See International Application WO2004/056744 which discloses adamantyl acetamides as inhibitors of 11-β-HSD, International Application WO2005/108360 which discloses pyrrolidin-2-one and piperidin-2-one derivatives as inhibitors of 11-β-HSD, and International Application WO2005/108361 which discloses adamantyl pyrrolidin-2-one derivatives as inhibitors of 11-β-HSD. In spite of the number of treatments for diseases that involve 11-β-HSD1, the current therapies suffer from one or more inadequacies, including poor or incomplete efficacy, unacceptable side effects, and contraindications for certain patient populations. Thus, there remains a need for an improved treatment using alternative or improved pharmaceutical agents that inhibit 11-β-HSD1 and treat the diseases that could benefit from 11-β-HSD1 inhibition. The present invention provides such a contribution to the art based on the finding that a novel class of compounds has a potent and selective inhibitory activity on 11-β-HSD1. The present invention is distinct in the particular structures and their activities. There is a continuing need for new methods of treating diabetes, metabolic syndrome, and cognitive disorders, and it is an object of this invention to meet these and other needs.

The present invention provides a compound structurally represented by formula I:

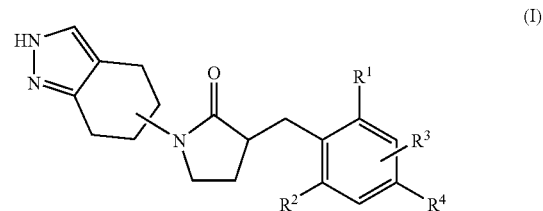

or a pharmaceutically acceptable salt thereof, wherein $R^1$ is —H, -halogen, —O—$CH_3$ (optionally substituted with one to three halogens), or —$CH_3$ (optionally substituted with one to three halogens);

$R^2$ is —H, -halogen, —O—$CH_3$ (optionally substituted with one to three halogens), or —$CH_3$ (optionally substituted with one to three halogens);

$R^3$ is —H or -halogen;

$R^4$ is

—OH, -halogen, -cyano, —($C_1$-$C_4$)alkyl(optionally substituted with one to three halogens), —($C_1$-$C_6$)alkoxy (optionally substituted with one to three halogens), —$SCF_3$, —C(O)O($C_1$-$C_4$)alkyl, —O—$CH_2$—C(O)$NH_2$, —($C_3$-$C_8$)cycloalkyl, —O-phenyl-C(O)O—($C_1$-$C_4$)alkyl, —$CH_2$-phenyl, —$NHSO_2$—($C_1$-$C_4$)alkyl, —$NHSO_2$-phenyl($R^{21}$)($R^{21}$), —($C_1$-$C_4$)alkyl-C(O)N($R^{10}$)($R^{11}$), —C(O)N($R^{10}$)($R^{11}$),

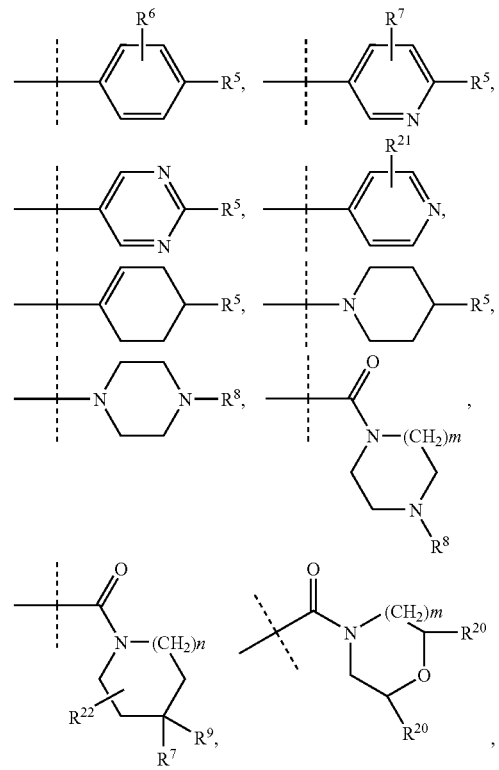

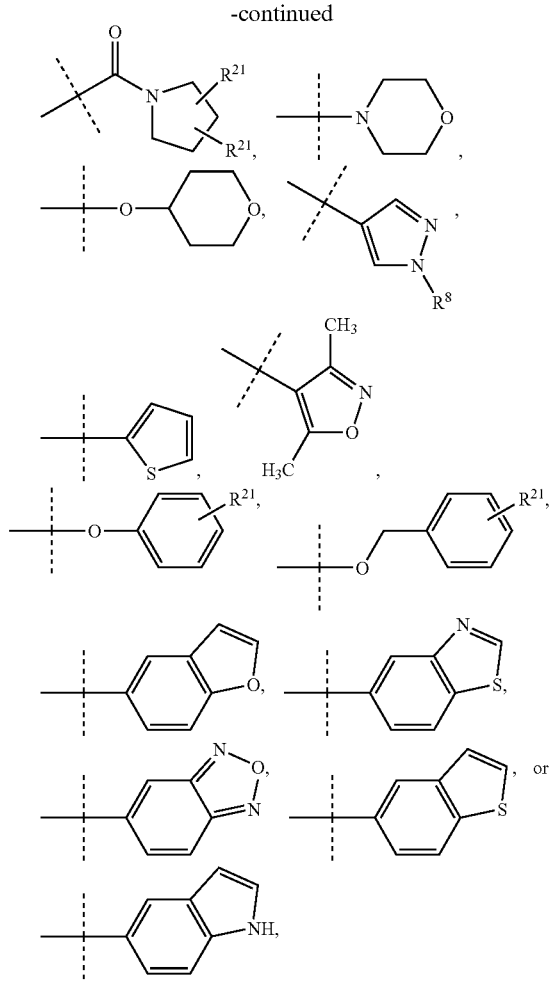

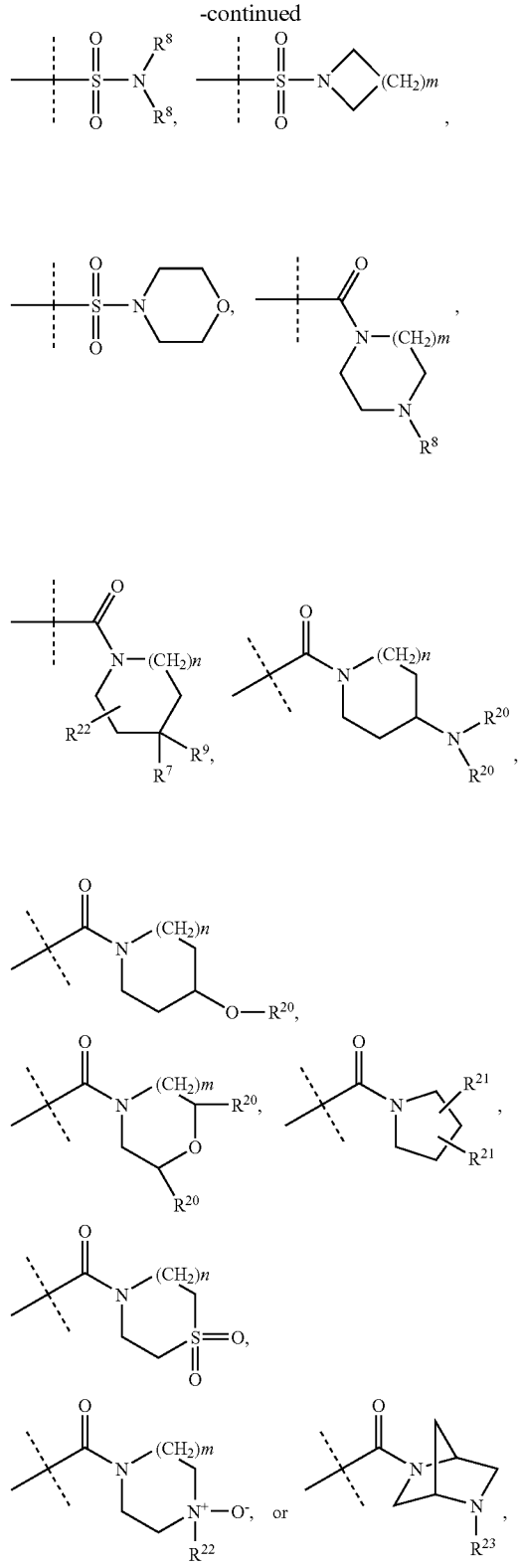

wherein the dashed line represents the point of attachment to the $R^4$ position in formula I; wherein m is 1, 2, or 3; wherein n is 0, 1, or 2, and wherein when n is 0, then "$(CH_2)n$" is a bond;

$R^5$ is
—H, -halogen, —OH, —CN, —$(C_1$-$C_4)$alkyl(optionally substituted with 1 to 3 halogens), —C(O)OH, —C(O)O—$(C_1$-$C_4)$alkyl, —C(O)—$(C_1$-$C_4)$alkyl, —O—$(C_1$-$C_4)$alkyl(optionally substituted with 1 to 3 halogens), —$SO_2$—$(C_1$-$C_4)$alkyl, —N$(R^8)(R^8)$, -phenyl$(R^{21})(R^{21})$, —C(O)—NH—$(C_3$-$C_6)$cycloalkyl,

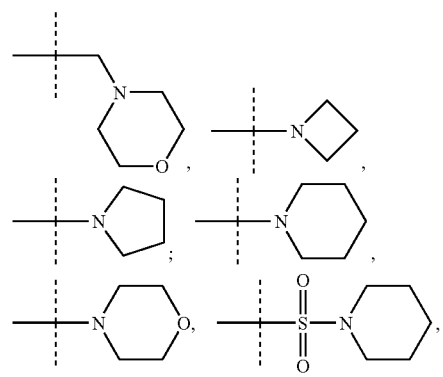

wherein the dashed line represents the point of attachment to the position indicated by $R^5$;

wherein m is 1, 2, or 3;

wherein n is 0, 1, or 2, and wherein when n is 0, then "$(CH_2)n$" is a bond;

$R^6$ is

—H, -halogen, —CN, —$(C_1-C_4)$alkyl(optionally substituted with 1 to 3 halogens), —O—$(C_1-C_4)$alkyl(optionally substituted with 1 to 3 halogens), or

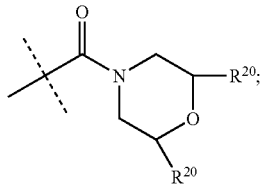

$R^7$ is

—H, -halogen, or —$(C_1-C_4)$alkyl(optionally substituted with 1 to 3 halogens);

$R^5$ is independently at each occurrence

—H, —$(C_1-C_6)$alkyl(optionally substituted with 1 to 3 halogens), —C(O)$(C_1-C_6)$alkyl(optionally substituted with 1 to 3 halogens), —C(O)—$(C_3-C_8)$cycloalkyl, —S$(O_2)$—$(C_3-C_8)$cycloalkyl or —S$(O_2)$—$(C_1-C_3)$alkyl(optionally substituted with 1 to 3 halogens);

$R^9$ is —H or -halogen;

$R^{10}$ and $R^{11}$ are each independently

—H or —$(C_1-C_4)$alkyl, or $R^{10}$ and $R^{11}$ taken together with the nitrogen to which they are attached form piperidinyl, piperazinyl, or pyrrolidinyl;

$R^{20}$ is independently at each occurrence —H, or —$(C_1-C_3)$alkyl(optionally substituted with 1 to 3 halogens);

$R^{21}$ is independently at each occurrence —H, -halogen, or —$(C_1-C_3)$alkyl(optionally substituted with 1 to 3 halogens);

$R^{22}$ is independently at each occurrence —H or —$(C_1-C_6)$alkyl(optionally substituted with 1 to 3 halogens); and $R^{23}$ is independently at each occurrence —H, —$(C_1-C_4)$alkyl, or —C(O)O—$(C_1-C_4)$alkyl.

The present invention provides compounds of formula I that are useful as potent and selective inhibition of 11-β-HSD1. The present invention further provides a pharmaceutical composition which comprises a compound of Formula I, or a pharmaceutical salt thereof, and a pharmaceutically acceptable carrier, diluent, or excipient. In addition, the present invention provides a method for the treatment of metabolic syndrome, and related disorders, which comprise administering to a patient in need thereof an effective amount of a compound of formula I or a pharmaceutically acceptable salt thereof.

In one embodiment, the present invention provides compounds of Formula I or a pharmaceutically acceptable salt thereof as described in detail above. While all of the compounds of the present invention are useful, certain of the compounds are particularly interesting and are preferred. The following listings set out several groups of preferred compounds.

In another embodiment the invention provides a compound structurally represented by formula Ia;

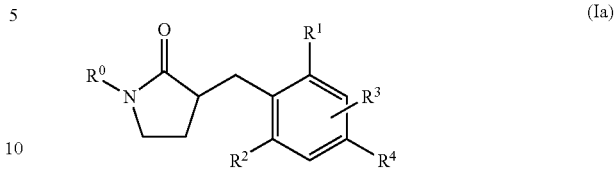

or a pharmaceutically acceptable salt thereof, wherein $R^0$ is

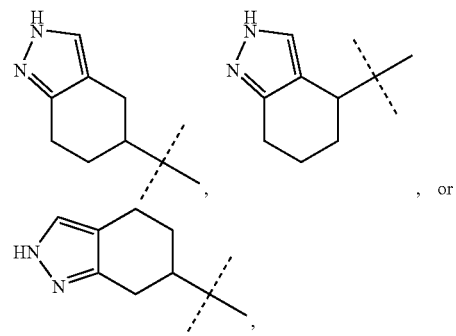

wherein the dashed line represents the point of attachment to the $R^0$ position in formula Ia;

$R^1$ is -halogen; $R^2$ is -halogen; $R^3$ is —H or -halogen; $R^4$ is

—OH, halogen, cyano, —$(C_1-C_4)$alkyl(optionally substituted with one to three halogens), —$(C_1-C_6)$alkoxy(optionally substituted with one to three halogens), —SCF$_3$, —C(O)O$(C_1-C_4)$alkyl, —O—CH$_2$—C(O)NH$_2$, —$(C_3-C_8)$cycloalkyl, —O-phenyl-C(O)O—$(C_1-C_4)$alkyl, —CH$_2$-phenyl, —NHSO$_2$—$(C_1-C_4)$alkyl, —NHSO$_2$-phenyl($R^{21}$)($R^{21}$), —$(C_1-C_4)$alkyl-C(O)N($R^{10}$)($R^{11}$),

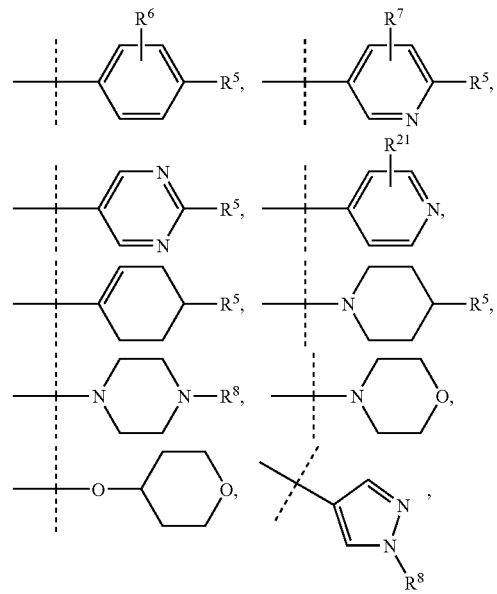

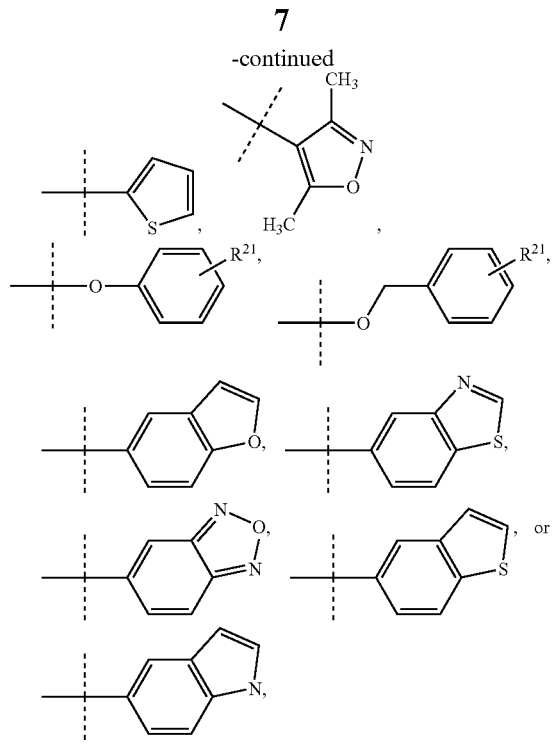

wherein the dashed line represents the point of attachment to the $R^4$ position in formula Ia;

$R^5$ is

—H, -halogen, —OH, —CN, —$(C_1-C_4)$alkyl(optionally substituted with 1 to 3 halogens), —C(O)OH, —C(O)O—$(C_1-C_4)$alkyl, —C(O)—$(C_1-C_4)$alkyl, —O—$(C_1-C_4)$alkyl(optionally substituted with 1 to 3 halogens), —$SO_2$—$(C_1-C_4)$alkyl, —N$(R^8)(R^8)$, -phenyl$(R^{21})(R^{21})$, —C(O)—NH—$(C_3-C_6)$cycloalkyl,

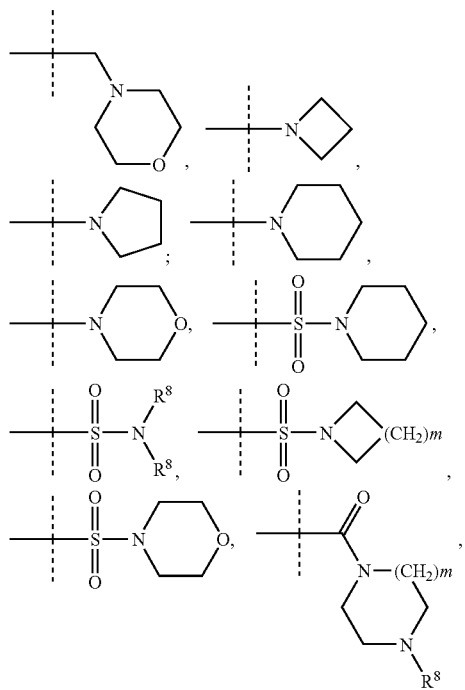

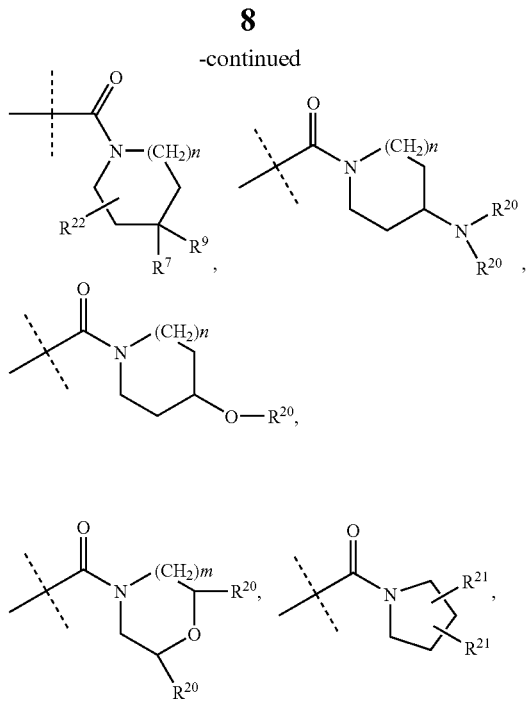

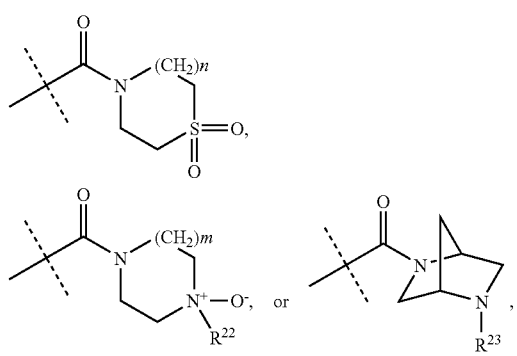

wherein the dashed line represents the point of attachment to the position indicated by $R^5$;

wherein m is 1, 2, or 3;

wherein n is 0, 1, or 2, and wherein when n is 0, then "$(CH_2)n$" is a bond;

$R^6$ is

—H, -halogen, —CN, or —$(C_1-C_4)$alkyl(optionally substituted with 1 to 3 halogens);

$R^7$ is

—H, -halogen, or —$(C_1-C_4)$alkyl(optionally substituted with 1 to 3 halogens);

$R^8$ is independently at each occurrence

—H, —$(C_1-C_6)$alkyl(optionally substituted with 1 to 3 halogens), —C(O)$(C_1-C_6)$alkyl(optionally substituted with 1 to 3 halogens), —C(O)—$(C_3-C_8)$cycloalkyl or —S$(O_2)$—$(C_1-C_3)$alkyl(optionally substituted with 1 to 3 halogens);

$R^9$ is —H or -halogen;

$R^{20}$ is independently at each occurrence —H, or —$(C_1-C_3)$alkyl(optionally substituted with 1 to 3 halogens);

$R^{21}$ is independently at each occurrence —H, -halogen, or —$(C_1-C_3)$alkyl(optionally substituted with 1 to 3 halogens);

$R^{22}$ is independently at each occurrence —H or —$(C_1-C_3)$alkyl(optionally substituted with 1 to 3 halogens); and $R^{23}$ is independently at each occurrence —H, —$(C_1$-$C_3)$alkyl, or —C(O)O—$(C_1$-$C_4)$alkyl.

In another embodiment the invention provides a compound structurally represented by formula Ia;

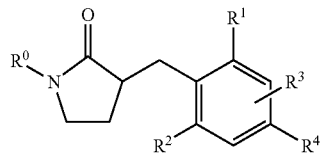
(Ia)

or a pharmaceutically acceptable salt thereof, wherein
$R^0$ is

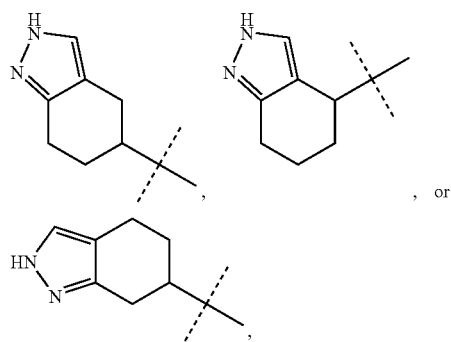, or

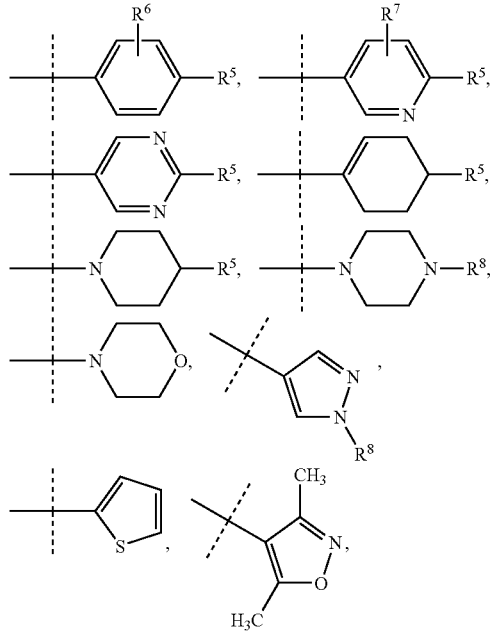, wherein the dashed line represents the point of attachment to the $R^0$ position in formula Ia;

$R^1$ is -chlorine, -fluorine, or -bromine; $R^2$ is chlorine, -fluorine, or -bromine; $R^3$ is —H or -halogen;

$R^4$ is

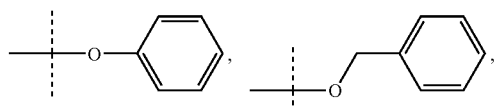

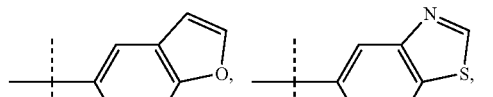

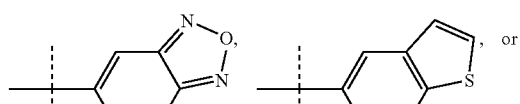

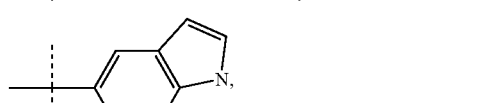

wherein the dashed line represents the point of attachment to the $R^4$ position in formula Ia;

$R^5$ is
—H, -halogen, —OH, —CN, —$(C_1$-$C_4)$alkyl(optionally substituted with 1 to 3 halogens), —C(O)OH, —C(O)O—$(C_1$-$C_4)$alkyl, —C(O)—$(C_1$-$C_4)$alkyl, —O—$(C_1$-$C_4)$alkyl(optionally substituted with 1 to 3 halogens), —$SO_2$—$(C_1$-$C_4)$alkyl, —N($R^8$)($R^8$), -phenyl($R^{21}$)($R^{21}$), —C(O)—NH—$(C_3$-$C_6)$cycloalkyl,

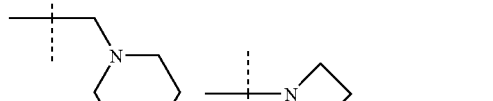

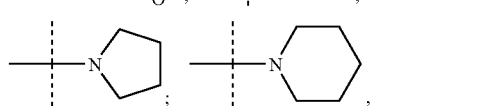

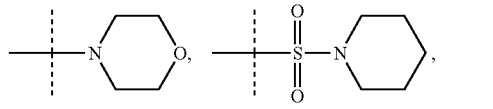

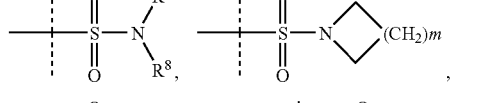

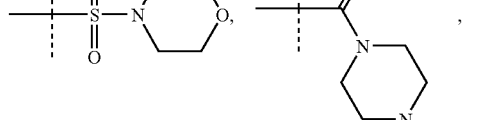

-continued

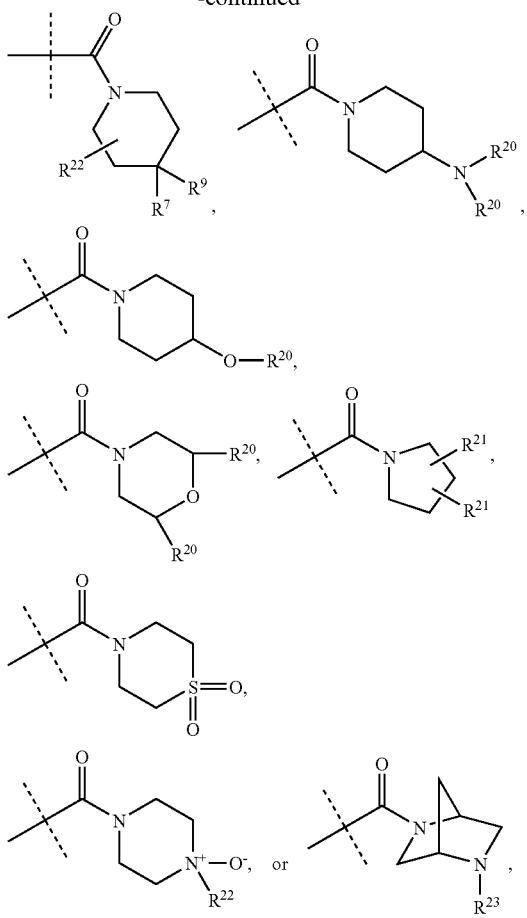

wherein the dashed line represents the point of attachment to the position indicated by R⁵;

wherein m is 1, 2, or 3;

R⁶ is
—H, -halogen, —CN, or —(C₁-C₄)alkyl(optionally substituted with 1 to 3 halogens);

R⁷ is
—H, -halogen, or —(C₁-C₄)alkyl(optionally substituted with 1 to 3 halogens);

R⁸ is independently at each occurrence
—H, —(C₁-C₆)alkyl(optionally substituted with 1 to 3 halogens), —C(O)(C₁-C₆)alkyl(optionally substituted with 1 to 3 halogens), —C(O)—(C₃-C₈)cycloalkyl or —S(O₂)—(C₁-C₃)alkyl(optionally substituted with 1 to 3 halogens);

R⁹ is —H or -halogen;

R²⁰ is independently at each occurrence —H, or —(C₁-C₃)alkyl(optionally substituted with 1 to 3 halogens);

R²¹ is independently at each occurrence —H, -halogen, or —(C₁-C₃)alkyl(optionally substituted with 1 to 3 halogens);

R²² is independently at each occurrence —H or —(C₁-C₃)alkyl(optionally substituted with 1 to 3 halogens); and R²³ is independently at each occurrence —H, —(C₁-C₃)alkyl, or —C(O)O—(C₁-C₄)alkyl.

In another embodiment the invention provides a compound structurally represented by formula Ia;

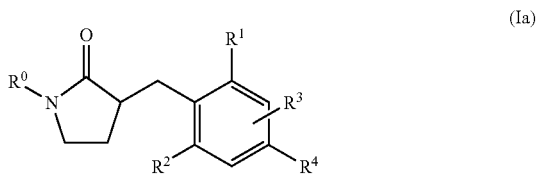

or a pharmaceutically acceptable salt thereof, wherein
R⁰ is

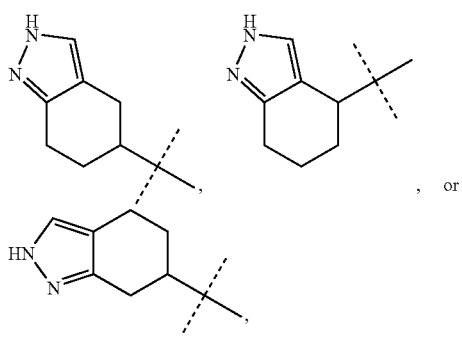

wherein the dashed line represents the point of attachment to the R⁰ position in formula Ia;

R¹ is -chlorine, -fluorine, or -bromine; R² is chlorine, -fluorine, or -bromine; R³ is —H or -halogen;

R⁴ is

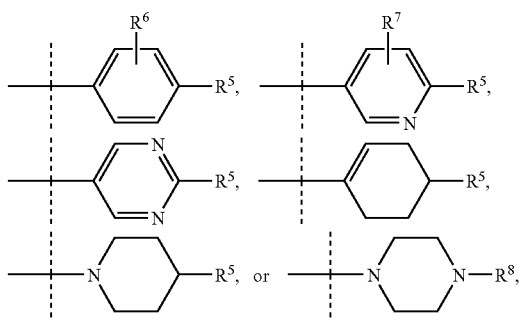

wherein the dashed line represents the point of attachment to the R⁴ position in formula Ia;

R⁵ is
—H, -halogen, —(C₁-C₄)alkyl(optionally substituted with 1 to 3 halogens), —C(O)OH, —C(O)O—(C₁-C₄)alkyl, —C(O)—(C₁-C₄)alkyl, —O—(C₁-C₄)alkyl(optionally substituted with 1 to 3 halogens), —SO₂—(C₁-C₄)alkyl, —N(R⁸)(R⁸),

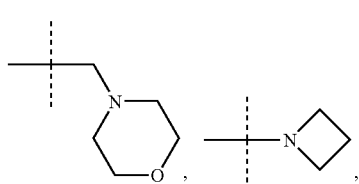

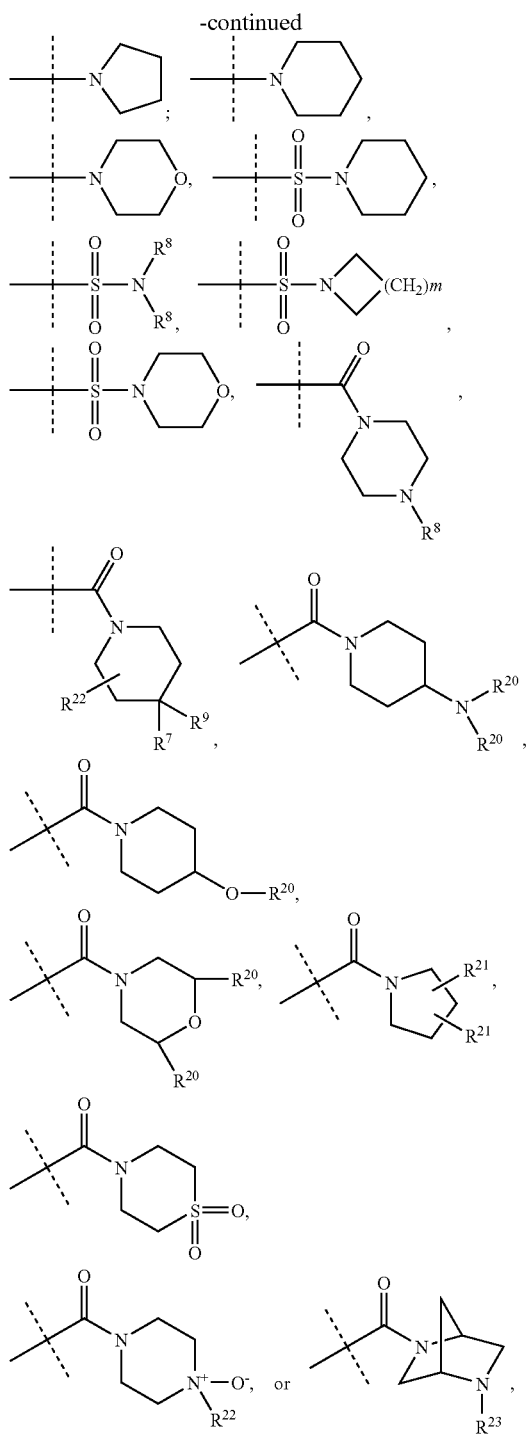

wherein the dashed line represents the point of attachment to the position indicated by R⁵;
wherein m is 1, 2, or 3;

R⁶ is
—H, -halogen, —CN, or —(C₁-C₄)alkyl(optionally substituted with 1 to 3 halogens);

R⁷ is
—H, -halogen, or —(C₁-C₄)alkyl(optionally substituted with 1 to 3 halogens);

R⁸ is independently at each occurrence
—H, —(C₁-C₆)alkyl(optionally substituted with 1 to 3 halogens), —C(O)(C₁-C₆)alkyl(optionally substituted with 1 to 3 halogens), —C(O)—(C₃-C₈)cycloalkyl or —S(O₂)—(C₁-C₃)alkyl(optionally substituted with 1 to 3 halogens);

R⁹ is —H or -halogen;

R²⁰ is independently at each occurrence —H, or —(C₁-C₃)alkyl(optionally substituted with 1 to 3 halogens);

R²¹ is independently at each occurrence —H, -halogen, or —(C₁-C₃)alkyl(optionally substituted with 1 to 3 halogens);

R²² is independently at each occurrence —H or —(C₁-C₃)alkyl(optionally substituted with 1 to 3 halogens); and R²³ is independently at each occurrence —H, —(C₁-C₃)alkyl, or —C(O)O—(C₁-C₄)alkyl.

In another embodiment the invention provides a compound structurally represented by formula Ia;

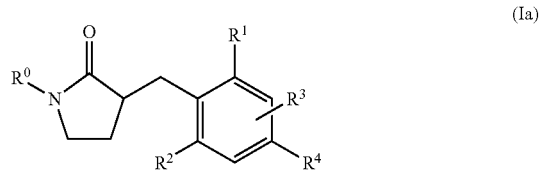

or a pharmaceutically acceptable salt thereof, wherein
R⁰ is

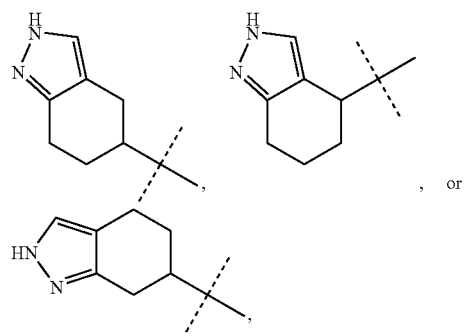

wherein the dashed line represents the point of attachment to the R⁰ position in formula Ia;

R¹ is -chlorine, -fluorine, or -bromine; R² is chlorine, -fluorine, or -bromine; R³ is —H or -halogen;

R⁴ is

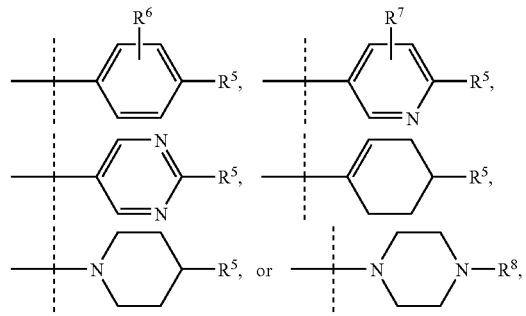

wherein the dashed line represents the point of attachment to the R⁴ position in formula Ia;

$R^5$ is

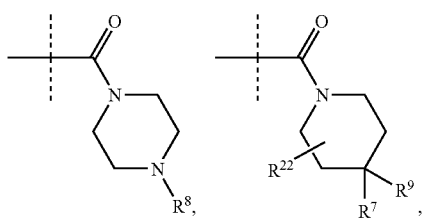

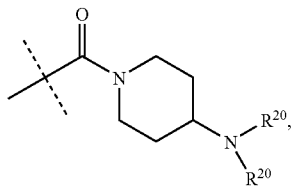

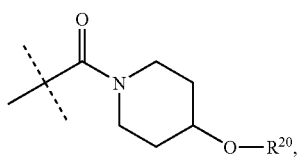

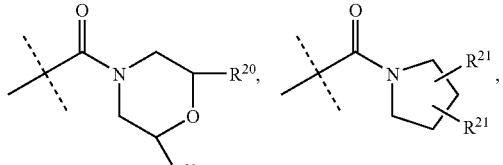

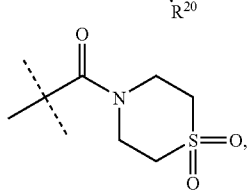

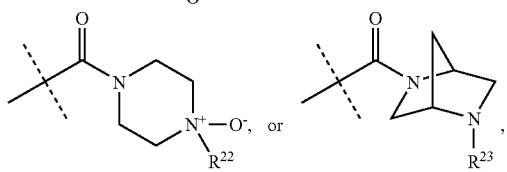

wherein the dashed line represents the point of attachment to the position indicated by $R^5$;

$R^6$ is
—H, -halogen, —CN, or —($C_1$-$C_4$)alkyl(optionally substituted with 1 to 3 halogens);

$R^7$ is
—H, -halogen, or —($C_1$-$C_4$)alkyl(optionally substituted with 1 to 3 halogens);

$R^8$ is independently at each occurrence
—H, —($C_1$-$C_6$)alkyl(optionally substituted with 1 to 3 halogens), —C(O)($C_1$-$C_6$)alkyl(optionally substituted with 1 to 3 halogens), —C(O)—($C_3$-$C_8$)cycloalkyl or —S($O_2$)—($C_1$-$C_3$)alkyl(optionally substituted with 1 to 3 halogens);

$R^9$ is —H or -halogen;

$R^{20}$ is independently at each occurrence —H, or —($C_1$-$C_3$)alkyl(optionally substituted with 1 to 3 halogens);

$R^{21}$ is independently at each occurrence —H, -halogen, or —($C_1$-$C_3$)alkyl(optionally substituted with 1 to 3 halogens);

$R^{22}$ is independently at each occurrence —H or —($C_1$-$C_3$)alkyl(optionally substituted with 1 to 3 halogens); and $R^{23}$ is independently at each occurrence —H, —($C_1$-$C_3$)alkyl, or —C(O)O—($C_1$-$C_4$)alkyl.

In another embodiment the invention provides a compound structurally represented by formula Ia;

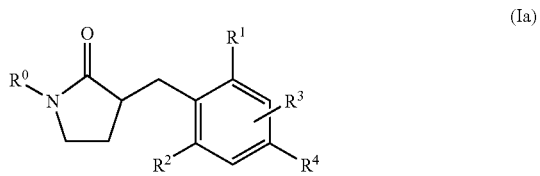

(Ia)

or a pharmaceutically acceptable salt thereof, wherein
$R^0$ is

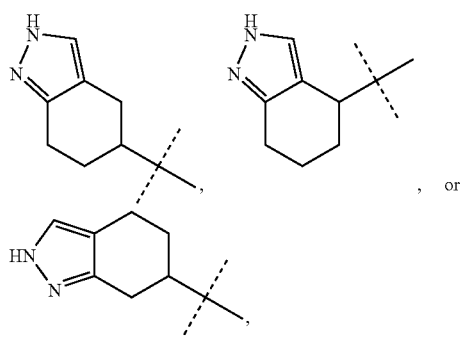

wherein the dashed line represents the point of attachment to the $R^0$ position in formula Ia;

$R^1$ is -chlorine, -fluorine, or -bromine; $R^2$ is chlorine, -fluorine, or -bromine; $R^3$ is —H or -halogen;

$R^4$ is

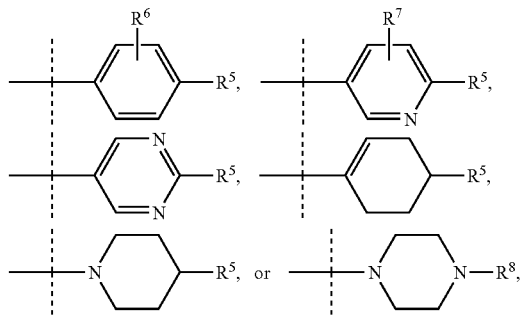

wherein the dashed line represents the point of attachment to the $R^4$ position in formula Ia;

$R^5$ is
—$SO_2$—($C_1$-$C_4$)alkyl,

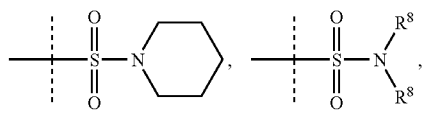

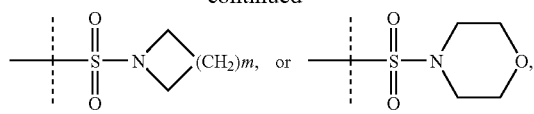

wherein the dashed line represents the point of attachment to the position indicated by $R^5$; wherein m is 1, 2, or 3;

$R^6$ is
—H, -halogen, —CN, or —$(C_1-C_4)$alkyl(optionally substituted with 1 to 3 halogens);

$R^7$ is
—H, -halogen, or —$(C_1-C_4)$alkyl(optionally substituted with 1 to 3 halogens); and $R^8$ is independently at each occurrence
—H, —$(C_1-C_6)$alkyl(optionally substituted with 1 to 3 halogens), —$C(O)(C_1-C_6)$alkyl(optionally substituted with 1 to 3 halogens), —$C(O)$—$(C_3-C_8)$cycloalkyl or —$S(O_2)$—$(C_1-C_3)$alkyl(optionally substituted with 1 to 3 halogens).

In another embodiment the invention provides a compound structurally represented by formula Ia;

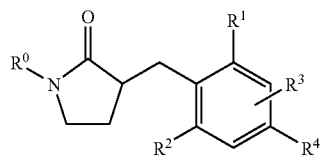
(Ia)

or a pharmaceutically acceptable salt thereof, wherein $R^0$ is

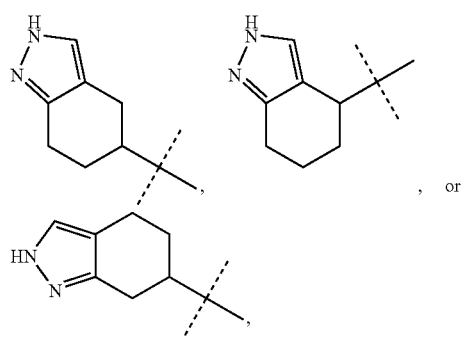

wherein the dashed line represents the point of attachment to the $R^0$ position in formula Ia;

$R^1$ is -chlorine, -fluorine, or -bromine; $R^2$ is chlorine, -fluorine, or -bromine; $R^3$ is —H or -halogen;

$R^4$ is

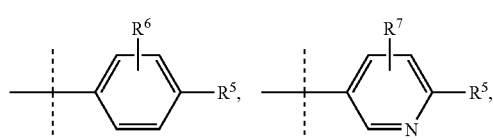

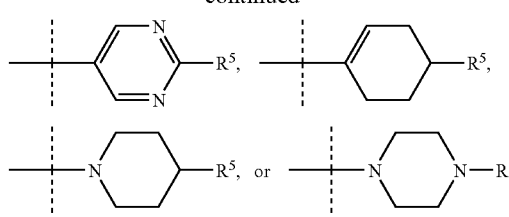

wherein the dashed line represents the point of attachment to the $R^4$ position in formula Ia;

$R^5$ is
—$N(R^8)(R^8)$,

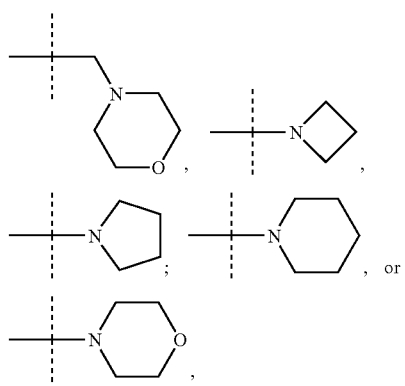

wherein the dashed line represents the point of attachment to the position indicated by $R^5$;

$R^6$ is
—H, -halogen, —CN, or —$(C_1-C_4)$alkyl(optionally substituted with 1 to 3 halogens);

$R^7$ is
—H, -halogen, or —$(C_1-C_4)$alkyl(optionally substituted with 1 to 3 halogens); and $R^8$ is independently at each occurrence
—H, —$(C_1-C_6)$alkyl(optionally substituted with 1 to 3 halogens), —$C(O)(C_1-C_6)$alkyl(optionally substituted with 1 to 3 halogens), —$C(O)$—$(C_3-C_8)$cycloalkyl or —$S(O_2)$—$(C_1-C_3)$alkyl(optionally substituted with 1 to 3 halogens).

In another embodiment the invention provides a compound structurally represented by formula Ib;

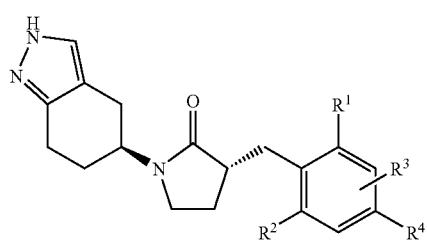
(Ib)

or a pharmaceutically acceptable salt thereof, wherein $R^1$ is -chlorine, -fluorine, or -bromine; $R^2$ is chlorine, -fluorine, or -bromine; $R^3$ is —H or -halogen;

$R^4$ is

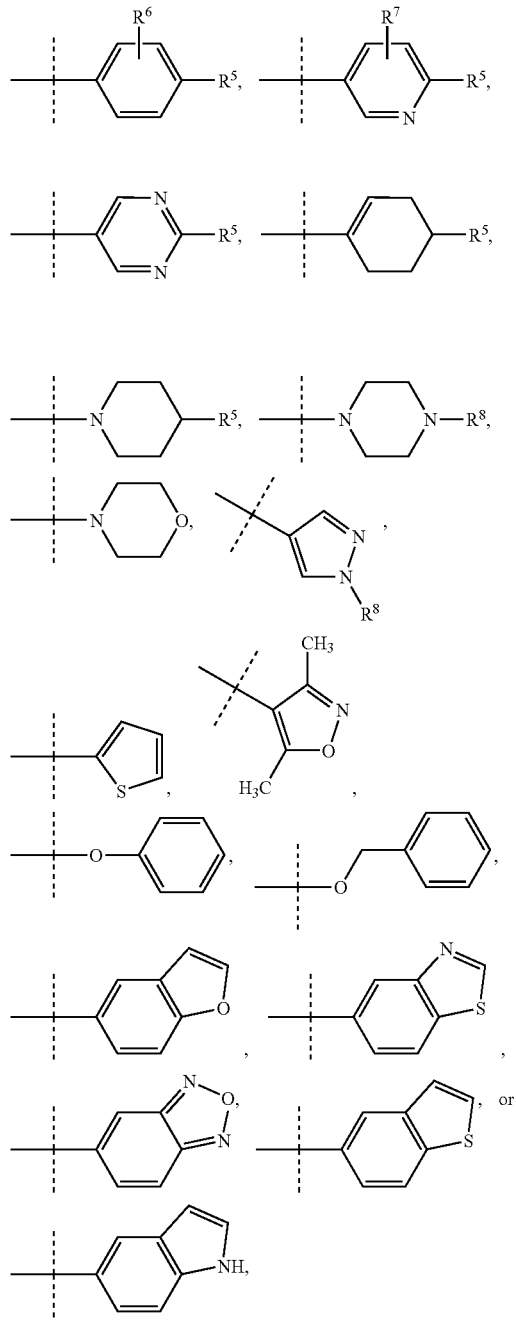

wherein the dashed line represents the point of attachment to the $R^4$ position in formula Ib;

$R^5$ is
 —H, -halogen, —OH, —CN, —($C_1$-$C_4$)alkyl(optionally substituted with 1 to 3 halogens), —C(O)OH, —C(O)O—($C_1$-$C_4$)alkyl, —C(O)—($C_1$-$C_4$)alkyl, —O—($C_1$-$C_4$)alkyl(optionally substituted with 1 to 3 halogens), —$SO_2$—($C_1$-$C_4$)alkyl, —N($R^8$)($R^8$), -phenyl($R^{21}$)($R^{21}$), —C(O)—NH—($C_3$-$C_6$)cycloalkyl,

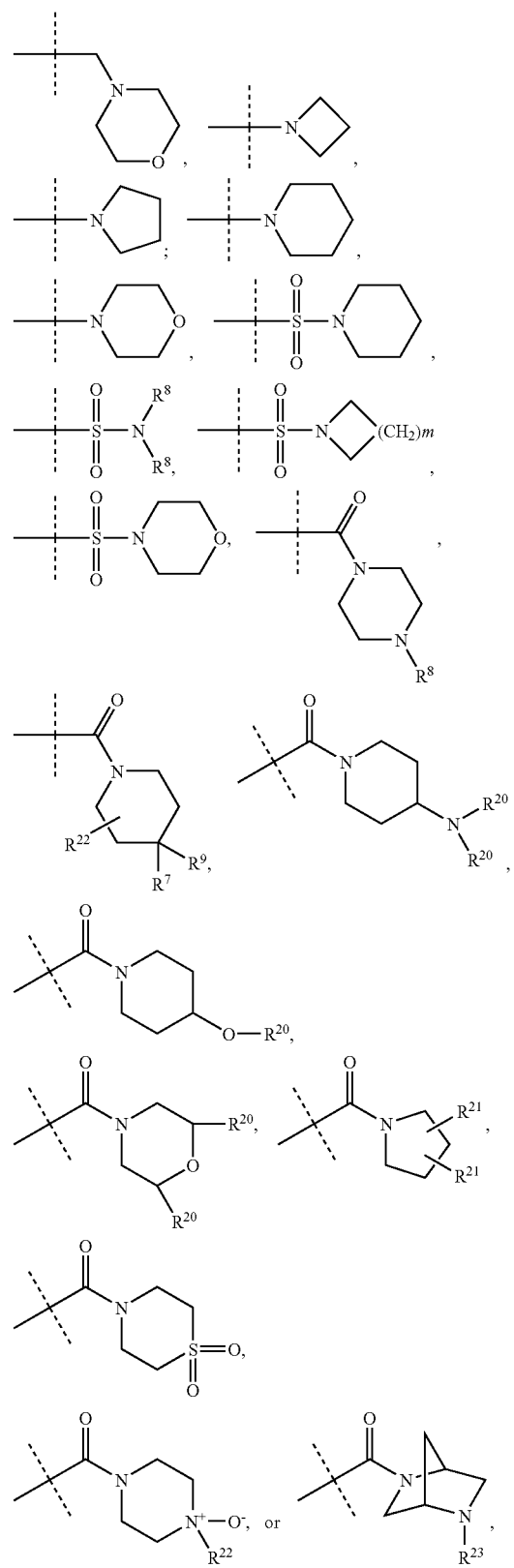

wherein the dashed line represents the point of attachment to the position indicated by $R^5$;

wherein m is 1, 2, or 3;

$R^6$ is
- —H, -halogen, —CN, or —$(C_1\text{-}C_4)$alkyl(optionally substituted with 1 to 3 halogens);

$R^7$ is
- —H, -halogen, or —$(C_1\text{-}C_4)$alkyl(optionally substituted with 1 to 3 halogens);

$R^8$ is independently at each occurrence
- —H, —$(C_1\text{-}C_6)$alkyl(optionally substituted with 1 to 3 halogens), —C(O)$(C_1\text{-}C_6)$alkyl(optionally substituted with 1 to 3 halogens), —C(O)—$(C_3\text{-}C_8)$cycloalkyl or —S$(O_2)$—$(C_1\text{-}C_3)$alkyl(optionally substituted with 1 to 3 halogens);

$R^9$ is —H or -halogen;

$R^{20}$ is independently at each occurrence —H, or —$(C_1\text{-}C_3)$ alkyl(optionally substituted with 1 to 3 halogens);

$R^{21}$ is independently at each occurrence —H, -halogen, or —$(C_1\text{-}C_3)$alkyl(optionally substituted with 1 to 3 halogens);

$R^{22}$ is independently at each occurrence —H or —$(C_1\text{-}C_3)$ alkyl(optionally substituted with 1 to 3 halogens); and $R^{23}$ is independently at each occurrence —H, —$(C_1\text{-}C_3)$ alkyl, or —C(O)O—$(C_1\text{-}C_4)$alkyl.

In another embodiment the invention provides a compound structurally represented by formula Ib;

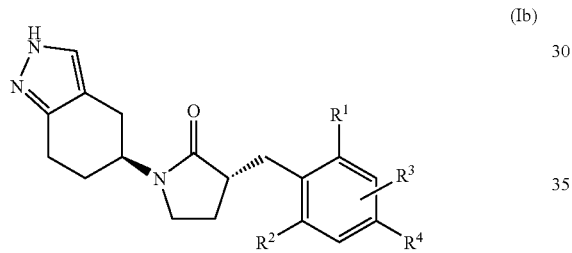

(Ib)

or a pharmaceutically acceptable salt thereof, wherein $R^1$ is -chlorine, -fluorine, or -bromine; $R^2$ is chlorine, -fluorine, or -bromine; $R^3$ is —H or -halogen;

$R^4$ is

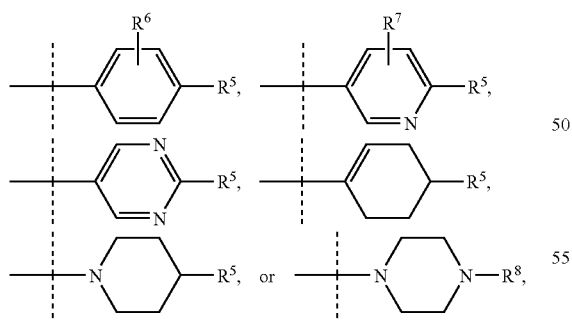

wherein the dashed line represents the point of attachment to the $R^4$ position in formula Ib;

$R^5$ is
- —H, -halogen, —$(C_1\text{-}C_4)$alkyl(optionally substituted with 1 to 3 halogens), —C(O)OH, —C(O)O—$(C_1\text{-}C_4)$alkyl, —C(O)—$(C_1\text{-}C_4)$alkyl, —O—$(C_1\text{-}C_4)$alkyl(optionally substituted with 1 to 3 halogens), —SO$_2$—$(C_1\text{-}C_4)$alkyl, —N$(R^8)(R^8)$,

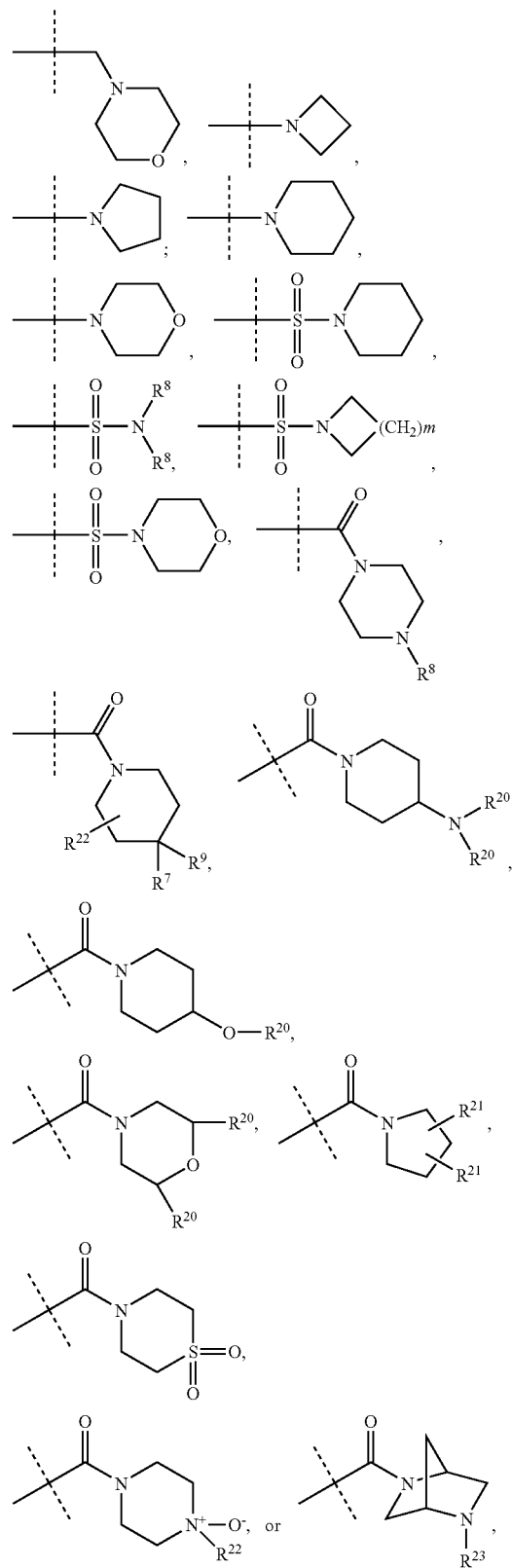

wherein the dashed line represents the point of attachment to the position indicated by $R^5$;

wherein m is 1, 2, or 3;

R⁶ is
- —H, -halogen, —CN, or —(C₁-C₄)alkyl(optionally substituted with 1 to 3 halogens);

R⁷ is
- —H, -halogen, or —(C₁-C₄)alkyl(optionally substituted with 1 to 3 halogens);

R⁸ is independently at each occurrence
- —H, —(C₁-C₆)alkyl(optionally substituted with 1 to 3 halogens), —C(O)(C₁-C₆)alkyl(optionally substituted with 1 to 3 halogens), —C(O)—(C₃-C₈)cycloalkyl or —S(O₂)—(C₁-C₃)alkyl(optionally substituted with 1 to 3 halogens);

R⁹ is —H or -halogen;

R²⁰ is independently at each occurrence —H, or —(C₁-C₃)alkyl(optionally substituted with 1 to 3 halogens);

R²¹ is independently at each occurrence —H, -halogen, or —(C₁-C₃)alkyl(optionally substituted with 1 to 3 halogens);

R²² is independently at each occurrence —H or —(C₁-C₃)alkyl(optionally substituted with 1 to 3 halogens); and R²³ is independently at each occurrence —H, —(C₁-C₃)alkyl, or —C(O)O—(C₁-C₄)alkyl.

In another embodiment the invention provides a compound structurally represented by formula Ib;

(Ib)

or a pharmaceutically acceptable salt thereof, wherein

R¹ is -chlorine, -fluorine, or -bromine; R² is chlorine, -fluorine, or -bromine; R³ is —H or -halogen;

R⁴ is wherein the dashed line represents the point of attachment to the R⁴ position in formula Ib;

R⁵ is wherein the dashed line represents the point of attachment to the position indicated by R⁵;

R⁶ is
- —H, -halogen, —CN, or —(C₁-C₄)alkyl(optionally substituted with 1 to 3 halogens);

R⁷ is
- —H, -halogen, or —(C₁-C₄)alkyl(optionally substituted with 1 to 3 halogens);

R⁸ is independently at each occurrence
- —H, —(C₁-C₆)alkyl(optionally substituted with 1 to 3 halogens), —C(O)(C₁-C₆)alkyl(optionally substituted with 1 to 3 halogens), —C(O)—(C₃-C₈)cycloalkyl or —S(O₂)—(C₁-C₃)alkyl(optionally substituted with 1 to 3 halogens);

R⁹ is —H or -halogen;

R²⁰ is independently at each occurrence —H, or —(C₁-C₃)alkyl(optionally substituted with 1 to 3 halogens);

R²¹ is independently at each occurrence —H, -halogen, or —(C₁-C₃)alkyl(optionally substituted with 1 to 3 halogens);

R²² is independently at each occurrence —H or —(C₁-C₃)alkyl(optionally substituted with 1 to 3 halogens); and $R^{23}$ is independently at each occurrence —H, —($C_1$-$C_3$) alkyl, or —C(O)O—($C_1$-$C_4$)alkyl.

In another embodiment the invention provides a compound structurally represented by formula Ib;

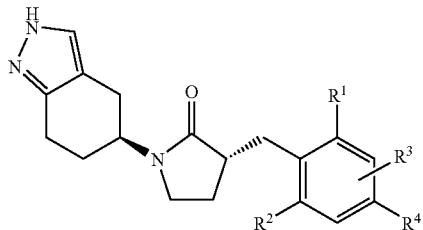

(Ib)

or a pharmaceutically acceptable salt thereof, wherein
$R^1$ is -chlorine, -fluorine, or -bromine; $R^2$ is chlorine, -fluorine, or -bromine; $R^3$ is —H or -halogen;
$R^4$ is

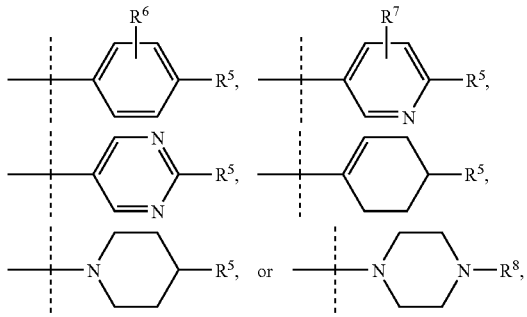

wherein the dashed line represents the point of attachment to the $R^4$ position in formula Ib;
$R^5$ is
—$SO_2$—($C_1$-$C_4$)alkyl,

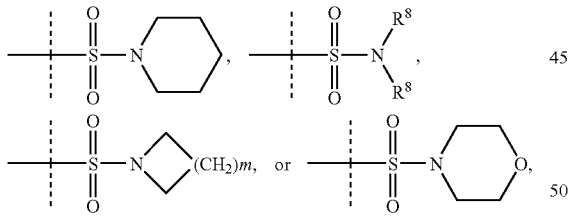

wherein the dashed line represents the point of attachment to the position indicated by $R^5$; wherein m is 1, 2, or 3;
$R^6$ is
—H, -halogen, —CN, or —($C_1$-$C_4$)alkyl(optionally substituted with 1 to 3 halogens);
$R^7$ is
—H, -halogen, or —($C_1$-$C_4$)alkyl(optionally substituted with 1 to 3 halogens); and
$R^8$ is independently at each occurrence
—H, —($C_1$-$C_6$)alkyl(optionally substituted with 1 to 3 halogens), —C(O)($C_1$-$C_6$)alkyl(optionally substituted with 1 to 3 halogens), —C(O)—($C_3$-$C_8$)cycloalkyl or —S($O_2$)—($C_1$-$C_3$)alkyl(optionally substituted with 1 to 3 halogens).

In another embodiment the invention provides a compound structurally represented by formula Ib;

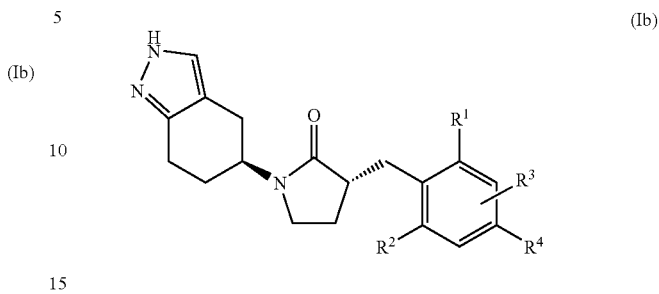

(Ib)

or a pharmaceutically acceptable salt thereof, wherein
$R^1$ is -chlorine, -fluorine, or -bromine; $R^2$ is chlorine, -fluorine, or -bromine; $R^3$ is —H or -halogen;
$R^4$ is

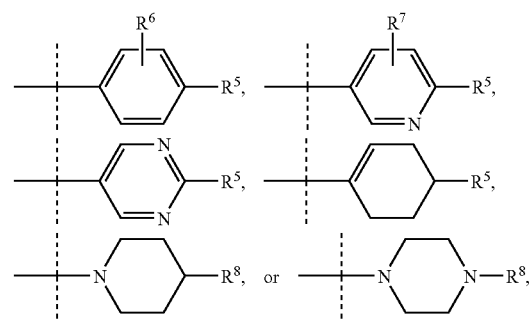

wherein the dashed line represents the point of attachment to the $R^4$ position in formula Ib;
$R^5$ is
—N($R^8$)($R^8$),

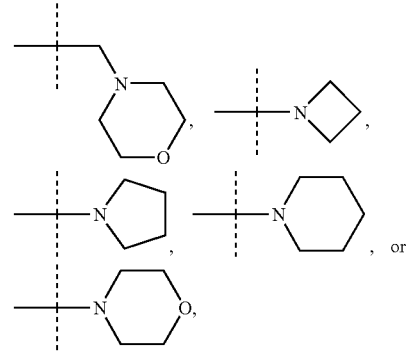

wherein the dashed line represents the point of attachment to the position indicated by $R^5$;
$R^6$ is
—H, -halogen, —CN, or —($C_1$-$C_4$)alkyl(optionally substituted with 1 to 3 halogens);
$R^7$ is
—H, -halogen, or —($C_1$-$C_4$)alkyl(optionally substituted with 1 to 3 halogens); and $R^8$ is independently at each occurrence
—H, —$(C_1$-$C_6)$alkyl(optionally substituted with 1 to 3 halogens), —$C(O)(C_1$-$C_6)$alkyl(optionally substituted with 1 to 3 halogens), —$C(O)$—$(C_3$-$C_8)$cycloalkyl or —$S(O_2)$—$(C_1$-$C_3)$alkyl(optionally substituted with 1 to 3 halogens).

In another embodiment the invention provides a compound structurally represented by formula Ia, or a pharmaceutically acceptable salt thereof, wherein $R^0$ is

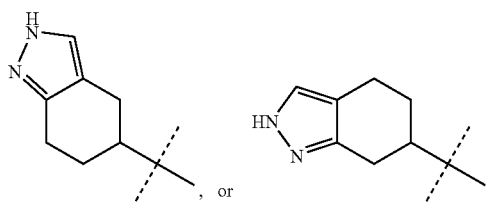

wherein the dashed line represents the point of attachment to the $R^0$ position in formula Ia; $R^1$ is chlorine; $R^2$ is -chlorine; $R^3$ is —H;

$R^4$ is

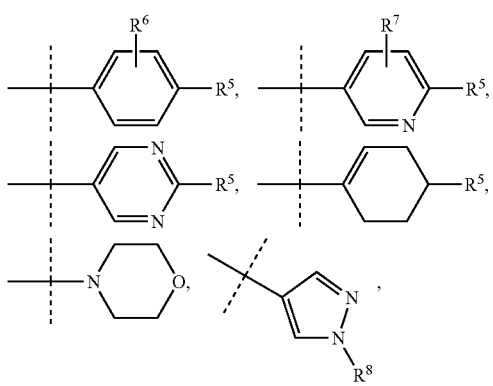

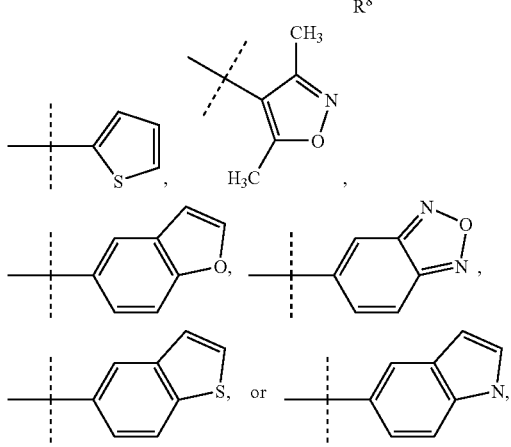

wherein the dashed line represents the point of attachment to the $R^4$ position in formula Ia;

$R^5$ is
—H, -chlorine, -fluorine, —$CH_3$, —$CF_3$, -0-$CF_3$, —$SO_2$-$CH_3$, —$C(CH_3)_3$, —$CH(CH_3)_2$, —O—$CH(CH_3)_2$, —$C(O)O$—$CH_3$, —N(—$CH_3$)(—$CH_3$),

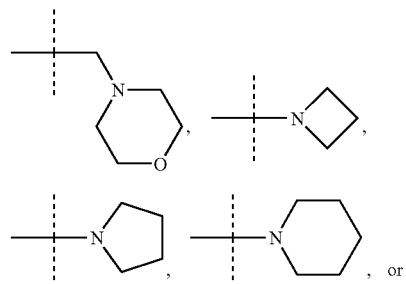

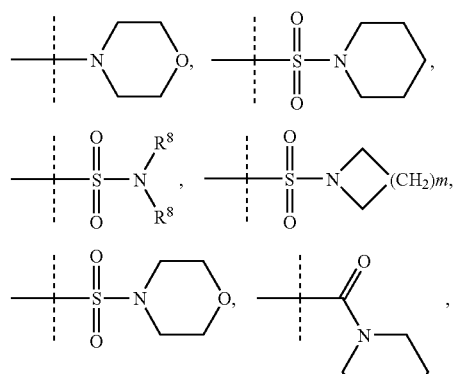

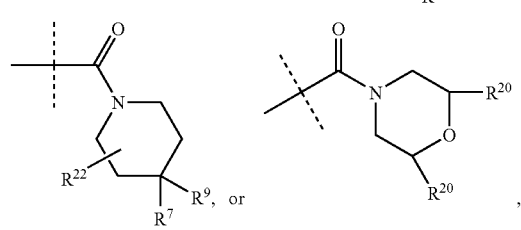

wherein the dashed line represents the point of attachment to the position indicated by $R^5$;

$R^6$ is —H, -chlorine, -fluorine, -bromine, —$CH_3$, or —$CF_3$;

$R^7$ is —H, -chlorine, -fluorine, or -bromine;

$R^8$ is independently at each occurrence —H, —$CH_3$, —$CH_2$—$CH_3$, —$C(CH_3)_3$, or —$CH(CH_3)_2$;

$R^9$ is —H or -chlorine, -fluorine, or -bromine;

$R^{20}$ is independently at each occurrence —H or —$CH_3$; and $R^{22}$ is independently at each occurrence —H.

In another embodiment the invention provides a compound structurally represented by the formula;

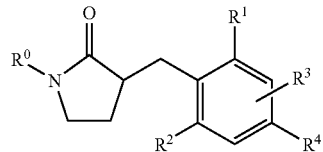

or a pharmaceutically acceptable salt thereof, wherein

R⁰ is

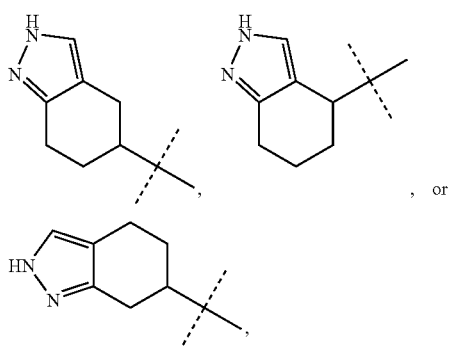

, or wherein the dashed line represents the point of attachment to the R⁰ position;

R¹ is —H, —Cl, —F, or —CH₃; R² is —Cl, —F, or —CH₃; R³ is —H, or —F;

R⁴ is —OCH₃, —F, —Br, —Cl, —OH, —CF₃, —O—CH(CH₃)₂, —O—CH₂—C(O)NH₂, —C(O)N(R¹⁰)(R¹¹),

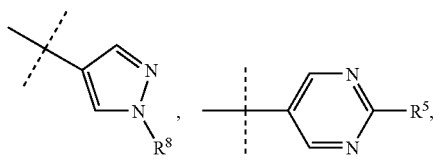

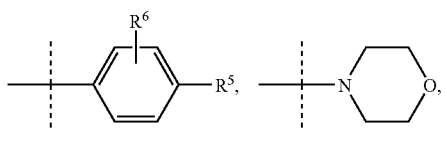

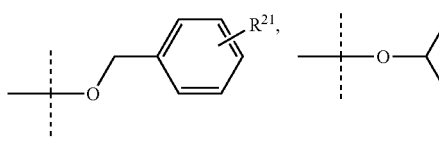

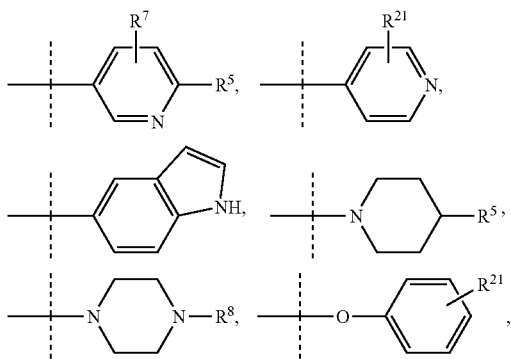

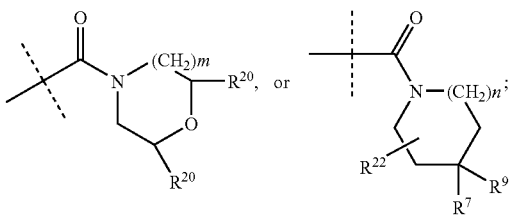

R⁵ is —H, —C(O)—NH-cyclopropyl, —CN, —F, —OCF₃, —Cl, —CF₃, —O—CH(CH₃)₂, —CH₃, —C(O)OH, —N(R⁸)(R⁸), —OH, —SO₂—CH₃, -phenyl(R²¹)(R²¹),

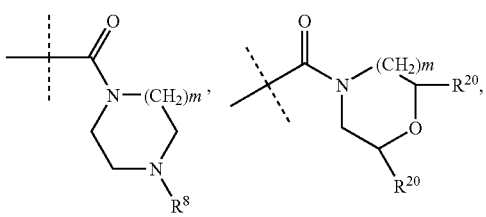

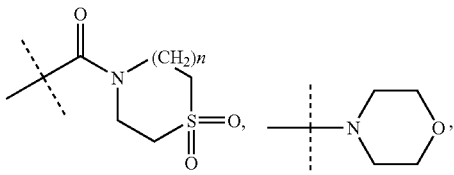

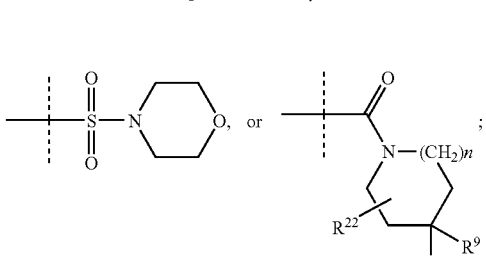

wherein m is 1 and n is 1;

R⁶ is —H, —CN, —OCF₃, —OCH₃, or

R⁷ is —H, —F, or —CF₃;
R⁸ is —H, —CH₃, —S(O₂)—CH₃, —CF₃, or —C(O)—CH₃;
R⁹ is —H or —F; R¹⁰ is —CH₂CH(CH₃)₂;
R¹¹ is —H; R²⁰ is —H; R²¹ is —F or —H; and R²² is —H.

In another embodiment the invention provides a compound structurally represented by the formula;
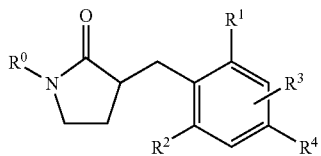
or a pharmaceutically acceptable salt thereof, wherein $R^0$ is
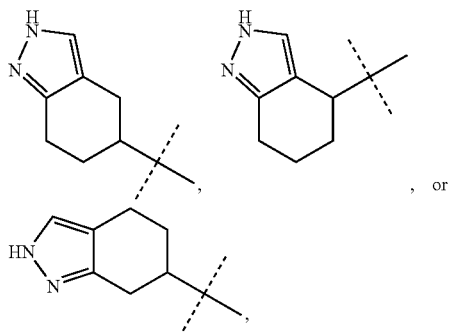
wherein the dashed line represents the point of attachment to the $R^0$ position;
$R^1$ is —H, —Cl, —F, or —$CH_3$; $R^2$ is —Cl, —F, or —$CH_3$; $R^3$ is —H or —F; and
$R^4$ is —$OCH_3$, —F, —Br, —Cl, —OH, —$CF_3$, —O—CH$(CH_3)_2$, —O—$CH_2$—C(O)—$NH_2$, —C(O)—NH—$CH_2CH(CH_3)_2$,
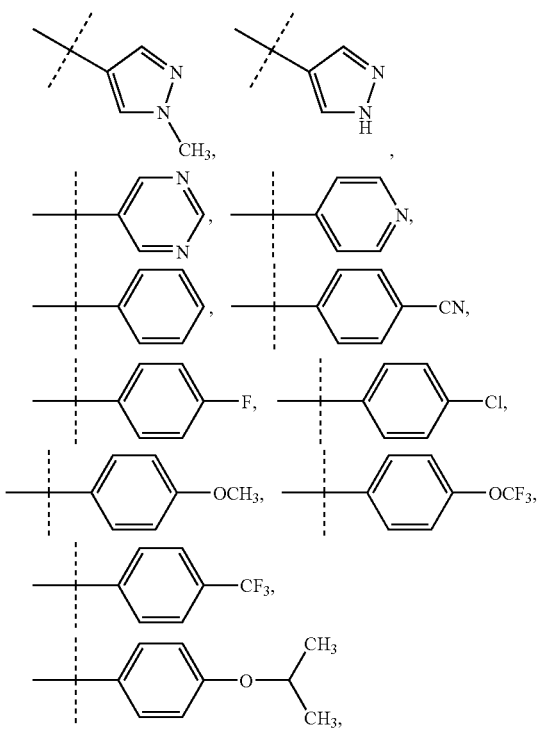
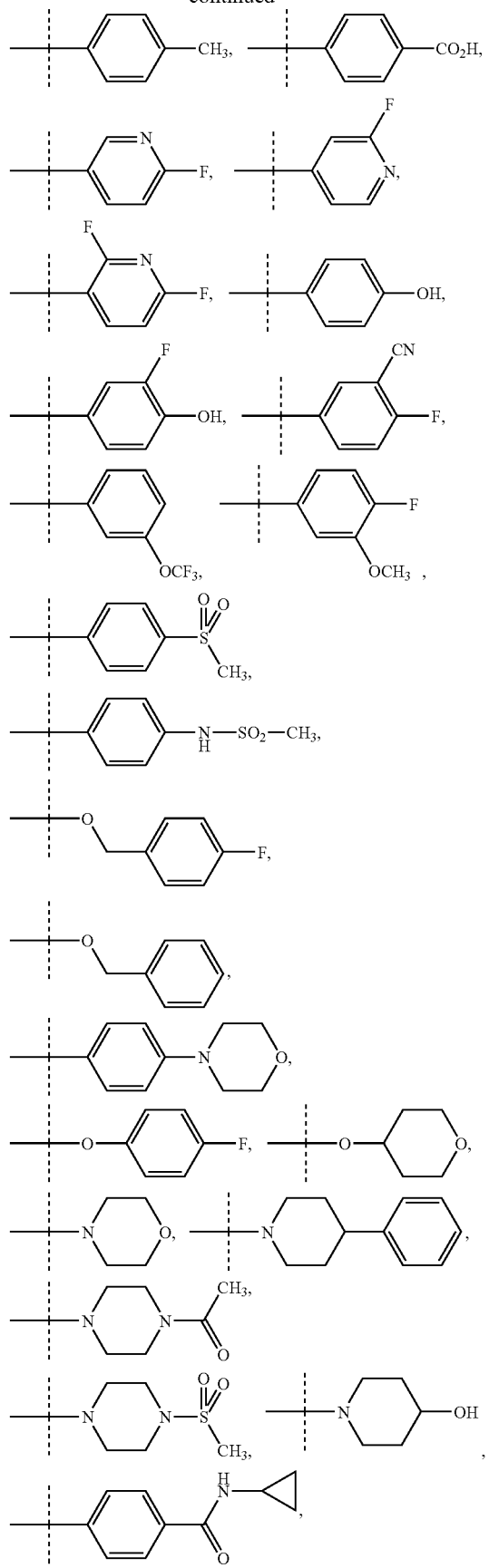

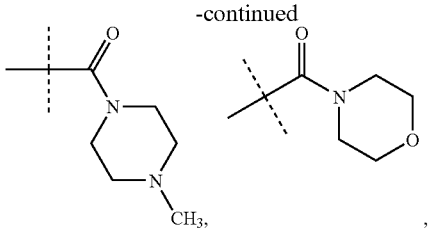
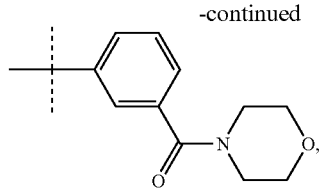
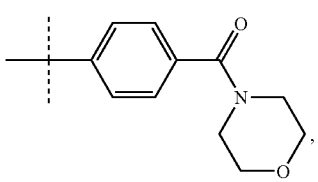
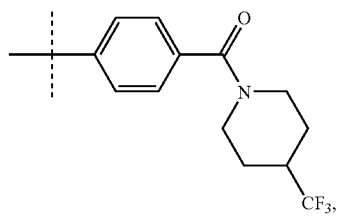
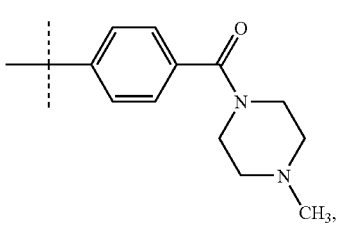
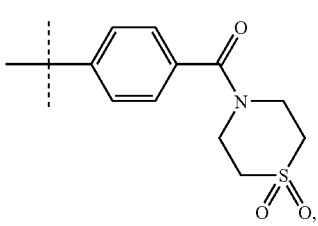
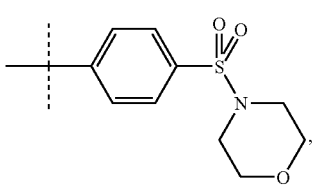
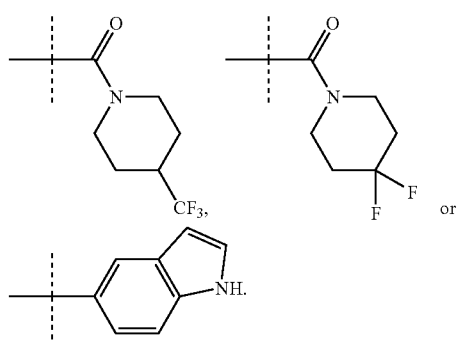

Other embodiments of the invention are provided wherein each of the embodiments described herein above is further narrowed as described in the following preferences. Specifically, each of the preferences below is independently combined with each of the embodiments above, and the particular combination provides another embodiment in which the variable indicated in the preference is narrowed according to the preference.

Preferably embodiments of the invention are structurally represented by the formula:

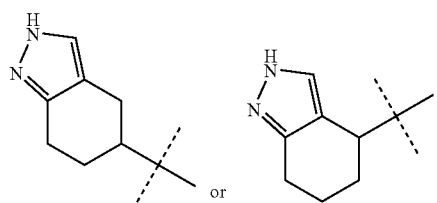

wherein $R^0$ is

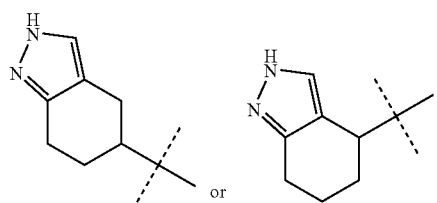

or

Preferably embodiments of the invention are structurally represented by the formula:

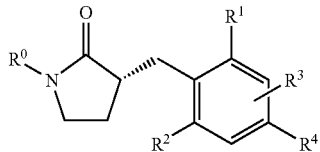

wherein $R^0$ is

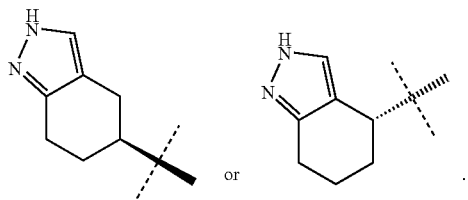

Preferably $R^0$ is

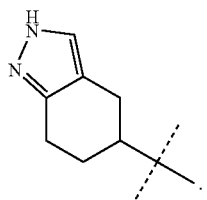

Preferably $R^0$ is

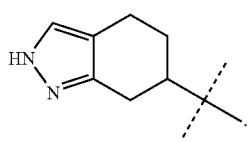

Preferably $R^0$ is

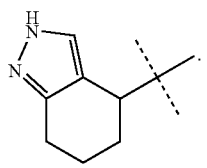

Preferably $R^1$ is -halogen. Preferably $R^1$ is —$CH_3$. Preferably $R^1$ is -chlorine, -fluorine, or -bromine. Preferably $R^1$ is -chlorine. Preferably $R^1$ is -fluorine. Preferably $R^1$ is -bromine. Preferably $R^2$ is -halogen. Preferably $R^2$ is —$CH_3$. Preferably $R^2$ is -chlorine, -fluorine, or -bromine. Preferably $R^2$ is chlorine. Preferably $R^2$ is -fluorine. Preferably $R^2$ is -bromine. Preferably $R^1$ is -chlorine and $R^2$ is -chlorine.

Preferably $R^3$ is —H. Preferably $R^3$ is -halogen.

Preferably $R^4$ is

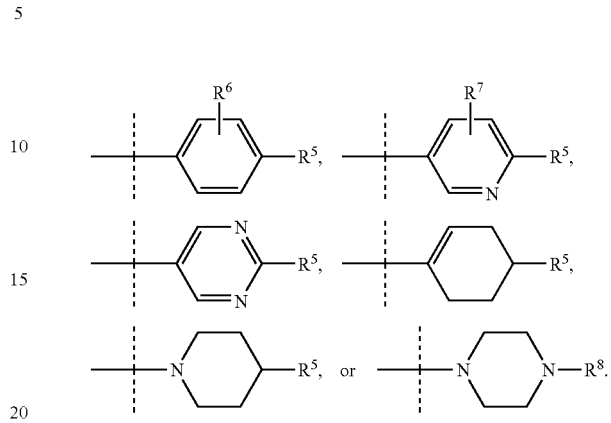

Preferably $R^4$ is

Preferably $R^4$ is

Preferably $R^4$ is

Preferably $R^4$ is

Preferably R⁴ is
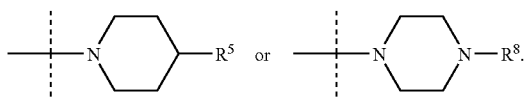
Preferably R⁴ is
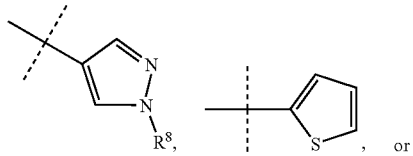
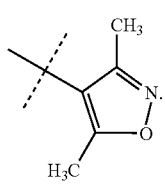
Preferably R⁴ is
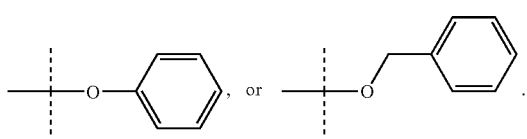
Preferably R⁴ is
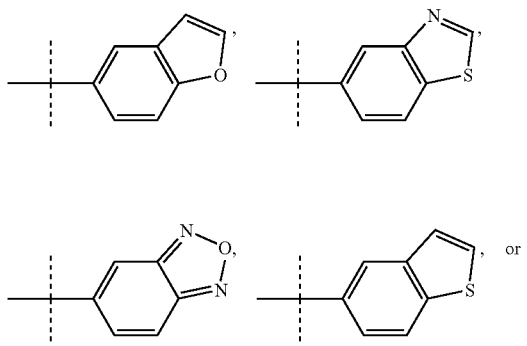
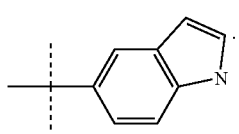
Preferably R⁴ is
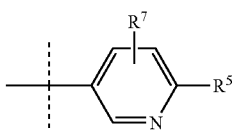
and R⁷ is hydrogen. Preferably R⁴ is
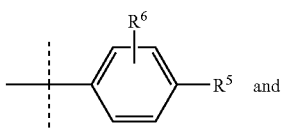
R⁶ is hydrogen.
Preferably R⁵ is —N(R⁸)(R⁸),
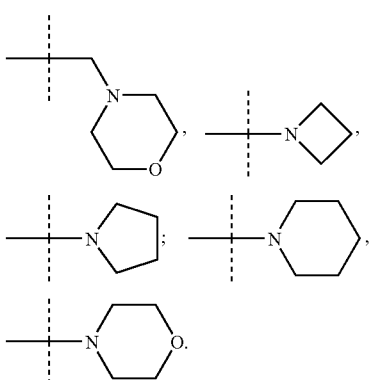
Preferably R⁵ is —SO₂—(C₁-C₄)alkyl,
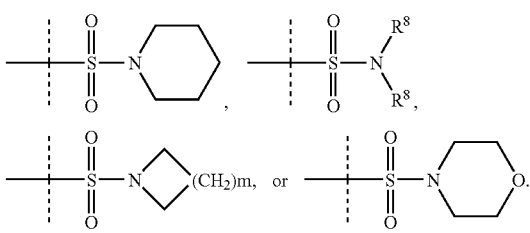
Preferably R⁵ is
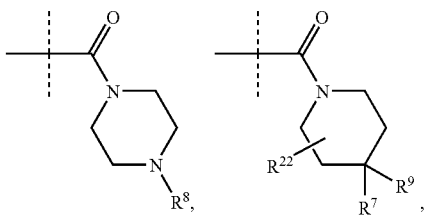

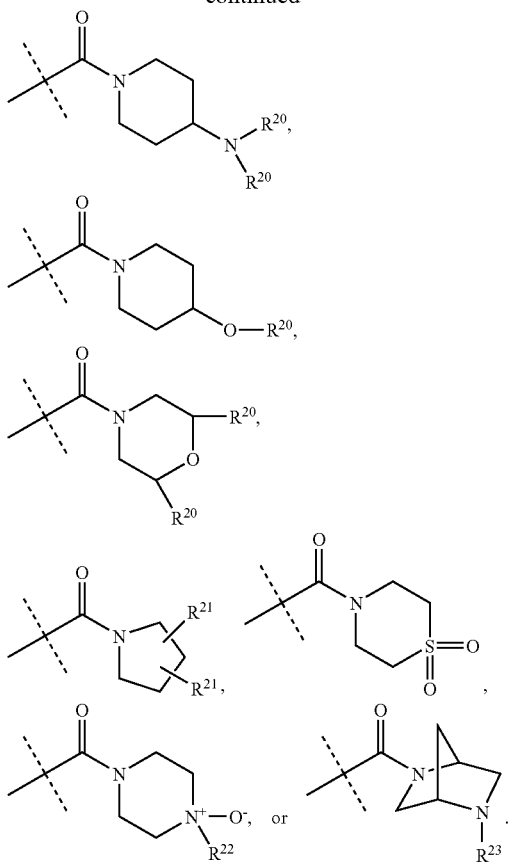

Preferably R⁵ is

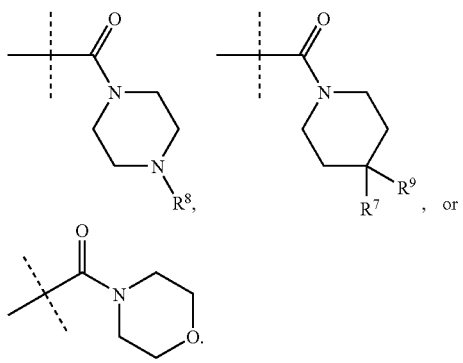

Preferably R⁵ is chlorine or fluorine. Preferably R⁵ is fluorine.

Preferably R⁶ is —H. Preferably R⁶ is -halogen. Preferably R⁶ is —(C₁-C₄)alkyl(optionally substituted with 1 to 3 halogens). Preferably R⁷ is —H. Preferably R⁷ is -halogen, or —(C₁-C₄)alkyl(optionally substituted with 1 to 3 halogens). Preferably R⁷ is -halogen. Preferably R⁷ is —(C₁-C₄)alkyl(optionally substituted with 1 to 3 halogens).

Preferably R⁸ is independently at each occurrence —H. Preferably R⁸ is independently at each occurrence —(C₁-C₃) alkyl. Preferably R⁸ is independently at each occurrence —CH₃.

Preferably R⁹ is —H. Preferably R⁹ is -halogen. Preferably R⁷ is -fluorine and R⁹ is -fluorine.

A preferred embodiment of the invention are compounds of the formula 3-(3,5-Dichloro-4'-fluoro-biphenyl-4-ylmethyl)-1-(4,5,6,7-tetrahydro-2H-indazol-5-yl)-pyrrolidin-2-one, or pharmaceutically acceptable salts thereof. Another preferred embodiment is (3R)-3-[3,5-Dichloro-4'-fluoro[1,1'-biphenyl]-4-yl)methyl]-1-[(5S)-4,5,6,7-tetrahydro-1H-indazol-5-yl]-2-pyrrolidinone or a pharmaceutically acceptable salt thereof. Another preferred embodiment is (3R)-3-(3,5-Dichloro-4'-fluoro-biphenyl-4-ylmethyl)-1-(4,5,6,7-tetrahydro-1H-indazol-4-yl)-pyrrolidin-2-one or a pharmaceutically acceptable salt thereof. A further embodiment of the invention are the novel intermediate preparations described herein which are useful for preparing the 11-β-HSD1 inhibitors according to formula I and the embodiments described herein. A further embodiment of the invention are the novel intermediate preparations described herein which are useful for preparing (3R)-3-[3,5-Dichloro-4'-fluoro[1,1'-biphenyl]-4-yl)methyl]-1-[(5S)-4,5,6,7-tetrahydro-1H-indazol-5-yl]-2-pyrrolidinone or a pharmaceutically acceptable salt thereof.

Patients with type 2 diabetes often develop "insulin resistance" which results in abnormal glucose homeostasis and hyperglycemia leading to increased morbidity and premature mortality. Abnormal glucose homeostasis is associated with obesity, hypertension, and alterations in lipid, lipoprotein, and apolipoprotein metabolism. Type 2 diabetics are at increased risk of developing cardiovascular complications, e.g., atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are important in the management and treatment of diabetes mellitus. Many patients who have insulin resistance but have not developed type 2 diabetes are also at risk of developing "Syndrome X" or "Metabolic syndrome". Metabolic syndrome is characterized by insulin resistance along with abdominal obesity, hyperinsulinemia, high blood pressure, low HDL, high VLDL, hypertension, atherosclerosis, coronary heart disease, and chronic renal failure. These patients are at increased risk of developing the cardiovascular complications listed above whether or not they develop overt diabetes mellitus.

Due to their inhibition of 11-β-HSD1, the present compounds are useful in the treatment of a wide range of conditions and disorders in which inhibition of 11-β-HSD1 is beneficial. These disorders and conditions are defined herein as "diabetic disorders" and "metabolic syndrome disorders". One of skill in the art is able to identify "diabetic disorders" and "metabolic syndrome disorders" by the involvement of 11-β-HSD1 activity either in the pathophysiology of the disorder, or in the homeostatic response to the disorder. Thus, the compounds may find use for example to prevent, treat, or alleviate, diseases or conditions or associated symptoms or sequalae, of "Diabetic disorders" and "metabolic syndrome disorders".

"Diabetic disorders" and "metabolic syndrome disorders" include, but are not limited to, diabetes, type 1 diabetes, type 2 diabetes, hyperglycemia, hyper insulinemia, beta-cell rest, improved beta-cell function by restoring first phase response, prandial hyperglycemia, preventing apoptosis, impaired fasting glucose (IFG), metabolic syndrome, hypoglycemia, hyper-/hypokalemia, normalizing glucagon levels, improved LDL/HDL ratio, reducing snacking, eating disorders, weight loss, polycystic ovarian syndrome (PCOS), obesity as a consequence of diabetes, latent autoimmune diabetes in adults (LADA), insulitis, islet transplantation, pediatric diabetes, gestational diabetes, diabetic late complications, micro-/ macroalbuminuria, nephropathy, retinopathy, neuropathy, diabetic foot ulcers, reduced intestinal motility due to glucagon administration, short bowel syndrome, antidiarrheic, increasing gastric secretion, decreased blood flow, erectile dysfunction, glaucoma, post surgical stress, ameliorating organ tissue injury caused by reperfusion of blood flow after ischemia, ischemic heart damage, heart insufficiency, congestive heart failure, stroke, myocardial infarction, arrhythmia, premature death, anti-apoptosis, wound healing, impaired glucose tolerance (IGT), insulin resistance syndromes, metabolic syndrome, syndrome X, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc. Thus the present invention also provides a method of treatment of "Diabetic disorders" and "metabolic syndrome disorders" while reducing and or eliminating one or more of the unwanted side effects associated with the current treatments.

In addition, the present invention provides a compound of Formula I, or a pharmaceutical salt thereof, or a pharmaceutical composition which comprises a compound of Formula I, or a pharmaceutical salt thereof, and a pharmaceutically acceptable carrier, diluent, or excipient: for use in inhibiting 11-β-HSD1 activity; for use in inhibiting a 11-β-HSD1 activity mediated cellular response in a mammal; for use in reducing the glycemic level in a mammal; for use in treating a disease arising from excessive 11-β-HSD1 activity; for use in treating diabetic and other metabolic syndrome disorders in a mammal; and for use in treating diabetes, metabolic syndrome, obesity, hyperglycemia, atherosclerosis, ischemic heart disease, stroke, neuropathy, and wound healing. Thus, the methods of this invention encompass a prophylactic and therapeutic administration of a compound of Formula I.

The present invention further provides the use of a compound of Formula I, or a pharmaceutical salt thereof for the manufacture of a medicament for inhibiting 11-β-HSD1 activity; for the manufacture of a medicament for inhibiting 11-β-HSD1 activity mediated cellular response in a mammal; for the manufacture of a medicament for reducing the glycemic level in a mammal; for the manufacture of a medicament for treating a disease arising from excessive 11-β-HSD1 activity; for the manufacture of a medicament for treating diabetic and other metabolic syndrome disorders in a mammal; and for the manufacture of a medicament for preventing or treating diabetes, metabolic syndrome, obesity, hyperglycemia, atherosclerosis, ischemic heart disease, stroke, neuropathy, and improper wound healing.

The present invention further provides a method of treating conditions resulting from excessive 11-β-HSD1 activity in a mammal; a method of inhibiting 11-β-HSD1 activity in a mammal; a method of inhibiting a 11-β-HSD1 activity mediated cellular response in a mammal; a method of reducing the glycemic level in a mammal; a method of treating diabetic and other metabolic syndrome disorders in a mammal; a method of preventing or treating diabetes, metabolic syndrome, obesity, hyperglycemia, atherosclerosis, ischemic heart disease, stroke, neuropathy, and improper wound healing; said methods comprising administering to a mammal in need of such treatment a 11-β-HSD1 activity inhibiting amount of a compound of Formula I, or a pharmaceutically acceptable salt thereof, or a pharmaceutical composition which comprises a compound of Formula I, or a pharmaceutical salt thereof, and a pharmaceutically acceptable carrier, diluent, or excipient.

In addition, the present invention provides a pharmaceutical composition which comprises a compound of Formula I, or a pharmaceutical salt thereof, and a pharmaceutically acceptable carrier, diluent, or excipient: adapted for use in inhibiting 11-β-HSD1 activity; adapted for use in inhibiting 11-β-HSD1 activity mediated cellular responses; adapted for use in reducing the glycemic level in a mammal; adapted for use in treating diabetic and other metabolic syndrome disorders in a mammal; and adapted for use in preventing or treating diabetes, metabolic syndrome, obesity, hyperglycemia, atherosclerosis, ischemic heart disease, stroke, neuropathy, and wound healing.

In a further aspect of the invention the present compounds are administered in combination with one or more further active substances in any suitable ratios. Such further active substances may for example be selected from antidiabetics, antiobesity agents, antihypertensive agents, agents for the treatment of complications resulting from or associated with diabetes and agents for the treatment of complications and disorders resulting from or associated with obesity. The following listing sets out several groups of combinations. It will be understood that each of the agents named may be combined with other agents named to create additional combinations.

Thus, in a further embodiment of the invention the present compounds may be administered in combination with one or more antidiabetics.

Suitable antidiabetic agents include insulin, insulin analogues and derivatives such as those disclosed in EP 792 290 (Novo Nordisk A/S), for example $N^{\epsilon B29}$-tetradecanoyl des (B30) human insulin, EP 214 826 and EP 705 275 (Novo Nordisk A/S), for example $Asp^{B28}$ human insulin, U.S. Pat. No. 5,504,188 (Eli Lilly), for example $Lys^{B28}$ $Pro^{B29}$ human insulin, EP 368 187 (Aventis), for example Lantus®, GLP-1 and GLP-1 derivatives such as those disclosed in WO 98/08871 (Novo Nordisk A/S), as well as orally active hypoglycemic agents.

The orally active hypoglycemic agents preferably comprise imidazolines, sulphonylureas, biguanides, meglitinides, oxadiazolidinediones, thiazolidinediones, insulin sensitizers, insulin secretagogues, such as glimepiride, α-glucosidase inhibitors, agents acting on the ATP-dependent potassium channel of the P-cells for example potassium channel openers such as those disclosed in WO 97/26265, WO 99/03861 and WO 00/37474 (Novo Nordisk A/S), or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), GLP-1 antagonists, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, activators of glucokinase (GK) such as those disclosed in WO 00/58293, WO 01/44216, WO 01/83465, WO 01/83478, WO 01/85706, WO 01/85707, and WO 02/08209 (Hoffman-La Roche) or those disclosed in WO 03/00262, WO 03/00267 and WO 03/15774 (AstraZeneca), GSK-3 (glycogen synthase kinase-3) inhibitors, compounds modifying the lipid metabolism such as antilipidemic agents such as HMG CoA inhibitors (statins), compounds lowering food intake, PPAR (Peroxisome proliferator-activated receptor) ligands including the PPAR-alpha, PPAR-gamma and PPAR-delta subtypes, and RXR (retinoid X receptor) agonists, such as ALRT-268, LG-1268 or LG-1069.

In another embodiment, the present compounds are administered in combination with insulin or an insulin analogue or derivative, such as $N^{\epsilon B29}$-tetradecanoyl des (B30) human insulin, Asp$^{B28}$ human insulin, Lys$^{B28}$ Pro$^{B29}$ human insulin, Lantus®, or a mix-preparation comprising one or more of these.

In a further embodiment of the invention the present compounds are administered in combination with a sulphonylurea such as glibenclamide, glipizide, tolbautamide, chloropamidem, tolazamide, glimepride, glicazide and glyburide.

In another embodiment of the invention the present compounds are administered in combination with a biguanide, for example, metformin.

In yet another embodiment of the invention the present compounds are administered in combination with a meglitinide, for example, repaglinide or nateglinide.

In still another embodiment of the invention the present compounds are administered in combination with a thiazolidinedione insulin sensitizer, for example, troglitazone, ciglitazone, pioglitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation).

In still another embodiment of the invention the present compounds may be administered in combination with an insulin sensitizer, for example, such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 such as ragaglitazar (NN 622 or (–)DRF 2725) (Dr. Reddy's Research Foundation) and WO 00/23425, WO 00/23415, WO 00/23451, WO 00/23445, WO 00/23417, WO 00/23416, WO 00/63153, WO 63196, WO 00/63209, WO 00/63190 and WO 00/63189 (Novo Nordisk A/S).

In a further embodiment of the invention the present compounds are administered in combination with an α-glucosidase inhibitor, for example, voglibose, emiglitate, miglitol or acarbose.

In another embodiment of the invention the present compounds are administered in combination with an agent acting on the ATP-dependent potassium channel of the β-cells, for example, tolbutamide, glibenclamide, glipizide, glicazide, BTS-67582 or repaglinide.

In yet another embodiment of the invention the present compounds may be administered in combination with nateglinide.

In still another embodiment of the invention the present compounds are administered in combination with an antilipidemic agent or antihyperlipidemic agent for example cholestyramine, colestipol, clofibrate, gemfibrozil, lovastatin, pravastatin, simvastatin, pitavastatin, rosuvastatin, probucol, dextrothyroxine, fenofibrate or atorvastin.

In still another embodiment of the invention the present compounds are administered in combination with compounds lowering food intake.

In another embodiment of the invention, the present compounds are administered in combination with more than one of the above-mentioned compounds for example in combination with metformin and a sulphonylurea such as glyburide; a sulphonylurea and acarbose; nateglinide and metformin; repaglinide and metformin, acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

General terms used in the description of compounds herein described bear their usual meanings.

As used herein, the terms "(C$_1$-C$_3$)alkyl", "(C$_1$-C$_4$)alkyl" or "(C$_1$-C$_6$)alkyl" refer to straight-chain or branched-chain saturated aliphatic groups of the indicated number of carbon atoms, such as methyl, ethyl, n-propyl, isopropyl, n-butyl, isobutyl, sec-butyl, t-butyl, and the like. The term "(C$_1$-C$_6$) alkoxy" represents a C$_1$-C$_6$ alkyl group attached through an oxygen and include moieties such as, for example, methoxy, ethoxy, n-propoxy, isopropoxy, and the like. The term "halogen" refers to fluoro, chloro, bromo, and iodo. The term "(C$_3$-C$_8$) cycloalkyl" refers to a saturated or partially saturated carbocycle ring of from 3 to 8 carbon atoms, typically 3 to 7 carbon atoms. Examples of (C$_3$-C$_8$) cycloalkyl include but are not limited to cyclopropyl, cyclobutyl, cyclopentyl, cyclohexyl, cycloheptyl, and the like.

The term "optionally substituted," or "optional substituents," as used herein, means that the groups in question are either unsubstituted or substituted with one or more of the substituents specified. When the groups in question are substituted with more than one substituent, the substituents may be the same or different. Furthermore, when using the terms "independently," "independently are," and "independently selected from" mean that the groups in question may be the same or different. Certain of the herein defined terms may occur more than once in the structural formulae, and upon such occurrence each term shall be defined independently of the other.

It is understood that guinea pigs, dogs, cats, rats, mice, hamsters, and primates, including humans, are examples of patients within the scope of the meaning of the term "patient". Preferred patients include humans. The term "patient" includes livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. The patient to be treated is preferably a mammal, in particular a human being.

The terms "treatment", "treating" and "treat", as used herein, include their generally accepted meanings, i.e., the management and care of a patient for the purpose of preventing, reducing the risk in incurring or developing a given condition or disease, prohibiting, restraining, alleviating, ameliorating, slowing, stopping, delaying, or reversing the progression or severity, and holding in check and/or treating existing characteristics, of a disease, disorder, or pathological condition, described herein, including the alleviation or relief of symptoms or complications, or the cure or elimination of the disease, disorder, or condition. The present method includes both medical therapeutic and/or prophylactic treatment, as appropriate.

As used herein, the term "therapeutically effective amount" means an amount of compound of the present invention that is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated.

"Composition" means a pharmaceutical composition and is intended to encompass a pharmaceutical product comprising the active ingredient(s) including compound(s) of Formula I, and the inert ingredient(s) that make up the carrier. Accordingly, the pharmaceutical compositions of the present invention encompass any composition made by admixing a compound of the present invention and a pharmaceutically acceptable carrier.

The term "substantially pure" refers to pure crystalline form of a compound comprising greater than about 90% of the desired crystalline form, and preferably, greater than about 95% of the desired crystal form.

The term "suitable solvent" refers to any solvent, or mixture of solvents, inert to the ongoing reaction that sufficiently solubilizes the reactants to afford a medium within which to effect the desired reaction.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

The compounds of the present invention may have one or more chiral centers and may exist in a variety of stereoisomeric configurations. As a consequence of these chiral centers the compounds of the present invention can occur as racemates, as individual enantiomers or mixtures of enantiomers, as well as diastereomers and mixtures of diastereomers. All such racemates, enantiomers, diastereomers and mixtures are within the scope of the present invention, whether pure, partially purified, or unpurified mixtures. For the examples provided herein, when a molecule which contains a chiral center or centers of known configuration is presented, its stereochemistry is designated in the name and in the structural representation of the molecule. If the stereochemistry is unknown or undefined its stereochemistry is not designated in the name or in the structural representation of the molecule. Embodiments of the invention include the Examples provided herein, and although the Example provided may be of one chiral or conformational form, or a salt thereof, further embodiments of the invention include all other stereoisomeric and or conformational forms of the examples described, as well as pharmaceutically acceptable salts thereof. These embodiments include any isolated enantiomers, diastereomers, and or conformers of these structures, as well as any mixtures containing more than one form.

Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention. Furthermore, some of the compounds of the present invention may exist in different tautomeric forms and it is intended that any tautomeric forms which the compounds are able to form are included within the scope of the present invention.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

The compounds of Formula I, can be prepared by one of ordinary skill in the art following a variety of procedures, some of which are illustrated in the procedures and schemes set forth below. The particular order of steps required to produce the compounds of Formula I is dependent upon the particular compound to being synthesized, the starting compound, and the relative lability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Preparations, Examples and Procedures are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The optimal time for performing the reactions of the Schemes, Preparations, Examples and Procedures can be determined by monitoring the progress of the reaction via conventional chromatographic techniques. Furthermore, it is preferred to conduct the reactions of the invention under an inert atmosphere, such as, for example, argon, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The terms and abbreviations used in the instant Schemes, Preparations, Examples and Procedures have their normal meanings unless otherwise designated. For example, as used herein, the following terms have the meanings indicated: "psi" refers to pounds per square inch; "TLC" refers to thin layer chromatography; "HPLC" refers to high performance liquid chromatography; "$R_f$" refers to retention factor; "$R_t$" refers to retention time; "δ" refers to part per million downfield from tetramethylsilane; "MS" refers to mass spectrometry, Observed Mass indicates [M+H] unless indicated otherwise. "MS (APCi) refers to atmospheric pressure chemical ionization mass spectrometry, "UV" refers to ultraviolet spectrometry, "$^1$H NMR" refers to proton nuclear magnetic resonance spectrometry. "LCMS" refers to liquid chromatography-mass spectrometry, "GC/MS" refers to gas chromatography/mass spectrometry. "IR" refers to infra red spectrometry, and the absorption maxima listed for the IR spectra are only those of interest and not all of the maxima observed. "RT" refers to room temperature.

"THF" refers to tetrahydrofuran, "LAH" refers to lithium aluminum hydride, "LDA" refers to lithium diisopropylamide, "DMSO" refers to dimethylsulfoxide, "DMF" refers to dimethylforamide, "HCl" refers to hydrochloric acid, "EtOAc" refers to ethyl acetate, "Pd—C" refers to palladium on carbon, "DCM" refers to dichloromethane, "DMAP" refers to dimethylaminopyridine, "LiHMDS" refers to Lithium Hexamethyldisilisane, "TFA" refers to trifluoroacetic acid, "EDAC" refers to N-Ethyl-N'-(3-dimethylaminopropyl)carbodiimide hydrochloride, "HOBT" refers to 1-Hydroxy benzotriazole, "Bn-9-BBN" refers to Benzyl-9-borabicyclo[3.3.1]nonane, "Pd(dppf)Cl$_2$" refers to [1,1'-Bis (diphenylphosphino)-ferrocene)dichloropalladium(II), "EDCI" refers to N-Ethyl-N'-(3-dimethylaminopropyl)carbodiimide hydrochloride, "DBU" refers to 1,8-Diazabicyclo [5.4.0]undecene-7, "TBSCl" refers to tert-butyl-dimethyl-silanyloxymethyl chloride, "NBS" refers to N-Bromosuccinimide, "TsOH" refers to p-toluenesulfonic acid, "DCE" refers to dichloroethane, "DAST" refers to (Diethylamino)sulfur trifluoride, "EA/H" refers to ethyl acetate/hexanes mixture, "Pd$_2$(dba)$_3$" refers to Bis(dibenzylideneacetone)palladium, "BINAP" refers to 2,2'-Bis (diphenylphospino-1,1'-binaphthalene, "NMP" refers to N-Methylpyrrollidine, "TMSCN" refers to Trimethylsilyl cyanide, "TBAF" refers to Tetrabutylammonium fluoride, "Tf$_2$O" refers to trifluoromethanesulfonic anhydride, "TBSO" refers to tert-butyl-dimethyl-silanyloxy, "OTf" refers to trifluoromethanesulfonate, MeTi(Oi-Pr)$_3$ refers to methyltitanium triisopropoxide, "BBr$_3$" refers to boron tribromide, "PBr$_3$" refers to phosphorous tribromide, "Pd (PPh$_3$)$_4$" refers to tetrakis(triphenylphoshine)palladium (0), "OAc" refers to acetate, "DME" refers to dimethylethane, "Et$_2$O" refers to diethyl ether, "(Ph$_3$P)$_4$Pd" refers to tetrakis (triphenylphoshine)palladium (0), "DMFDMA" refers to N,N-dimethylformamide dimethyl acetal, "Et$_3$N" refers to triethylamine, "tBu" refers to t-butyl, "DIPEA" refers to diisopropylethyl amine, "EDC" refers to -(3-Dimethylaminopropyl)-3-ethylcarbodiimide hydrochloride, "HOAc" refers to acetic acid, "boc" refers to t-butoxycarbonyl. In a structure, "Ph" refers to phenyl, "Me" refers to methyl, "Et" refers to ethyl, "Bn" refers to benzyl, "MeOH" refers to methanol, "OTf" refers to trifluoromethanesulfonate, "TIPSO" refers to triisopropylsilanyloxy, "TBSO" refers to tert-butyl-dimethyl-silanyloxy, "NaBH(OAc)$_3$" refers to sodium triacetoxyborohydride, "[Ir(cod)Cl]$_2$" refers to Di-chlorobis((1,2,5,6-eta)-1,5-cyclooctadiene)diiridium.

The Examples provided herein are illustrative of the invention claimed herein and are not intended to limit the scope of the claimed invention in any way. The preparations and examples are named using AutoNom 2.2 in ChemDraw Ultra, or AutoNom 2000 in MDL ISIS/Draw version 2.5 SP 1 from MDL Information Systems, Inc., or where provided by Chemical Abstracts Services.

A Varian INOVA 400 MHz spectrometer is used to obtain $^1$H NMR Specta the in the solvent indicated. An Agilent HP1100 instrument equipped with a Mass Spectrometer (Agilent MSD SL) is used to obtain LCMS. A Waters Xterra C18 (2.1×50 mm, 3.5 micron) is used as stationary phase and a standard method is a gradient of 5-100% acetonitrile/methanol (50:50) with 0.2% ammonium formate over 3.5 minutes then held at 100% B for 0.5 minutes at a column temperature of 50° C. and a flow rate of 1.0 mL/min. Another standard method is a gradient of 5-100% acetonitrile/methanol (50:50) with 0.2% ammonium formate over 7.0 minutes then held at 100% B for 1.0 minutes at a column temperature of 50° C. and a flow rate of 1.0 mL/min. Additional MS analysis via Agilent MSD (loop machine) is standard Flow injection Analysis (FIA), no column is present and flow is 0.5 ml/min of 80% MeOH with 6.5 mM Ammonium Acetate for 30 secs run time.

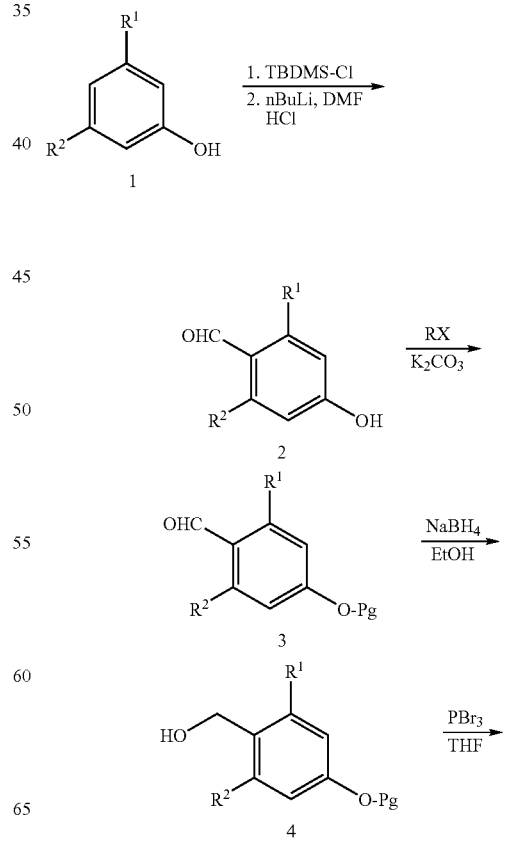

Scheme A

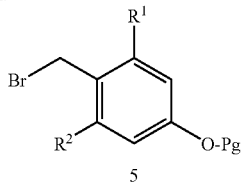

In Scheme A, an optionally substituted phenol (1) is protected (e.g, with TBSCl) and then is converted to the aldehyde (2). Compound 2 is reacted with a compound containing a protecting group (Pg) and leaving group (Lg) to give the ether compound 3. Pg can be —$CH_3$ or —$CH_2$-phenyl and Lg can be mesylate or halo. Preferably, the Lg-Pg compound is I—$CH_3$ or Br—$CH_2$-phenyl. The aldehyde is reduced to form the alcohol (4) and then converted to compound 5. Preferably, compound 4 is halogenated with $PBr_3$ to give the 2-bromomethyl compound.

Protection and deprotection of the compounds to form compounds of formula I and others are well known to the skilled artisan and are described in the literature. (For example, see: Greene and Wuts, *Protective Groups in Organic Synthesis*, Third Edition, John Wiley and Sons Inc., 1999).

Preparation 1 tert-butyl-(3,5-dichloro-phenoxy)-dimethyl-silane

Dissolve 3,5 dichlorophenol (1 kg, 6.13 mol) in 3 L dimethylformamide and cool to 0° C. Add imidazole (918.74 g, 6.75 mol), followed by tertbutyldimethylsilyl chloride (1017.13 g, 6.75 mol). Warm the mixture to room temperature and stir for 15 min. Pour into water (6 L) and extract with ether (4 L). Wash the organic layer with water 2 times, 10% aqueous lithium chloride solution then brine before drying over sodium sulfate. Filter and concentrate under vacuum to 135 g of an oil.

Preparation 2

2,6-dichloro-4-hydroxy-benzaldehyde

Dissolve tert-butyl-(3,5-dichloro-phenoxy)-dimethyl-silane (425 g, 1.5 mol) in 4 L dry tetrahydrofuran and cool to −68° C. Slowly add 1.1 equivalents of sec-butyl lithium (103.1 g, 1.61 mol) at −68° C. (~1.75 hr). After addition is complete stir the reaction at −70° C. for 30 min. Add dimethylformamide (168.5 g, 2.3 mol) and stir the reaction at −70° C. for 1 hr. Add 1 M hydrochloric acid in water (3.5 L) and allow the reaction to warm to room temperature.

Pour the reaction mixture into ether (5 L), wash with water then brine. Dry over sodium sulfate and concentrate under vacuum to an orange solid. Triturate with cold dichloromethane and filter to recover 250 g (80%) pale yellow solid.

Preparation 3

2,6-dichloro-4-methoxy-benzaldehyde

Combine 2,6-dichloro-4-hydroxy-benzaldehyde (120 g, 628.24 mmol) and potassium carbonate (173.65 g, 1256.5 mmol) in 900 mL dimethylformamide and treat with iodomethane (107 g, 753.9 mmol). Stir the reaction at room temperature for 3 hours. Filter off solids and pour into 6 L of water. Filter solids, wash several times with water, air dry and dissolve in ethyl acetate. Wash with water, followed by brine then dry over sodium sulfate. Filter and concentrate under vacuum to ~100 mL volume, at which point, solids start to crash out. Filter then concentrate down the filtrate to yield a second crop. Wash with hexane, combine all solids and vacuum dry to yield 112.3 g of off-white, solid: $^1$H NMR (400 MHz, $CDCl_3$) δ 10.41 (s, 1H), 6.90 (s, 2H), 3.87 (s, 3H).

Preparation 4

2,6-dichloro-4-benzyloxy-benzaldehyde

Treat a mixture of 2,6-dichloro-4-hydroxy-benzaldehyde (250 g, 1.3 mol) and potassium carbonate (361.8 g, 2.62 mol) in 2 L dimethylformamide with benzyl bromide (268.64 g, 1.57 mol). Stir the reaction at room temperature for 1 hour. Filter off solids and pour into 12 L of water. Filter off solid, wash several times with water, air dry and dissolve in ethyl acetate. Dry over magnesium sulfate, filter and concentrate under vacuum to ~1.5 L. Allow to sit overnight then filter. Wash solid with minimal amount of hexane and vacuum dry. Concentrate the filtrate under vacuum and triturate with hexane to yield a second crop of product which when combined with the first crop equals 245 g white crystals. Repeat to obtain a third crop of 80 g as a light-tan powder (88% overall yield): $^1$H NMR (400 MHz, DMSO-$d_6$) δ 10.26 (s, 1H), 7.43 (m, 5H), 7.28 (s, 2H), 5.25 (s, 2H).

Preparation 5

(2,6-dichloro-4-methoxy-phenyl)-methanol

Suspend 2,6-dichloro-4-methoxy-benzaldehyde (112 g, 546 mmol) in 1500 mL ethanol and cool in an ice bath to 7° C. Add sodium borohydride (20.67, 546 mmol) portionwise to obtain a solution. Remove the ice bath and stir for 2 hours. Carefully add reaction mixture to saturated ammonium chloride solution (~4 L) and stir until fully quenched. Extract with dichloromethane (3×1 L) and dry the combined organic extracts over sodium sulfate. Filter and concentrate under vacuum to yield 113 g of a light-tan solid: $^1$H NMR (400 MHz, $CDCl_3$) δ 6.86 (s, 2H), 4.86 (s, 2H), 3.78 (s, 3H), 2.07 (s, 1H).

Preparation 6

(2,6-dichloro-4-benzyloxy-phenyl)-methanol

Prepare the title compound essentially by the method of Preparation 5 starting from 2,6-dichloro-4-benzyloxy-benzaldehyde: $^1$H NMR (400 MHz, DMSO-$d_6$) δ 7.38 (m, 4H), 7.33 (m, 1H), 7.12 (s, 2H), 5.14 (s, 2H), 5.05 (t, 1H), 4.59 (d, 2H).

Preparation 7

2-bromomethyl-1,3-dichloro-5-methoxy-benzene

Dissolve (2,6-dichloro-4-methoxy-phenyl)-methanol (113 g, 545.76 mmol) in 1200 mL dry tetrahydrofuran and cool to 0° C. under nitrogen. Add $PBr_3$ (59.1 g, 218.3 mmol) under nitrogen and stir at 0° C. for 30 minutes. Pour into saturated aqueous sodium bicarbonate and extract with ethyl acetate.

Dry and concentrate under vacuum to obtain 129.4 g product as an off-white solid: $^1$H NMR (400 MHz, CDCl$_3$) δ 6.88 (s, 2H), 4.73 (s, 2H), 3.79 (s, 3H).

Preparation 8

2-bromomethyl-1,3-dichloro-5-benzyloxy-benzene

Prepare the title compound essentially by the method of Preparation 6 in an 89% yield starting from 2,6-dichloro-4-benzyloxy-phenyl)-methanol: ES MS (m/z): 347 (M+1).

Scheme B

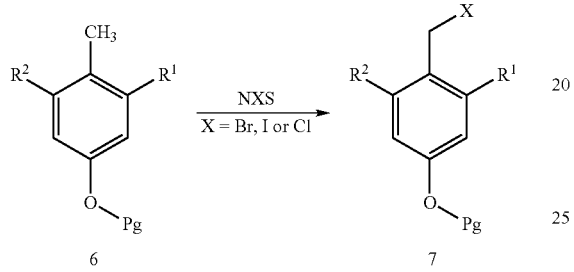

In Scheme B, treatment of substituted methyl benzene 6 with NXS (X=Cl, N-chlorosuccinamide; X=Br, N-bromosuccinamide; X=I, N-iodosuccinamide) in presence of benzoyl peroxide in CCl$_4$ under reflux to afford the corresponding benzyl halide 7.

Preparation 9

2-Chloro-4-methoxy-1-methyl-benzene

Heat a solution of 3-chloro-4-methylphenol (15 g, 0.11 mol), iodomethane (9.8 mL, 0.16 mol), and potassium carbonate (22 g, 0.16 mol) in DMF (200 mL) to 50° C. and stir for 2 hr. Cool the reaction to room temperature and quench with 1N aqueous HCl. Extract the aqueous with diethyl ether (Et$_2$O). Wash the organic with brine, dry over MgSO$_4$, and filter. Remove the solvent to afford 16.4 g (100%) of the desired product.

Preparation 10

1-Bromomethyl-2-chloro-4-methoxy-benzene

Heat a solution of 2-chloro-4-methoxy-1-methyl-benzene (2.0 g, 13 mmol), N-bromosuccinimide (2.7 g, 15 mmol), and benzoyl peroxide (50 mg) in CCl$_4$ (50 mL) to reflux and stir for 3 hr. Cool the reaction to room temperature and quench with water. Extract the aqueous with CH$_2$Cl$_2$, dry over MgSO$_4$, and filter. Remove the solvent to afford 3.0 g (98%) of the desired product.

Scheme C

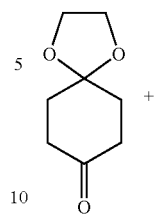

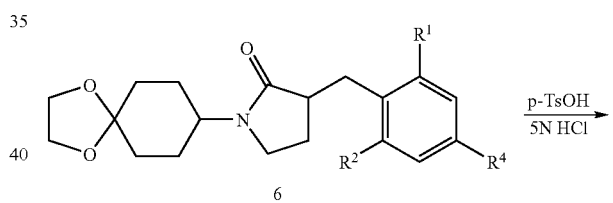

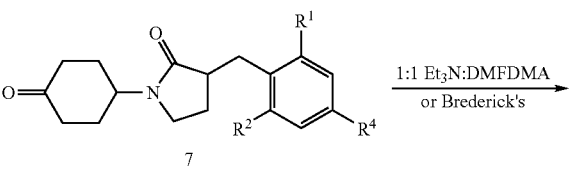

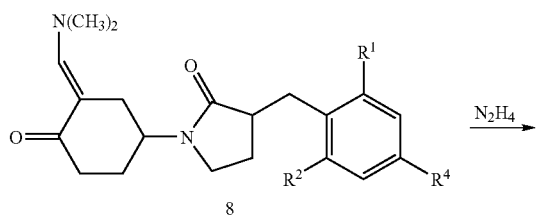

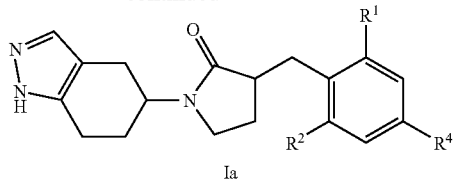

Ia

In Scheme C, treatment of 1,4-dioxa-spiro[4.5]decan-8-one with hydrochloride salt of 4-amino-butyric acid ethyl ester in presence of NaBH(OAc)$_3$ affords 1-(1,4-dioxa-spiro[4.5]dec-8-yl)-pyrrolidin-2-one. Alkylation is achieved by using LDA and benzyl bromide 5 to give desired lactam 6. Removal of the ketal protection under acidic condition gives ketone 7. Compound 8 is prepared by treatment of ketone 7 with dimethoxymethyl-dimethyl-amine or Brederick's reagent. Treatment of 8 with hydrazine to provide pyrazole Ia.

Preparation 11

1-(1,4-Dioxa-spiro[4.5]dec-8-yl)-pyrrolidin-2-one

Dissolve 1,4-dioxaspiro{4.5}decan-8-one (100 g, 640.3 mmol), methyl-4-aminobutyrate hydrochloride (98.5 g, 640.3 mmol), triethylamine (90 mL, 640.3 mmol) and dichloromethane (2 L) and stir at room temperature. Add Sodium triacetoxyborohydride (135.7 g, 640.3 mmol) stir 17 h at room temperature. Quench with water (1 L), separate, wash the aqueous layer with dichloromethane (3×500 mL), combine the organic phases and dry over anhydrous sodium sulfate, filter and concentrate. Purify the material on a 1.5 kg silica column, 6 inches in diameter, and eluted with 8:2 hexanes/ethyl acetate to 95:5 ethyl acetate/methanol to give 73 g of the title compound as a waxy brown solid. $^1$H NMR (CDCl$_3$) δ 3.99-4.10 (m, 1H), 3.93 (s, 4H), 3.32-3.36 (m, 2H), 2.36-2.40 (m, 2H), 1.94-2.03 (m, 2H), 1.65-1.83 (m, 8H).

Preparation 12

3-(2,6-Dichloro-4-methoxy-benzyl)-1-(1,4-dioxa-spiro[4.5]dec-8-yl)-pyrrolidin-2-one Cool a solution of 1-(1,4-Dioxa-spiro[4.5]dec-8-yl)-pyrrolidin-2-one (5 g, 22.2 mmol) in tetrahydrofuran (100 mL) to −78° C. under nitrogen purge. Add LDA (2.0 M, 15 mL, 30 mmol) at a rate such that the internal reaction temperature did not reach above −67° C. Stir 30 min at −78° C., add a solution of 2-bromomethyl-1,3-dichloro-5-methoxy-benzene, 6.6 g, 24.4 mmol) in THF (20 mL) over a 1-2 minute period, remove the cold bath and allow reaction to warm over 3 hr. Quench the reaction with saturated aqueous ammonium chloride (100 mL), extract with ethyl acetate (3×100 mL), combine the extracts and dry over anhydrous sodium sulfate. Purify on silica column eluting with 8:2 hexanes:ethyl acetate to 1:1 hexanes:ethyl acetate to afford the product as a ivory solid, 6.5 g, 71%. $^1$H NMR (CDCl$_3$) δ 6.86 (s, 2H), 4.06-4.12 (m, 1H), 3.94 (s, 4H), 3.77 (s, 3H), 3.32-3.41 (m, 2H), 3.15-3.21 (m, 1H), 2.83-2.97 (m, 2H), 1.68-2.04 (m, 8H). LCMS m+1 414.

TABLE 1

Prepare the Preparations in Table 1 essentially as described in Preparation 12 except for 2-bromomethyl-1,3-dichloro-5-methoxy-benzene is replaced by the reagent as indicated in column 3.

| Preparation | Structure and Chemical name | Reagent | Physical data |
| --- | --- | --- | --- |
| 13 | 1-(1,4-Dioxa-spiro[4.5]dec-8-yl)-3-(2,4,6-trifluoro-benzyl)-pyrrolidin-2-one | Br-CH$_2$-C$_6$H$_2$F$_3$ (2,4,6-trifluorobenzyl bromide) | MS (m/z): 370 (M + 1) |
| 14 | 3-(2-Chloro-4-fluoro-benzyl)-1-(1,4-dioxa-spiro[4.5]dec-8-yl)-pyrrolidin-2-one | Br-CH$_2$-C$_6$H$_3$ClF (2-chloro-4-fluorobenzyl bromide) | MS (m/z): 368 (M + 1) |
| 15 | 3-(2-Chloro-4-methoxy-benzyl)-1-(1,4-dioxa-spiro[4.5]dec-8-yl)-pyrrolidin-2-one | Br-CH$_2$-C$_6$H$_3$Cl(OCH$_3$) (2-chloro-4-methoxybenzyl bromide) | MS (m/z): 385 (M + 1) |

TABLE 1-continued

Prepare the Preparations in Table 1 essentially as described in Preparation 12 except for 2-bromomethyl-1,3-dichloro-5-methoxy-benzene is replaced by the reagent as indicated in column 3.

| Preparation | Structure and Chemical name | Reagent | Physical data |
| --- | --- | --- | --- |
| 16 | 3-(2,4-Dihloro-benzyl)-1-(1,4-dioxa-spiro[4.5]dec-8-yl)-pyrrolidin-2-one | (2,4-dichlorobenzyl bromide) | MS (m/z): 385 (M + 1) |
| 17 | 3-(2-Chloro-4-bromo-benzyl)-1-(1,4-dioxa-spiro[4.5]dec-8-yl)-pyrrolidin-2-one | (2-chloro-4-bromobenzyl bromide) | MS (m/z): 429 (M + 1) |

Preparation 18

3-(2,6-Dichloro-4-methoxy-benzyl)-1-(4-oxo-cyclohexyl)-pyrrolidin-2-one

Dissolve 3-(2,6-Dichloro-4-methoxy-benzyl)-1-(1,4-dioxa-spiro[4.5]dec-8-yl)-pyrrolidin-2-one (6.5 g, 15.7 mmol) in acetone (100 mL), add p-toluenesulfonic acid hydrate (3 g, 15.7 mmol) and stir for 24 hr at room temp. Add 5N HCl (10 mL) and heat to 45° C. for 1 hr. Reaction progress can be monitored by TLC. Concentrate the reaction mixture, dilute with saturated aqueous sodium hydrogen carbonate (500 mL) and extract with ethyl acetate (3×150 mL). Wash the combined extracts with water (100 mL) and brine (100 mL), dry over anhydrous sodium sulfate, filtered, and concentrate to about 50 mL volume, dilute with hexanes (50 mL) and filter to give 5.5 g, 95%, as a white solid. 1H NMR (CDCl$_3$) δ 6.78 (s, 2H), 4.44-4.52 (m, 1H), 3.78 (s, 3H), 3.37-3.47 (m, 1H), 3.29-3.36 (m, 1H), 3.15-3.23 (m, 2H), 2.39-2.62 (m, 4H), 1.80-2.11 (m, 6H). LCMS m+1 370.

TABLE 2

Prepare the Preparations in Table 2 essentially as described in Preparation 18 substituting the indicated synthetic reagent as indicated in column 3.

| Preparation | Chemical name | Synthetic Reagent | Physical data |
| --- | --- | --- | --- |
| 19 | 1-(4-Oxo-cyclohexyl)-3-(2,4,6-trifluoro-benzyl)-pyrrolidin-2-one | 1-(1,4-Dioxa-spiro[4.5]dec-8-yl)-3-(2,4,6-trifluoro-benzyl)-pyrrolidin-2-one | MS (m/z): 326 (M + 1) |
| 20 | 3-(2-Chloro-4-fluoro-benzyl)-1-(4-oxo-cyclohexyl)-pyrrolidin-2-one | 3-(2-Chloro-4-fluoro-benzyl)-1-(1,4-dioxa-spiro[4.5]dec-8-yl)-pyrrolidin-2-one | MS (m/z): 324 (M + 1) |
| 21 | 3-(2-Chloro-4-methoxy-benzyl)-1-(4-oxo-cyclohexyl)-pyrrolidin-2-one | 3-(2-Chloro-4-methoxy-benzyl)-1-(1,4-dioxa-spiro[4.5]dec-8-yl)-pyrrolidin-2-one | MS (m/z): 336 (M + 1) |
| 22 | 3-(2,4-Dichloro-benzyl)-1-(4-oxo-cyclohexyl)-pyrrolidin-2-one | 3-(2,4-Dihloro-benzyl)-1-(1,4-dioxa-spiro[4.5]dec-8-yl)-pyrrolidin-2-one | MS (m/z): 340 (M + 1) |
| 23 | 3-(2-Chloro-4-bromo-benzyl)-1-(4-oxo-cyclohexyl)-pyrrolidin-2-one | 3-(2-Chloro-4-bromo-benzyl)-1-(1,4-dioxa-spiro[4.5]dec-8-yl)-pyrrolidin-2-one | MS (m/z): 441 (M + 1) |

Preparation 24

3-(2,6-Dichloro-4-methoxy-benzyl)-1-(3-dimethylaminomethylene-4-oxo-cyclohexyl)-pyrrolidin-2-one Heat a mixture of 3-(2,6-Dichloro-4-methoxy-benzyl)-1-(4-oxo-cyclohexyl)-pyrrolidin-2-one (5 g, 13.5 mmol), triethylamine (20 mL) and N,N-dimethylformamide dimethylacetal (20 mL) in a 140° C. oil bath to dryness. Cooling the reaction a bit, add another portion of triethylamine (20 mL) and N,N-dimethylformamidedimethylacetal (20 mL) heat to 140° C. again to dryness. Remove organics under vacuum and monitor reaction progress via LCMS and NMR: $^1$H NMR (CDCl$_3$) δ 7.50-7.53 (m, 1H), 6.86 (s, 2H), 4.24-4.33 (m, 1H), 3.76 (s, 3H), 3.44-3.46 (m, 2H), 3.19-3.28 (m, 1H), 3.08 (s, 3H), 3.05 (s, 3H), 2.86-2.97 (m, 2H), 2.56-2.69 (m, 1H), 2.43-2.52 (m, 2H), 1.83-2.03 (m, 3H). MS (m/z): 425 (M+1).

TABLE 3

Prepare the Preparations in Table 3 essentially as described in Preparation 24 substituting the indicated synthetic reagent.

| Preparation | Chemical structure | Synthetic Reagent |
|---|---|---|
| 25 | 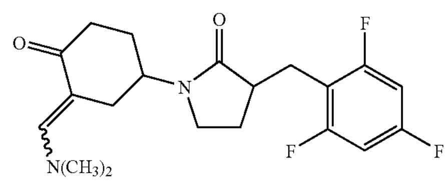 | 1-(4-Oxo-cyclohexyl)-3-(2,4,6-trifluoro-benzyl)-pyrrolidin-2-one |
| 26 | 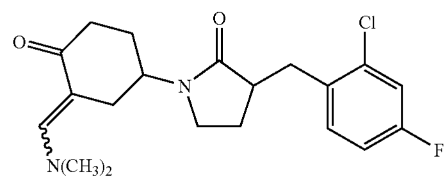 | 3-(2-Chloro-4-fluoro-benzyl)-1-(4-oxo-cyclohexyl)-pyrrolidin-2-one |
| 27 | 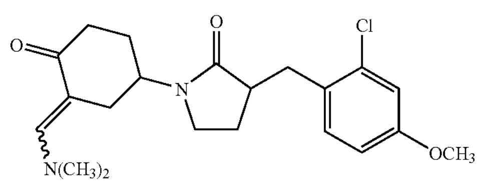 | 3-(2-Chloro-4-methoxy-benzyl)-1-(4-oxo-cyclohexyl)-pyrrolidin-2-one |
| 28 | 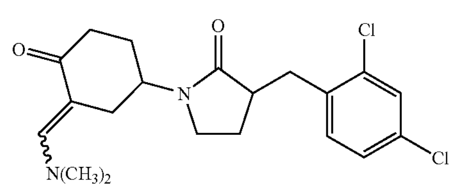 | 3-(2,4-Dichloro-benzyl)-1-(4-oxo-cyclohexyl)-pyrrolidin-2-one |
| 29 | 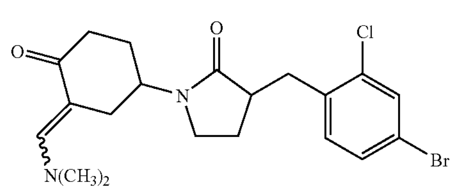 | 3-(2-Chloro-4-bromo-benzyl)-1-(4-oxo-cyclohexyl)-pyrrolidin-2-one |

Scheme D

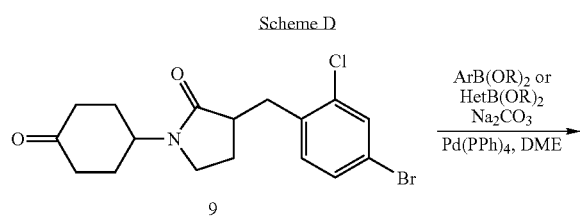

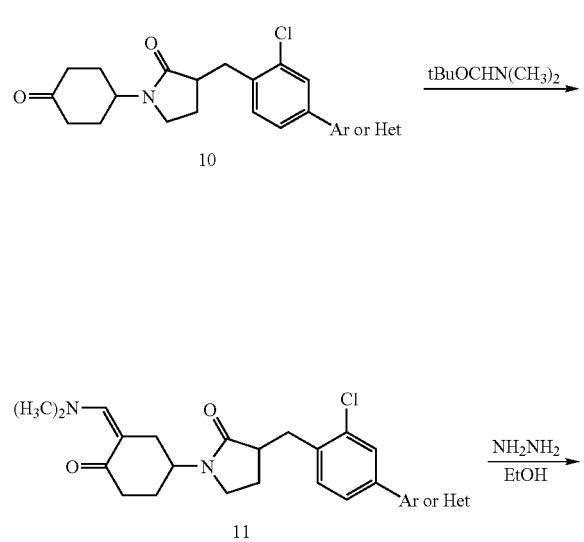

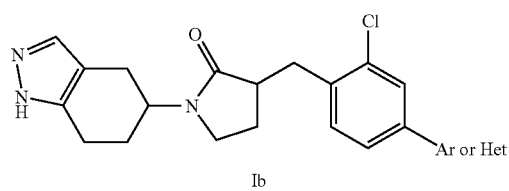

In Scheme D, compound 10 is prepared by treatment of compound 9 with various aryl boronic acids or esters under standard Suzuki coupling conditions, i.e. Pd(PPh)$_4$, Na$_2$CO$_3$ in DME. Treatment of ketone 10 with Brederick's reagent affords compound 11. The pyrazole Ib is prepared by treatment of 11 with hydrazine.

Preparation 30

3-[2-Chloro-4-(1-methyl-1H-pyrazol-4-yl)-benzyl]-1-(4-oxo-cyclohexyl)-pyrrolidin-2-one Combine 3-(4-Bromo-2-chloro-benzyl)-1-(4-oxo-cyclohexyl)-pyrrolidin-2-one (0.5, 1.3 mmol), 1-Methyl-4-(4,4,5,5-tetramethyl-[1,3,2]dioxaborolan-2-yl)-1H-pyrazole (0.814 g, 3.9 mmol), sodium carbonate (0.689 g, 6.5 mmol) in DME (8 mL)/H$_2$O (3 mL) and degas with a stream of nitrogen. Add (Ph$_3$P)$_4$Pd (0.150 g, 0.13 mmol), and stir at 80° C. for 17 hour under nitrogen atmosphere. Cool to ambient temperature and add ethyl acetate (20 mL) and water (10 mL). Extract the aqueous phase with ethyl acetate (2×20 mL), dry (sodium sulfate) and condense under reduced pressure. Chromatography (silica, EtOAc) yields 0.287 g (42%) as a white solid MS (m/z): 386 (M+1).

Preparation 31

3-[2-Chloro-4-(1-methyl-1H-pyrazol-4-yl)-benzyl]-1-(3-dimethylaminomethylene-4-oxo-cyclohexyl)-pyrrolidin-2-one Heat a mixture of 3-[2-Chloro-4-(1-methyl-1H-pyrazol-4-yl)-benzyl]-1-(4-oxo-cyclohexyl)-pyrrolidin-2-one (0.287 g, 0.745 mmol), and Brederick's reagent (0.17 mL) in toluene (3 mL) to 90° C. for 30 minutes. Remove organics under vacuum to give 0.327 g of an oil to be used without additional purification. MS (m/z): 441 (M+1).

Scheme E

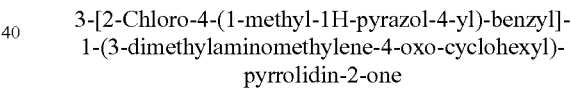
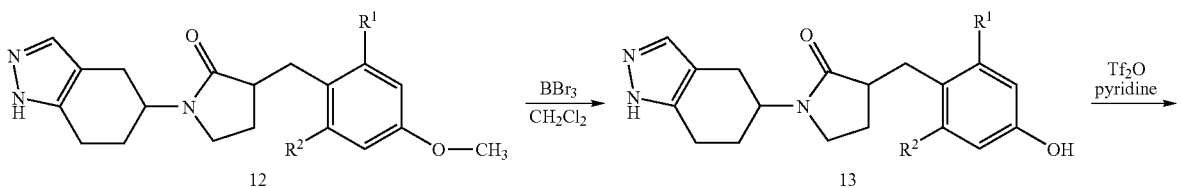

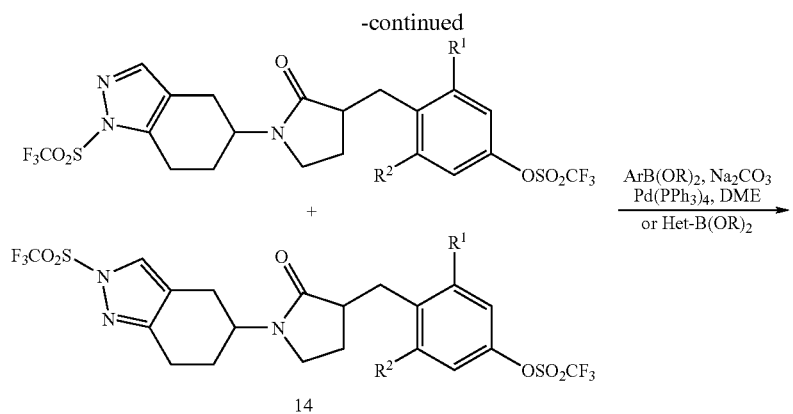

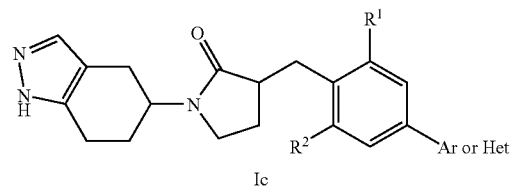

In Scheme E, treatment of compound 12 with BBr$_3$ gives phenol 13 which can be subsequently triflated to afford compound 14 using Tf$_2$O in presence of pyridine. Ic can be prepared by using various boronic acids or esters under standard Suzuki coupling conditions, i.e. Pd(PPh$_3$)$_4$ and Na$_2$CO$_3$ in DME.

Preparation 32

3-(2,6-Dichloro-4-hydroxy-benzyl)-1-(4,5,6,7-tetrahydro-2H-indazol-5-yl)-pyrrolidin-2-one Dissolve 3-(2,6-Dichloro-4-methoxy-benzyl)-1-(4,5,6,7-tetrahydro-2H-indazol-5-yl)-pyrrolidin-2-one (Example 1) (15.0 g, 38 mmol) in methylene chloride (1.5 L) and cool to 0° C. Treat with boron tribromide (19.9 mL, 190 mmol) dropwise over 30 minutes and allow reaction mixture to warm to room temperature. Stir for 28 h at room temperature, re-cool in an ice-bath, add methanol (38 mL) carefully over 15 minutes to the stirred reaction mixture. Remove organic solvents by rotary evaporator, and dissolve the residue in 4:1 chloroform/isopropyl alcohol (600 mL) and water (100 mL). Neutralize to pH 7 using 5 N NaOH, separate, reserve the organics and extract the aqueous layer with two portions of chloroform/isopropyl alcohol. Dry the combined organics over sodium sulfate, filter and evaporate to a solid and vacuum dry at 90° C. to yield 10.7 g (75%) of the titled compound. MS (m/z): 380 (m+1).

Preparation 33

Trifluoro-methanesulfonic acid 3,5-dichloro-4-[2-oxo-1-(2-trifluoromethanesulfonyl-4,5,6,7-tetrahydro-2H-indazol-5-yl)-pyrrolidin-3-ylmethyl]-phenyl ester

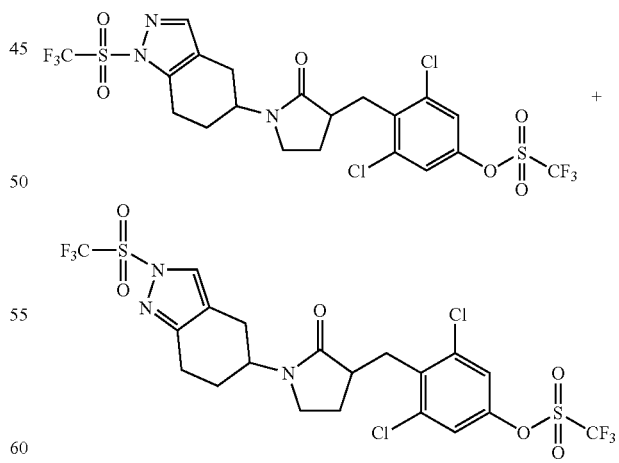

Dissolve 3-(2,6-Dichloro-4-hydroxy-benzyl)-1-(4,5,6,7-tetrahydro-2H-indazol-5-yl)-pyrrolidin-2-one (5.0 g, 13.2 mmol) in pyridine (32 mL) and cool to 0° C. Treat with triflic anhydride (7.1 mL, 42 mmol) dropwise over 5 minutes and allow reaction mixture to warm to room temperature. Stir for 4 h at room temperature under nitrogen atmosphere, add water and dilute with ethyl acetate/diethyl ether and separate. Wash organics with water, brine, and dry over sodium sulfate. Chromatography (silica, 75:25 hexanes/ethyl acetate, CAM stain to visualize the fractions) yields 4.97 g (58%) as a mixture of N1/N2 triflate isomers. MS (m/z): 645 (m+1).

Combine Trifluoro-methanesulfonic acid 3,5-dichloro-4-[2-oxo-1-(2-trifluoromethanesulfonyl-4,5,6,7-tetrahydro-2H-indazol-5-yl)-pyrrolidin-3-ylmethyl]-phenyl ester (1.0 g, 1.55 mmol), 4-Carboxymethylphenyl boronic acid (0.416 g, 2.3 mmol), sodium carbonate (2.3 ml of 2.0 M, 5.4 mmol) in Scheme F

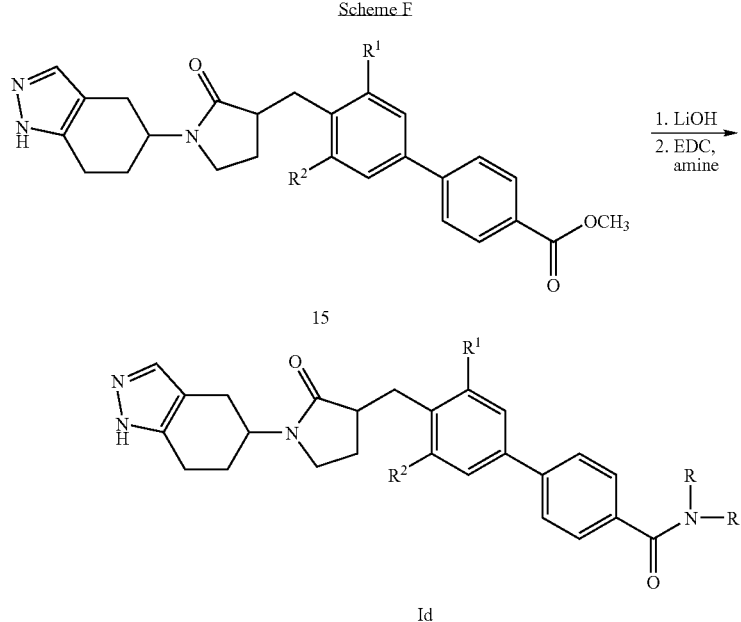

In Scheme F, Id is prepared from compound 15 which is first hydrolyzed to acid and subsequently coupled with various amines in the presence of EDC.

Preparation 34

Trifluoro-methanesulfonic acid 3-(3,5-Dichloro-4'-carboxymethyl-biphenyl-4-ylmethyl)-1-(4,5,6,7-tetrahydro-2H-indazol-5-yl)-pyrrolidin-2-one

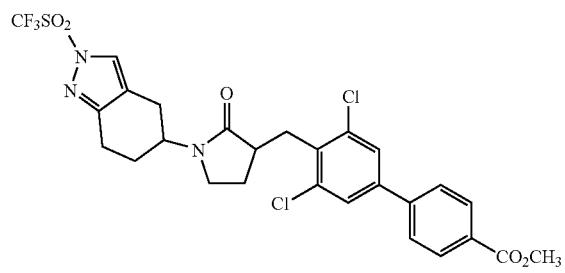

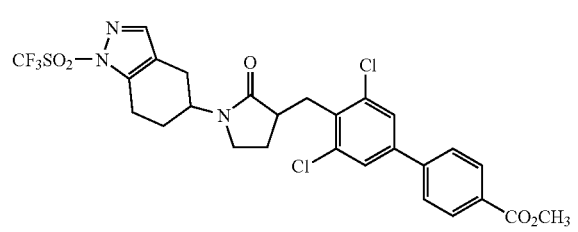

DME (12 mL) and degas with a stream of nitrogen. Add $(Ph_3P)_4Pd$ (0.078 g, 0.15 mmol), and stir at 80° C. for 17 hour under nitrogen atmosphere. Cool to ambient temperature and add ethyl acetate (20 mL) and water (10 mL). Extract the aqueous phase with ethyl acetate (2×20 mL), dry (sodium sulfate) and condense under reduced pressure. Chromatography (silica, 95:5 $CH_2Cl_2$/Methanol) yields 0.750 g as a white solid MS (m/z): 632 (M+2).

Preparation 35

3-(2,6-Dichloro-4-hydroxy-benzyl)-1-(4,5,6,7-tetrahydro-2H-indazol-5-yl)-pyrrolidin-2-one Combine Example 7 (Isomer 1, see Examples 7-10) 3-(2,6-Dichloro-4-methoxy-benzyl)-1-(4,5,6,7-tetrahydro-2H-indazol-5-yl)-pyrrolidin-2-one (0.38 g, 0.96 mmol), $BBr_3$ (5.3 mL of a 1.0 M, 5.3 mmol) in dichloroethane (20 mL) at 0° C., allow reaction to warm to room temperature and stir for 7 hours. Cool to 0° C., quench with methanol, neutralize with 5.0 N NaOH, extract product with 3:1 $CHCl_3$/isopropyl alcohol and dry over sodium sulfate. Chromatography (silica, 95:5:$CHCl_3$/EtOH/$NH_3$) yields 0.290 g as a white solid. MS (m/z): 380 (M+1).

Scheme G

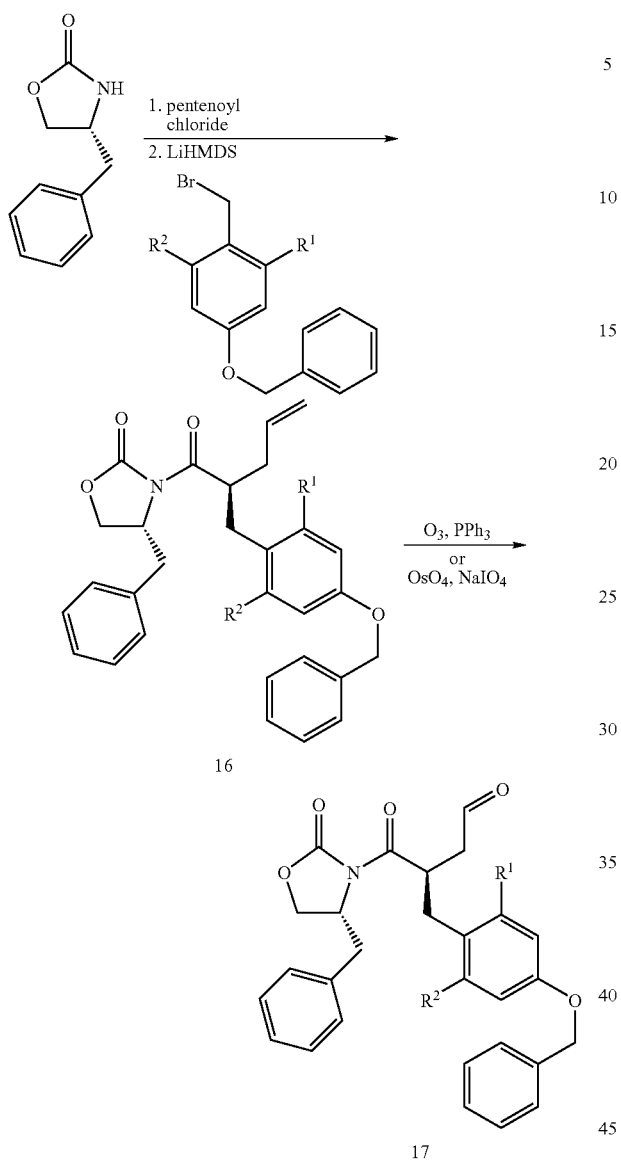

In Scheme G, compound 16 is prepared from 4-benzyl-oxazolidin-2-one which is first acylated with pentenoyl chloride and subsequently alkylated with various benzyl bromide upon pre-treatment of LiHMDS. Oxidation of vinyl group in compound 16 can be achieved by treatment with ozone and PPh$_3$ or OsO$_4$ in presence of NaIO4 to afford aldehyde 17.

Preparation 36

(R)-4-benzyl-3-pent-4-enoyl-oxazolidin-2-one

Flush with nitrogen a 12 L 3-neck round bottom flask equipped with mechanical stirrer, internal temperature probe/N$_2$ inlet, and 1 L addition funnel for 20 min, then add (R)-4-benzyl-2-oxazolidinone (250 g, 1.41 mol). Dilute with THF (1.8 L) and cool in a dry ice/acetone bath until the internal temperature is –74° C. Transfer a 1.6M hexanes solution of n-butyllithium (970 mL, 1.552 mol) to the addition funnel via cannula, and add to the oxazolidinone solution at a rate such that the internal temperature does not reach above –65° C. After the addition is complete, allow the reaction to stir in the cooling bath 30 min. Transfer 4-pentenoyl chloride (175 mL, 1.585 mol) to the addition funnel and add dropwise to the anion solution over a 25 min period. Stir the reaction for 45 min in the cooling bath. Remove the cooling bath and stir the reaction 18 hr as it slowly reaches room temperature. Dilute the mixture with 1N aqueous hydrochloric acid (1.5 L) and diethyl ether (1.0 L). Separate the layers and wash the organic phase with water (2×1 L) then brine (1 L). Extract the combined aqueous washes with ether (1 L). Dry the combined organic phases over anhydrous magnesium sulfate, filter, and concentrate to 390 g of a tan oil. Purify this material by silica gel chromatography using hexanes:ethyl acetate to obtain 345 g (94.5%) of a clear, yellow oil.

Preparation 37

(R)-4-benzyl-3-[(S)-2-(4-benzyloxy-2,6-dichloro-benzyl)-pent-4-enoyl]-oxazolidin-2-one Stir a mixture of (R)-4-benzyl-3-pent-4-enoyl-oxazolidin-2-one (345 g, 1.33 mol) and THF (1.8 L) in a 12 L 3-neck round bottom flask, with internal temperature probe/nitrogen inlet and addition funnel, under a nitrogen atmosphere and cool to –75° C. Transfer 1 M LiHMDS (1.6 L) to the addition funnel and add at a rate such that the internal temperature does not reach above –60° C. After the addition is complete, allow the reaction to stir at –25° C. for 30 min then cool to about –60° C. At this point add solid 2-bromomethyl-1,3-dichloro-5-benzyloxy-benzene portionwise over 5 min. When the addition is complete, transfer the reaction vessel to a –10° C. acetone bath and maintain the internal reaction temperature below 10° C. for 1 hr. Cool the mixture to 0° C. then quench with 2 L aqueous 1N hydrochloric acid. Transfer the mixture to a 22 L separatory funnel and dilute with 2.5 L water and 2 L ether. Separate the layers and extract the aqueous layer with ether. Dry the combined organic phase over anhydrous magnesium sulfate, filter and concentrate to 800 g of a thick oil. Purify by silica gel chromatography using hexanes:ethyl acetate to obtain 597 g, (86%) of a colorless oil.

Preparation 38

(R)-4-((R)-4-Benzyl-2-oxo-oxazolidin-3-yl)-3-(4-benzyloxy-2,6-dichloro-benzyl)-4-oxo-butyraldehyde Cool a mixture of (R)-4-benzyl-3-[(S)-2-(4-benzyloxy-2,6-dichloro-benzyl)-pent-4-enoyl]-oxazolidin-2-one (100 g, 190.68 mmol) and dichloromethane (800 mL) to –74° C. Bubble ozone, produced via the A-113 ozone generator at a rate of 75%, through the reaction via carrier air at a rate of 5 CFM until the solution takes on a blue color (approx 3 hr). Add triphenylphosphine (60 g, 228.8 mmol) as a solution in 200 mL dichloromethane and allow the reaction to stir while reaching room temperature over night. Concentrate the solution under vacuum and purify by silica gel chromatography using a gradient of 20-50% ethyl acetate in hexanes to obtain 82.1 g (82%) of the product as a white foam: MS (m/z): 526 (M+).

Alternatively, treat a mixture of (R)-4-benzyl-3-[(S)-2-(4-benzyloxy-2,6-dichloro-benzyl)-pent-4-enoyl]-oxazolidin-2-one (0.96 g, 1.8 mmol), THF (21 mL) and water (7 mL) with 2.5% osmium tetroxide in t-butanol (46 mg, 0.18 mmol). Add sodium periodate (1.17 g, 5.5 mmol) and stir the reaction 4 hr at room temperature. Quench the reaction with water and extract with ethyl acetate. Wash the organic phase with aqueous 1N sodium thiosulfate then brine. Dry the organic layer over magnesium sulfate, filter, and concentrate under vacuum. Purify the crude material by silica gel chromatography using hexanes:ethyl acetate to elute the pure product.

Concentrate the fractions containing product under vacuum to afford 0.46 g (48%) of desired product. MS (m/z): 526 (M+).

Scheme H

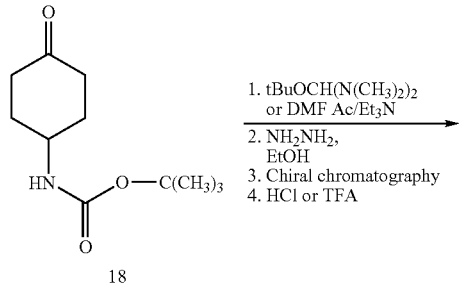

In Scheme H, ketone 18 is converted pyrazole using Brederick's reagent followed by treatment of N₂H₄ in EtOH. Enantiomerically pure amine 19 is received upon chiral chromatography separation of enantiomers and subsequently removal of Boc group under acidic condition, i.e. HCl or TFA.

Preparation 39

(+/−)-(4,5,6,7-Tetrahydro-2H-indazol-5-yl)-carbamic acid tert-butyl ester

Boil a mixture of (4-oxo-cyclohexyl)-carbamic acid tert-butyl ester (10 g, 0.469 mol), N,N-Dimethylformamide dimethyl acetal (100 mL) and Et₃N (100 mL) to dryness in a 140° C. oil bath for 30 minutes. Add an additional 100 mL of each reagent and allow to boil out. Repeat this step a third time for a total of 300 mL each DMFDMA and Et₃N. Concentrate the mixture containing (3-dimethylaminomethylene-4-oxo-cyclohexyl)-carbamic acid tert-butyl ester to a glass, re-dissolve in 250 mL ethanol, and then add 65 mL hydrazine hydrate and stir the reaction overnight at room temp. Concentrate the mixture, take up in 500 mL EtOAc and wash with 2×500 mL water. Extract the aqueous layer with 150 mL EtOAc, and wash the combined organic layers with 250 mL brine, dry on anhydrous MgSO₄, filter, and concentrate. Chromatography (silica, ethyl acetate) to give 87 g as a light yellow solid. MS (m/z): 237.

Obtain the single enantiomers by chiral chromatography (Chiralpak AD-H, 4.6×150 mm, 80:10:10, C7 (hexanes)/3A/MeOH w/0.2% DMEA, 0.6 ml/min, @235 nm) yielding:
Isomer 1 (retention time=6.8 minutes, % e.e. >99, $[\alpha]^{25}_D$ −41.7 (c 1, MeOH)
Isomer 2 (retention time=9.5 minutes, % e.e. >95, $[\alpha]^{25}_D$ 40.7 (c 1, MeOH)

Preparation 40

4,5,6,7-Tetrahydro-2H-indalzol-5-ylamine (free-base)

Combine Isomer 1 (from Preparation 39), (−)-(4,5,6,7-Tetrahydro-2H-indazol-5-yl)-carbamic acid tert-butyl ester, (5.3 g, 22.3 mmol) in CH₂Cl₂ (200 ml), treat with TFA (16.5 ml, 223 mmol) and stir at room temperature for 3 h. Remove the solvent under reduced pressure giving a thick, oil. Isolation of free-base via solid phase extraction (50 grams, Megabond Elut, Varian, 0.79 milliequivalents/g of resin) using Methanol to wet resin, followed by elution with a 95:5 solution of CH₂Cl₂/Methanol and finally a 95:5 solution of CH₂Cl₂/7 M NH₃ Methanol gives 2.66 g (86%) of a tan oil that solidifies upon standing.

Preparation 41

4,5,6,7-Tetrahydro-2H-indalzol-5-ylamine (free-base)

Combine Isomer 2 (from Preparation 39), (+)-(4,5,6,7-Tetrahydro-2H-indazol-5-yl)-carbamic acid tert-butyl ester, (5.01 g, 2.11 mmol) in CH₂Cl₂ (200 ml), treat with TFA (16.0 ml, 211 mmol) and stir at room temperature for 3 h. Remove the solvent under reduced pressure giving a thick, oil. Isolation of free-base via solid phase extraction (50 grams, Megabond Elut, Varian, 0.79 milliequivalents/g of resin) using Methanol to wet resin, followed by elution with a 95:5 solution of CH₂Cl₂/Methanol and finally a 95:5 solution of CH₂Cl₂/7 M NH₃ Methanol gives 2.1 g (71%) of a tan oil that solidifies upon standing.

Scheme I

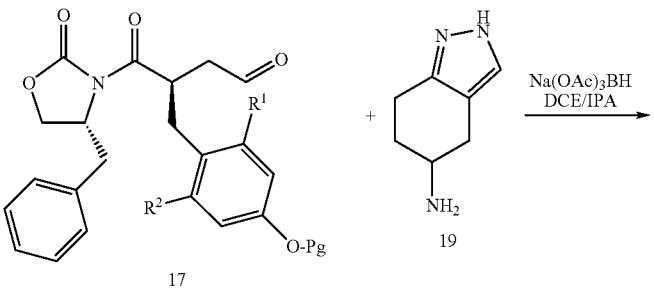

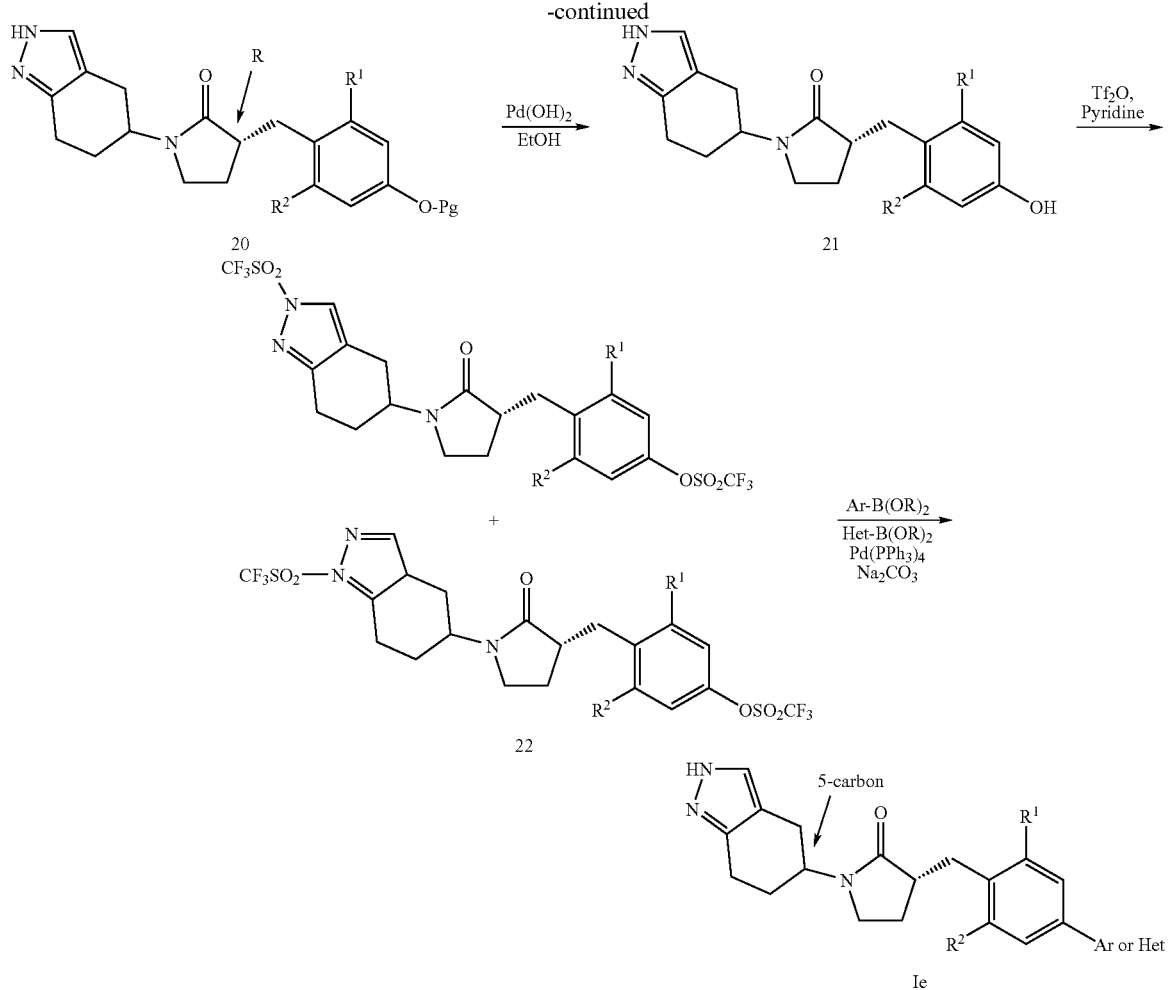

In Scheme I, treatment of aldehyde 17 with amine 19 in presence of NaBH(OAc)$_3$ affords pyrazole 20. Removal of benzyl protecting group under hydrogenation in the presence of Pd(OH)$_2$ to give phenol 21 which is subsequently converted to triflate 22. Ie is prepared by treatment of triflate 22 with various boronic acids or esters under standard Suzuki coupling conditions, i.e. Pd(PPh$_3$)$_4$ and Na$_2$CO$_3$.

In Scheme I, compound 19 can be either enantiomer. The reaction of compound 17 with 19 results forms the "R" stereo configuration at the C-3 designated with the arrow. In compound 1e, the stereo designation at C-3 in the pyrrolidinone is "R" and the stereo designation at C-5 in the tetrahydroindazole is determined by the stereo configuration in compound 19.

Preparation 42

(3R,5S)-3-(4-Hydroxy-2,6-dichloro-benzyl)-1-(4,5,6,7-tetrahydro-2H-indazol-5-yl)-pyrrolidin-2-one Dissolve (3R,5S)-3-(4-Benzyloxy-2,6-dichloro-benzyl)-1-(4,5,6,7-tetrahydro-2H-indazol-5-yl)-pyrrolidin-2-one (Example 35) (8.79 g, 18.7 mmol) in absolute ethanol (60 mL), treat with 20% Pd(OH)$_2$ (6.0 g) and stir at 30 psi hydrogen pressure. After 6 h, ESMS shows starting material consumed and product formed. Remove the catalyst by filtration, rinse with ethanol and evaporate to a dark foam. Filtration through 50 g SCX mega-bond elut using 95:5 CH$_2$Cl$_2$/MeOH followed by 95:5 CH$_2$Cl$_2$/7.0 M NH$_3$/MeOH yields 5.6 g (79%) as an amorphous solid MS (m/z): 380 (M+1)

Preparation 43

(3R,5S)-Trifluoro-methanesulfonic acid 3,5-dichloro-4-[2-oxo-1-(2-trifluoromethanesulfonyl-4,5,6,7-tetrahydro-2H-indazol-5-yl)-pyrrolidin-3-ylmethyl]-phenyl ester

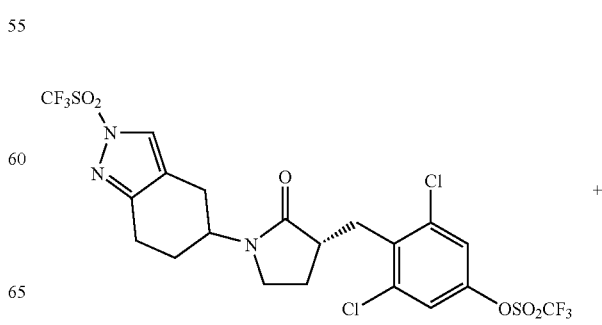

-continued

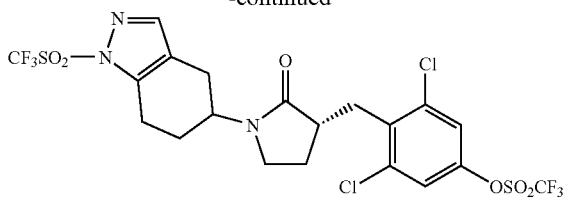

Dissolve (3R,5S)-3-(4-Hydroxy-2,6-dichloro-benzyl)-1-(4,5,6,7-tetrahydro-2H-indazol-5-yl)-pyrrolidin-2-one (Preparation 42) (5.56 g, 14.6 mmol) in dry pyridine (35 mL), cool to 0° C. and add triflic anhydride (7.4 ml, 44 mmol) drop-wise over 60 seconds. Allow reaction to warm to room temperature and stirring continued for 3.0 h under nitrogen atmosphere. Quench the reaction with water (20 mL), and dilute with ethyl acetate (75 mL). Separate the layers, wash the organics with 0.1 N HCl (2×), brine and dry over sodium sulfate. Filtration and evaporation yields 7.71 g (80%) of an amorphous orange solid. MS (m/z): 645 (M+1).

Preparation 44

1-Chloro-3,4-difluoro-2-iodomethyl-5-trifluoromethyl-benzene

Treat a solution of 1-chloro-2-chloromethyl-3,4-difluoro-5-trifluoromethyl-benzene (1.0 g, 3.8 mmol) in acetone (10 mL) with sodium iodide (2.8 g, 19 mmol) and stir the reaction 1 hr at room temperature. Dilute the reaction in EtOAc (50 mL) and filter. Concentrate the filtrate to afford 1.35 g (100%) of product. $^1$H NMR (d$_6$-CDCl$_3$) δ 7.39 (d, 1H, J=5.7 Hz), 4.46 (d, 2H, J=2.2 Hz).

Preparation 45

(R)-4-Benzyl-3-[(S)-2-(6-chloro-2,3-difluoro-4-trifluoromethyl-benzyl)-pent-4-enoyl]-oxazolidin-2-one Cool a solution of (R)-4-Benzyl-3-pent-4-enoyl-oxazolidin-2-one (0.94 g, 3.6 mmol) in THF (10 mL) to −78° C. Treat this solution dropwise with 10M LiHMDS in THF (4 mL, 4.0 mmol) and stir at −78° C. for 30 minutes. Treat the solution with 1-Chloro-3,4-difluoro-2-iodomethyl-5-trifluoromethyl-benzene (1.35 g, 3.8 mmol) and allowed to slowly warm to room temperature. The reaction stirs 4 hr at room temperature. Quench the reaction with 1N HCl (aqueous) and extracted with Et$_2$O. Wash the organic with brine, dry over MgSO$_4$, filter, and remove the solvent. Purify the crude by silica gel column chromatography using Hexanes:EtOAc to elute the pure product. Remove the solvent to afford 0.725 g (41%) of desired product. MS (m/e): 488 (M+1).

Preparation 46

(R)-4-((R)-4-Benzyl-2-oxo-oxazolidin-3-yl)-3-(6-chloro-2,3-difluoro-4-trifluoromethyl-benzyl)-4-oxo-butyraldehyde Treat a solution of (R)-4-Benzyl-3-[(S)-2-(6-chloro-2,3-difluoro-4-trifluoromethyl-benzyl)-pent-4-enoyl]-oxazolidin-2-one (Preparation 45) (0.72 g, 1.5 mmol) in THF (9 mL) and water (3 mL) with 2.5% OsO$_4$ in tBuOH (1.5 g, 0.15 mmol). Then, add sodium periodate (0.96 g, 4.5 mmol) to the solution and stir the reaction for 4 hr at room temperature. Quench the reaction with water and extract with EtOAc. Wash the organic with 1N sodium thiosulfate and brine. Separate the organic, dry over MgSO$_4$, filter, and remove the solvent. Purify the crude by silica gel column chromatography using Hexanes:EtOAc to elute the pure product. Remove the solvent to afford 0.60 g (82%) of desired product. MS (m/e): 490 (M+1).

Preparation 47

(3R,5R)-3-(2,6-Dichloro-4-hydroxy-benzyl)-1-(4,5,6,7-tetrahydro-2H-indazol-5-yl)-pyrrolidin-2-one Dissolve (3R,5R)-3-(4-Benzyloxy-2,6-dichloro-benzyl)-1-(4,5,6,7-tetrahydro-2H-indazol-5-yl)-pyrrolidin-2-one (Example 57) (0.977 g, 2.1 mmol) in THF (90 mL), treat with 20% Pd(OH)$_2$ (0.977 g) and stir at 30 psi hydrogen pressure. After stirring overnight, ESMS shows 2:1 product to starting material. Remove the catalyst by filtration, rinse with ethanol and evaporate to a dark foam. Chromatography (silica, 95:5 CH$_2$Cl$_2$/EtOH/NH$_3$) yields 0.26 g (33%) of the titled compound as an amorphous solid MS (m/z): 380 (M+1).

Preparation 48

(3R,5R)-Trifluoro-methanesulfonic acid 3,5-dichloro-4-[2-oxo-1-(2-trifluoromethanesulfonyl-4,5,6,7-tetrahydro-2H-indazol-5-yl)-pyrrolidin-3-ylmethyl]-phenyl ester

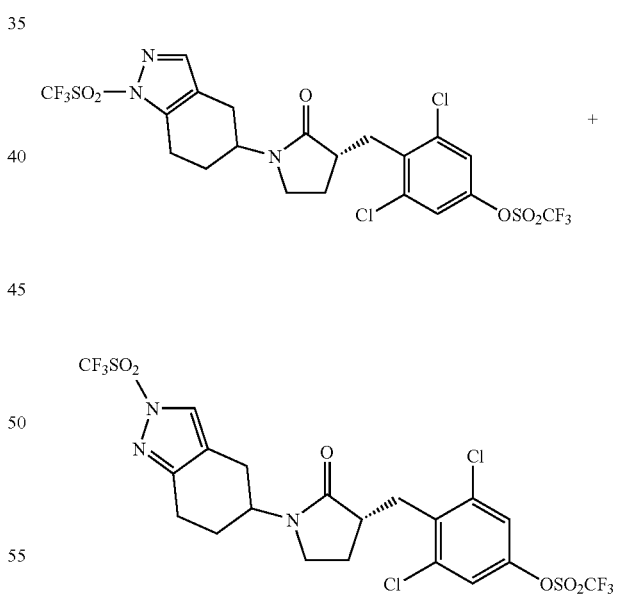

Dissolve (3R,5R)-3-(4-Hydroxy-2,6-dichloro-benzyl)-1-(4,5,6,7-tetrahydro-2H-indazol-5-yl)-pyrrolidin-2-one (Preparation 47) (0.261 g, 0.86 mmol) in dry pyridine (2.0 mL), cool to 0° C. and add triflic anhydride (0.359 ml, 2.1 mmol) drop-wise over 60 seconds. Allow reaction to warm to room temperature and continue stirring for 4.0 h under nitrogen atmosphere. Quench the reaction with water (20 mL) and dilute with ethyl acetate (75 mL). Separate the layers, wash the organics with 0.1 N HCl (2×), brine and dry over sodium sulfate. Filtration and chromatography (silica, 95:5 CH$_2$Cl$_2$/MeOH) yields 0.34 g (77%) of an amorphous orange solid. MS (m/z): 645 (M+1)

Preparation 49

(3R,5S)-5-[3-(4-Benzyloxy-2,6-dichloro-benzyl)-2-oxo-pyrrolidin-1-yl]-4,5,6,7-tetrahydro-indazole-2-carboxylic acid tert-butyl ester and (3R,5S)-5-[3-(4-Benzyloxy-2,6-dichloro-benzyl)-2-oxo-pyrrolidin-1-yl]-4,5,6,7-tetrahydro-indazole-1-carboxylic acid tert-butyl ester

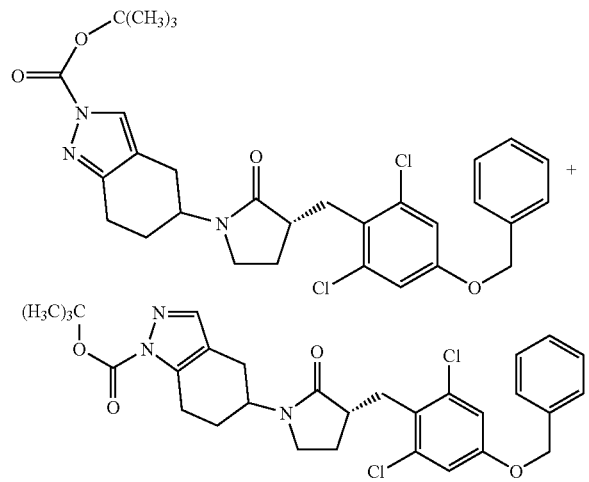

Treat a solution of (3R,5S)-3-(4-benzyloxy-2,6-dichloro-benzyl)-1-(4,5,6,7-tetrahydro-2H-indazol-5-yl)-pyrrolidin-2-one (Example 35) (0.429 g, 0.91 mmol) and pyridine (0.144 g, 1.82 mmol) in CH$_2$Cl$_2$ (15 mL) with di-tert-butyl dicarbonate (0.24 g, 1.10 mmol) and stir for 5 hours at room temperature under N$_2$. Extract the reaction with 1N HCl and water. Dry the organic layer with Na$_2$SO$_4$, remove the solvent in vacuo to afford crude product, and purify on silica using a 0 to 100% ethyl acetate in hexanes gradient to afford 0.443 g (85%) of the titled products as a mixture. R$_f$=0.15 and 0.05 (1/1 hexanes/ethyl acetate).

Preparation 50

(3R,5S)-5-[3-(2,6-Dichloro-4-hydroxy-benzyl)-2-oxo-pyrrolidin-1-yl]-4,5,6,7-tetrahydro-indazole-2-carboxylic acid tert-butyl ester and (3R,5S)-5-[3-(2,6-Dichloro-4-hydroxy-benzyl)-2-oxo-pyrrolidin-1-yl]-4,5,6,7-tetrahydro-indazole-1-carboxylic acid tert-butyl ester

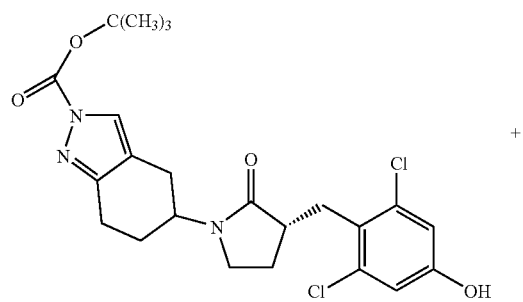

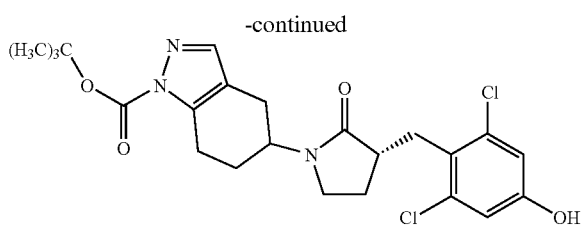

Sparge with N$_2$ and then H$_2$ a mixture of (3R,5S)-5-[3-(4-benzyloxy-2,6-dichloro-benzyl)-2-oxo-pyrrolidin-1-yl]-4,5,6,7-tetrahydro-indazole-2-carboxylic acid tert-butyl ester and (3R,5S)-5-[3-(4-benzyloxy-2,6-dichloro-benzyl)-2-oxo-pyrrolidin-1-yl]-4,5,6,7-tetrahydro-indazole-1-carboxylic acid tert-butyl ester (Preparation 49) (0.44 g, 0.77 mmol) and 20% Pd(OH)$_2$ on carbon (0.44 g) in ethyl acetate (50 mL). Stir the mixture under a balloon of H$_2$ for 16 hours at room temperature. Treat the mixture with Na$_2$SO$_4$ and then filter through hyflow to remove the catalyst and remove the solvent in vacuo to afford 0.388 g (100%) of the titled products as a mixture. R$_f$=0.42 (9/1 CH$_2$Cl$_2$/methanol).

Preparation 51

1-Bromo-3-bromomethyl-2,4-dichloro-benzene

Treat a mixture of 2,6-dichlorotoluene (50.0 g, 0.31 mol), iodine (0.10 g, 0.39 mmol), and 325 mesh iron powder (0.70 g, 12.5 mmol) in CCl$_4$ (60 mL) dropwise with bromine (52.8 g, 0.33 mol) over 20 minutes and is stir for 3 hours at room temperature. Pour the mixture into ice water and extract with 1,2-dichloroethane. Wash the organic layer with saturated sodium bisulfite and dry using Na$_2$SO$_4$. Remove the solvent in vacuo to afford 76.01 g (100%) 1-bromo-2,4-dichloro-3-methyl-benzene.

Treat a mixture of 1-bromo-2,4-dichloro-3-methyl-benzene (76.01 g, 0.316 mol) and N-bromosuccinimide (59.2 g, 0.332 mol) in CCl$_4$ (500 mL) with benzoyl peroxide (0.77 g, 3.18 mmol) and is heat to reflux for 6 hours under N$_2$. Cool the reaction mixture to 0° C. and filter using hexanes to rinse the solids. Extract the filtrate with water and saturated NaHCO$_3$. Dry the organic layer (Na$_2$SO$_4$) and remove the solvent in vacuo to afford 97.89 g (97%) of the titled product. R$_f$=0.34 (100% hexanes).

Preparation 56

Ethyl 2-(4-bromo-2-chlorobenzyl)pent-4-enoate

Add LDA (5.27 mL, 10.5 mmol, 2.0 M) into a solution of ethyl pent-4-enoate (0.9 g, 7.0 mmol), in THF (125 mL) at −78° C. and stir for 15 minutes. Add 4-bromo-2-chlorobenzyl bromide (3.3 g, 10.5 mmol) and warm reaction to room temperature. Quench with ammonium chloride solution, extract the reaction mixture with methylene chloride and wash the organic layer with brine. Dry over sodium sulfate, filter and concentrate. Purify the residue with silica gel column (hexanes) to afford the title compound (1.65 g, 73%) as colorless oil.

Preparation 57

Ethyl 2-(4-bromo-2-chlorobenzyl)-4-oxobutanoate.

Add sodium periodate (41 g, 190 mmol) into a solution of ethyl 2-(4-bromo-2-chlorobenzyl)pent-4-enoate (21 g, 63 mmol), 2.5 wt % OsO$_4$ (64 g, 6.3 mmol) in THF (400 mL) and water (160 mL) and stir for 2 hours. Extract the reaction mixture with ethyl acetate, wash the organic layer with sodium thiosulfate solution and brine. Dry over sodium sulfate, filter and concentrate. Purify the residue with silica gel column to afford the title compound (15.9 g, 75%) as colorless oil: $^1$H NMR (CDCl$_3$) 9.73 (s, 1H), 7.53 (d, J=2.0 Hz, 1H), 7.32 (dd, J=8.20, 2.0 Hz, 1H), 7.08 (d, J=8.2 Hz, 1H), 4.05-4.15 (m, 2H), 3.20-3.28 (m, 1H), 3.07-3.15 (m, 1H), 2.84-2.92 (m, 2H), 2.53-2.61 (m, 1H), 1.51-1.21 (m, 3H).

Preparation 58

(4,4-Difluoro-piperidin-1-yl)-[4-(4,4,5,5-tetramethyl-[1,3,2]dioxaborolan-2-yl)-phenyl]-methanone Step 1. Dissolve 4-Bromobenzoic acid (4.98 g, 24 mmol), 4,4,-Difluorpiperidine hydrochloride (4.3 g, 27 mmol), HOBt (4.09 g, 29 mmol) and DIPEA (15.5 mL, 89 mmol) in THF (50 ml). Add EDC (5.7 g, 29 mmol) and stir at room temperature for 24 hours. Dilute reaction with ethyl acetate, wash with 0.1 N HCl, sodium bicarbonate (sat), brine, dry over sodium sulfate, filter and evaporate to an oil yielding (4-Bromo-phenyl)-(4,4-difluoro-piperidin-1-yl)-methanone as the titled product: MS (m/z): 305 (M+1)

Step 2. Add (4-Bromo-phenyl)-(4,4-difluoro-piperidin-1-yl)-methanone (3.0 g, 9.86 mmol), Bis(pinacolato)diborane (2.74 g, 10.7 mmol), Potassium acetate (2.9 g, 29 mmol), [1,1'-Bis(diphenylphosphino)-ferrocene]palladium(II) Chloride (0.804 g, 0.9 mmol) in DMSO (20 mL) and stir at 80° C. for 17 hours. Cool, dilute with ethyl acetate, wash with brine (5×), dry over sodium sulfate, filter and evaporate. Chromatography (silica, CH$_2$Cl$_2$/MeOH, 98:2) provides 1.7 g (47%) of (4,4-Difluoro-piperidin-1-yl)-[4-(4,4,5,5-tetramethyl-[1,3,2]dioxaborolan-2-yl)-phenyl]-methanone.

Preparation 59

4-Benzyloxy-2,6-dimethyl-benzaldehyde

Treat a solution of 2,6-Dimethyl-4-hydroxybenzaldehyde (4.0 g, 27 mmol) and benzyl bromide (3.3 mL, 28 mmol) in DMF (50 mL) with Potassium carbonate (4.5 g, 32 mmol). Heat the reaction to 60° C. and stir for 1 hr. Cool the reaction and quench with 1N aqueous HCl. Extract the aqueous with Et$_2$O. Wash the organic with brine, dry over MgSO$_4$, and filter. Remove the solvent to afford 6.4 g (100%) of product. $^1$H NMR (d$_6$-CDCl$_3$) δ 10.46 (s, 1H), 7.31-7.43 (m, 5H), 6.65 (s, 2H), 5.08 (s, 2H), 2.58 (s, 6H).

Preparation 60

(4-Benzyloxy-2,6-dimethyl-phenyl)-methanol

Treat a solution of 4-Benzyloxy-2,6-dimethyl-benzaldehyde (6.4 g, 27 mmol) in Methanol (60 mL) with Sodium borohydride (0.82 g, 22 mmol). Stir the reaction for 1 hr at room temperature. Quench the reaction with a saturated solution of sodium bicarbonate in water and extract with Et$_2$O. Wash the organic with brine, dry over MgSO$_4$, and filter. Remove the solvent to afford 6.3 g (97%) of product. $^1$H NMR (d$_6$-CDCl$_3$) δ 7.31-7.43 (m, 5H), 6.65 (s, 2H), 5.01 (s, 2H), 4.66 (s, 2H), 2.38 (s, 6H).

Preparation 61

5-Benzyloxy-2-bromomethyl-1,3-dimethyl-benzene

Cool a solution of (4-Benzyloxy-2,6-dimethyl-phenyl)-methanol (5.70 g, 24 mmol) in THF (100 mL) to 0° C. Treat the solution with Phosphorous tribromide (0.9 mL, 9.4 mmol) and stir the reaction for 2 hr at 0° C. Quench the reaction with water and extract with Et$_2$O. Wash the organic with brine, dry over MgSO$_4$, and filter. Remove the solvent to afford 7.1 g (99%) of product. $^1$H NMR (d$_6$-CDCl$_3$) δ 7.31-7.43 (m, 5H), 6.65 (s, 2H), 5.01 (s, 2H), 4.56 (s, 2H), 2.38 (s, 6H).

Preparation 62

(R)-4-Benzyl-3-[(S)-2-(4-benzyloxy-2,6-dimethyl-benzyl)-pent-4-enoyl]-oxazolidin-2-one Cool a solution of (R)-4-Benzyl-3-pent-4-enoyl-oxazolidin-2-one (4.8 g, 19 mmol) in THF (100 mL) to −78° C. Treat the solution dropwise with 10M LiHMDS in THF (20 mL, 20 mmol) and stir at −78° C. for 30 minutes. Treat the solution with 5-Benzyloxy-2-bromomethyl-1,3-dimethyl-benzene (6.8 g, 22 mmol) and allow to slowly warm to room temperature. The reaction stirs 3 hr at room temperature. Quench the reaction with 1N HCl (aqueous) and extract with Et$_2$O. Wash the organic with brine, dry over MgSO$_4$, filter, and remove the solvent. Purify the crude by silica gel column chromatography using Hexanes:EtOAc to elute the pure product. Remove the solvent to afford 7.0 g (78%) of desired product. MS (m/e): 484 (M+1).

Preparation 63

(R)-4-((R)-4-Benzyl-2-oxo-oxazolidin-3-yl)-3-(4-benzyloxy-2,6-dimethyl-benzyl)-4-oxo-butyraldehyde Treat a solution of (R)-4-Benzyl-3-[2-(4-benzyloxy-2,6-dimethyl-benzyl)-pent-4-enoyl]-oxazolidin-2-one (7.5 g, 16 mmol) in THF (120 mL) and water (40 mL) with 2.5% OsO$_4$ in tBuOH (16 g, 1.6 mmol). Add Sodium periodate (10 g, 47 mmol) to the solution and stir the reaction for 3 hr at room temperature. Quench the reaction with water and extract with EtOAc. Wash the organic with 1N sodium thiosulfate and brine. Separate the organic, dry over MgSO$_4$, filter, and remove the solvent. Purify the crude by silica gel column chromatography using Hexanes:EtOAc to elute the pure product. Remove the solvent to afford 3.25 g (43%) of desired product. MS (m/e): 486 (M+1).

Preparation 64

(R)-3-(4-Benzyloxy-2,6-dimethyl-benzyl)-1-(4,5,6,7-tetrahydro-2H-indazol-5-yl)-pyrrolidin-2-one Combine a solution of (R)-4-((R)-4-Benzyl-2-oxo-oxazolidin-3-yl)-3-(4-benzyloxy-2,6-dimethyl-benzyl)-4-oxo-butyraldehyde (3.0 g, 6.2 mmol) and racemic 4,5,6,7-Tetrahydro-2H-indazol-5-ylamine (0.85 g, 6.2 mmol) in Dichloroethane (50 mL) and Acetonitrile (50 mL). Treat the solution with sodium triacetoxyborohydride (6.6 g, 31 mmol) and stir 1 hr at room temperature. Treat the reaction with N,N-Diisopropylethylamine (5.6 mL, 31 mmol) and stir overnight at room temperature. Concentrate the reaction to a residue. Quench the residue with saturated sodium carbonate and extract with EtOAc. Wash the organic with brine, dry over MgSO$_4$, filter, and remove the solvent. Purify the crude by silica gel column chromatography using CH$_2$Cl$_2$ and 2M Ammonia in MeOH to elute the pure product. Remove the solvent to afford 1.66 g (62%) of desired product. MS (m/e): 430 (M+1).

Preparation 65

(R)-3-(4-Hydroxy-2,6-dimethyl-benzyl)-1-(4,5,6,7-tetrahydro-2H-indazol-5-yl)-pyrrolidin-2-one Treat a solution of (R)-3-(4-Benzyloxy-2,6-dimethyl-benzyl)-1-(4,5,6,7-tetrahydro-2H-indazol-5-yl)-pyrrolidin-2- one (Preparation 64) (1.65 g, 3.8 mmol) in EtOH (20 mL) with Palladium Hydroxide on carbon (1.7 g). Purge the solution with Hydrogen and pressurize to 35 psi. The reaction stirs 2 days at 35 psi of hydrogen. Filter the reaction through celite to remove catalyst. Purify the crude by silica gel column chromatography using $CH_2Cl_2$ and 2M Ammonia in MeOH to elute the pure product. Remove the solvent to afford 0.85 g (65%) of desired product. MS (m/e): 340 (M+1).

Preparation 66

Trifluoro-methanesulfonic acid 3,5-dimethyl-4-[(R)-2-oxo-1-(2-trifluoromethanesulfonyl-4,5,6,7-tetrahydro-2H-indazol-5-yl)-pyrrolidin-3-ylmethyl]-phenyl ester Cool a solution of (R)-3-(4-Hydroxy-2,6-dimethyl-benzyl)-1-(4,5,6,7-tetrahydro-2H-indazol-5-yl)-pyrrolidin-2-one (Preparation 65) (0.85 g, 2.5 mmol) in Pyridine (20 mL) to 0° C. and treat with Trifluoromethanesulfonic anhydride (1.3 mL, 7.5 mmol). Allow the reaction to warm to room temperature. After stirring for 2 hr at room temperature, quench the reaction with 1N HCl and extract with EtOAc. Wash the organic with brine, dry over $MgSO_4$, and filter. Remove the solvent to afford 1.05 g (70%) of desired product. MS (m/e): 604 (M+1).

sodium sulfate, filter and concentrate. Add diethyl ether to the residuer. Filter the resulting white precipitate and air dry to afford 19.1 g of the title compound (88%). MS (m/z): 250 (M+).

Preparation 68

(3-Oxo-cyclohexyl)-carbamic acid benzyl ester

Treat a solution of (3-hydroxy-cyclohexyl)-carbamic acid benzyl ester (15.5 g, 62.24) in dichloromethane (300 mL) with PCC (16.73 g, 77.81 mmol) and stir the mixture at room temperature for 12 hours. Filter the reaction mixture through celite. Remove the solvent in vacuo. Purify the residue on silica gel column using 25% to 50% ethyl acetate in hexanes gradient to afford 12.6 g (82%) of the title compound. MS (m/z): 248 (M+).

Preparation 69

(4,5,6,7-Tetrahydro-1H-indazol-4-yl)-carbamic acid benzyl ester

Stir a mixture of (3-Oxo-cyclohexyl)-carbamic acid benzyl ester (12.3 g, 49.8 mmol), toluene (60 mL) and tert-butoxybis

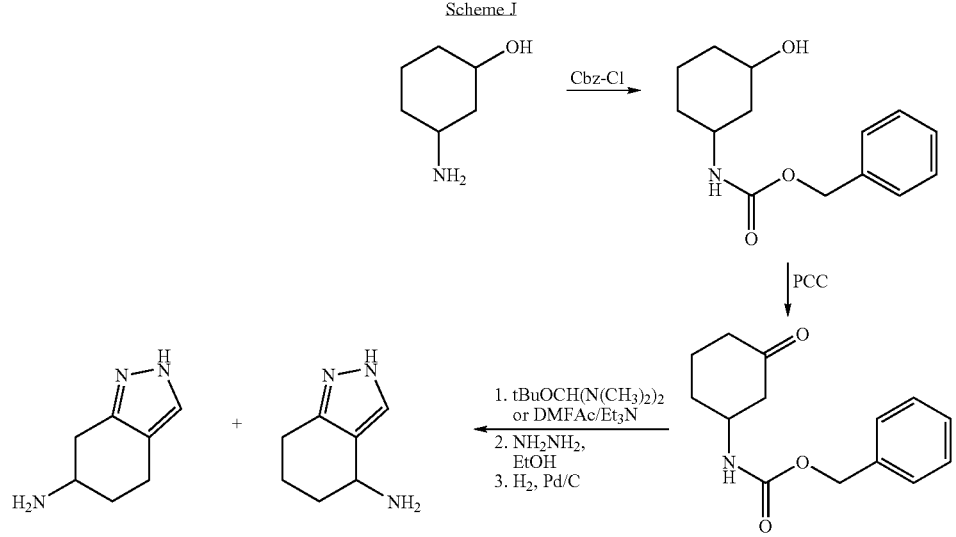

In Scheme J, 4 or 6 amino 4,5,6,7-tetrahydro-2H-indazol can be prepared from 3-amino-cyclohexanol of which the amino group is first protected by Cbz followed by oxidation of alcohol to ketone using PCC. The tetrahydroindazol ring is constructed by first treatment of ketone with Brederick's reagent and subsequently with $N_2H_4$. Deprotection of Cbz group under hydrogenation affords desired 4 and 6 amino 4,5,6,7-tetrahydro-2H-indazols as a mixture.

Preparation 67

(3-Hydroxy-cyclohexyl)-carbamic acid benzyl ester

Treat a mixture of 3-hydroxycyclohexyl amine (10 g, 86.96 mmol), potassium carbonate (18 g, 130 mmol), ethyl acetate (150 mL) and water (70 mL) with benzyl chloroformate (22.17 g, 130 mmol). Stir the reaction at room temperature for 12 hours. Separate the organic layer, dry the organic over (dimethylamino)methane (9.53 g, 54.77 mmol) at 90° C. for 1.5 hour. Cool the reaction and remove the solvent in vacuo. To the residue, add methanol (60 mL) and hydrazine hydrate (2.74 g, 54.77 mmol). Stir the reaction at room temperature for 3 hours. Remove the solvent in vacuo. To the residue, add ethyl acetate and wash with water. After drying the organic layer over sodium sulfate, filter and concentrate to afford 9.8 g of the title compound with 80% purity.

Preparation 70

4,5,6,7-Tetrahydro-1H-indazol-4-ylamine

Stir a mixture of (4,5,6,7-tetrahydro-1H-indazol-4-yl)-carbamic acid benzyl ester (3.5 g) methanol (50 mL) and palladium on carbon (10%, 0.7 g) on a hydrogenation parr shaker under 50 psi for 3 hours. Remove the reaction from parr shaker and filter the mixture through celite. Concentrate the filtrate to afford 1.7 g of the title compound.

Scheme K

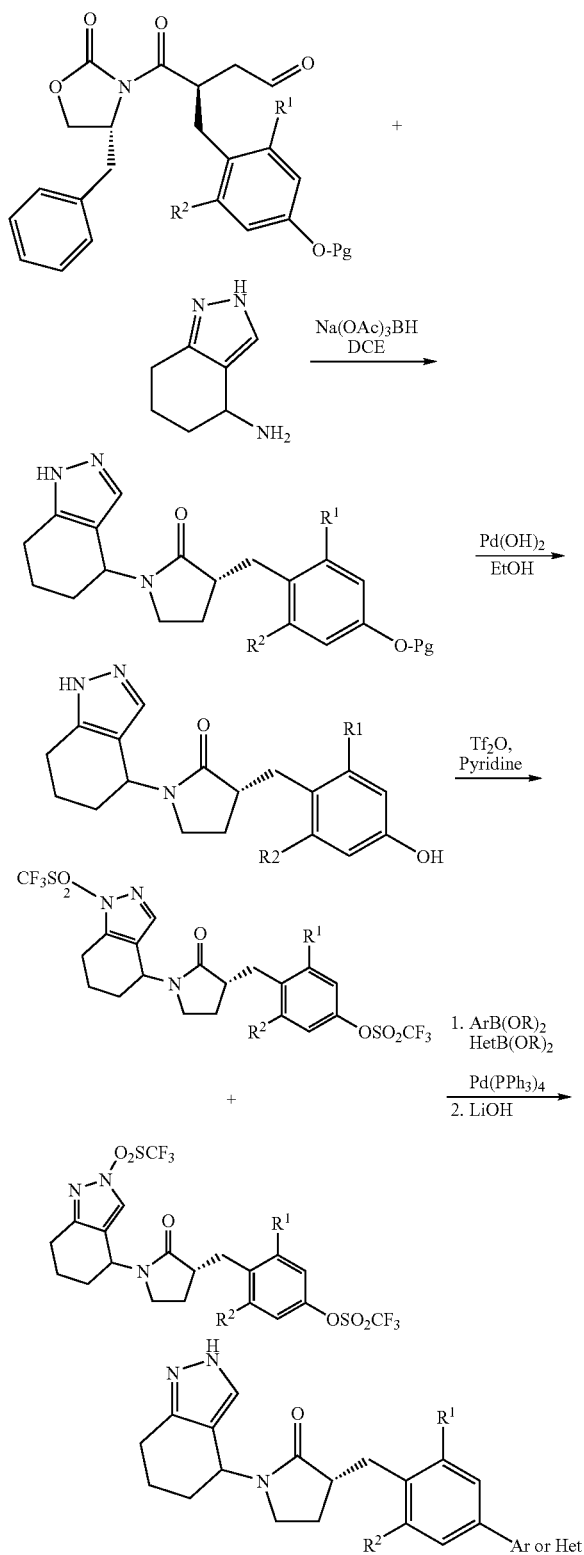

In Scheme K, treatment of aldehyde with 4-amino-4,5,6,7-tetrahydro-2H-indazol in presence of NaBH(OAc)$_3$ affords pyrazole. Removal of benzyl protecting group under hydrogenation in the presence of Pd(OH)$_2$ to give phenol which is subsequently converted to triflate. The final product is prepared by treatment of triflate with various boronic acids or esters under standard Suzuki coupling conditions, i.e. Pd(PPh$_3$)$_4$ and Na$_2$CO$_3$.

Preparation 71

(R)-3-(4-Benzyloxy-2,6-dichloro-benzyl)-1-(4,5,6,7-tetrahydro-1H-indazol-4-yl)-pyrrolidin-2-one To a solution of (R)-4-((R)-4-Benzyl-2-oxo-oxazolidin-3-yl)-3-(4-benzyloxy-2,6-dichloro-benzyl)-4-oxo-butyraldehyde, Preparation 38, (2 g, 3.81 mmol) in DCE (75 mL) at room temperature, add 4,5,6,7-tetrahydro-1H-indazol-4-ylamine (0.66 g, 4.77 mmol) and sodium triacetoxy borohydride (2.42 g, 11.45 mmol). Stir the reaction at room temperature for 12 h and at 50° C. for 1 hour. Cool the reaction, dilute with dichloromethane and wash with water. After drying the organic layer over sodium sulfate, filter and concentrate under vacuum. Purify the residue by silica gel chromatography with 50% ethyl acetate in hexane to 100% ethyl acetate to afford 1.32 g of the title compound. MS (m/z): 470 (M+).

Preparation 72

(R)-3-(2,6-Dichloro-4-hydroxy-benzyl)-1-(4,5,6,7-tetrahydro-1H-indazol-4-yl)-pyrrolidin-2-one To a solution of (R)-3-(4-benzyloxy-2,6-dichloro-benzyl)-1-(4,5,6,7-tetrahydro-1H-indazol-4-yl)-pyrrolidin-2-one (1.32 g) in ethanol (50 mL), add palladium hydroxide on carbon (10%, 0.65 g). Stir the mixture under hydrogenation (50 psi) at room temperature for 3 hours. Filter the mixture through celite. Remove the solvent in vacuo to afford 0.93 g of the title compound. MS (m/z): 380 (M+).

Preparation 73

Trifluoro-methanesulfonic acid 3,5-dichloro-4-[(R)-2-oxo-1-(1-trifluoromethanesulfonyl-4,5,6,7-tetrahydro-1H-indazol-4-yl)-pyrrolidin-3-ylmethyl]-phenyl ester and Trifluoro-methanesulfonic acid 3,5-dichloro-4-[(R)-2-oxo-1-(2-trifluoromethanesulfonyl-4,5,6,7-tetrahydro-2H-indazol-4-yl)-pyrrolidin-3-ylmethyl]-phenyl ester

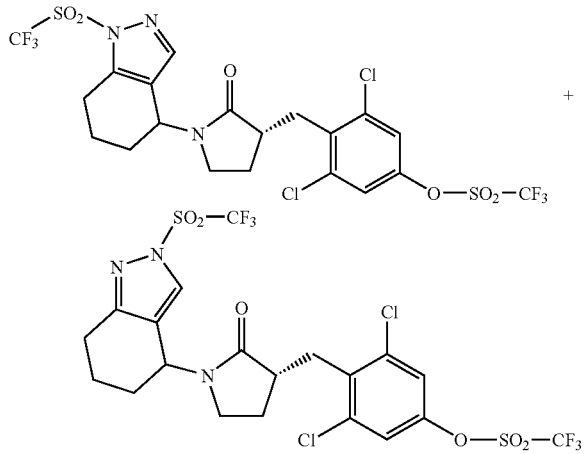

Treat a 0° C. solution of (R)-3-(2,6-dichloro-4-hydroxy-benzyl)-1-(4,5,6,7-tetrahydro-1H-indazol-4-yl)-pyrrolidin-2-one (0.93 g, 2.45 mmol) and pyridine (0.97 g, 12.27 mmol)

in CH$_2$Cl$_2$ (20 mL) with trifluoromethanesulfonic anhydride (2.07 g, 7.36 mmol) for 20 minutes. Warm up the reaction to room temperature and stir for 30 minutes. Dilute the reaction with CH$_2$Cl$_2$ and wash with 1N HCl and water. Dry the organic layer (Na$_2$SO$_4$) and remove the solvent. Purify the residue via silica gel chromatography to afford 1.45 g of the mixed titled products. MS (m/z): 644 (M+).

Preparation 74

5-[3-(4'-Carboxy-3,5-dichloro-biphenyl-4-ylmethyl)-2-oxo-pyrrolidin-1-yl]-4,5,6,7-tetrahydro-indazole-2-carboxylic acid tert-butyl ester Treat a 0° C. solution of (3R,5S)-3-[2,6-Dichloro-4-(morpholine-4-carbonyl)-benzyl]-1-(4,5,6,7-tetrahydro-2H-indazol-5-yl)-pyrrolidin-2-one, Example 73, (0.066 g, 0.14 mmol) in CH$_2$Cl$_2$ (5 mL) and pyridine (2.0 mL) with Boc anhydride (0.036 g, 0.16 mmol) for 5 hours. Warm up the reaction to room temperature, dilute with CH$_2$Cl$_2$ and wash with 1N HCl and water. Dry the organic layer (Na$_2$SO$_4$) and remove the solvent to afford 0.074 g of the mixed titled products.

Preparation 75

(4-Trifluoromethyl-piperidin-1-yl)-[4-(4,4,5,5-tetramethyl-[1,3,2]dioxaborolan-2-yl)-phenyl]-methanone Step 1. Dissolve 4-Bromobenzoic acid (4.98 g, 24 mmol), 4-Trifluoromethyl-piperidine hydrochloride (4.3 g, 27 mmol), HOBt (4.09 g, 29 mmol) and DIPEA (15.5 mL, 89 mmol) in THF (50 ml). Add EDC (5.7 g, 29 mmol) and stir at room temperature for 24 hours. Dilute reaction with ethyl acetate, wash with 0.1 N HCl, sodium bicarbonate (sat), brine, dry over sodium sulfate, filter and evaporate to an oil yielding (4-Bromo-phenyl)-(4-Trifluoromethyl-piperidin-1-yl)-methanone as the titled product.

Step 2. Add (4-Bromo-phenyl)-(4-Trifluoromethyl-piperidin-1-yl)-methanone (3.13 g, 9.86 mmol), Bis(pinacolato) diborane (2.74 g, 10.7 mmol), Potassium acetate (2.9 g, 29 mmol), [1,1'-Bis(diphenylphosphino)-ferrocene]palladium (II) Chloride (0.804 g, 0.9 mmol) in DMSO (20 mL) and stir at 80° C. for 17 hours. Cool, dilute with ethyl acetate, wash with brine (5×), dry over sodium sulfate, filter and evaporate. Chromatography (silica, CH$_2$Cl$_2$/MeOH, 97:3) provides 1.04 g (27%) of (4,Trifluoromethyl-piperidin-1-yl)-[4-(4,4,5,5-tetramethyl-[1,3,2]dioxaborolan-2-yl)-phenyl]-methanone.

Scheme M

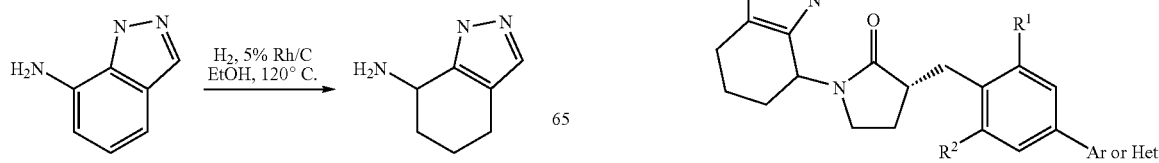

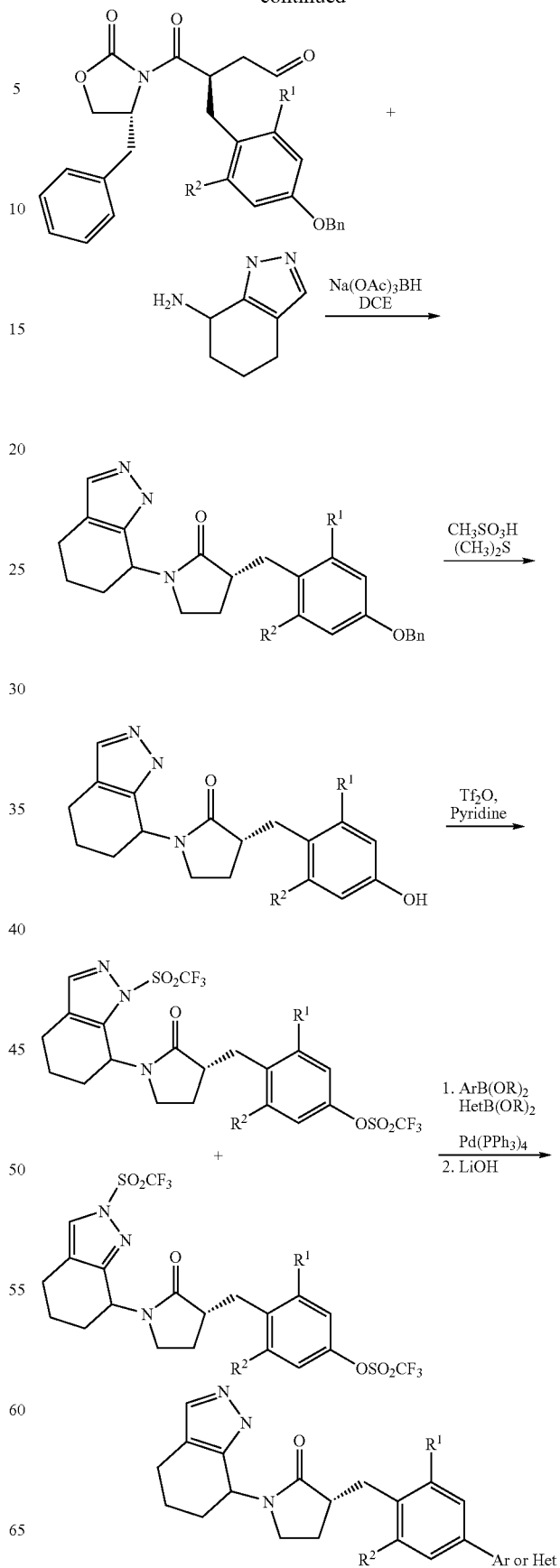

In Scheme M, 4,5,6,7-Tetrahydro-1H-indazol-7-ylamine is prepared from 1H-indazol-7-ylamine under hydrogenation using 5% Rh/C as a catalyst. Treatment of 4,5,6,7-Tetrahydro-1H-indazol-7-ylamine with aldehyde in presence of NaBH(OAc)$_3$ affords pyrazole. Removal of benzyl protecting group using CH$_3$SO$_3$H in the presence of dimethylsulfide gives phenol which is subsequently converted to triflate. The final product is prepared by treatment of triflate with various boronic acids or esters under standard Suzuki coupling conditions, i.e. Pd(PPh$_3$)$_4$ and Na$_2$CO$_3$.

Preparation 76

4,5,6,7-Tetrahydro-1H-indazol-7-ylamine

Combine 1H-indazol-7-ylamine (5.0 g, 37.6 mmol) and 5% Rh/C (2.45 g) in ethanol (120 mL) and heat at 120° C. for 48 hours under ~1000 psi H$_2$. Cool the reaction and filter through hyflo. Remove the solvent in vacuo and purify the crude product with 5% 2 M NH$_3$ in MeOH in CH$_2$Cl$_2$ to afford 1.43 g (28%) of the titled product. MS (m/z): 138 (M+1).

Preparation 77

(3R)-3-(4-Benzyloxy-2,6-dichloro-benzyl)-1-(4,5,6, 7-tetrahydro-1H-indazol-7-yl)-pyrrolidin-2-one Add a solution of (R)-4-((R)-4-benzyl-2-oxo-oxazolidin-3-yl)-3-(4-benzyloxy-2,6-dichloro-benzyl)-4-oxo-butyraldehyde, Preparation 38, (9.95 g, 18.9 mmol) in CH$_2$Cl$_2$ (300 mL) to a solution of 4,5,6,7-tetrahydro-1H-indazol-7-ylamine (2.60 g, 19.00 mmol) in acetonitrile (300 mL) and stir for 30 minutes at room temperature under N$_2$. Add sodium triacetoxyborohydride (12.02 g, 56.9 mmol) to the reaction and stir for 72 hours. Remove the solvent in vacuo and extract solid with ethyl acetate, water and saturated NaHCO$_3$. Dry the organic layer (Na$_2$SO$_4$), filter and concentrate under vacuum. Purify the residue by silica gel chromatography with a gradient of 0 to 10% methanol in CH$_2$Cl$_2$ to afford 2.53 g (28%) of the title compound. MS (m/z): 470 (M+).

Preparation 78

(3R)-3-(2,6-Dichloro-4-hydroxy-benzyl)-1-(4,5,6,7-tetrahydro-1H-indazol-7-yl)-pyrrolidin-2-one To a solution of (R)-3-(4-benzyloxy-2,6-dichloro-benzyl)-1-(4,5,6,7-tetrahydro-1H-indazol-7-yl)-pyrrolidin-2-one (2.46 g, 5.23 mmol) in dimethylsulfide (28 mL), add methane sulfonic acid (8.23 g, 85.7 mmol) and stir the mixture vigorously under at room temperature for 18 hours. Remove the solvent in vacuo and dilute the residue with water, adjust the pH to pH=7 with 5 N NaOH, and extract the mixture several times with ethyl acetate and THF. After drying the combined organic layer (Na$_2$SO$_4$), filter and concentrate under vacuum to afford 2.20 g (100%) of the title compound. MS (m/z): 381 (M+).

Preparation 79

Trifluoro-methanesulfonic acid 3,5-dichloro-4-[(R)-2-oxo-1-(1-trifluoromethanesulfonyl-4,5,6,7-tetrahydro-1H-indazol-7-yl)-pyrrolidin-3-ylmethyl]-phenyl ester and Trifluoro-methanesulfonic acid 3,5-dichloro-4-[(R)-2-oxo-1-(2-trifluoromethanesulfonyl-4,5,6,7-tetrahydro-2H-indazol-7-yl)-pyrrolidin-3-ylmethyl]-phenyl ester

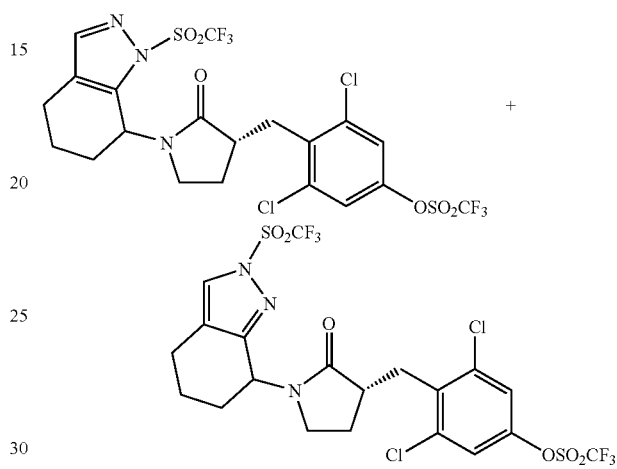

Treat a 0° C. solution of (R)-3-(2,6-dichloro-4-hydroxy-benzyl)-1-(4,5,6,7-tetrahydro-1H-indazol-7-yl)-pyrrolidin-2-one (2.10 g, 5.52 mmol) in pyridine (50 mL) drop-wise with triflic anhydride (4.99 g, 17.7 mmol) and stir at 0° C. for 15 minutes. Warm up the reaction to room temperature and stir for 90 minutes. Dilute the reaction with CH$_2$Cl$_2$ and wash with 1N HCl (3×300 mL). Dry the organic layer (Na$_2$SO$_4$) and the remove the solvent to afford 2.93 g (82%) of the mixed titled products. MS (m/z): 645 (M+).

Scheme N

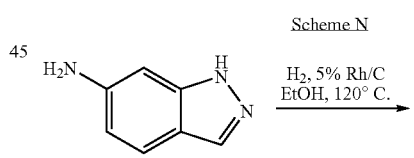

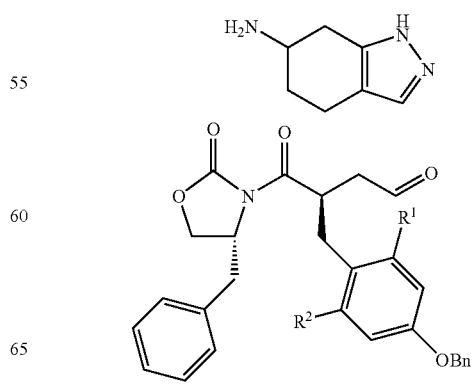

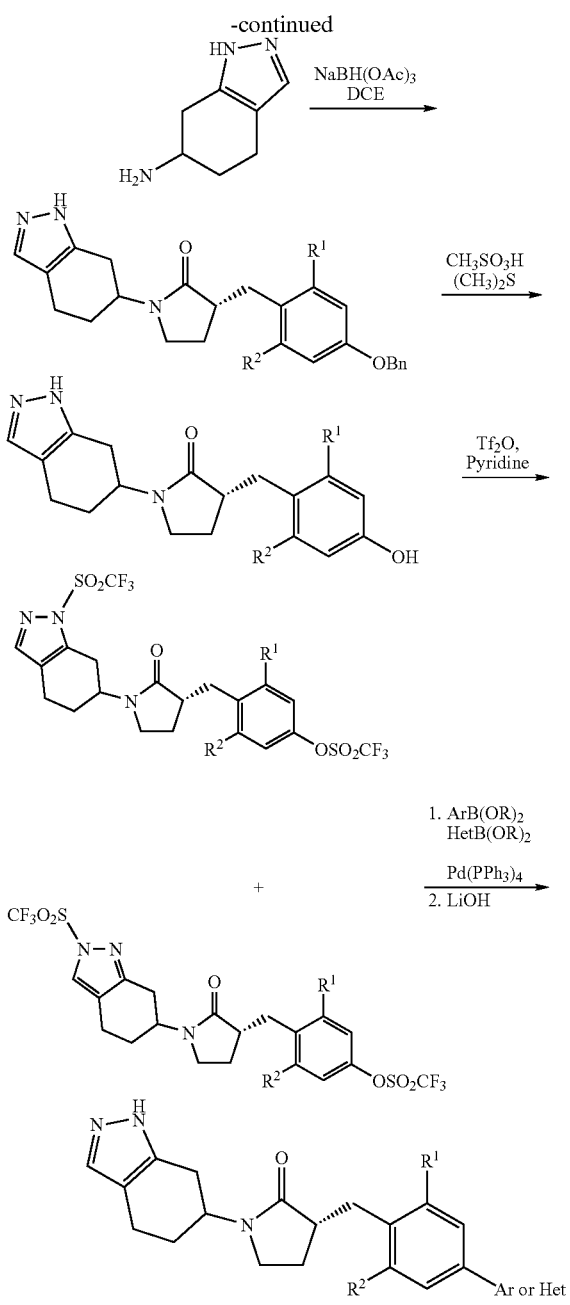

72 hours under ~1000 psi $H_2$. Cool the reaction and filter through hyflo. Remove the solvent in vacuo and purify the crude product with 10% 2 M $NH_3$ in MeOH in $CH_2Cl_2$ and re-purify mixed fractions with 15% 2 M $NH_3$ in MeOH in $CH_2Cl_2$ to afford 4.80 g (37%) of the titled product. MS (m/z): 138 (M+1).

Preparation 81

(3R)-3-(4-Benzyloxy-2,6-dichloro-benzyl)-1-(4,5,6,7-tetrahydro-1H-indazol-6-yl)-pyrrolidin-2-one Add a solution of (R)-4-((R)-4-benzyl-2-oxo-oxazolidin-3-yl)-3-(4-benzyloxy-2,6-dichloro-benzyl)-4-oxo-butyraldehyde, Preparation 38, (8.17 g, 15.5 mmol) in $CH_2Cl_2$ (100 mL) to a solution of 4,5,6,7-tetrahydro-1H-indazol-6-ylamine (2.13 g, 15.5 mmol) in acetonitrile (200 mL) and stir for 30 minutes at room temperature under $N_2$. Add sodium triacetoxyborohydride (9.89 g, 46.7 mmol) to the reaction and stir for 18 hours. Remove the solvent in vacuo and extract solid with ethyl acetate, water and saturated $NaHCO_3$. Dry the organic layer ($Na_2SO_4$), filter and concentrate under vacuum. Purify the residue by silica gel chromatography with a gradient of 0 to 10% methanol in $CH_2Cl_2$ to afford 3.93 g (54%) of the title compound. MS (m/z): 470 (M+).

Preparation 82

(3R)-3-(2,6-Dichloro-4-hydroxy-benzyl)-1-(4,5,6,7-tetrahydro-1H-indazol-6-yl)-pyrrolidin-2-one To a solution of (3R)-3-(4-benzyloxy-2,6-dichloro-benzyl)-1-(4,5,6,7-tetrahydro-1H-indazol-6-yl)-pyrrolidin-2-one (3.93 g, 8.36 mmol) in dimethylsulfide (45 mL), add methane sulfonic acid (13.23 g, 138 mmol) and stir the mixture vigorously under nitrogen atmosphere at room temperature for 18 hours. Remove the solvent in vacuo and dilute the residue with water, adjust the pH to pH=7 with 5 N NaOH, and extract the mixture several times with ethyl acetate and THF. After drying the combined organic layer ($Na_2SO_4$), filter and concentrate under vacuum to afford 3.60 g (100%) of the title compound. MS (m/z): 381 (M+).

Preparation 83

Trifluoro-methanesulfonic acid 3,5-dichloro-4-[(R)-2-oxo-1-(1-trifluoromethanesulfonyl-4,5,6,7-tetrahydro-1H-indazol-6-yl)-pyrrolidin-3-ylmethyl]-phenyl ester and Trifluoro-methanesulfonic acid 3,5-dichloro-4-[(R)-2-oxo-1-(2-trifluoromethanesulfonyl-4,5,6,7-tetrahydro-2H-indazol-6-yl)-pyrrolidin-3-ylmethyl]-phenyl ester

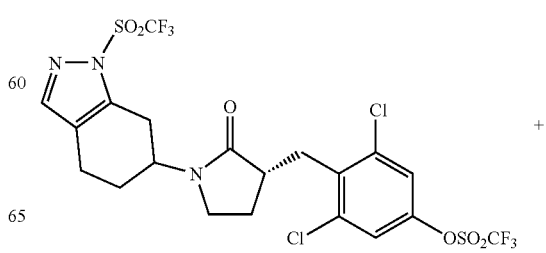

In Scheme N, 4,5,6,7-Tetrahydro-1H-indazol-6-ylamine is prepared from 1H-indazol-6-ylamine under hydrogenation using 5% Rh/C as a catalyst. Treatment of 4,5,6,7-Tetrahydro-1H-indazol-6-ylamine with aldehyde in presence of $NaBH(OAc)_3$ affords pyrazole. Removal of benzyl protecting group using $CH_3SO_3H$ in the presence of dimethylsulfide gives phenol which is subsequently converted to triflate. The final product is prepared by treatment of triflate with various boronic acids or esters under standard Suzuki coupling conditions, i.e. $Pd(PPh_3)_4$ and $Na_2CO_3$.

Preparation 80

4,5,6,7-Tetrahydro-1H-indazol-6-ylamine

Combine 1H-indazol-6-ylamine (12.45 g, 93.6 mmol) and 5% Rh/C (6.13 g) in ethanol (300 mL) and heat at 120° C. for -continued

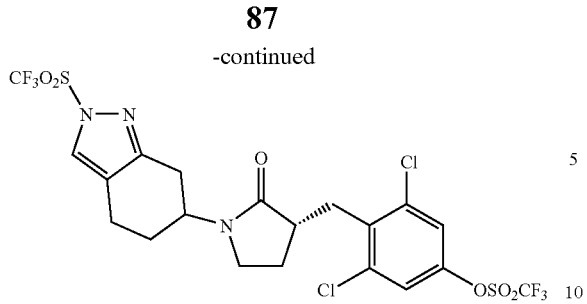

Treat a 0° C. solution of (R)-3-(2,6-dichloro-4-hydroxybenzyl)-1-(4,5,6,7-tetrahydro-1H-indazol-6-yl)-pyrrolidin-2-one (3.58 g, 9.42 mmol) in pyridine (100 mL) drop-wise with triflic anhydride (8.52 g, 30.2 mmol) and stir at 0° C. for 15 minutes. Warm up the reaction to room temperature and stir for 90 minutes. Dilute the reaction with $CH_2Cl_2$ and wash with 1N HCl (3×600 mL). Dry the organic layer ($Na_2SO_4$) and remove the solvent to afford 5.12 g (84%) of the mixed titled products. MS (m/z): 645 (M+).

Preparation 84

7-(4,4,5,5-Tetramethyl-[1,3,2]dioxaborolan-2-yl)-imidazo[1,2-a]pyridine

Combine 7-chloro-imidazo[1,2-a]pyridine (500.4 g, 3.28 mol), bis(pinacolato)diboron (999 g; 3.93 mol), tricyclohexylphosphine (92 g; 328.06 mmoles), and potassium acetate (483 g; 4.92 mol), in diglyme (4 L) and water (4.83 mL) and stir for 5 min. Add palladium (II) acetate (36.81 g; 163.96 mmoles) and more diglyme (1 L) and heat to 100° C. for 17 hours. Cool the reaction and add potassium carbonate (340 g; 2.46 moles) and stir 18 hr. Filter reaction slurry and wash solids with diglyme (2×1 L). Slurry the solids in water (5 L) and then filter and wash with water (2×1 L) and heptane (1 L). Dry the solid in a vacuum oven at 60° C. to afford 695.1 g (90%) of the titled product. MS (m/z): 245 (M+1).

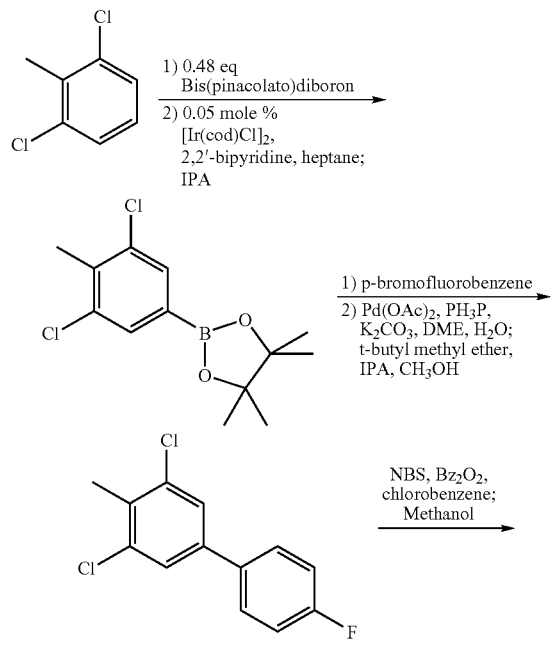

Scheme O

In Scheme O, dichlorotoluene is converted to the boronate using Ir catalyzed C—H activation. The boronate is coupled with p-bromofluorbenzene in a Suzuki reaction to afford the biary toluene. The biaryl toluene is brominated in the benzylic position using NBS under radical bromination conditions.

Preparation 85

4-Bromomethyl-3,5-dichloro-4'-fluoro-biphenyl

Step 1) Heat a mixture of 1,3-dichlorotoluene (250 mL, 1.95 moles), heptane (625 mL), Bis(pinacolato)diboron (237.9 g; 937 mmoles), 2,2'-Bipyridine (3.08 g, 19.47 mmoles), and Di-chlorobis((1,2,5,6-eta)-1,5-cyclooctadiene)diiridium (0.662 g; 0.98 mmoles) at 100° C. for 4 h. Cool the mixture to 55° C. and add 940 mL of t-butyl methyl ether. The solution is passed through 133 g of flash silica gel and the silica gel is rinsed with 200 mL of t-butyl methyl ether. Replace the solvent with isopropanol (approximately 1 L) and stir the slurry at 5° C. for 1 hr. Collect the solid by filtration and rinse with 200 mL of cold isopropanol. Dry the solid under vacuum to afford 410 g (73% yield) of 2-(3,5-dichloro-4-methyl-phenyl)-4,4,5,5-tetramethyl-[1,3,2]dioxaborolane as an off-white solid. $^1$H NMR (CDCl$_3$, 500 MHz) δ 1.34 (12H, s), 2.48 (3H, s), 7.68 (2H, s).

Step 2) To a suspension of 2-(3,5-Dichloro-4-methyl-phenyl)-4,4,5,5-tetramethyl-[1,3,2]dioxaborolane (119 g; 414.64 mmoles) in 1,2-dimethoxyethane (240 mL) under nitrogen, add p-bromofluorobenzene (57 mL; 518.54 mmoles), water (120 mL), potassium carbonate (115.7 g; 828.79 mmoles), triphenylphosphine (2.72 g; 10.37 mmoles) and Pd(OAc)$_2$ (0.47 g; 2.09 mmoles). Heat the mixture at 80° C. for 12 h and then allow to cool to room temperature. To the mixture, add 240 mL of t-butyl methyl ether and 480 mL of water, and then separate the layers. Wash the organic layer with an aqueous solution of TMT (Trithiocyanuric acid, trisodium salt hydrate, 5 g) in 120 mL, followed by saturated aqueous NaCl (120 mL). Solvent exchange the organic layer into approximately 600 mL of isopropanol to afford a slurry. Add water (120 mL) and cool the slurry to 3° C. Collect the solid by filtration and wash with 120 mL of cold methanol. Dry the solid under vacuum to afford 92.8 g of 3,5-dichloro-4'-fluoro-4-methyl-biphenyl as a light yellow solid. $^1$H NMR (CDCl$_3$, 500 MHz) δ 2.49 (3H, s), 7.13 (2H, t, J=9 Hz), 7.46 (2H, s), 7.49 (2H, dd, J=9, 5 Hz).

Alternate Step 2) Stir a slurry of 2-(3,5-dichloro-4-methyl-phenyl)-4,4,5,5-tetramethyl-[1,3,2]dioxaborolane (300 g, 1.05 moles) in 2 L of isopropanol under a blanket of nitrogen. Add p-bromofluorobenzene 61619 (150 mL; 1.36 moles) followed by an aqueous solution of potassium carbonate (160.5 g; 1.15 moles) in 300 mL water. Rinse the addition funnel with 400 mL isopropanol. Add triphenylphosphine (12.3 g; 46.89 mmoles) and Pd(OAc)$_2$ (2.35 g; 10.47 mmoles) and heat the mixture at 75° C. for 8 h. Add water (300 mL) and allow the mixture to cool to room temperature to afford a slurry. Cool the slurry in an ice bath, collect the solid by filtration and rinse with 350 mL of 6:1 IPA-water. Dry the solid in a vacuum oven at room temperature overnight to afford 345 g of crude product. Suspend the crude product in 2.2 L of ethanol and heat at 70° C. to afford a solution. Add Darco (35 g) and stir for 30 min. Filter the mixture through a pad of Hyflo (Celite) and allow the solution to cool to room temperature to afford a slurry. Cool the slurry to 5° C., collect the solid by filtration, and rinse with cold ethanol (530 mL). Dry the solid under vacuum to afford 230 g of 3,5-dichloro-4'-fluoro-4-methyl-biphenyl as an off-white solid (86% yield).

Step 3) To a suspension of 3,5-dichloro-4'-fluoro-4-methyl-biphenyl (138 g; 541 mmoles) in 965 mL acetonitrile, add N-Bromosuccinimide (109 g; 603 mmoles), and then add an additional 140 mL of ACN (rinse). Add benzoyl peroxide (1.37 g; 5.5 mmoles) and heat the mixture at 80° C. for 2.5 h. Add sodium thiosulfate (1.75 g) in 276 mL water and allow the mixture to gradually cool. Add to the mixture another 138 mL water at 55° C. and seed crystals of 4-bromomethyl-3,5-dichloro-4'-fluoro-biphenyl. After the slurry is at room temperature, add another 280 mL of water and cool the slurry in an ice bath. Collect the solid by filtration, rinse with 275 mL of cold methanol and dry to afford 170 g (94%) of 4-bromomethyl-3,5-dichloro-4'-fluoro-biphenyl as a solid.

Optional Purification—decreases main impurity from 2% to 1%. Slurry a 100 g portion of the above material in 200 mL of ACN and heat to 75° C. Add methanol (200 mL) as the temperature is allowed to cool to 54° C. Cool the slurry in an ice bath and collect the solid by filtration. Dry the solid under vacuum to afford 79.5 g of 4-bromomethyl-3,5-dichloro-4'-fluoro-biphenyl as a solid. $^1$H NMR (DMSO-$d_6$, 500 MHz) δ 4.81 (2H, s), 7.31 (2H, t, J=9 Hz), 7.82 (2H, dd, J=9, 5 Hz), 7.83 (2H, s).

Alternate Step 3) Clean a 55 gallon glass lined reactor. Charge 3,5-dichloro-4'-fluoro-4-methyl-biphenyl (7712 g) and chlorobenzene (77 L) and initiate stirring. Add NBS (6457 g) and continue stirring. Add benzoyl peroxide (73 g) and continue stirring and slowly heat the reaction to 85° C. After the exotherm has subsided, continue to heat the reaction mixture to 120° C. and maintain this reaction temperature until the reaction is deemed complete by GC (1-2 h). Cool the reaction mixture to 50° C. to 55° C. and quench the reaction mixture with Sodium thiosulfate pentahydrate (224 g) in Water (25.4 L) and stir the mixture for a minimum of 30 minutes. Separate the layers. Wash the organic layer with Water (1×20 L). Back extract the aqueous washes (steps 8 and 10) with Chlorobenzene (1×6 L). Combine the organic layers, dry with MgSO$_4$, add charcoal and stir well. Filter the mixture through a Buchner funnel using a glass fiber filter, wash with methylene chloride (3×500 mL). Concentrate the filtrate to ~3 L of total volume; co-evaporate the red oil with isopropanol (3×7 L) to remove any residual Chlorobenzene (methanol may be substituted for isopropanol). Transfer the wide mouth round bottom flask to a cooling bath and dilute the oil with methanol (5 L) and stir vigorously until the product precipitates. Dilute the mixture with additional methanol (10 L) and stir at room temperature overnight. Cool the mixture to 0° C. to 5° C. (ice/water bath) for a minimum of 2 hours. Filter the solid onto a Buchner funnel using a polypropylene filter cloth. Wash the solids with methanol (3×4 L, -20° C.). Tray the solids and dry in a vacuum oven at 25° C. to 30° C. for a minimum of 12 hours.

Scheme P

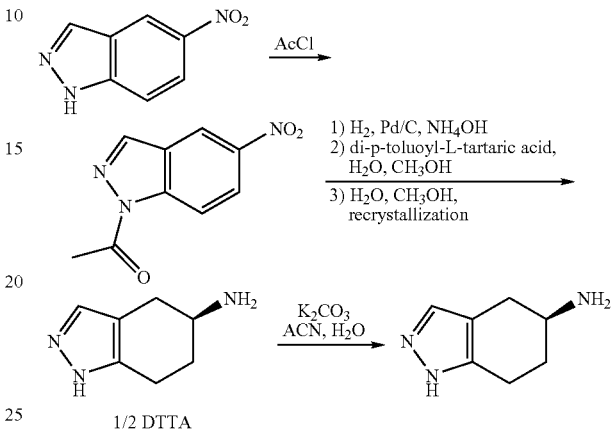

In Scheme P, 5-nitroindazole is protected as the N-acetyl derivative and then the nitro group and benzene ring are reduced under hydrogenation conditions in the presence of ammonia. The ammonia leads to deacylation under the reduction conditions. The resulting racemic amine is resolved using di-p-toluoyltartartic acid. The resulting resolved salt is freebased by stirring a slurry of the salt with potassium carbonated in ACN/water. Alternatively, the acetyl protected can be avoided and the 5-nitroindazole can be reduced directly.

Alternate Amine Preparation without Acetyl Protecting Group

Heat a mixture of 25 g of 5-nitroindazole, 500 mL of 8.3 M ammonium hydroxide and 25 g of 50% water wet 10% palladium on carbon at 100° C. under 200 psi of hydrogen for 24 hours. Purify a 10 g portion of this mixture by chromatography using NH$_3$/MeOH/CH$_2$Cl$_2$ to afford 235 mg (58% calculated yield) of racemic amine (R,S)-(4,5,6,7-tetrahydro-1H-indazol-5-yl)amine. The racemic amine is resolved as described in Preparation 86.

Preparation 86

(S)-(4,5,6,7-Tetrahydro-1H-indazol-5-yl)amine.½ DTTA

Step 1) Dissolve commercially available 5-nitroindazole (100 g, 613 mmoles) in 2 L of THF and then add triethylamine (260 mL; 1.87 moles). Stir the solution at room temp until all the solid went into the solution, and then add acetic acid anhydride (94 g; 927 mmoles). After 2 h at room temperature, add 2 L of EtOAc and extract the mixture with 1 N HCl (2×800 mL). Wash the organic layer with aqueous sodium bicarbonate followed by saturated aqueous NaCl. Dry the organic layer with magnesium sulfate and concentrate to a thick slurry. Add t-Butyl methyl ether (300 mL) and filter the slurry. Collect the solid, rinse with t-butyl methyl ether, and dry under vacuum to afford 113 g (90%) of 1-(5-nitro-indazol-1-yl)-ethanone a pale yellow solid. $^1$H NMR (500 MHz, CDCl$_3$) δ 8.70 (d, 1H, J=2.0 Hz), 8.58 (d, 1H, J=9.5 Hz), 8.44 (dd, 1H J=7.0, 2.0 Hz), 8.31 (s, 1H), 2.84 (s, 1H).

Step 2) Pressurize, with 200 psi of hydrogen, a mixture of 100 g of 1-(5-nitro-indazol-1-yl)-ethanone and 100 g of 10%

Pd/C (50% water wet) in 2 L of concentrated ammonium hydroxide (7.7 M) and heat at 100° C. for 24 h. Allow the mixture to cool to room temperature, filter through Hyflo (Celite), and rinse with ammonium hydroxide. Evaporate the solvent under vacuum to about 300-400 g. Add methanol (100 mL) and remove the solvent under vacuum to afford 310 g of solution. Dilute this solution with 1.8 L of methanol and add slowly di-p-toluoyl-L-tartaric acid (DTTA) (37.7 g, 97.6 mmoles) in 250 mL of warm methanol slowly, and then rinse in with 250 mL of methanol. After 30 min, collect the solid by filtration and rinse with methanol (3×100 mL). Dry the solid under vacuum to afford 52.9 g of a white solid. Slurry a portion of this solid (50 g) in 1.5 L of methanol and heat at reflux for 1 h. Allow the slurry to cool to room temperature. Collect the solid by filtration and dry under vacuum to afford 47.5 g of a white solid. Slurry a portion of this solid (47.3 g) in 1.42 L of 1:1 MeOH/water at 75° C. for 1 h and allow to cool to room temperature. Collect the solid and dry under vacuum to afford 42.3 g of resolved salt, (S)-(4,5,6,7-tetrahydro-1H-indazol-5-yl)amine.½DTTA, as a white solid, 96% ee. (An alternate procedure using 71 volumes (mL/g) of 1:2 methanol/water affords a similar ee in one reslurry.) MS (m/z): 138 (M+1 for amine).

Preparation 87

(S)-(4,5,6,7-Tetrahydro-1H-indazol-5-yl)amine

Add 5.98 g (8.0 mmoles) of (S)-(4,5,6,7-tetrahydro-1H-indazol-5-yl)amine.½ DTTA, 5.58 g (40 mmoles) of potassium carbonate, 72 mL of acetonitrile and 1.45 mL of water to a flask and heat at reflux for 16 h. Allow to cool to room temperature and filter. Rinse the solids with acetonitrile (2×10 mL) and evaporate the filtrate under vacuum to an oil. Add 10 mL of acetonitrile and seed with (S)-(4,5,6,7-tetrahydro-1H-indazol-5-yl)amine. After 1.5 h, filter the slurry, rinse with 3 mL of acetonitrile and dry under vacuum to afford 0.73 g (33%) of amine (S)-(4,5,6,7-tetrahydro-1H-indazol-5-yl) amine as a white solid. MS (m/z): 138 (M+1).

Crystallized (S)-(4,5,6,7-tetrahydro-1H-indazol-5-yl) amine is dissolved in ACN and used in the reductive amination portion of Example 88. Alternatively, this amine is used in Example 88 by carrying forward the amine dissolved in the ACN solution without isolation of the crystalline amine.

Scheme Q

1) TMSCl, Me₂NEt, THF
2) LiHMDS, THF, -70° C.
3) 4-Bromomethyl-3,5-dichloro-4'-fluoro-biphenyl
4) H₃PO₄, H₂O
5) EtOAc, heptane, xtl

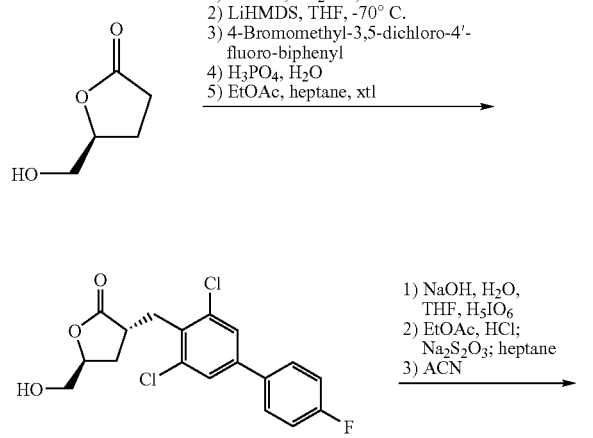

1) NaOH, H₂O, THF, H₅IO₆
2) EtOAc, HCl; Na₂S₂O₃; heptane
3) ACN

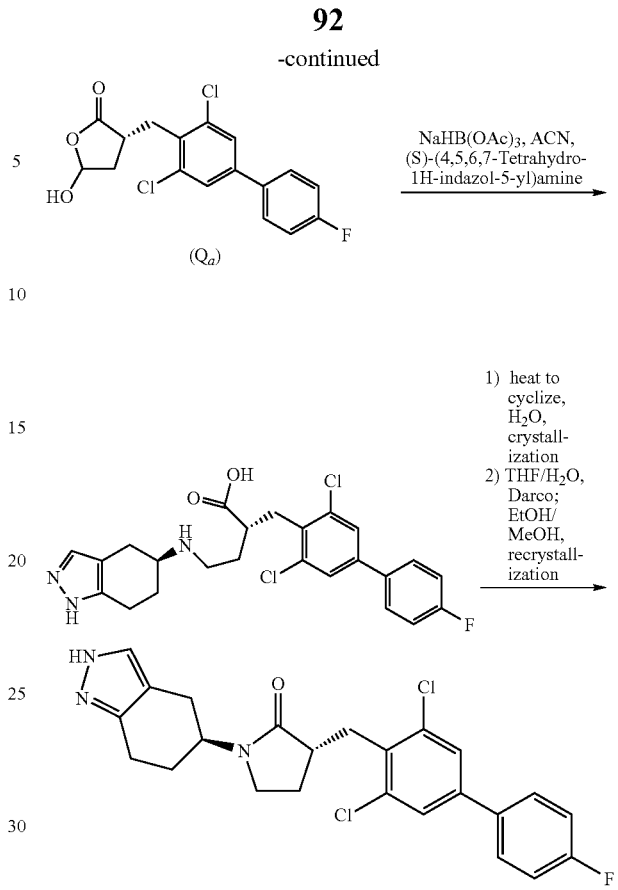

NaHB(OAc)₃, ACN, (S)-(4,5,6,7-Tetrahydro-1H-indazol-5-yl)amine 1) heat to cyclize, H₂O, crystallization
2) THF/H₂O, Darco; EtOH/MeOH, recrystallization In Scheme Q, the lactone-alcohol is protected in situ as the TMS ether and alkylated using LiHMDS as base with the biaryl benzyl bromide from Preparation 85. The TMS protecting group is removed during the workup. The alkylated lactone is opened under basic conditions to afford the diol-carboxylate. Diol cleavage with periodic acid affords the aldehyde. Neutralization during workup affords the aldehyde in the closed form after trapping by the carboxylic acid moiety. The closed form of the aldehyde is converted to the uncyclized intermediate amino acid by reductive amination. Heating of the intermediate affords the lactam product.

One of skill in the art will recognize the intermediate $Q_a$ from Scheme Q can be represented as illustrated below and may exist in equilibrium with several forms as shown. The representation of $Q_a$ therefore includes each of these forms:

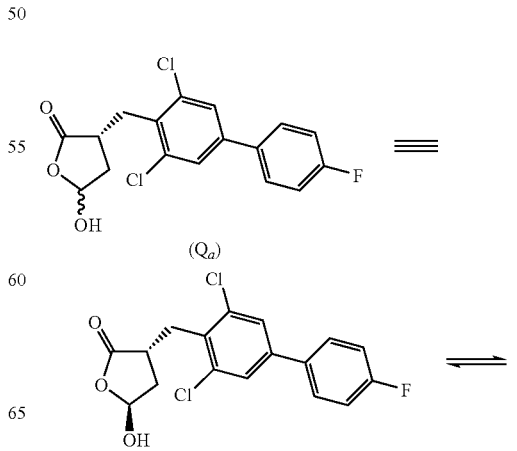

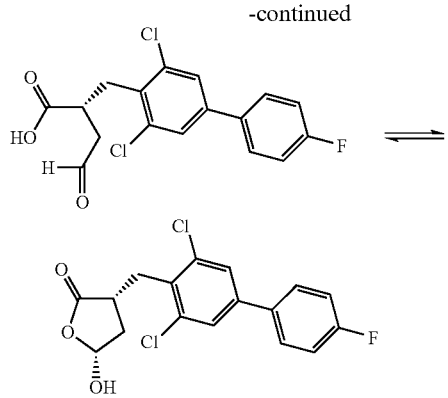

Preparation 88

(3R,5S)-3-(3,5-Dichloro-4'-fluoro-biphenyl-4-ylmethyl)-5-hydroxymethyl-dihydro-furan-2-one Dissolve commercially available (S)-5-hydroxymethyl-dihydro-furan-2-one (33.0 g, 284 mmoles) in 450 mL of THF, and then add 31.2 g (427 mmoles) of dimethylethylamine along with 50 mL of THF (rinse). Place the mixture under nitrogen and cool in an ice/water bath. Add trimethylsilyl chloride 39.8 mL (313 mmoles) while maintaining the temperature below 13° C. Filter the mixture and rinse the cake with THF (2×100 mL). Cool the solution of TMS (trimethylsilyl) protected lactone to −78° C. and add 4-bromomethyl-3,5-dichloro-4'-fluoro-biphenyl (71.2 g, 213 mmoles). Add a 1 M solution of lithium hexamethyldisilazide in THF (264 mL, 264 mmoles) over 1 h at −65 to −78° C. After stirring for 1 h, add a 600 mL solution of 120 mL of conc. phosphoric acid in water. After stirring for 10 min at room temperature, add 1 L of ethyl acetate and stir the mixture for 10 min. The layers separate. Wash the organic layer with water (2×500 mL). Evaporate the solvent down to a solution of approximately 250 mL and add an additional 250 mL of EtOAc. Evaporate the solvent until a solution of approximately 300-350 mL remains. Heat the mixture to reflux and add 494 mL of heptane. Allow the slurry to cool to room temperature, collect the solids by filtration, and rinse with heptane (2×100 mL). Dry the solid under vacuum to afford 62.1 g (59%) of the titled compound. MS (m/z): 369 (M+1, $^{35}$Cl), 371 (M+1, $^{37}$Cl).

Preparation 89

Alternative procedure for preparation of (3R,5S)-3-(3,5-Dichloro-4'-fluoro-biphenyl-4-ylmethyl)-5-hydroxymethyl-dihydro-furan-2-one:

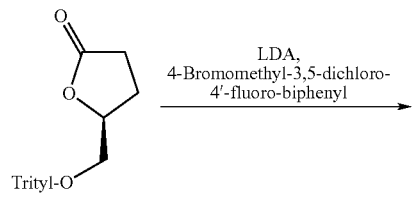

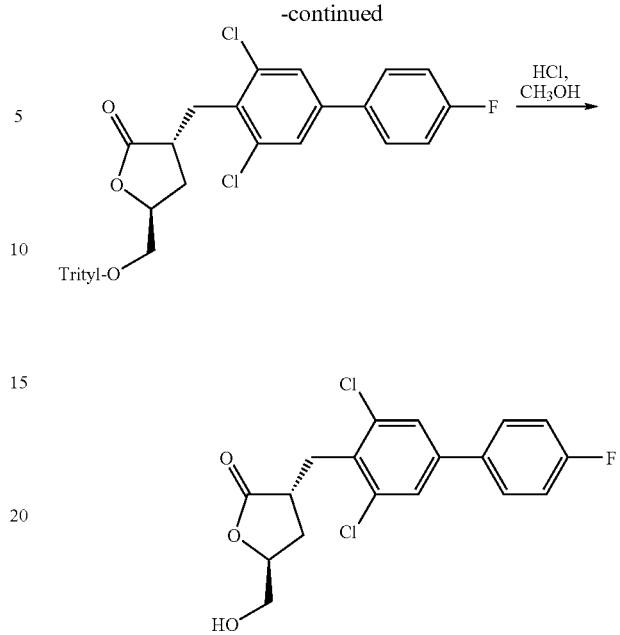

To 50 mL of THF and 2.4 mL (16.9 mmoles) of diisopropylamine at −78° C., add 10.6 mL of n-BuLi (1.6 M in hexane). Warm the solution to −25° C. and then recool to -78° C. Add a solution of 5.5 g of (S)-5-trityloxymethyl-dihydro-furan-2-one (prepared using the literature procedure, Chakraborty, T. K; et al, Tetrahedron, 2004, 60, 8329-8339; can also be purchased) in 60 mL of THF over 15 min. After 1 h, add a solution of 5.64 g (16.9 mmoles) of 4-bromomethyl-3,5-dichloro-4'-fluoro-biphenyl in 40 mL of THF over 20 min. Allow the mixture to warm to 15° C. overnight and partition between aqueous ammonium chloride and dichloromethane. Separate the layers, wash the organic layer with brine and dry over sodium sulfate. Evaporate the solvent to afford a foam.

Redissolve (3R,5S)-3-(3,5-Dichloro-4'-fluoro-biphenyl-4-ylmethyl)-5-trityloxymethyl-dihydro-furan-2-one in 30 mL of dichloromethane and 50 mL of methanol containing 0.5 mL of concentrate HCl. Stir the mixture overnight and neutralize with aqueous sodium bicarbonate. Most of the methanol and dichloromethane are removed. Extract the product with ethyl acetate. Wash the organic layers with water and then brine. Evaporate the solvent and chromatograph the product on flash silica gel using 5 to 25% acetone in methylene chloride. Evaporate the product containing fractions and recrystallize from ethyl acetate and heptane to afford 2.5 g (44% yield) of (3R,5S)-3-(3,5-dichloro-4'-fluoro-biphenyl-4-ylmethyl)-5-hydroxymethyl-dihydro-furan-2-one.

Preparation 90

(R)-3-(3,5-Dichloro-4'-fluoro-biphenyl-4-ylmethyl)-5-hydroxy-dihydro-furan-2-one To (3R,5S)-3-(3,5-dichloro-4'-fluoro-biphenyl-4-ylmethyl)-5-hydroxymethyl-dihydro-furan-2-one (375 g, 1.015 mmoles) dissolved in 5 vols of THF, add 750 mL of 2 N NaOH. After 40 min, add periodic acid (375 g, 1,644 mmoles), dissolved in 1,125 mL of water, over 17 min ($T_{max}$ 33° C.). Add EtOAc (3 L) followed by 800 mL of 5.0 N HCl and 600 mL of water. Agitate the layers and then separate.

Wash the organic layer with 100 g of sodium thiosulfate in 1 L of water, then 1 L of water, and then 700 mL of saturated NaCl in water. Dry the organic layer over sodium sulfate and then solvent exchange into 4 volumes (1500 mL) of heptane. Collect the solid by filtration and dry under vacuum. Reslurry the resulting solid in 3 volumes (1 L) of acetonitrile at 55° C. Cool the mixture in an ice bath and collect the solid by filtration. Dry the solid under vacuum to afford 273 g (78% yield) of the title compound as a white solid. MS (m/z): 355 (M+1, $^{35}$Cl), 357 (M+1, $^{37}$Cl).

Preparation 91

Isolation of Uncyclized intermediate (R)-2-(3,5-Dichloro-4'-fluoro-biphenyl-4-ylmethyl)-4-[(S)-(4,5,6,7-tetrahydro-1H-indazol-5-yl)amino]-butyric acid To a solution of 0.30 g (2.2 mmoles) of (S)-(4,5,6,7-tetrahydro-1H-indazol-5-yl)amine in 15 mL of ACN at 43° C., add 0.732 g (2.05 mmoles) of (R)-3-(3,5-Dichloro-4'-fluoro-biphenyl-4-ylmethyl)-5-hydroxy-dihydro-furan-2-one. Heat the mixture at 50° C. for 0.5 h and allow to cool to room temperature. Add 0.70 g (3.3 mmoles) of sodium triacetoxyborohydride. After 2.5 h, add an additional charge of sodium triacetoxyborohydride (100 mg). After 1 h, heat to 50° C. and add 15 mL of water slowly. Allow to cool to room temperature and stir the slurry overnight. Collect the solids by filtration and rinse with water (2×5 mL). Stir the wet cake with 15 mL of acetonitrile and filter. Rinse the cake with acetonitrile (2×5 mL) and dry in a vacuum oven to afford 0.65 g (62%) of the title compound as a solid. MS (m/z): 476 (M+1, $^{35}$Cl), 478 (M+1, $^{37}$Cl).

Scheme R

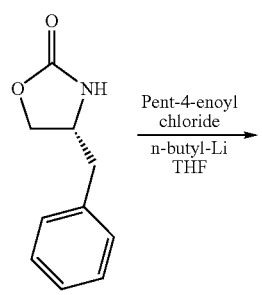

Pent-4-enoyl chloride
n-butyl-Li
THF

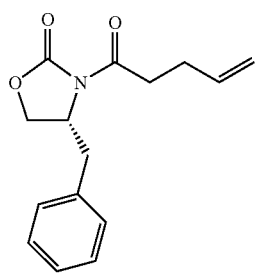

4-Bromomethyl-3,5-dichloro-4'-fluoro-biphenyl
LiHMDS
THF

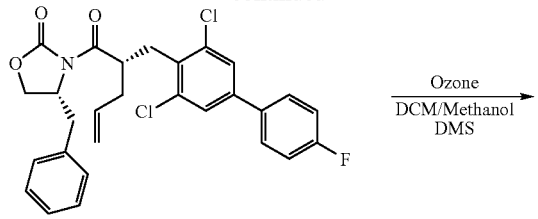

Ozone
DCM/Methanol
DMS

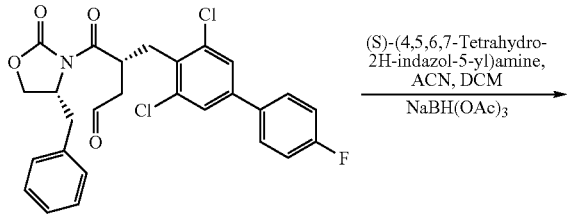

(S)-(4,5,6,7-Tetrahydro-2H-indazol-5-yl)amine,
ACN, DCM
NaBH(OAc)$_3$

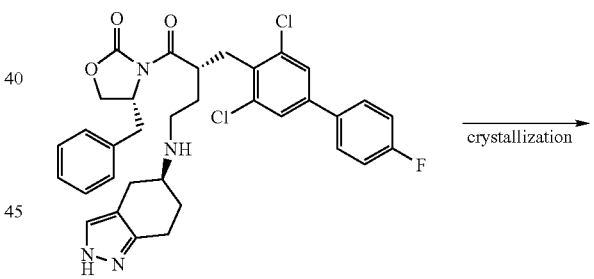

crystallization

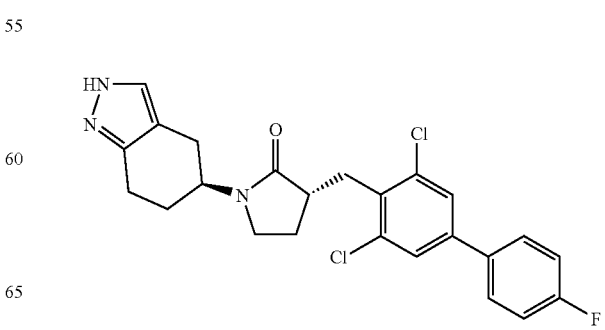

In Scheme R, the chiral oxazolidinone is acylated with pent-4-enoyl chloride and alkylated with 4-bromoethyl-3,5-dichloro-4'-fluoro-biphenyl to form the alkene compound with the alpha chiral center set. The biphenyl compound is ozonized to form the aldehyde. Reductive amination of the aldehyde with the chiral amino indazole affords an acyclic intermediate which cyclizes under the reaction conditions to afford the lactam.

Preparation 92

(R)-4-Benzyl-3-pent-4-enoyl-oxazolidin-2-one

Dissolve (R)-4-Benzyl-2-oxazolidinone (5.906 g, 33.33 mmoles) and 4-Pentenoyl chloride (4.54 g, 38.33 mmoles) in THF (50 mL). Cool the mixture in a dry ice acetone bath, and add n-Butyl Lithium (36.66 mmoles; 14.66 mL; 10.12 g) dropwise at −78° C. Stir the mixture at −78° C. for 30 min and then warm to ambient temperature. Quench the solution with 60 ml of sat. ammonium chloride, and then extract with 60 ml MTBE. Separate the organics and dry over magnesium sulfate. Filter the drying agent and concentrate under vacuum to an oil (6.96 g). LCMS=100% 260 amu (M+1).

Preparation 93

(R)-4-Benzyl-3-[(S)-2-(3,5-dichloro-4'-fluoro-biphenyl-4-ylmethyl)-pent-4-enoyl]-oxazolidin-2-one Dissolve (R)-4-Benzyl-3-pent-4-enoyl-oxazolidin-2-one (3.86 mmoles; 1.00 g) in THF (2 mL) and cool the mixture in a dry ice acetone bath. Add Lithium Bis(trimethylsilyl)amide (4.24 mmoles; 4.24 mL) dropwise at −78° C. under nitrogen. Stir the mixture at −78° C. for 10 minutes, and then warm to −25° C. for 1 hour. Cool the mixture back down to −78° C. and add 4-Bromomethyl-3,5-dichloro-4'-fluoro-biphenyl (4.43 mmoles; 1.48 g) in THF (2 mL) dropwise at −78° C. Warm the reaction to ambient temp. After stirring overnight, the LCMS analysis indicated 2 peaks. Purify the mixture over silica gel using hexane to 1:1 EtOAc/hexanes to obtain 1.3 g oil/foam. WY=65.8%, LCMS=89.6% (M+1=512.0).

Preparation 94
(R)-4-((R)-4-Benzyl-2-oxo-oxazolidin-3-yl)-3-(3,5-dichloro-4'-fluoro-biphenyl-4-ylmethyl)-4-oxo-butyraldehyde Dissolve (R)-4-Benzyl-3-[(S)-2-(3,5-dichloro-4'-fluoro-biphenyl-4-ylmethyl)-pent-4-enoyl]-oxazolidin-2-one (1.95 mmoles; 1.00 g) in dichloromethane (10 ml) and methanol (1 mL). Cool the mixture to −78° C. in a dry ice acetone bath and add ozone subsurface to the reaction with an exotherm to −71° C. The reaction turns blue, and then sweep with nitrogen to a clear color. Add dimethyl sulfide (2 mL; 27.20 mmoles) dropwise at −78° C. Warm the solution to ambient temperature and then test with KI starch paper (test is negative). Remove the solvents under vacuum, extract with MTBE, wash with pH=7 buffer, water, and brine. Concentrate the organics under vacuum to give a white non-crystalline solid (0.81 g). LCMS (M+1=515.39).

Preparation 95

(R)-3-(3,5-Dichloro-4'-t-butoxycarbonyl-biphenyl-4-ylmethyl)-1-(1-trifluoromethanesulfonyl-4,5,6,7-tetrahydro-1H-indazol-4-yl)-pyrrolidin-2-one and (R)-3-(3,5-Dichloro-4'-t-butoxycarbonyl-biphenyl-4-ylmethyl)-1-(2-trifluoromethanesulfonyl-4,5,6,7-tetrahydro-2H-indazol-4-yl)-pyrrolidin-2-one

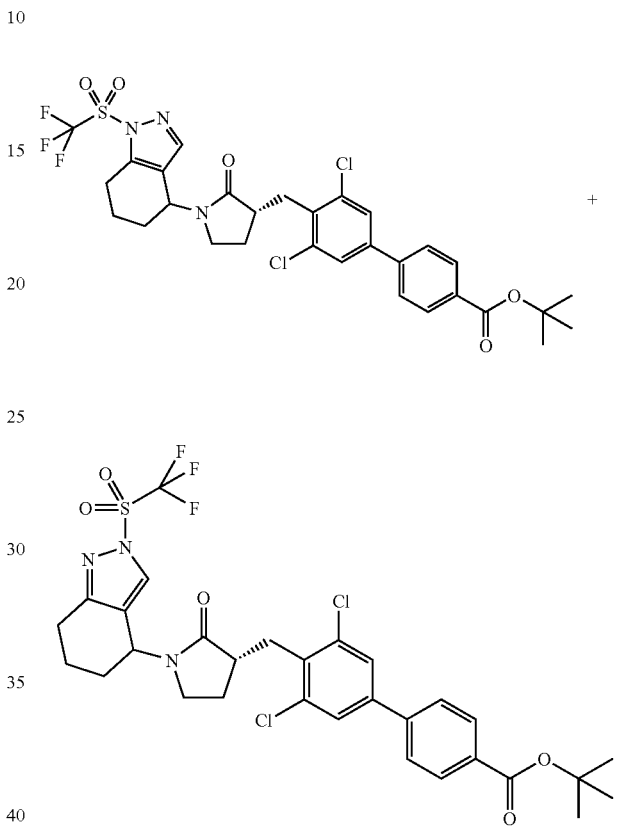

Bring a mixture of Preparation 73 (0.66 g, 1.02 mmol), 4-t-butoxycarbonylphenylboronic acid (0.27 g, 1.23 mmol), sodium carbonate (0.33 g, 3.07 mmol) in THF (15 mL) and water (5 mL) to 60° C. To the mixture at 60° C., add Pd(PPh₃)₄ (0.06 g, 0.05 mmol). Raise the reaction temperature to 80° C. and stir the reaction for 1 hour. Cool the reaction, dilute with ethyl acetate and, wash with water and brine. Dry the organic layer (Na₂SO₄), remove the solvent in vacuo, and purify the crude product on silica gel using 100% hexane to 50% ethyl acetate in hexane to afford 0.61 g of the titled mixture. MS 672 (M+).

Preparation 96

(R)-3-(3,5-Dichloro-4'-hydroxycarbonyl-biphenyl-4-ylmethyl)-1-(1-trifluoromethanesulfonyl-4,5,6,7-tetrahydro-1H-indazol-4-yl)-pyrrolidin-2-one (R)-3-(3,5-Dichloro-4'-hydroxycarbonyl-biphenyl-4-ylmethyl)-1-(2-trifluoromethanesulfonyl-4,5,6,7-tetrahydro-2H-indazol-4-yl)-pyrrolidin-2-one Treat a solution of Preparation 98 (0.61 g) in CH₂Cl₂ (4 mL) with trifluoroacedic acid (2 mL) at 25° C. for 3 hours. Concentrate the reaction in vacuo to afford 0.5 g of the titled mixture. MS (m/z): 615 (M−).

Preparation 97
2-[3,5-Dichloro-4'-(4-trifluoromethyl-piperidine-1-carbonyl)-biphenyl-4-ylmethyl]-5-(1-trifluoromethanesulfonyl-4,5,6,7-tetrahydro-1H-indazol-4-yl)-pyrrolidin-2-one, and 2-[3,5-Dichloro-4'-(4-trifluoromethyl-piperidine-1-carbonyl)-biphenyl-4-ylmethyl]-5-(2-trifluoromethanesulfonyl-4,5,6,7-tetrahydro-2H-indazol-4-yl)-pyrrolidin-2-one
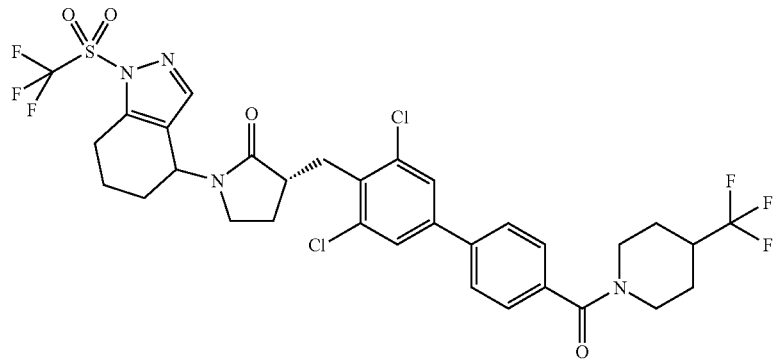
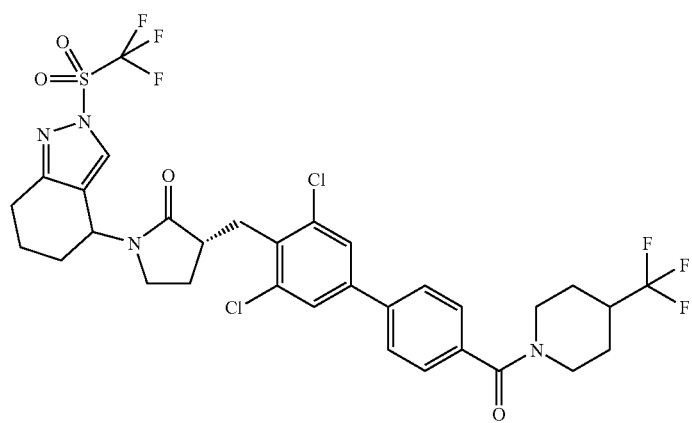

Treat a solution of Preparation 99 (0.5 g, 0.81 mmol) in CH₂Cl₂ (25 mL) with 1,1'-carbonyldiimidazole (0.27 g, 1.62 mmol) at 25° C. for 0.5 hour. To the mixture, add 4-trifluoromethylpiperidine hydrochloride (0.23 g, 1.22 mmol) and diisopropylethylamine (0.21 mL, 1.22 mmol). Stir the reaction at 25° C. for 12 hours. Dilute the reaction with CH₂Cl₂ and wash with HCL (1N) and water. Dry the organic layer (Na₂SO₄), remove the solvent in vacuo, and purify the crude product on silica gel using 50% ethyl acetate in hexane to afford 0.36 g of the titled mixture. MS (m/z): 751 (M+).

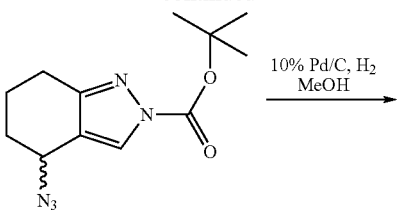

Scheme S

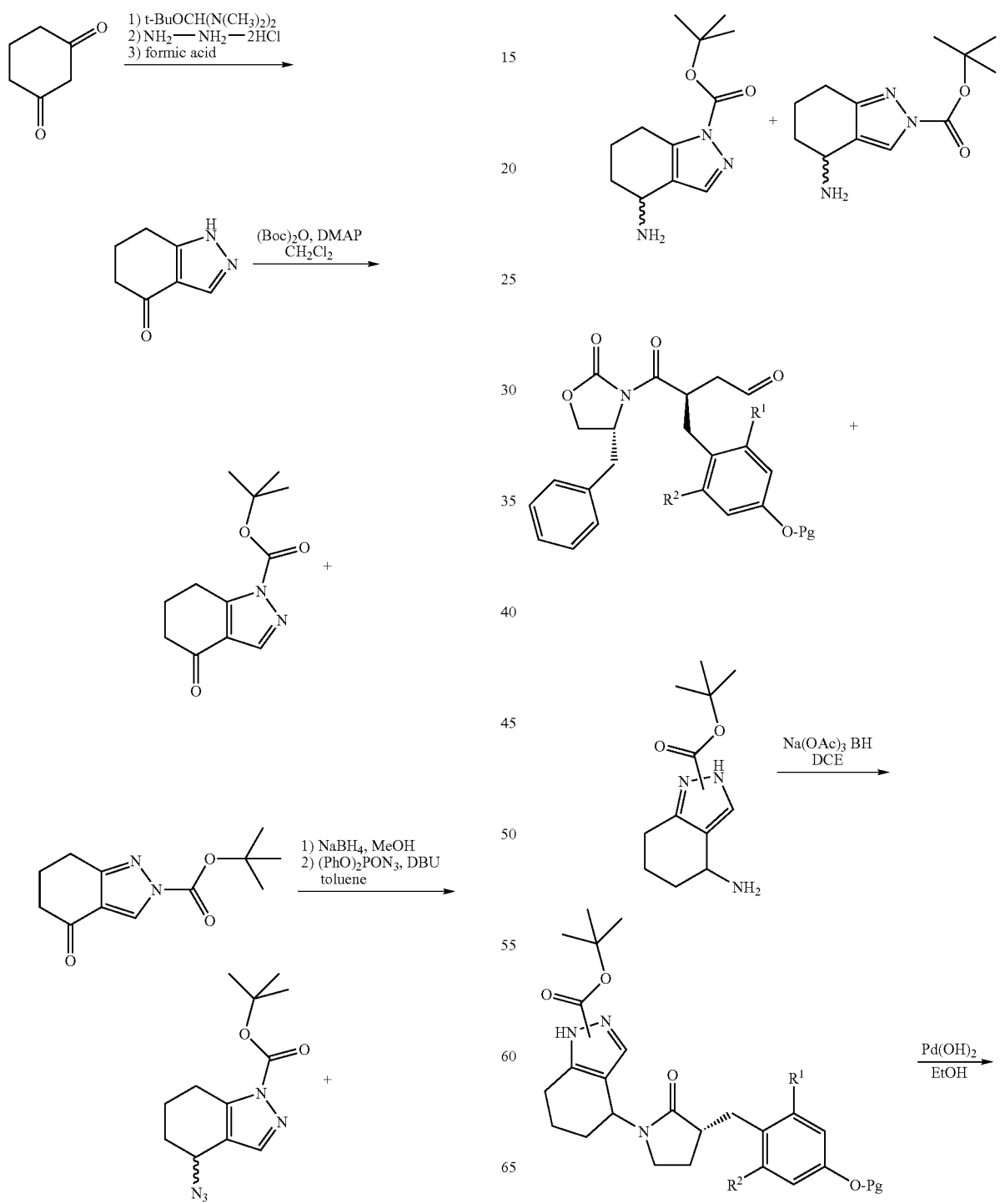

-continued

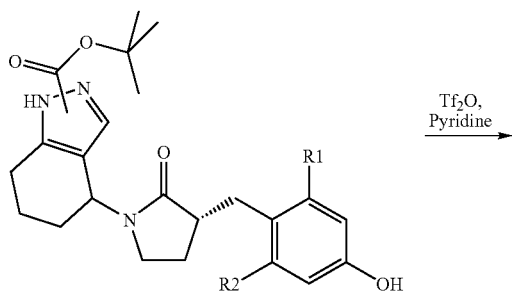

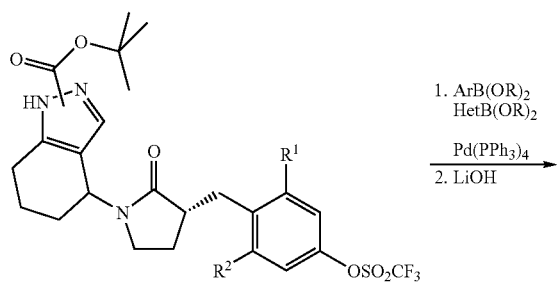

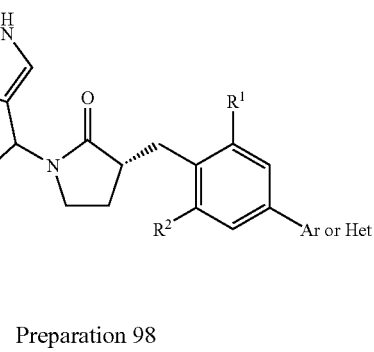

Preparation 98

2,5,6,7-Tetrahydro-indazol-4-one

To 1,3-cyclohexane dione (22.4 g, 0.19 mol), add tert-butoxybis(dimethylamino)methane (23.1 g, 0.19 mol). Stir the reaction at room temperature for 5 minutes. Add hydrazine dihydrochloride (20.55 g, 0.19 mol) to the reaction and stir at room temperature for 1 hour. Add formic acid (50 mL) to the mixture. Bring the reaction to 100° C. and stirred for 2 hours. Cool the reaction and extract with 3:1 chloroform:IPA (10×60 mL each). Combine the organics and dry over sodium sulfate. After filtration and concentration, load the residue on silica gel column and flash with ethyl acetate to afford 21.6 g (82%) of the desired product as white-grey solid. NMR matches the structure. MS (m/z): 137 [M+H]$^+$.

Preparation 99

4-Oxo-4,5,6,7-tetrahydro-indazole-1-carboxylic acid tert-butyl ester and 4-Oxo-4,5,6,7-tetrahydro-indazole-2-carboxylic acid tert-butyl ester

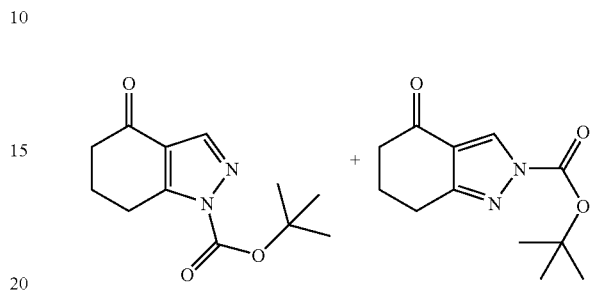

To a mixture of 2,5,6,7-tetrahydro-indazol-4-one (23.0 g, 169 mmol) in dichloromethane (750 mL), is add N,N-dimethyl-4-pyridinamine (25.02 g, 203 mmol) and di-t-butyldicarbonate (44.2 g, 230 mmol). Stir the mixture at room temperature for 45 minutes. Concentrate the reaction to ⅓ of its volume, load on silica gel column, and flash with 50% ethyl acetate in hexanes to afford 30.1 g (75%) of the desired product as a mixture of the two isomers.

Preparation 100

4-Hydroxy-4,5,6,7-tetrahydro-indazole-1-carboxylic acid tert-butyl ester, 4-Hydroxy-4,5,6,7-tetrahydro-indazole-2-carboxylic acid tert-butyl ester and 4,5,6,7-Tetrahydro-2H-indazol-4-ol

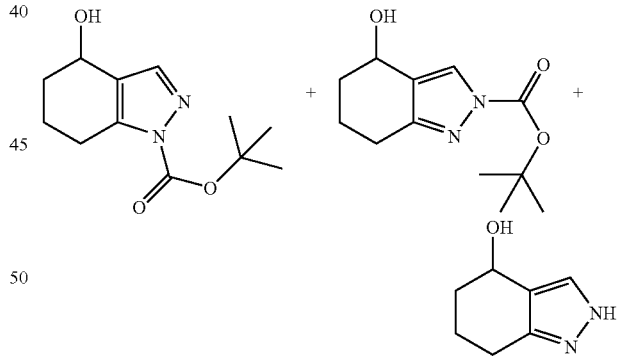

To the mixture of 4-oxo-4,5,6,7-tetrahydro-indazole-1-carboxylic acid tert-butyl ester and 4-oxo-4,5,6,7-tetrahydro-indazole-2-carboxylic acid tert-butyl ester (30.0 g, 127 mmol) in dichloromethane, add sodium tetrahydroborate (6.31 g, 165 mmol). Stir the reaction at room temperature for 1 hour. TLC indicates less than 10% conversion. To the mixture, add methanol (5 mL) and stir for 1 hour. TLC indicates the reaction is completed. Load the reaction mixture on silica gel column and flash with ethyl acetate to afford 10.2 g (34%) of the desired product as a colorless oil, and then flash with 20% methanol in dichloromethane to afford 7 g (40%) of the des boc product 4,5,6,7-tetrahydro-2H-indazol-4-ol. LCMS (loop): 139 (M-Boc+H)$^+$.

Preparation 101

4-Azido-4,5,6,7-tetrahydro-indazole-1-carboxylic acid tert-butyl ester and 4-Azido-4,5,6,7-tetrahydro-indazole-2-carboxylic acid tert-butyl ester

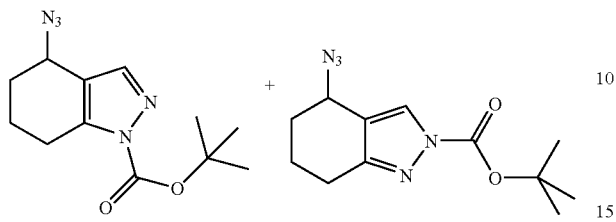

To the 4-hydroxy-4,5,6,7-tetrahydro-indazole-1-carboxylic acid tert-butyl ester and 4-hydroxy-4,5,6,7-tetrahydro-indazole-2-carboxylic acid tert-butyl ester (1.86 g, 7.81 mmol) in toluene (35 mL), add diphenylphosphonic azide (3.01 g, 2.36 g) and 1,8-diazabicyclo[5.4.0]undec-7-ene (1.66 g, 10.9 mmol). Stir the mixture at 80° C. for 1.5 hour, and then cool the reaction and concentrate. Dissolve the residue in dichloromethane, load on silica gel column, and flash with 25% ethyl acetate in hexanes to afford 1.83 g (89%) of the desired product as colorless oil. About 5% of diphenylphosphonic azide in the product but carried on as is).

Preparation 102

4-Amino-4,5,6,7-tetrahydro-indazole-1-carboxylic acid tert-butyl ester and 4-Amino-4,5,6,7-tetrahydro-indazole-2-carboxylic acid tert-butyl ester

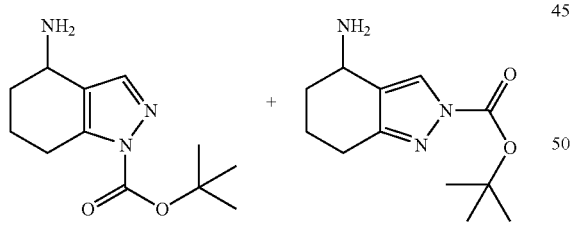

To a solution of the 4-azido-4,5,6,7-tetrahydro-indazole-1-carboxylic acid tert-butyl ester and 4-azido-4,5,6,7-tetrahydro-indazole-2-carboxylic acid tert-butyl ester (1.83 g, 6.95 mmol) in methanol (100 mL) in a hydrogenation bottle, add 10% palladium on carbon (0.36 g). Stir the mixture under hydrogen (30 psi) for 1 hour. Filter the reaction through celite to remove the catalyst. Concentrate the filtrate and purify via SCX column to afford 1.44 g (87%) of the desired product as colorless oil.

Preparation 103

(R)-4-[3-(4-Benzyloxy-2,6-dichloro-benzyl)-2-oxo-pyrrolidin-1-yl]-4,5,6,7-tetrahydro-indazole-1-carboxylic acid tert-butyl ester and (R)-4-[3-(4-Benzyloxy-2,6-dichloro-benzyl)-2-oxo-pyrrolidin-1-yl]-4,5,6,7-tetrahydro-indazole-2-carboxylic acid tert-butyl ester

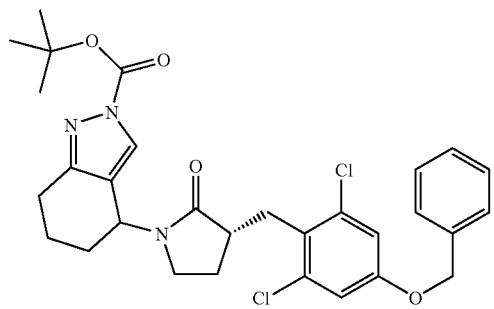

To the amine mixture 4-amino-4,5,6,7-tetrahydro-indazole-1-carboxylic acid tert-butyl ester/4-amino-4,5,6,7-tetrahydro-indazole-2-carboxylic acid tert-butyl ester (6.85 g, 28.9 mmol) in 1,2-dichloroethane (40 mL), add (R)-4-((R)-4-benzyl-2-oxo-oxazolidin-3-yl)-3-(4-benzyloxy-2,6-dichloro-benzyl)-4-oxo-butyraldehyde (15.2 g, 28.9 mmol) and sodium triacetoxyborohydride (19.1 g, 86.6 mmol). Stir the mixture at room temperature for 1 hour and then at 70° C. for 1 hour. Cool the reaction and concentrate. Partition the residue between ethyl acetate and water, dry the organic layer, and purify the residue on silica gel column to afford 15 g (91%) of the desired product as a mixture.

Preparation 104

(R)-4-[3-(2,6-Dichloro-4-hydroxy-benzyl)-2-oxo-pyrrolidin-1-yl]-4,5,6,7-tetrahydro-indazole-1-carboxylic acid tert-butyl ester and (R)-4-[3-(2,6-Dichloro-4-hydroxy-benzyl)-2-oxo-pyrrolidin-1-yl]-4,5,6,7-tetrahydro-indazole-2-carboxylic acid tert-butyl ester

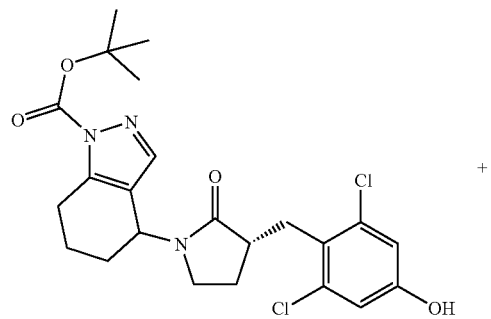

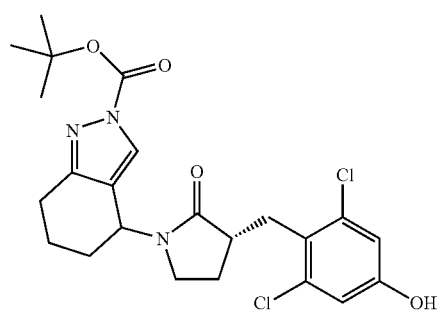

To a solution of (R)-4-[3-(4-benzyloxy-2,6-dichloro-benzyl)-2-oxo-pyrrolidin-1-yl]-4,5,6,7-tetrahydro-indazole-1-carboxylic acid tert-butyl ester and (R)-4-[3-(4-benzyloxy-2,6-dichloro-benzyl)-2-oxo-pyrrolidin-1-yl]-4,5,6,7-tetrahydro-indazole-2-carboxylic acid tert-butyl ester (15.0 g, 26.3 mmol) in methanol (250 mL) in a round bottom flask, add 20% palladium hydroxide on carbon (3.0 g). Stir the reaction mixture under a hydrogen balloon for 1 hour. Filter through celite and concentrate the residue to afford 11.36 g (90%) of the desired mixed product as white solid.

Preparation 105

(R)-4-[3-(2,6-Dichloro-4-trifluoromethanesulfonyloxy-benzyl)-2-oxo-pyrrolidin-1-yl]-4,5,6,7-tetrahydro-indazole-1-carboxylic acid tert-butyl ester and (R)-4-[3-(2,6-Dichloro-4-trifluoromethanesulfonyloxy-benzyl)-2-oxo-pyrrolidin-1-yl]-4,5,6,7-tetrahydro-indazole-2-carboxylic acid tert-butyl ester

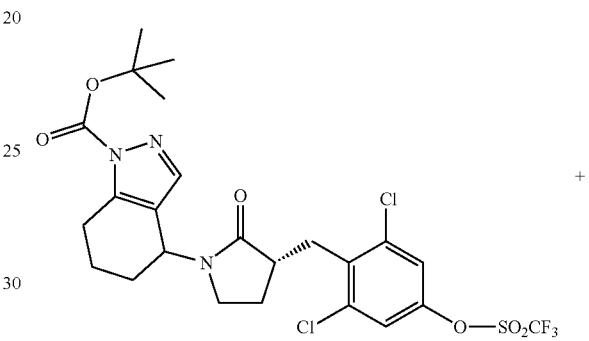

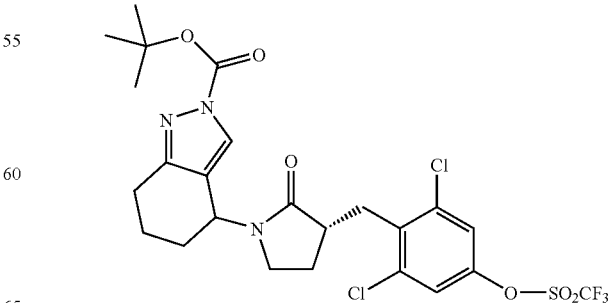

Cool a solution of the (R)-4-[3-(2,6-dichloro-4-hydroxy-benzyl)-2-oxo-pyrrolidin-1-yl]-4,5,6,7-tetrahydro-indazole-1-carboxylic acid tert-butyl ester and (R)-4-[3-(2,6-dichloro-4-hydroxy-benzyl)-2-oxo-pyrrolidin-1-yl]-4,5,6,7-tetrahydro-indazole-2-carboxylic acid tert-butyl ester (11.4 g, 23.7 mmol) in pyridine (20 mL) to 0° C. and add trifluoromethanesulfonic anhydride (8.67 g, 30.7 mmol). Stir the reaction from 0° C. for 30 minutes and at room temperature for 1 hour. Dilute the reaction with dichloromethane and wash three times with HCl (1N). Separate the organic and dry over sodium sulfate, filter, concentrate to give crude product, and then purify by flash chromatography with 50% ethyl acetate in hexane to afford 10.6 g (73%) desired product as a mixture of two regioisomers.

EXAMPLE 1

(±)3-(2,6-Dichloro-4-methoxy-benzyl)-1-(4,5,6,7-tetrahydro-2H-indazol-5-yl)-pyrrolidin-2-one

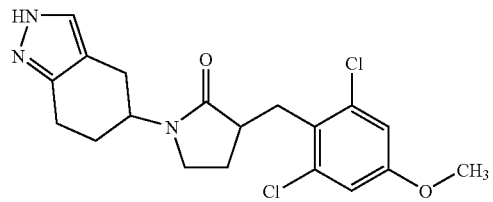

Dissolve 3-(2,6-Dichloro-4-methoxy-benzyl)-1-(3-dimethylaminomethylene-4-oxo-cyclohexyl)-pyrrolidin-2-one in ethanol (Preparation 24) (50 mL), and hydrazine hydrate (2.6 mL, 54 mmol) stir the resulting orange solution for 3 days at room temp. Concentrate the mixture to dryness, dilute with ethanol (15 mL) and ether (20 mL), cooled to 0° C. and filter to give 3.6 g, 68%, as a tan solid. MS (m/z): 394 (M+1).

TABLE 4

Prepare the Examples in Table 4 essentially as described in Example 1 substituting the preparation indicated in column labeled Preparation.

| Example | Structure and Chemical name | Preparation | Physical data |
|---|---|---|---|
| 2 | 1-(4,5,6,7-Tetrahydro-2H-indazol-5-yl)-3-(2,4,6-trifluoro-benzyl)-pyrrolidin-2-one | 25 | MS (m/z): 351 (M + 1) |
| 3 | 3-(2-Chloro-4-fluoro-benzyl)-1-(4,5,6,7-tetrahydro-2H-indazol-5-yl)-pyrrolidin-2-one | 26 | MS (m/z): 347 (M + 1) |

TABLE 4-continued

Prepare the Examples in Table 4 essentially as described in Example 1 substituting the preparation indicated in column labeled Preparation.

| Example | Structure and Chemical name | Preparation | Physical data |
|---|---|---|---|
| 4 | 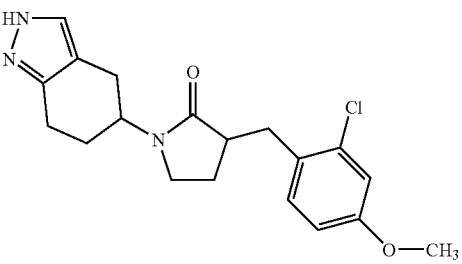<br>3-(2-Chloro-4-methoxy-benzyl)-1-(4,5,6,7-tetrahydro-2H-indazol-5-yl)-pyrrolidin-2-one | 27 | MS (m/z): 360 (M + 1) |
| 5 | 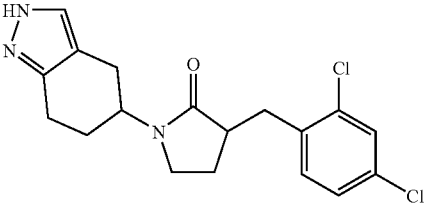<br>3-(2,4-Dichloro-benzyl)-1-(4,5,6,7-tetrahydro-2H-indazol-5-yl)-pyrrolidin-2-one | 28 | MS (m/z): 364 (M + 1) |
| 6 | 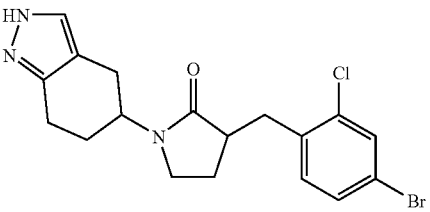<br>3-(4-Bromo-2-chloro-benzyl)-1-(4,5,6,7-tetrahydro-2H-indazol-5-yl)-pyrrolidin-2-one | 29 | MS (m/z): 410 (M + 2) |

EXAMPLES 7-10

3-(2,6-Dichloro-4-methoxy-benzyl)-1-(4,5,6,7-tetrahydro-2H-indazol-5-yl)-pyrrolidin-2-one

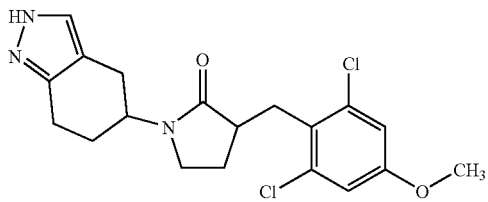

The four component mixture (Example 1) can be separated into individual enantiomers via chiral chromatography (Chiralpak AD-H, 4.6×150 mm, 40/60 Isopropyl alcohol/hexanes/0.2% DMEA, flow=0.6 ml/min, 290 nm).

The following enantiomers can be isolated by the procedure above.

| Example | Retention Time (min) | % ee | Isomer Number | $[\alpha]^{23}$D (c 0.5, CHCl$_3$) |
|---|---|---|---|---|
| 7 | 7.088 | >99 | Isomer 1 | −32 |
| 8 | 8.872 | >99 | Isomer 2 | +17 |
| 9 | 11.084 | >99 | Isomer 3 | +29 |
| 10 | 14.064 | >96 | Isomer 4 | −16 |

EXAMPLE 11

3-[2-Chloro-4-(1-methyl-1H-pyrazol-4-yl)-benzyl]-1-(4,5,6,7-tetrahydro-2H-indazol-5-yl)-pyrrolidin-2-one

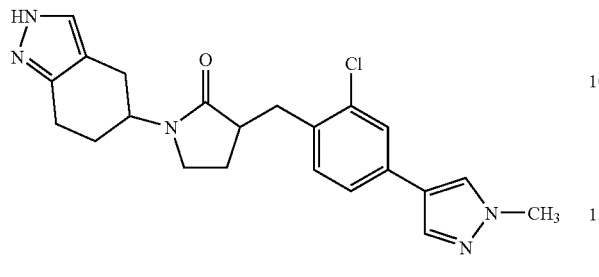

Dissolve 3-[2-Chloro-4-(1-methyl-1H-pyrazol-4-yl)-benzyl]-1-(3-dimethylaminomethylene-4-oxo-cyclohexyl)-pyrrolidin-2-one (Preparation 30) (0.327 g, 0.745 mmol) in methanol (3.0 mL), and hydrazine hydrate (0.038 mL) stir the resulting orange solution for 17 hours at room temperature. Filter the mixture, rinse with cold methanol and vacuum dry to 0.138 g of a solid. MS (m/z): 410 (M+1).

EXAMPLE 12

3-[2,6-Dichloro-4-(1-methyl-1H-pyrazol-4-yl)-benzyl]-1-(4,5,6,7-tetrahydro-2H-indazol-5-yl)-pyrrolidin-2-one

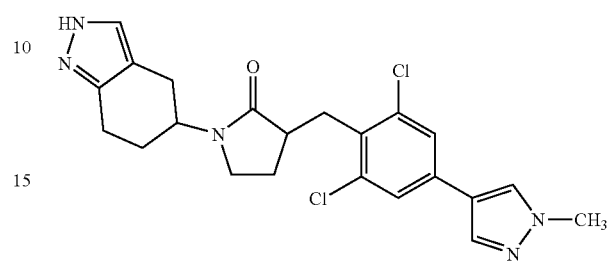

Combine trifluoro-methanesulfonic acid 3,5-dichloro-4-[2-oxo-1-(2-trifluoromethanesulfonyl-4,5,6,7-tetrahydro-2H-indazol-5-yl)-pyrrolidin-3-ylmethyl]phenyl ester (Preparation 33) (0.5, 0.77 mmol), 1-methyl-4-(4,4,5,5-tetramethyl-[1,3,2]dioxaborolan-2-yl)-1H-pyrazole (0.484 g, 2.3 mmol), sodium carbonate (2.7 ml of 2.0 M, 5.4 mmol) in DME (12 mL) and degas with a stream of nitrogen. Add $(Ph_3P)_4Pd$ (0.089 g, 0.07 mmol), and stir at 80° C. for 4 hour under nitrogen atmosphere. Cool to ambient temperature and add ethyl acetate (20 mL) and water (10 mL). Extract the aqueous phase with ethyl acetate (2×20 mL), dry (sodium sulfate) and condense under reduced pressure. Chromatography (silica, 95:5 $CH_2Cl_2$/MeOH) yields 0.144 g (42%) as a white solid MS (m/z): 445 (M+1).

TABLE 5

Prepare the Examples in Table 5 essentially as described in Example 12 with substitution for 1-methyl-4-(4,4,5,5-tetramethyl-[1,3,2]dioxaborolan-2-yl)-1H-pyrazole by the reagent indicated in the column labeled Synthetic Reagent.

| Example | Structure and Chemical name | Synthetic Reagent | Physical data |
| --- | --- | --- | --- |
| 13 | 3-(2,6-Dichloro-4-pyrimidin-5-yl-benzyl)-1-(4,5,6,7-tetrahydro-2H-indazol-5-yl)-pyrrolidin-2-one | pyrimidin-5-yl boronic acid | MS (m/z): 443 (M + 1) |

… TABLE 5-continued

Prepare the Examples in Table 5 essentially as described in Example 12 with substitution for 1-methyl-4-(4,4,5,5-tetramethyl-[1,3,2]dioxaborolan-2-yl)-1H-pyrazole by the reagent indicated in the column labeled Synthetic Reagent.

| Example | Structure and Chemical name | Synthetic Reagent | Physical data |
|---|---|---|---|
| 14 | 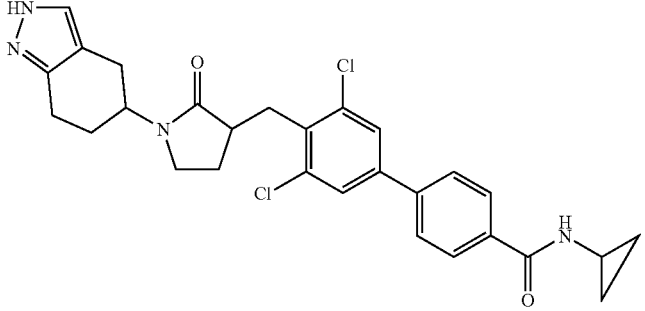<br>3′,5′-Dichloro-4′-[2-oxo-1-(4,5,6,7-tetrahydo-2H-indazol-5-yl)-pyrrolidin-3-ylmethyl]-biphenyl-4-carboxylic acid cyclopropylamide | 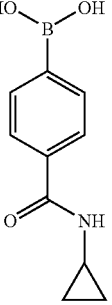 | MS (m/z): 524 (M + 1) |
| 15 | 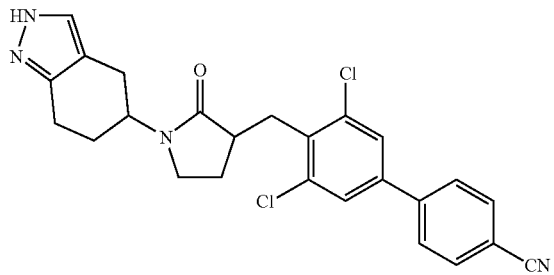<br>3-(3,5-Dichloro-4′-cyano-biphenyl-4-ylmethyl)-1-(4,5,6,7-tetrahydro-2H-indazol-5-yl)-pyrrolidin-2-one | 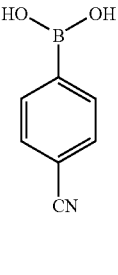 | MS (m/z): 467 (M + 1) |
| 16 | 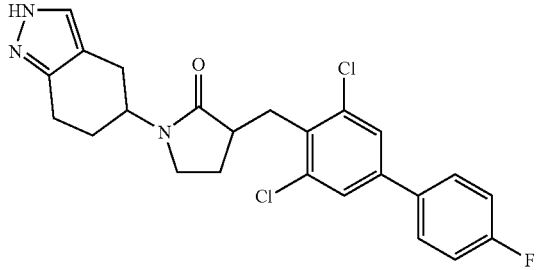<br>3-(3,5-Dichloro-4′-fluoro-biphenyl-4-ylmethyl)-1-(4,5,6,7-tetrahydro-2H-indazol-5-yl)-pyrrolidin-2-one | 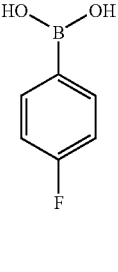 | MS (m/z): 459 (M + 1) |
| 17 | 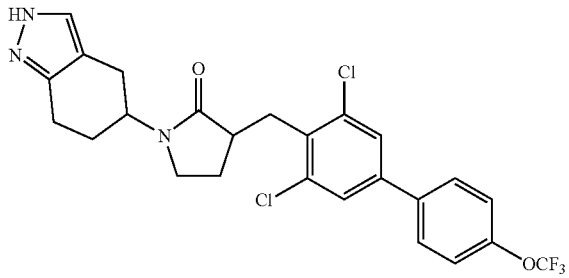<br>3-(3,5-Dichloro-4′-trifluoromethoxy-biphenyl-4-ylmethyl)-1-(4,5,6,7-tetrahydro-2H-indazol-5-yl)-pyrrolidin-2-one | 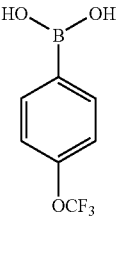 | MS (m/z): 526 (M + 2) |

TABLE 5-continued

Prepare the Examples in Table 5 essentially as described in Example 12 with substitution for 1-methyl-4-(4,4,5,5-tetramethyl-[1,3,2]dioxaborolan-2-yl)-1H-pyrazole by the reagent indicated in the column labeled Synthetic Reagent.

| Example | Structure and Chemical name | Synthetic Reagent | Physical data |
|---|---|---|---|
| 18 | 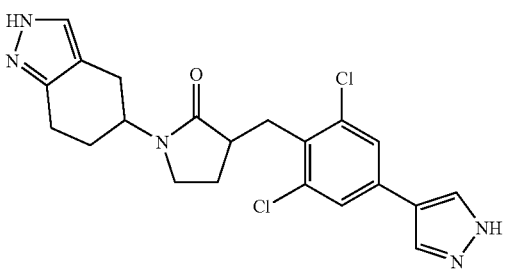<br>3-[2,6-Dichloro-4-(1H-pyrazol-4-yl)-benzyl]-1-(4,5,6,7-tetrahydro-2H-indazol-5-yl)-pyrrolidin-2-one | 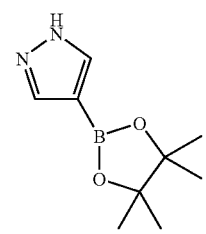 | MS (m/z): 431 (M + 1) |
| 19 | 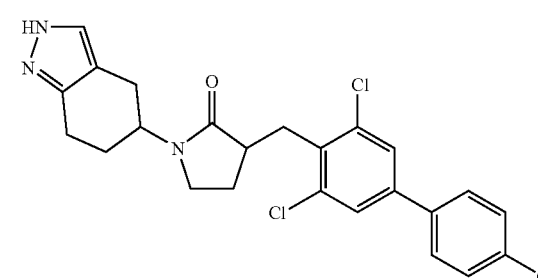<br>3-(3,5-Dichloro-4'-chloro-biphenyl-4-ylmethyl)-1-(4,5,6,7-tetrahydro-2H-indazol-5-yl)-pyrrolidin-2-one | 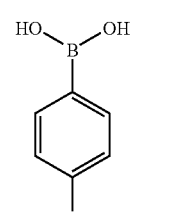 | MS (m/z): 475 (M + 1) |
| 20 | 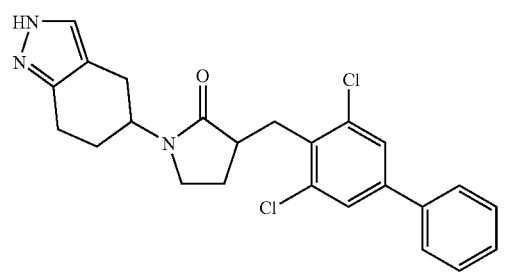<br>3-(3,5-Dichloro-biphenyl-4-ylmethyl)-1-(4,5,6,7-tetrahydro-2H-indazol-5-yl)-pyrrolidin-2-one | 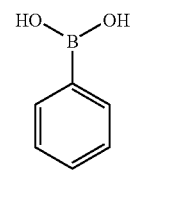 | MS (m/z): 441 (M + 1) |
| 21 | 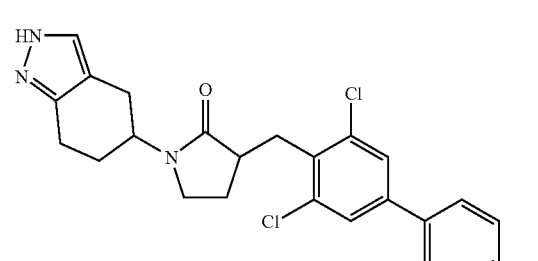<br>3-(3,5-Dichloro-4'-trifluoromethyl-biphenyl-4-ylmethyl)-1-(4,5,6,7-tetrahydro-2H-indazol-5-yl)-pyrrolidin-2-one | 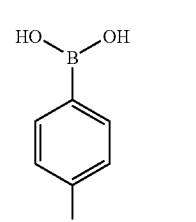 | MS (m/z): 510 (M + 1) |

TABLE 5-continued

Prepare the Examples in Table 5 essentially as described in Example 12 with substitution for 1-methyl-4-(4,4,5,5-tetramethyl-[1,3,2]dioxaborolan-2-yl)-1H-pyrazole by the reagent indicated in the column labeled Synthetic Reagent.

| Example | Structure and Chemical name | Synthetic Reagent | Physical data |
|---|---|---|---|
| 22 | 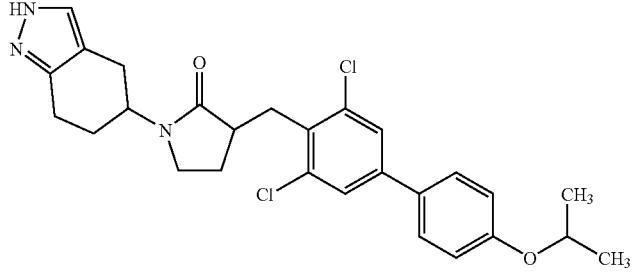<br>3-(3,5-Dichloro-4'-isopropoxy-biphenyl-4-ylmethyl)-1-(4,5,6,7-tetrahydro-2H-indazol-5-yl)-pyrrolidin-2-one | 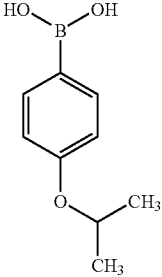 | MS (m/z): 499 (M + 1) |
| 23 | 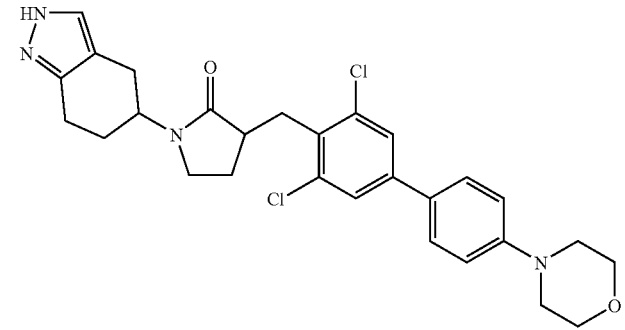<br>3-(3,5-Dichloro-4'-morpholin-4-yl-biphenyl-4-ylmethyl)-1-(4,5,6,7-tetrahydro-2H-indazol-5-yl)-pyrrolidin-2-one | 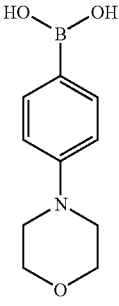 | MS (m/z): 526 (M + 1) |
| 24 | 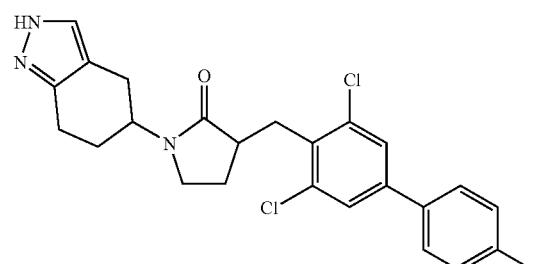<br>3-(3,5-Dichloro-4'-methyl-biphenyl-4-ylmethyl)-1-(4,5,6,7-tetrahydro-2H-indazol-5-yl)-pyrrolidin-2-one | 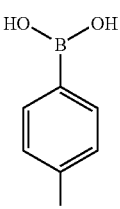 | MS (m/z): 454 (M + 1) |

TABLE 5-continued

*Prepare the Examples in Table 5 essentially as described in Example 12 with substitution for 1-methyl-4-(4,4,5,5-tetramethyl-[1,3,2]dioxaborolan-2-yl)-1H-pyrazole by the reagent indicated in the column labeled Synthetic Reagent.*

| Example | Structure and Chemical name | Synthetic Reagent | Physical data |
|---|---|---|---|
| 25 | 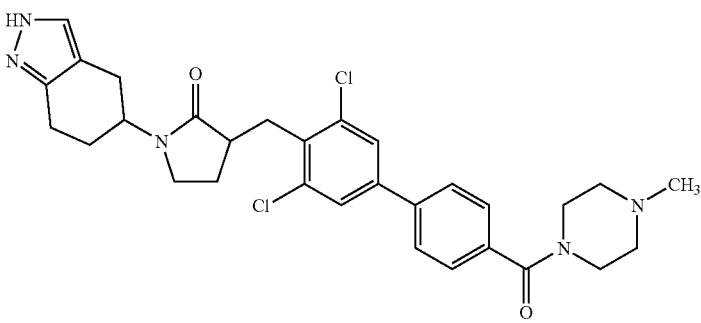<br>3-[3,5-Dichloro-4'-(4-methyl-piperazine-1-carbonyl)-biphenyl-4-ylmethyl]-1-(4,5,6,7-tetrahydro-2H-indazol-5-yl)-pyrrolidin-2-one | 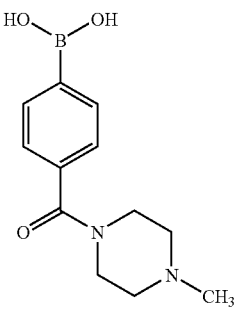 | MS (m/z): 567 (M + 1) |
| 25a | 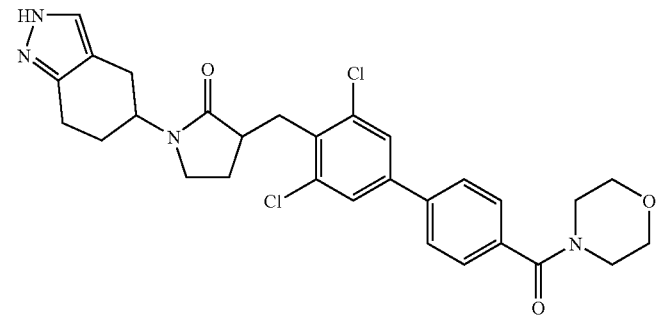<br>3-[3,5-Dichloro-4'-(morpholine-4-carbonyl)-biphenyl-4-ylmethyl]-1-(4,5,6,7-tetrahydro-2H-indazol-5-yl)-pyrrolidin-2-one | 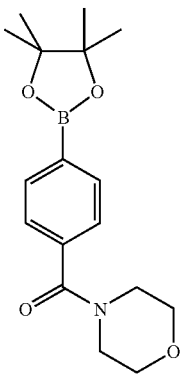 | MS (m/z): 554 (M + 1). |
| 25b | 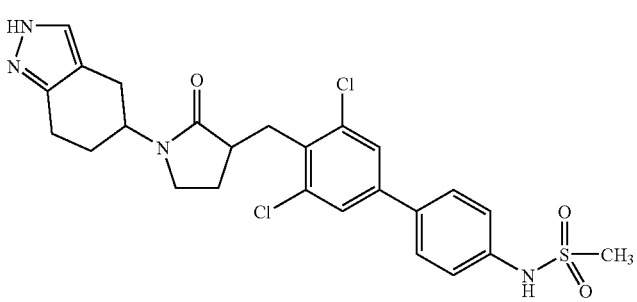<br>3-[3,5-Dichloro-4'-(N-methanesulfonamide)-biphenyl-4-ylmethyl]-1-(4,5,6,7-tetrahydro-2H-indazol-5-yl)-pyrrolidin-2-one | 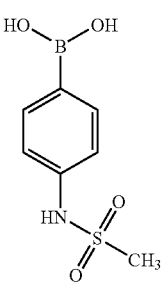 | MS (m/z): 534 (M + 1). |

EXAMPLE 26

3-(3,5-Dichloro-4'-carboxyl-biphenyl-4-ylmethyl)-1-(4,5,6,7-tetrahydro-2H-indazol-5-yl)-pyrrolidin-2-one

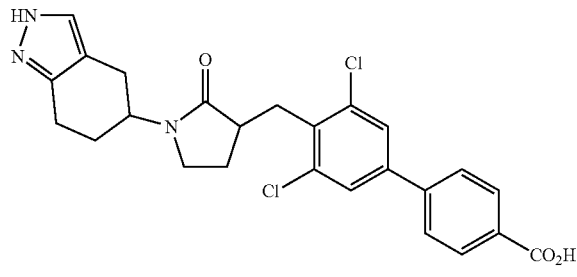

Combine trifluoro-methanesulfonic acid 3-(3,5-Dichloro-4'-carboxymethyl-biphenyl-4-ylmethyl)-1-(4,5,6,7-tetrahydro-2H-indazol-5-yl)-pyrrolidin-2-one (Preparation 34) (0.75 g, 1.18 mmol), lithium hydroxide (0.49 g, 11.8 mmol) in dioxane (15 mL) and water (5 ml) and stir at room temperature for 17 hour under nitrogen atmosphere. Neutralize to pH 7.0 with 1 N HCl, evaporate to a solid, dilute with water extract with 3:1 $CHCl_3$/Isopropyl alcohol (4×75 mL). Dry (sodium sulfate) the combined organics and condense under reduced pressure. Chromatography (silica, 93:7 $CH_2Cl_2$/MeOH) yields 0.12 g as a white solid MS (m/z): 485 (M+1).

EXAMPLE 27

3-[3,5-Dichloro-4'-(1,1-dioxo-1l6-thiomorpholin-4-yl-1-carbonyl)-biphenyl-4-ylmethyl]-1-(4,5,6,7-tetrahydro-2H-indazol-5-yl)-pyrrolidin-2-one

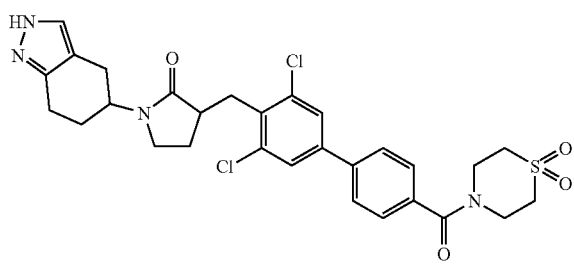

Combine 3-(3,5-Dichloro-4'-carboxyl-biphenyl-4-ylmethyl)-1-(4,5,6,7-tetrahydro-2H-indazol-5-yl)-pyrrolidin-2-one (0.057 g, 0.117 mmol), EDCI (0.029 g, 0.153 mmol), thiomorpholine dioxide (0.029 g, 0.153 mmol) in DMF (2.0 mL) and stir at room temperature for 17 hour under nitrogen atmosphere. Dilute with ethyl acetate and water, wash the organics layer with water, dry (sodium sulfate) and condense under reduced pressure. Chromatography (silica, 97:3 $CH_2Cl_2$/methanol) yields 0.046 g as a white solid MS (m/z): 601 (M+1).

Scheme T

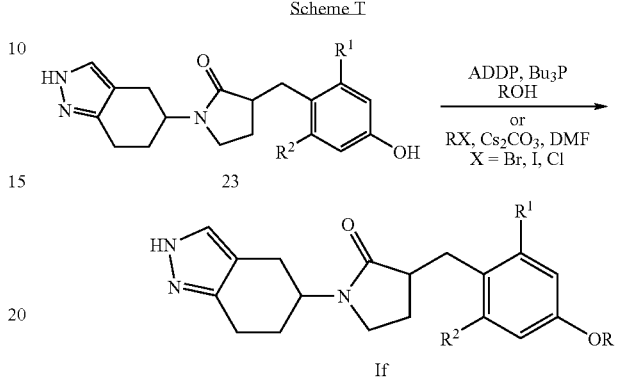

In Scheme T, Phenol 23 is alkylated to afford If under Mitsunobu condition using corresponding alcohol in presence of ADDP and $Bu_3P$. If can also be prepared by direction alkylation of phenol 23 with alkyl halides in presence of $Cs_2CO_3$ in DMF.

EXAMPLE 28

3-(2,6-Dichloro-4-isopropoxy-benzyl)-1-(4,5,6,7-tetrahydro-2H-indazol-5-yl)-pyrrolidin-2-one Hydrochloride

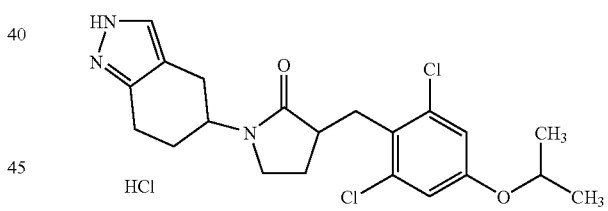

Combine 3-(2,6-Dichloro-4-hydroxy-benzyl)-1-(4,5,6,7-tetrahydro-2H-indazol-5-yl)-pyrrolidin-2-one (1.0 g, 2.26 mmol) (Preparation 32), isopropyl alcohol (1.0 mL, 13.1 mmol), ADDP (0.994 g, 3.9 mmol) in THF (40 mL) and DMF (15 mL) and add $nBu_3P$ stir at 60° C. for 17 h under nitrogen atmosphere. Add an additional 0.75 equivalents of each reagent and stir an additional 24 h at 60° C. Cool to room temperature and evaporate to a solid. Initial purification using SCX Mega-bond Elut (Varian, 0.79 meq/g) eluting the non-basic components with 9:1 methylene chloride/methanol followed by elution of product using 9:1 methylene chloride/7.0 $NH_3$/MeOH. Chromatography (silica, 95:5:$CHCl_3$/EtOH/$NH_3$) yields 0.700 g as a white solid. Dissolve the free-base in diethyl ether/methylene chloride and treat with 1.2 equivalents of HCl (1.0 M in ether) and evaporate to a powder MS (m/z): 422 (M+1).

TABLE 6

Prepare the Examples in Table 6 essentially as described in Example 28 with substitution for isopropyl alcohol by the reagent indicated in the column labeled Synthetic Reagent.

| Example | Structure and Chemical name | Synthetic Reagent | Physical data |
|---|---|---|---|
| 29 | 3-[2,6-Dichloro-4-(4-fluoro-benzyloxy)-benzyl]-1-(4,5,6,7-tetrahydro-2H-indazol-5-yl)-pyrrolidin-2-one | 4-fluorobenzyl alcohol | MS (m/z): 490 (M + 1) |
| 30 | 3-[2,6-Dichloro-4-(tetrahydro-pyran-4-yloxy)-benzyl]-1-(4,5,6,7-tetrahydro-2H-indazol-5-yl)-pyrrolidin-2-one | tetrahydro-4-pyranol | MS (m/z): 465 (M + 1) |

Note-
Chromatography (C18 Xterra MS (19 × 100 5 um), 55:45 MeCN/NH$_4$CO$_3$ (10 mM, pH 10)

EXAMPLE 31

3-(2,6-Dichloro-4-isopropoxy-benzyl)-1-(4,5,6,7-tetrahydro-2H-indazol-5-yl)-pyrrolidin-2-one

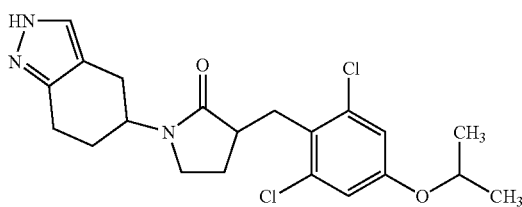

Combine 3-(2,6-Dichloro-4-hydroxy-benzyl)-1-(4,5,6,7-tetrahydro-2H-indazol-5-yl)-pyrrolidin-2-one from Preparation 35 (0.29 g, 0.765 mmol), isopropyl alcohol (0.58 mL, 7.6 mmol), ADDP (0.29 g, 1.14 mmol) in THF (12 mL) and add nBu$_3$P stir at 60° C. for 17 h under nitrogen atmosphere. Add an additional 0.75 equivalents of each reagent and stir an additional 24 h at 60° C. Cool to room temperature and evaporate to a solid. Initial purification using SCX Megabond Elut (Varian, 0.79 meq/g) eluting the non-basic components with 9:1 methylene chloride/MeOH followed by elution of product using 9:1 methylene chloride/7.0 NH$_3$/MeOH. Chromatography (silica, 95:5:CHCl$_3$/EtOH/NH$_3$) yields 0.065 g as a white solid. MS (m/z): 422 (M+1).

EXAMPLE 32

(±) 2-{3,5-Dichloro-4-[2-oxo-1-(4,5,6,7-tetrahydro-2H-indazol-5-yl)-pyrrolidin-3-ylmethyl]-phenoxy}-acetamide

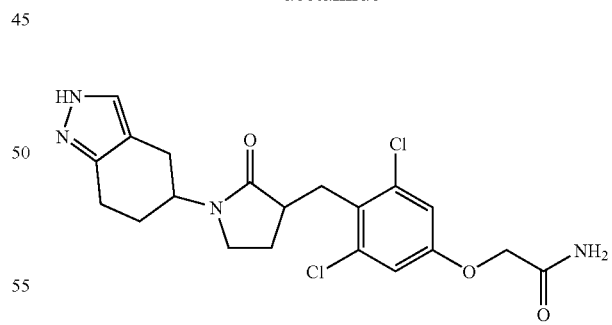

Combine 3-(2,6-Dichloro-4-hydroxy-benzyl)-1-(4,5,6,7-tetrahydro-2H-indazol-5-yl)-pyrrolidin-2-one, (Preparation 32)(0.25 g, 0.66 mmol), cesium carbonate (0.322 g, 0.99 mmol), bromoacetamide (0.136 g, 0.99 mmol) in DMF (5.0 mL) and stir at room temperature for 17 hours under nitrogen atmosphere. Cool to room temperature and evaporate to a solid. Initial purification using SCX Mega-bond Elut (Varian, 0.79 meq/g) eluting the non-basic components with 9:1 methylene chloride/MeOH followed by elution of product using 9:1 methylene chloride/7.0 NH$_3$/MeOH. Chromatography

EXAMPLE 33

(±)3-(2-Chloro-4-hydroxy-benzyl)-1-(4,5,6,7-tetrahydro-2H-indazol-5-yl)-pyrrolidin-2-one

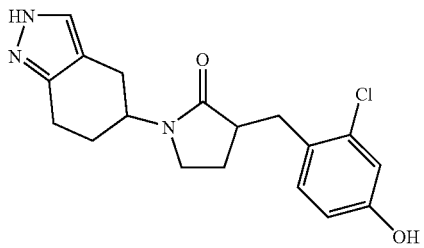

Cool a solution of 3-(2-Chloro-4-methoxy-benzyl)-1-(4,5,6,7-tetrahydro-2H-indazol-5-yl)-pyrrolidin-2-one (3.0 g, 8.3 mmol) in dichloroethane (100 mL) to −78° C. Treat the solution with 1.0M Boron tribromide in CH$_2$Cl$_2$ (46 mL, 46 mmol) and allow the reaction to warm to room temp and stir for 4 hr. Then, cool the reaction to 0° C. and quench with water. Extract the organic with CHCl$_3$, wash with brine, dry over MgSO$_4$, filter, and remove the solvent. Purify the crude by silica gel column chromatography using 10% EtOH in CHCl$_3$ to elute the pure product. Remove the solvent to afford 2.24 g (78%) of product. MS (m/e): 364 (M+1).

EXAMPLE 34

3-(2-Chloro-4-isopropoxy-benzyl)-1-(4,5,6,7-tetrahydro-2H-indazol-5-yl)-pyrrolidin-2-one

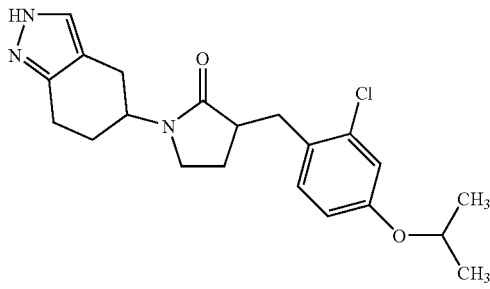

Treat a solution of 3-(2-chloro-4-hydroxy-benzyl)-1-(4,5,6,7-tetrahydro-2H-indazol-5-yl)-pyrrolidin-2-one (0.2 g, 0.58 mmol) and 2-Iodopropane (0.06 mL, 0.64 mmol) in DMF (4 mL) with potassium carbonate (0.1 g, 0.7 mmol) and stir reaction overnight at room temp. Quench the reaction with 1N HCl and extract with EtOAc. Wash the organic with brine, dry over MgSO$_4$, filter, and remove the solvent. Purify the crude by silica gel column chromatography and remove the solvent to afford 0.11 g (48%) of product. MS (m/e): 388 (M+1).

EXAMPLE 35

(3R,5S)-(−)-3-(4-Benzyloxy-2,6-dichloro-benzyl)-1-(4,5,6,7-tetrahydro-2H-indazol-5-yl)-pyrrolidin-2-one

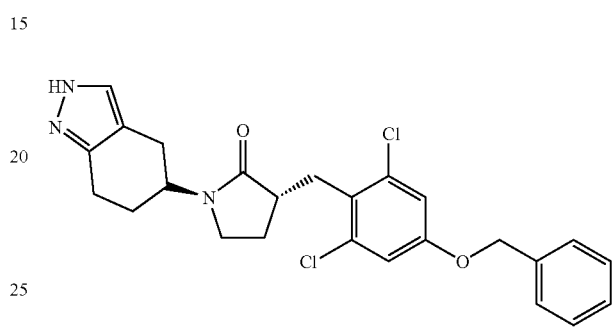

Suspend Preparation 40 (4,5,6,7-Tetrahydro-2H-indalzol-5-ylamine) (3.01 g, 21.9 mmol in DCE (150 mL) and treat with enough IPA (6.0 mL) to form a solution. Dissolve (R)-4-((R)-4-Benzyl-2-oxo-oxazolidin-3-yl)-3-(4-benzyloxy-2,6-dichloro-benzyl)-4-oxo-butyraldehyde (Preparation 38) (11.5 g, 21.9 mmol) in DCE (40 mL) and add to the amine solution at room temperature under nitrogen atmosphere. Stir for 17 h, add Na(OAc)$_3$BH (13.7 g, 76 mmol) and stir at room temperature for 2 h followed by diisopropylethylamine (DIPEA) (16 mL, 93 mmol) and stir at room temperature for an additional 1 h.

When the amine is no longer detected, remove the DCE by evaporation, replace with 300 mL of ethyl acetate, quench the resulting mixture with water, and separate. Wash the organics with several portions of NaHCO$_3$ (sat), dry over sodium sulfate and evaporate to a foam. Initial purification over 50 g Mega-bond Elut first using 95:5 CH$_2$Cl$_2$/methanol to elute the non-basic components of the reaction mixture followed by product using 95:5 CH$_2$Cl$_2$/7.0 M NH$_3$/methanol. Chromatography (silica, 97:3 CH$_2$Cl$_2$/methanol/NH$_3$) provides 5.32 g (52%) as an amorphous solid. MS (m/z): 472 (M+2), $[\alpha]^{25}_D$ −25 (c 1, methanol).

EXAMPLE 36

(3R-5S)-(−)-3-(3,5-Dichloro-4'-fluoro-biphenyl-4-ylmethyl)-1-(4,5,6,7-tetrahydro-2H-indazol-5-yl)-pyrrolidin-2-one This compound is synonomous with and identifiable as (3R)-3-[3,5-Dichloro-4'-fluoro[1,1'-biphenyl]-4-yl)methyl]-1-[(5S)-4,5,6,7-tetrahydro-1H-indazol-5-yl]-2-pyrrolidinone (C18 Xterra MS, 19×100 5 um, 55:45 MeCN/NH$_4$CO$_3$, 10 mM, pH 10) yields 0.095 g of a white solid. MS (m/z): 437 (M+1).

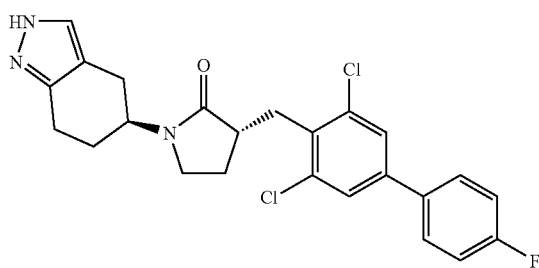

Dissolve (3R,5S)-Trifluoro-methanesulfonic acid 3,5-dichloro-4-[2-oxo-1-(2-trifluoromethanesulfonyl-4,5,6,7-tetrahydro-2H-indazol-5-yl)-pyrrolidin-3-ylmethyl]-phenyl ester (Preparation 43) (7.3 g, 11.3 mmol) in DME (90 mL) and de-gas with a stream of nitrogen for 5.0 minutes. Add 4-fluorophenyl boronic acid (3.17 g, 22.6 mmol), followed by 2.0 M sodium carbonate (28.2 mL, 56 mmol) and continue de-gas. Add Pd(PPh$_3$)$_4$ (0.65 g, 0.565 mmol) and heat to 80° C. for 17 hours. Hydrolysis of N1/N2-triflate regioisomers is accomplished by cooling to room temperature, adding LiOH (10 equivalents) and stirring for 30 minutes. Dilute with ethyl acetate and water, separate and save both layers. Adjust the pH of the aqueous layer pH 9 with NaHCO$_3$, and back extract with three portions of ethyl acetate. Combine the organic layers, dry over sodium sulfate and evaporate to 7.4 g. Purification over SCX (mega-bond elut, 95:5 CH$_2$Cl$_2$/MeOH then 95:5 CH$_2$Cl$_2$/MeOH/NH$_3$) yields 4.93 g of basic component. Chromatography (silica 95:5 CH$_2$Cl$_2$/MeOH/1% NH$_3$) yields 3.86 g (74%) of an amorphorous foam. MS (m/z): 460 (M+1). Chiral HPLC analysis (Chiralpak AD-H, 0.46×15 cm, 60:40:0.23A ethanol/heptane/DMEA, flow=0.6 ml/min, UV: 250 nm) 9.8 minutes (>99% ee). [α]$^{23}_D$ −20 (c 1, DMSO)

TABLE 7

Prepare the Examples in Table 7 essentially as described in Example 36 substituting the reagent indicated in the column labeled Synthetic Reagent.

| Example | Structure and Chemical name | Synthetic Reagent | Physical data |
|---|---|---|---|
| 37 | (3R,5S)-3-[2,6-Dichloro-4-(1-methyl-1H-pyrazol-4-yl)-benzyl]-1-(4,5,6,7-tetrahydro-2H-indazol-5-yl)-pyrrolidin-2-one | | MS (m/z): 446 (M + 1) |
| 38 | (3R,5S)-3-(3,5-Dichloro-4'-trifluoromethoxy-biphenyl-4-ylmethyl)-1-(4,5,6,7-tetrahydro-2H-indazol-5-yl)-pyrrolidin-2-one | | MS (m/z): 524 (M + 1) |

TABLE 7-continued

Prepare the Examples in Table 7 essentially as described in Example 36 substituting the reagent indicated in the column labeled Synthetic Reagent.

| Example | Structure and Chemical name | Synthetic Reagent | Physical data |
|---|---|---|---|
| 39 | 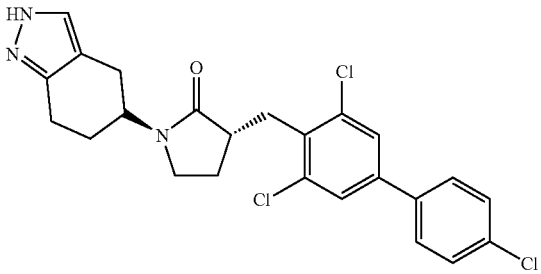<br>(3R,5S)-1-(4,5,6,7-Tetrahydro-2H-indazol-5-yl)-3-(3,5,4'-trichloro-biphenyl-4-ylmethyl)-pyrrolidin-2-one | 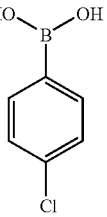 | MS (m/z): 475 (M + 1) |
| 40 | 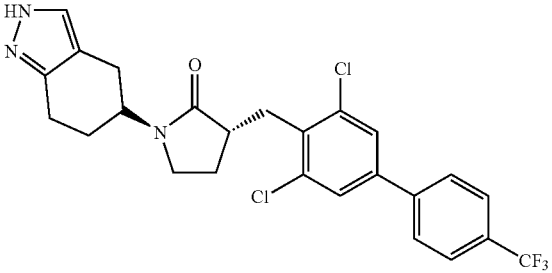<br>(3R,5S)-3-(3,5-Dichloro-4'-trifluoromethyl-biphenyl-4-ylmethyl)-1-(4,5,6,7-tetrahydro-2H-indazol-5-yl)-pyrrolidin-2-one | 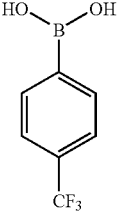 | MS (m/z): 510 (M + 2) |
| 41 | 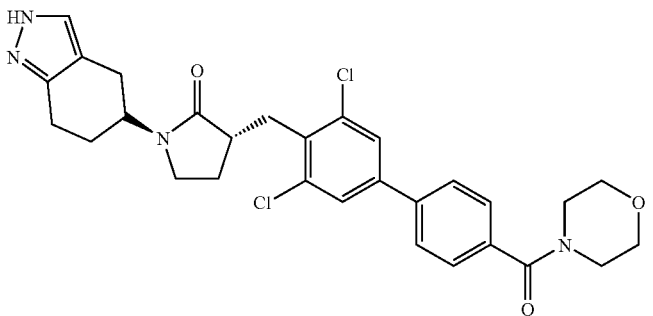<br>(3R,5S)-3-[3,5-Dichloro-4'-(morpholine-4-carbonyl)-biphenyl-4-ylmethyl]-1-(4,5,6,7-tetrahydro-2H-indazol-5-yl)-pyrrolidin-2-one | 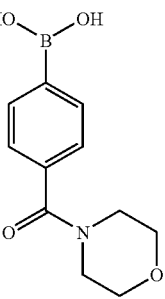 | MS (m/z): 555 (M + 2) |
| 42 | 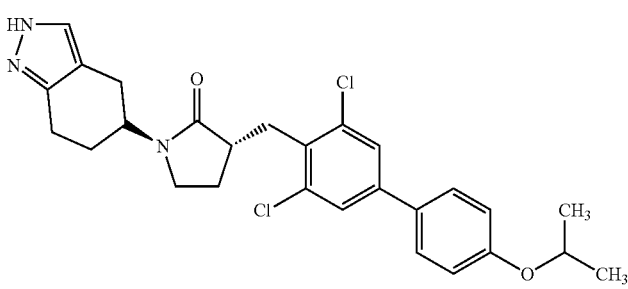<br>(3R,5S)-3-(3,5-Dichloro-4'-isopropoxy-biphenyl-4-ylmethyl)-1-(4,5,6,7-tetrahydro-2H-indazol-5-yl)-pyrrolidin-2-one | 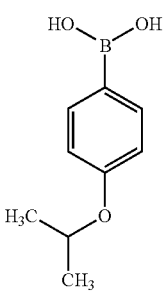 | MS (m/z): 500 (M + 2) |

TABLE 7-continued

Prepare the Examples in Table 7 essentially as described in Example 36 substituting the reagent indicated in the column labeled Synthetic Reagent.

| Example | Structure and Chemical name | Synthetic Reagent | Physical data |
|---|---|---|---|
| 43 | 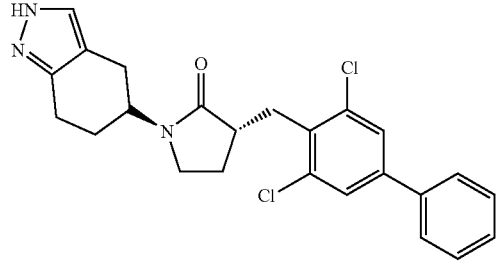<br>(3R,5S)-3-(3,5-Dichloro-biphenyl-4-ylmethyl)-1-(4,5,6,7-tetrahydro-2H-indazol-5-yl)-pyrrolidin-2-one | 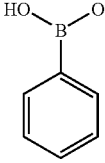 | MS (m/z): 442 (M + 2) |
| 44 | 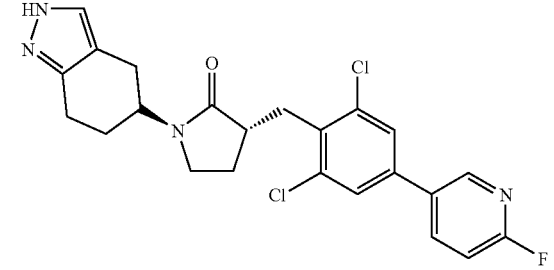<br>(3R,5S)-3-[2,6-Dichloro-4-(6-fluoro-pyridin-3-yl)-benzyl]-1-(4,5,6,7-tetrahydro-2H-indazol-5-yl)-pyrrolidin-2-one | 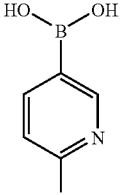 | MS (m/z): 461 (M + 2) |
| 45 | 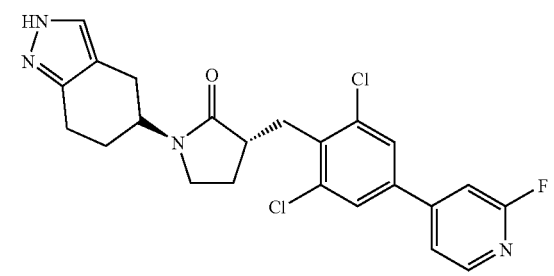<br>(3R,5S)-3-[2,6-Dichloro-4-(2-fluoro-pyridin-4-yl)-benzyl]-1-(4,5,6,7-tetrahydro-2H-indazol-5-yl)-pyrrolidin-2-one | 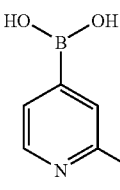 | MS (m/z): 461 (M + 2) |

TABLE 7-continued

Prepare the Examples in Table 7 essentially as described in Example 36 substituting the reagent indicated in the column labeled Synthetic Reagent.

| Example | Structure and Chemical name | Synthetic Reagent | Physical data |
|---|---|---|---|
| 46 | 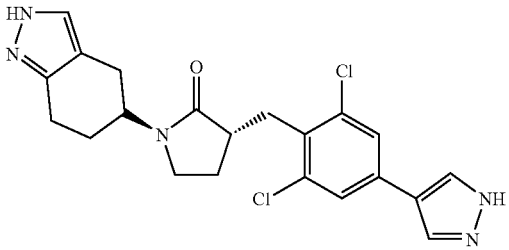<br>(3R,5S)-3-[2,6-Dichloro-4-(1H-pyrazol-4-yl)-benzyl]-1-(4,5,6,7-tetrahydro-2H-indazol-5-yl)-pyrrolidin-2-one | 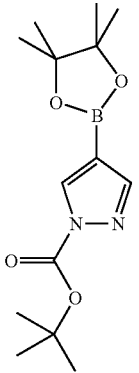 | MS (m/z): 432 (M + 2) |
| 47 | 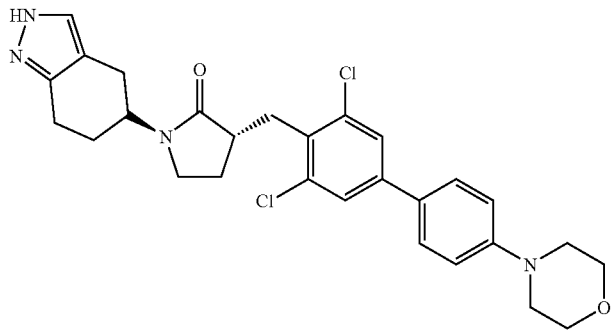<br>(3R,5S)-3-(3,5-Dichloro-4'-morpholin-4-yl-biphenyl-4-ylmethyl)-1-(4,5,6,7-tetrahydro-2H-indazol-5-yl)-pyrrolidin-2-one | 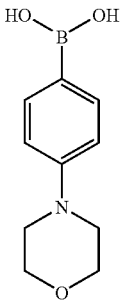 | MS (m/z): 526 (M + 1) |
| 48 | 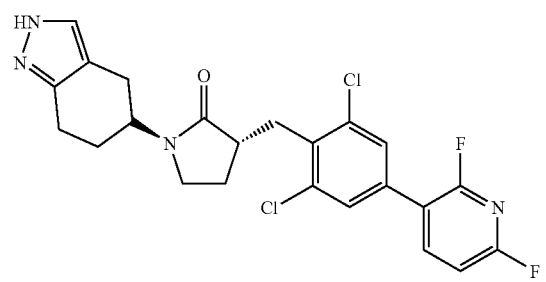<br>(3R,5S)-3-[2,6-Dichloro-4-(2,6-difluoro-pyridin-3-yl)-benzyl]-1-(4,5,6,7-tetrahydro-2H-indazol-5-yl)-pyrrolidin-2-one | 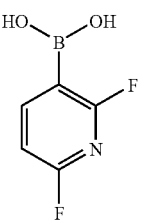 | MS (m/z): 579 (M − 1) |

TABLE 7-continued

Prepare the Examples in Table 7 essentially as described in Example 36
substituting the reagent indicated in the column labeled Synthetic Reagent.

| Example | Structure and Chemical name | Synthetic Reagent | Physical data |
|---|---|---|---|
| 49 | 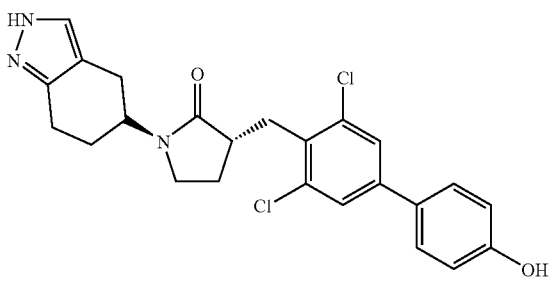<br>(3R,5S)-3-(3,5-Dichloro-4'-hydroxy-biphenyl-4-ylmethyl)-1-(4,5,6,7-tetrahydro-2H-indazol-5-yl)-pyrrolidin-2-one | 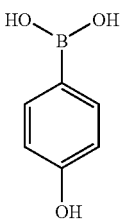 | MS (m/z): 456 (M + 1) |
| 50 | 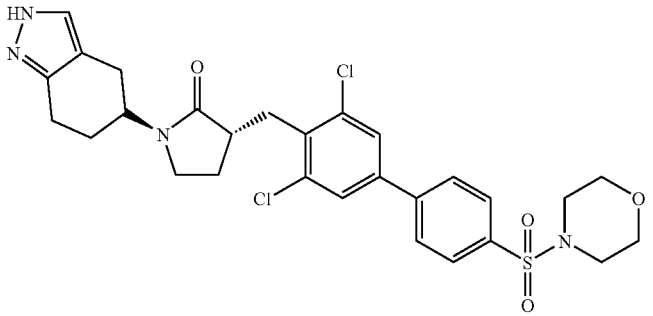<br>(3R,5S)-3-[3,5-Dichloro-4'-(morpholine-4-sulfonyl)-biphenyl-4-ylmethyl]-1-(4,5,6,7-tetrahydro-2H-indazol-5-yl)-pyrrolidin-2-one | 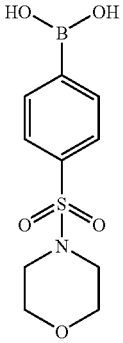 | MS (m/z): 590 (M + 1) |
| 51 | 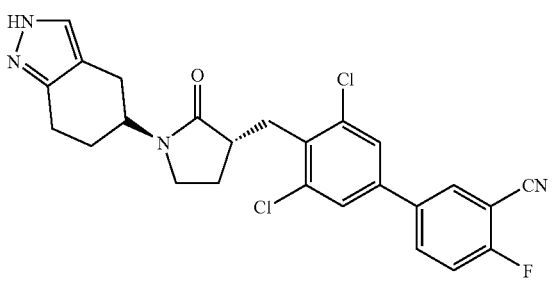<br>(3R,5S)-3-(3,5-Dichloro-4'-fluoro-3'-cyano biphenyl-4-ylmethyl)-1-(4,5,6,7-tetrahydro-2H-indazol-5-yl)-pyrrolidin-2-one | 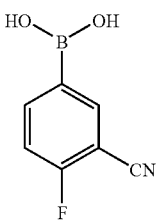 | MS (m/z): 484 (M − 1) |

TABLE 7-continued

Prepare the Examples in Table 7 essentially as described in Example 36 substituting the reagent indicated in the column labeled Synthetic Reagent.

| Example | Structure and Chemical name | Synthetic Reagent | Physical data |
|---|---|---|---|
| 52 | 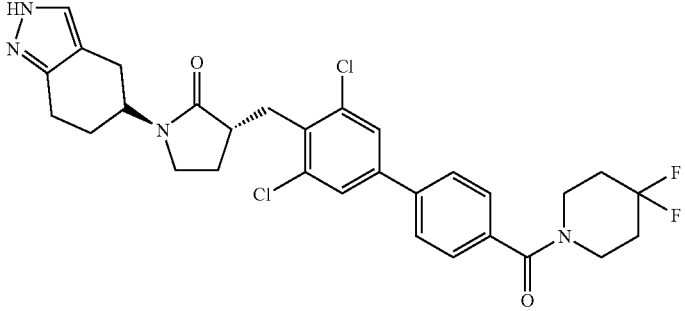<br>(3R,5S)-3-[3,5-Dichloro-4'-(4,4-difluoro-piperidine-1-carbonyl)-biphenyl-4-ylmethyl]-1-(4,5,6,7-tetrahydro-2H-indazol-5-yl)-pyrrolidin-2-one | 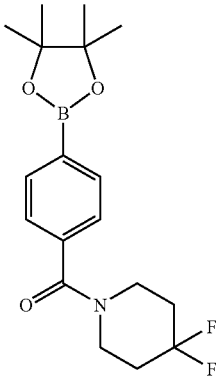 | MS (m/z): 589 (M + 1) |
| 53 | 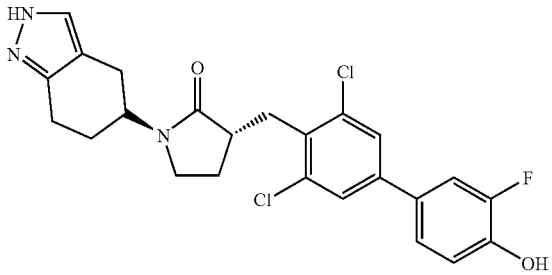<br>(3R,5S)-3-(3,5-Dichloro-3'-fluoro-4'-hydroxy-biphenyl-4-ylmethyl)-1-(4,5,6,7-tetrahydro-2H-indazol-5-yl)-pyrrolidin-2-one | 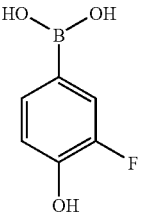 | MS (m/z): 475 (M + 1) |
| 54 | 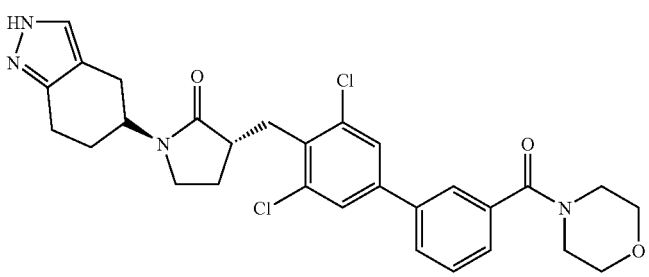<br>(3R,5S)-3-[3,5-Dichloro-3'-(morpholine-4-carbonyl)-biphenyl-4-ylmethyl]-1-(4,5,6,7-tetrahydro-2H-indazol-5-yl)-pyrrolidin-2-one | 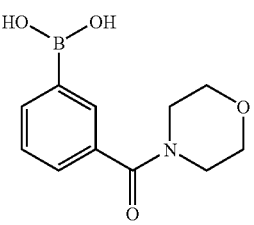 | MS (m/z): 554 (M + 1) |
| 55 | 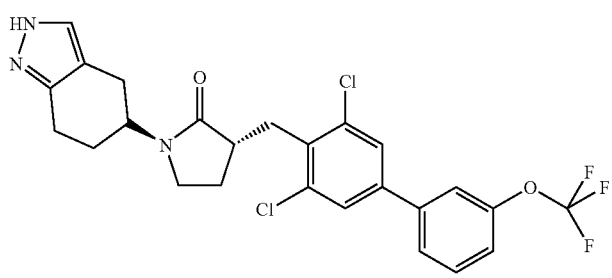<br>(3R,5S)-3-(3,5-Dichloro-3'-trifluoromethoxy-biphenyl-4-ylmethyl)-1-(4,5,6,7-tetrahydro-2H-indazol-5-yl)-pyrrolidin-2-one | 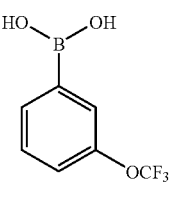 | MS (m/z): 525 (M + 1) |

TABLE 7-continued

Prepare the Examples in Table 7 essentially as described in Example 36
substituting the reagent indicated in the column labeled Synthetic Reagent.

| Example | Structure and Chemical name | Synthetic Reagent | Physical data |
|---|---|---|---|
| 56 | 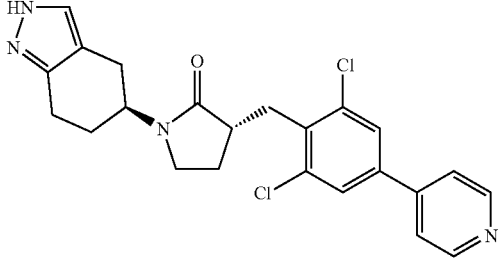<br>(3R,5S)-3-[3,5-Dichloro-4-pyridyl-4-ylmethyl]-1-(4,5,6,7-tetrahydro-2H-indazol-5-yl)-pyrrolidin-2-one | 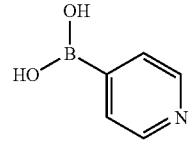 | MS (m/z): 441(M+). |
| 57 | 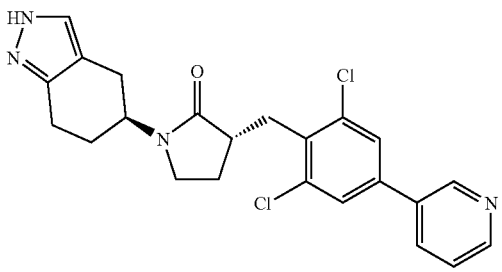<br>(3R,5S)-3-[3,5-Dichloro-3-pyridyl-4-ylmethyl]-1-(4,5,6,7-tetrahydro-2H-indazol-5-yl)-pyrrolidin-2-one | 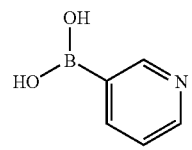 | MS (m/z): 441(M+) |
| *58 | 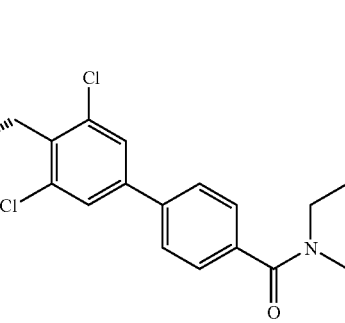<br>(3R,5S)-3-[3,5-Dichloro-4'-(4-trifluoromethyl-piperidine-1-carbonyl)-biphenyl-4-ylmethyl]-1-(4,5,6,7-tetrahydro-2H-indazol-5-yl)-pyrrolidin-2-one | 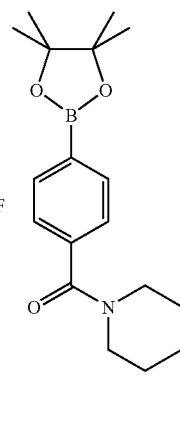 | MS (m/z): 619(M+) |

TABLE 7-continued

Prepare the Examples in Table 7 essentially as described in Example 36 substituting the reagent indicated in the column labeled Synthetic Reagent.

| Example | Structure and Chemical name | Synthetic Reagent | Physical data |
|---|---|---|---|
| *59 | 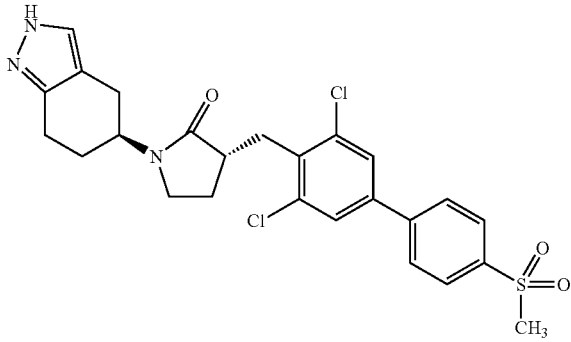<br>(3R,5S)-3-[3,5-Dichloro-4'-methanesulfonyl-biphenyl-4-ylmethyl]-1-(4,5,6,7-tetrahydro-2H-indazol-5-yl)-pyrrolidin-2-one | 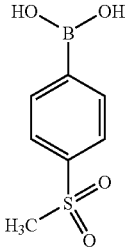 | MS (m/z): 518(M+) |
| *60 | 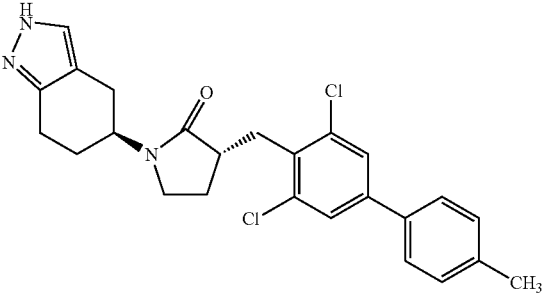<br>(3R,5S)-3-[3,5-Dichloro-4'-methyl-biphenyl-4-ylmethyl]-1-(4,5,6,7-tetrahydro-2H-indazol-5-yl)-pyrrolidin-2-one | 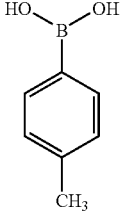 | MS (m/z): 454(M+) |
| *61 | 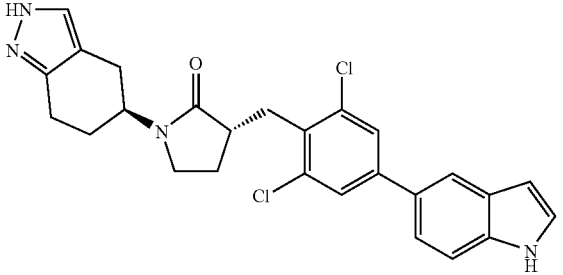<br>(3R,5S)-3-[2,6-Dichloro-4-(1H-indol-5-yl)-benzyl]-1-(4,5,6,7-tetrahydro-2H-indazol-5-yl)-pyrrolidin-2-one | 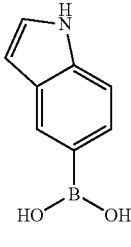 | MS (m/z): 479(M+) |

TABLE 7-continued

Prepare the Examples in Table 7 essentially as described in Example 36 substituting the reagent indicated in the column labeled Synthetic Reagent.

| Example | Structure and Chemical name | Synthetic Reagent | Physical data |
|---|---|---|---|
| 62 | 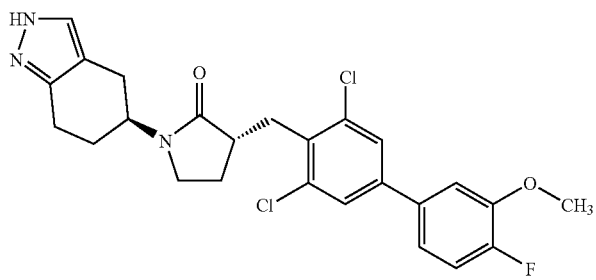<br>(3R,5S)-3-(3,5-Dichloro-4'-fluoro-3'-methoxy-biphenyl-4-ylmethyl)-1-(4,5,6,7-tetrahydro-2H-indazol-5-yl)-pyrrolidin-2-one | 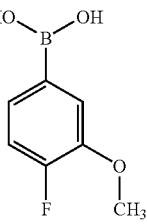 | MS (m/z): 488(M+) |

*Indicates substitution of tetrahydrofuran as solvent over dimethyl glycol.

EXAMPLE 63

(R)-3-(6-Chloro-2,3-difluoro-4-trifluoromethyl-benzyl)-1-(4,5,6,7-tetrahydro-2H-indazol-5-yl)-pyrrolidin-2-one

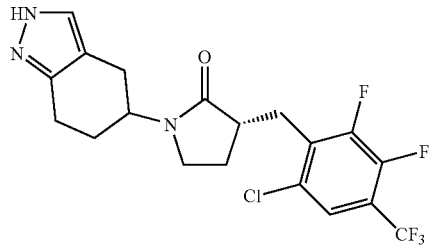

Combine a solution of (R)-4-((R)-4-Benzyl-2-oxo-oxazolidin-3-yl)-3-(6-chloro-2,3-difluoro-4-trifluoromethyl-benzyl)-4-oxo-butyraldehyde (Preparation 46) (0.30 g, 0.6 mmol) and 4,5,6,7-Tetrahydro-2H-indazol-5-ylamine (Preparation 40) (88 mg, 0.64 mmol) in CH$_2$Cl$_2$ (15 mL) and MeOH (1 mL) and treat the solution with HOAc (0.03 mL, 0.6 mmol). Stir the reaction for 30 min at room temperature, treat the reaction with sodium triacetoxyborohydride (0.39 g, 1.8 mmol), and stir overnight at room temperature. Quench the reaction with water and extract with EtOAc. Wash the organic with brine, dry over MgSO$_4$, filter, and remove the solvent. Purify the crude by SCX resin exchange column using 2M ammonia in MeOH to elute the pure product. Remove the solvent to afford 0.12 g (46%) of the title compound. MS (m/e): 434 (M+1).

EXAMPLE 64

(3R,5R)-3-(4-Benzyloxy-2,6-dichloro-benzyl)-1-(4,5,6,7-tetrahydro-2H-indazol-5-yl)-pyrrolidin-2-one

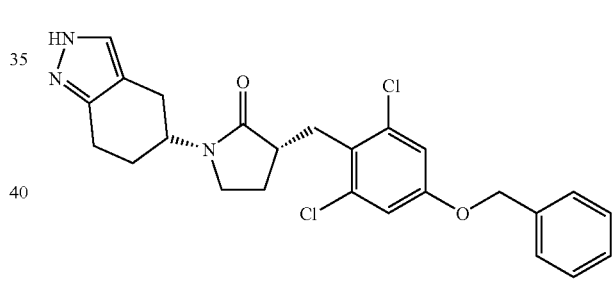

Suspend Preparation 41 (4,5,6,7-Tetrahydro-2H-indalzol-5-ylamine) (0.467 g, 3.4 mmol in THF (35 mL). Add HOAc (0.38 mL, 6.8 mmol) and (R)-4-((R)-4-Benzyl-2-oxo-oxazolidin-3-yl)-3-(4-benzyloxy-2,6-dichloro-benzyl)-4-oxo-butyraldehyde (Preparation 38) (1.38 g, 2.4 mmol) at room temperature under nitrogen atmosphere and stir for 17 h. Add Na(OAc)$_3$BH (2.076 g, 9.8 mmol) and stir at room temperature for 4 h. Quench with water, dilute with ethyl acetate, separate, the organics washed with several portions of NaHCO$_3$ (sat), brine, dried over sodium sulfate and evaporated to a foam. Purification (SCX Mega-bond Elut first using 95:5 CH$_2$Cl$_2$/MeOH to elute the non-basic components of the reaction mixture followed by product using 95:5 CH$_2$Cl$_2$/7.0 M NH$_3$/MeOH), provides 0.977 g (61%) as an amorphous solid. MS (m/z): 472 (M+2).

EXAMPLE 65

(3R,5R)-(+)-3-(3,5-Dichloro-4'-fluoro-biphenyl-4-ylmethyl)-1-(4,5,6,7-tetrahydro-2H-indazol-5-yl)-pyrrolidin-2-one

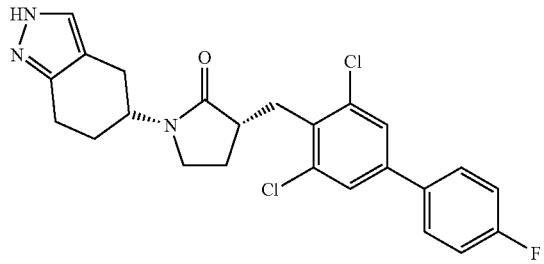

Dissolve (3R,5R)-Trifluoro-methanesulfonic acid 3,5-dichloro-4-[2-oxo-1-(2-trifluoromethanesulfonyl-4,5,6,7-tetrahydro-2H-indazol-5-yl)-pyrrolidin-3-ylmethyl]-phenyl ester (Preparation 48) (0.34, 0.527 mmol) in DME (5.0 mL) and de-gas with a stream of nitrogen for 5.0 minutes. Add 4-fluorophenyl boronic acid (0.22 g, 1.58 mmol), followed by 2.0 M sodium carbonate (1.8 mL, 3.7 mmol) and continue de-gas. Add Pd(PPh$_3$)$_4$ (0.061 g, 0.052 mmol) and heat to 80° C. for 17 hours. Dilute with ethyl acetate and water, separate and save both layers. The pH of the aqueous layer adjusted to ph 9 with NaHCO$_3$, and back extract with three portions of ethyl acetate. The organic layers are combined, dry over sodium sulfate and evaporate. Purification over SCX (megabond elut, 95:5 CH$_2$Cl$_2$/Methanol then 95:5 CH$_2$Cl$_2$/Methanol/NH$_3$) yields basic components. Chromatography (silica 95:5 CH$_2$Cl$_2$/Methanol/1% NH$_3$) yields 0.21 (88%) of the title compound as an amorphorous foam. MS (m/z): 460 (M+2). Chiral HPLC analysis (Chiralpak AD-H, 0.46×15 cm, 60:40:0.2 3A ethanol/heptane/DMEA, flow=0.6 ml/min, UV: 250 nm) 12.2 minutes (97.3% ee). [α]$^{23}$D 20 (c 1, DMSO).

Scheme U

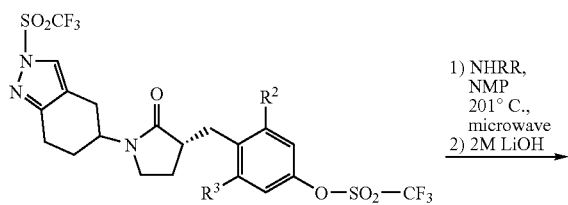

24

1) NHRR, NMP 201° C., microwave
2) 2M LiOH

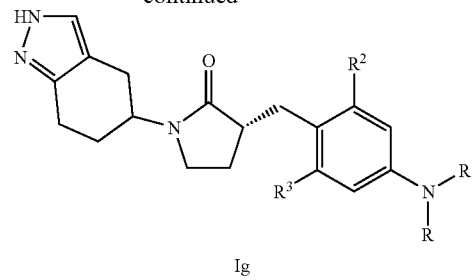

Ig

In Scheme U, compound Ig is formed by treating compound 24 with various amines (NHRR) under microwave at 201° C. followed by removal of triflate group from pyrazole nitrogen using 2M LiOH.

EXAMPLE 66

(3R,5S)-3-[2,6-Dichloro-4-(4-phenyl-piperidin-1-yl)-benzyl]-1-(4,5,6,7-tetrahydro-2H-indazol-5-yl)-pyrrolidin-2-one

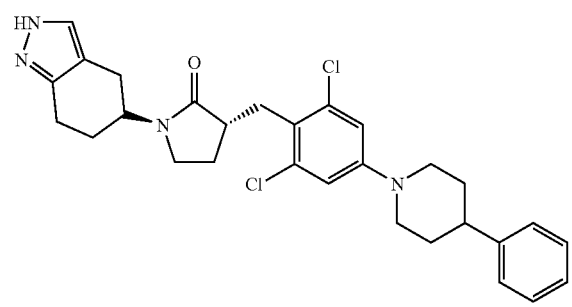

Heat a solution of (3R,5S)-Trifluoro-methanesulfonic acid 3,5-dichloro-4-[2-oxo-1-(2-trifluoromethanesulfonyl-4,5,6,7-tetrahydro-2H-indazol-5-yl)-pyrrolidin-3-ylmethyl]-phenyl ester (Preparation 43) (0.10 g, 0.155 mmol) and 4-phenylpiperidine (0.063 g, 0.39 mmol) in 1-methyl-2-pyrrolidine (2.5 mL) to 201° C. for 1.5 hours in a microwave reactor. Cool the reaction to room temperature and treat with 2M LiOH (1 mL) and stir for 16 hours at room temperature. Dilute the reaction with ethyl acetate and wash with water. Dry the organic layer (Na$_2$SO$_4$) and remove the solvent in vacuo to afford crude product. Purify with a 0 to 5% methanol in CH$_2$Cl$_2$ gradient to afford 0.039 g (48%) of the title compound. MS (m/z): 523 (M+).

TABLE 8

Prepare the Examples in Table 8 essentially as described in Example 66 substituting for 4-phenylpiperidine with the reagent indicated in the column labeled Synthetic Reagent.

| Example | Chemical Name | Synthetic Reagent | Physical Data |
|---|---|---|---|
| 67 | (3R,5S)-3-[(2,6-dichloro-4-morpholin-4-yl-benzyl)-1-(4,5,6,7-tetrahydro-2H-indazol-5-yl)-pyrrolidin-2-one | morpholine | MS (m/z) 449 (M+) |
| 68 | (3R,5S)-3-(2,6-dichloro-4-piperidin-1-yl-benzyl)-1-(4,5,6,7-tetrahydro-2H-indazol-5-yl)-pyrrolidin-2-one | piperidine | MS (m/z) 447 (M+) |
| 69 | (3R,5S)-3-[4-(4-acetyl-piperazin-1-yl-2,6-dichloro-benzyl]-1-(4,5,6,7-tetrahydro-2H-indazol-5-yl)-pyrrolidin-2-one | 1-acetylpiperazine | MS (m/z) 490 (M+) |

TABLE 8-continued

Prepare the Examples in Table 8 essentially as described in Example 66 substituting for 4-phenylpiperidine with the reagent indicated in the column labeled Synthetic Reagent.

| Example | Chemical Name | Synthetic Reagent | Physical Data |
|---|---|---|---|
| 70 | 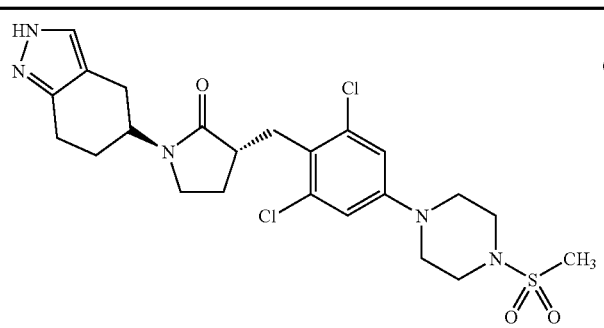<br>(3R,5S)-3-[2,6-dichloro-4-(4-methanesulfonyl-piperazin-1-yl)-benzyl]-1-(4,5,6,7-tetrahydro-2H-indazol-5-yl)-pyrrolidin-2-one | 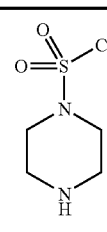 | MS (m/z) 526 (M+) |
| 71 | 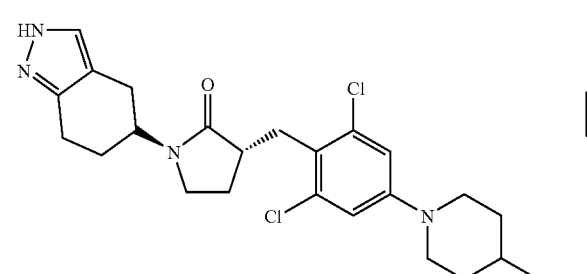<br>(3R,5S)-3-[2,6-dichloro-4-(4-hydroxy-piperidin-1-yl)-benzyl]-1-(4,5,6,7-tetrahydro-2H-indazol-5-yl)-pyrrolidin-2-one | 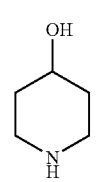 | MS (m/z) 463 (M+) |

EXAMPLE 72

(3R,5S)-3-[2,6-Dichloro-4-(4-fluoro-phenoxy)-benzyl]-1-(4,5,6,7-tetrahydro-2H-indazol-5-yl)-pyrrolidin-2-one

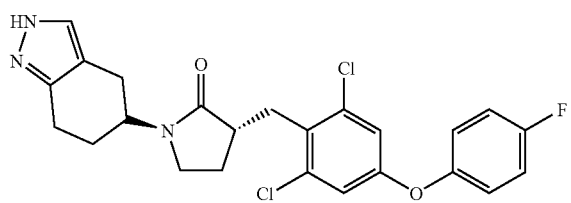

Treat a mixture of (3R,5S)-5-[3-(2,6-dichloro-4-hydroxy-benzyl)-2-oxo-pyrrolidin-1-yl]-4,5,6,7-tetrahydro-indazole-2-carboxylic acid tert-butyl ester and (3R,5S)-5-[3-(2,6-dichloro-4-hydroxy-benzyl)-2-oxo-pyrrolidin-1-yl]-4,5,6,7-tetrahydro-indazole-1-carboxylic acid tert-butyl ester (Preparation 50) (0.238 g, 0.495 mmol), 4-fluorophenyl boronic acid (0.139 g, 0.99 mmol), Et$_3$N (0.10 g, 0.99 mmol) and 4A molecular sieves (200 mg) in CH$_2$Cl$_2$ (8 mL) with copper (II) acetate (0.090 g, 0.49 mmol) and stir for 16 hours at room temperature under N$_2$. Remove the solvent in vacuo to afford crude product and purify on silica using a 0 to 100% ethyl acetate in hexanes gradient to afford 0.123 g (43%) of the N-Boc'd product (Rf=0.25, 2/1 ethyl acetate/hexanes). Dissolve in methanol (8 mL), treat with 2 M LiOH (1 mL), and stir overnight at room temperature. Dilute the reaction with ethyl acetate and wash with water. Dry the organic layer (Na$_2$SO$_4$) and remove the solvent in vacuo to afford crude product that is recrystallized from methanol/hexanes to afford 0.034 g (14%) of the title compound. MS (m/z): 474 (M+).

Scheme V

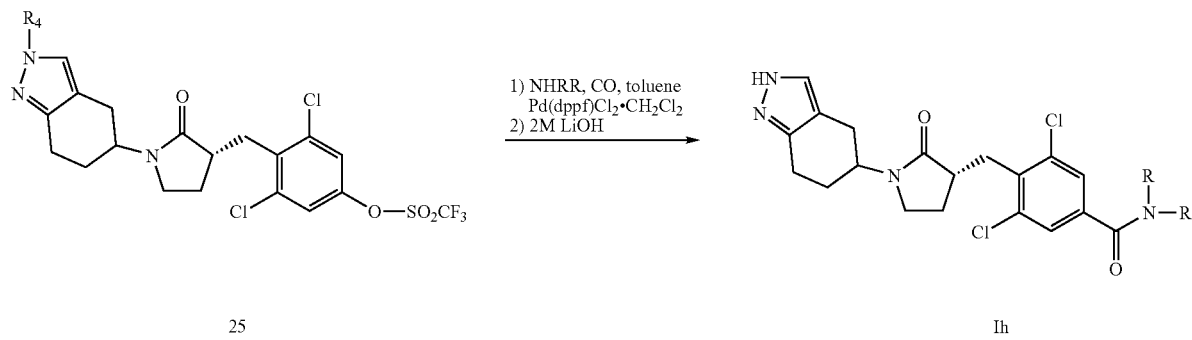

In Scheme V, compound Ih is formed by treating compound 25 with various amines (NHRR) under carbon monoxide and Pd(dppf)Cl$_2$ followed by removal of triflate group from pyrazole nitrogen using 2M LiOH.

EXAMPLE 73

(3R,5S)-3-[2,6-Dichloro-4-(morpholine-4-carbonyl)-benzyl]-1-(4,5,6,7-tetrahydro-2H-indazol-5-yl)-pyrrolidin-2-one

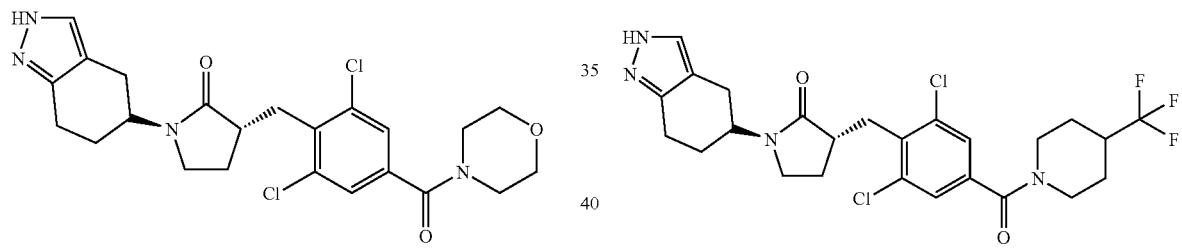

Dissolve (3R,5S)-Trifluoro-methanesulfonic acid 3,5-dichloro-4-[2-oxo-1-(2-trifluoromethanesulfonyl-4,5,6,7-tetrahydro-2H-indazol-5-yl)-pyrrolidin-3-ylmethyl]-phenyl ester (Preparation 43) (0.312 g, 0.48 mmol), in 4 ml of Argon-sparged toluene. Treat with morpholine (0.17 g, 1.94 mmol) and [1,1'-bis(diphenylphosphino)-ferrocene]dichloropalladium(II) (0.02 g, 0.024 mmol) and stir under 45 psi carbon monoxide pressure at 80° C. for 3 hr. LCMS shows consumption of starting material. Cool to ambient temperature and add ethyl acetate (50 ml) and water (10 ml). Extract the aqueous phase with ethyl acetate (50 ml). Wash the organic phases with 0.5 M aqueous HCl (2×10 ml), saturated sodium bicarbonate solution (10 ml) and brine (10 ml). Combine the organic phases, dry over magnesium sulfate and concentrate under reduced pressure. Dissolve the crude product in 5 ml of dimethoxyethane and treat with 2 M aqueous lithium hydroxide solution (1 ml). Stir for 2 hrs at ambient temperature. Dilute with ethyl acetate (50 ml) and water (10 ml) and extract the aqueous phase with ethyl acetate (50 ml). Wash the organic phases with water (10 ml) and brine (10 ml). Combine the organic phases, dry over sodium sulfate and concentrate under reduced pressure. Chromatography (silica, 95:5 CH$_2$Cl$_2$/2M NH$_3$ in MeOH) yields 0.170 g as a foam MS (m/z): 477 (M+1).

EXAMPLE 74

(3R,5S)-3-[2,6-Dichloro-4-(4-trifluoromethyl-piperidine-1-carbonyl)-benzyl]-1-(4,5,6,7-tetrahydro-2H-indazol-5-yl)-pyrrolidin-2-one Dissolve (3R,5S)-Trifluoro-methanesulfonic acid 3,5-dichloro-4-[2-oxo-1-(2-trifluoromethanesulfonyl-4,5,6,7-tetrahydro-2H-indazol-5-yl)-pyrrolidin-3-ylmethyl]-phenyl ester (Preparation 43) (0.307 g, 0.48 mmol) in 5 ml of argon-sparged toluene. Treat with 4-trifluoromethylpiperidine-HCl salt (0.27 g, 1.43 mmol), [1,1'-bis(diphenylphosphino)-ferrocene]dichloropalladium(II) (0.02 g, 0.024 mmol) and triethylamine (0.21 ml, 1.48 mmol). Stir under 48 psi carbon monoxide pressure at 80° C. for 4 hr. Add 3 ml of argon-sparged dimethyl formamide and more triethylamine (0.25 ml, 1.76 mmol). Heat at 80° C. for 5 hrs under 50 psi carbon monoxide pressure. LCMS shows consumption of starting material. Cool to ambient temperature and add ethyl acetate (50 ml) and water (10 ml). Extract the aqueous phase with ethyl acetate (50 ml). Wash the organic phases with water (10 ml) and brine (10 ml). Combine the organic phases, dry over sodium sulfate and concentrate under reduced pressure. Dissolve the crude product in 5 ml of dimethoxyethane and treat with 2 M aqueous lithium hydroxide solution (1 ml). Stir for 2 hrs at ambient temperature. Dilute with ethyl acetate (50 ml) and water (10 ml) and extract the aqueous phase with ethyl acetate (50 ml). Wash the organic phases with water (10 ml) and brine (10 ml). Combine the organic phases, dry over sodium sulfate and concentrate under reduced pressure.

Chromatography (silica, 97:3 CH$_2$Cl$_2$/2M NH$_3$ in MeOH) yields 0.080 g as a white solid MS (m/z): 543 (M+1).

EXAMPLE 75

(3R,5S)-3-[2,6-Dichloro-4-(4,4-difluoropiperidine-1-carbonyl)-benzyl]-1-(4,5,6,7-tetrahydro-2H-indazol-5-yl)-pyrrolidin-2-one

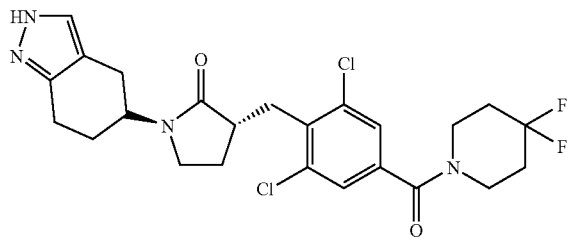

Dissolve (3R,5S)-Trifluoro-methanesulfonic acid 3,5-dichloro-4-[2-oxo-1-(2-trifluoromethanesulfonyl-4,5,6,7-tetrahydro-2H-indazol-5-yl)-pyrrolidin-3-ylmethyl]-phenyl ester (Preparation 43) (0.304 g, 0.48 mmol) in 5 ml of argon-sparged dimethylformamide. Treat with 4,4-difluoropiperidine-HCl salt (0.22 g, 1.41 mmol), catalyst: [1,1'-bis(diphenylphosphino)-ferrocene]dichloropalladium(II) (0.02 g, 0.024 mmol) and triethylamine (0.21 ml, 1.48 mmol). Stir under 40 psi carbon monoxide pressure at 80° C. for 5 hr. Add more catalyst (0.02 g, 0.024 mmol) and more triethylamine (0.25 ml, 1.76 mmol). Heat at 85° C. for 4 hrs at 50 psi carbon monoxide pressure. LCMS shows consumption of starting material. Cool to ambient temperature and add ethyl acetate (50 ml) and water (10 ml). Extract the aqueous phase with ethyl acetate (50 ml). Wash the organic phases with water (10 ml) and brine (10 ml). Combine the organic phases, dry over sodium sulfate and concentrate under reduced pressure. Dissolve the crude product in 5 ml of dimethoxyethane and treat with 2 M aqueous lithium hydroxide solution (1 ml). Stir for 2 hrs at ambient temperature. Dilute with ethyl acetate (50 ml) and water (10 ml) and extract the aqueous phase with ethyl acetate (50 ml). Wash the organic phases with water (10 ml) and brine (10 ml). Combine the organic phases, dry over sodium sulfate and concentrate under reduced pressure.

Chromatography (silica, 98:2 CH$_2$Cl$_2$/2M NH$_3$ in MeOH) yields 0.028 g as a foam MS (m/z): 511 (M+1).

EXAMPLE 76

3,5-Dichloro-N-isobutyl-4-[2-oxo-1-(4,5,6,7-tetrahydro-2H-indazol-5-yl)-pyrrolidin-3-ylmethyl]-benzamide

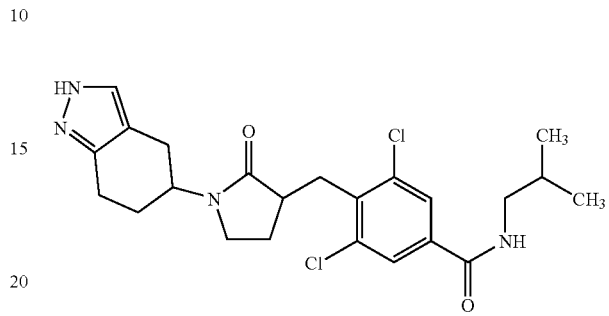

Dissolve trifluoro-methanesulfonic acid 3,5-dichloro-4-[2-oxo-1-(2-trifluoromethanesulfonyl-4,5,6,7-tetrahydro-2H-indazol-5-yl)-pyrrolidin-3-ylmethyl]-phenyl ester (Preparation 33) (0.229 g, 0.35 mmol), in 5 ml of Argon-sparged toluene. Treat with isopropyl amine (0.103 g, 1.42 mmol) and [1,1'-bis(diphenylphosphino)-ferrocene]dichloropalladium(II) (0.02 g, 0.024 mmol) and stir under 45 psi carbon monoxide pressure at 80° C. for 17 hr. LCMS shows consumption of starting material. Cool to ambient temperature and add ethyl acetate (50 ml) and water (10 ml). Extract the aqueous phase with ethyl acetate (50 ml). Wash the organic phases with 0.5 M aqueous HCl (2×10 ml), saturated sodium bicarbonate solution (10 ml) and brine (10 ml). Combine the organic phases, dry over magnesium sulfate and concentrate under reduced pressure. Dissolve the crude product in 5 ml of dimethoxyethane and treat with 2 M aqueous lithium hydroxide solution (1.6 ml). Stir for 24 hrs at ambient temperature. Dilute with ethyl acetate (50 ml) and water (10 ml) and extract the aqueous phase with ethyl acetate (50 ml). Wash the organic phases with water (10 ml) and brine (10 ml). Combine the organic phases, dry over sodium sulfate and concentrate under reduced pressure. Chromatography (silica, 95:5 CH$_2$Cl$_2$/2M NH$_3$ in MeOH) yields 0.073 g as a foam MS (m/z): 464 (M+1).

Scheme W

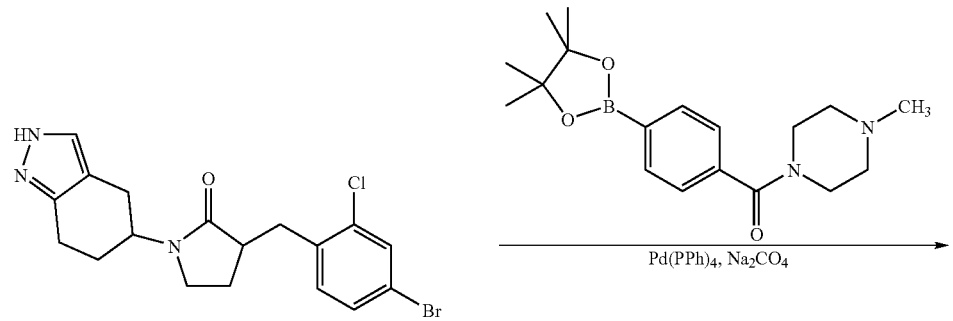

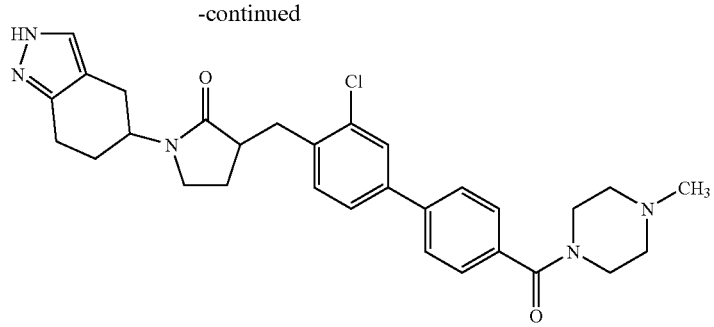

In Scheme W, 3-[3-Chloro-4'-(4-methyl-piperazine-1-carbonyl)-biphenyl-4-ylmethyl]-1-(4,5,6,7-tetrahydro-2H-indazol-5-yl)-pyrrolidin-2-one is prepared by treatment of 3-(4-Bromo-2-chloro-benzyl)-1-(4,5,6,7-tetrahydro-2H-indazol-5-yl)-pyrrolidin-2-one with (4-Methyl-piperazin-1-yl)-[4-(4,4,5,5-tetramethyl-[1,3,2]dioxaborolan-2-yl)-phenyl]-methanone in the presence of $Pd(PPh_3)_4$ and $Na_2CO_3$.

EXAMPLE 77

3-[3-Chloro-4'-(4-methyl-piperazine-1-carbonyl)-biphenyl-4-ylmethyl]-1-(4,5,6,7-tetrahydro-2H-indazol-5-yl)-pyrrolidin-2-one

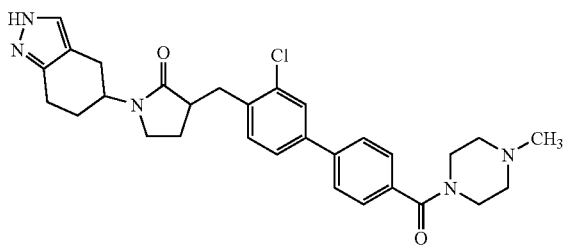

Dissolve 3-(4-Bromo-2-chloro-benzyl)-1-(4,5,6,7-tetrahydro-2H-indazol-5-yl)-pyrrolidin-2-one (Example 6) (0.471, 1.16 mmol) in DME (5.0 mL) and de-gas with a stream of nitrogen for 5.0 minutes. Add (4-Methyl-piperazin-1-yl)-[4-(4,4,5,5-tetramethyl-[1,3,2]dioxaborolan-2-yl)-phenyl]-methanone hydrochloride (0.114 g, 1.58 mmol), followed by 2.0 M sodium carbonate (2.03 mL, 4.06 mmol) and continue de-gas. Add $Pd(Ph_3)_4$ (0.134 g, 0.116 mmol) and heat to 80° C. for 17 hours. Dilute with ethyl acetate and water, separate and save both layers. The pH of the aqueous layer adjusted to ph 9 with 1.0 N HCl, and back extract with three portions of ethyl acetate. The organic layers are combined, dry over sodium sulfate and evaporate. Chromatography (silica 95:5 $CH_2Cl_2$/MeOH/1% $NH_3$) yields 0.08 g (0.6%) of the title compound as an amorphorous foam. MS (m/z): 533 (M+1).

EXAMPLE 78

3-(4-Bromo-2-chlorobenzyl)-1-(4,5,6,7-tetrahydro-2H-indazol-6-yl)pyrrolidin-2-one

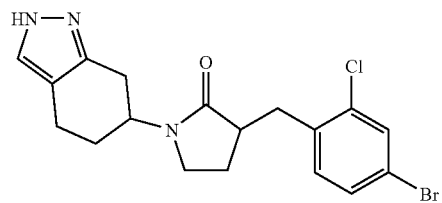

Combine ethyl 2-(4-bromo-2-chlorobenzyl)-4-oxobutanoate (0.92 g, 2.8 mmol), 4,5,6,7-tetrahydro-1H-indazol-6-amine hydrochloride (preparation 80) (490 mg, 2.8 mmol) and sodium triacetoxyborohydride (886 mg, 4.2 mmol) in dichloroethane (50 mL) and stir for 48 hours at room temperature. Add water and extract with $CH_2Cl_2$. Dry the organic layer over magnesium sulfate, filter and concentrate. Purify the residue by silica gel chromatography affords the title compound (428 mg, 68%): MS (m/z): 410 (M+2).

EXAMPLE 79

(R)-3-(4'-Fluoro-3,5-dimethyl-biphenyl-4-ylmethyl)-1-(4,5,6,7-tetrahydro-2H-indazol-5-yl)-pyrrolidin-2-one

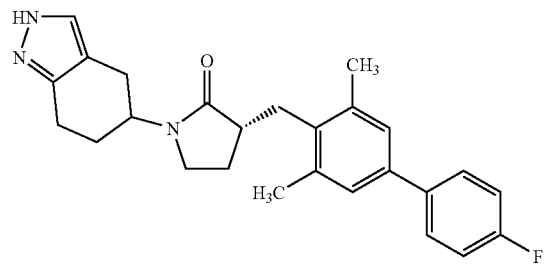

Purge a solution of Trifluoro-methanesulfonic acid 3,5-dimethyl-4-[(R)-2-oxo-1-(2-trifluoromethanesulfonyl-4,5,6,7-tetrahydro-2H-indazol-5-yl)-pyrrolidin-3-ylmethyl]-phenyl ester (Preparation 66) (1.05 g, 2.2 mmol), 4-Fluorophenylboronic acid (0.38 g, 2.7 mmol), and sodium carbonate (0.36 g, 3.4 mmol) in THF (15 mL) and water (5 mL) with nitrogen. Treat the reaction with Tetrakis(triphenylphosphine)palladium(0) (0.13 g, 0.1 mmol) and again purge with nitrogen. Heat the reaction to 80° C. and stir for 2 hr. Treat the reaction with 1N LiOH (5 mL) and cool to room temperature. Quench the reaction with 1N HCl. Extract the aqueous with EtOAc. Wash the organic with brine, dry over $MgSO_4$, and filter. Purify the crude by silica gel column chromatography using $CH_2Cl_2$ and 2M Ammonia in MeOH to elute the pure product. MS (m/e): 418 (M+1).

EXAMPLE 80

(3R)-3-(3,5-Dichloro-4'-fluoro-biphenyl-4-ylmethyl)-1-(4,5,6,7-tetrahydro-1H-indazol-4-yl)-pyrrolidin-2-one

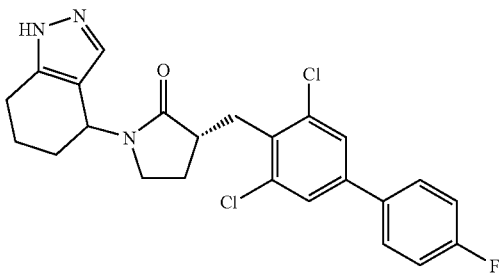

A mixture of trifluoro-methanesulfonic acid 3,5-dichloro-4-[(R)-2-oxo-1-(1-trifluoromethanesulfonyl-4,5,6,7-tetrahydro-1H-indazol-4-yl)-pyrrolidin-3-ylmethyl]-phenyl ester and trifluoro-methanesulfonic acid 3,5-dichloro-4-[(R)-2-oxo-1-(2-trifluoromethanesulfonyl-4,5,6,7-tetrahydro-2H-indazol-4-yl)-pyrrolidin-3-ylmethyl]-phenyl ester, Preparation 73, (0.49 g, 0.76 mmol), 4-fluorophenylboronic acid (0.13 g, 0.91 mmol), sodium carbonate (0.24 g, 2.28 mmol) in THF (20 mL) and water (6 mL) is brought to 60° C. To the mixture at 60° C., add $Pd(PPh_3)_4$ (0.044 g, 0.038 mmol). Raise the reaction temperature to 80° C. and stir the reaction for 1 hour. Cool the reaction, dilute with ethyl acetate and wash with water and brine. Dry the organic layer ($Na_2SO_4$) and remove the solvent in vacuo to afford crude product (0.45 g). Dissolve in THF (5 mL) and LiOH (2 N, 5 mL) and stir at room temperature for 1 hour. Quench the reaction with HCl (1N, 8 mL) and dilute with ethyl acetate and washed with water. Dry the organic layer ($Na_2SO_4$), remove the solvent in vacuo to afford crude product, and purify on silica gel column with 50% ethyl acetate in hexanes to 100% ethyl acetate to afford 0.25 g of the title product. MS (m/z): 458 (M+). Separate the two component mixture into individual enantiomers via preparative chiral chromatography (Chiralpak AD, 5×15 cm, 60/40 ethanol/heptane/0.2% DMEA, flow=40 mL/min, 260 nm). The analytical conditions are as follows: Chiralpak AD-H, 4.6×150 mm, 60/40 ethanol/heptane/0.2% DMEA, flow=0.6 mL/min, 260 nm.

| Example | Ret time (min) | % ee | Isomer | $[\alpha]^{23}D$ (c 1.0, DMSO) |
|---|---|---|---|---|
| 80a | 7.7 | >99 | Isomer 1 | −33.80 |
| 80b | 8.9 | 80 | Isomer 2 | |

EXAMPLE 81

3-[3,5-Dichloro-4'-(4-trifluoromethyl-piperidine-1-carbonyl)-biphenyl-4-ylmethyl]-1-(4,5,6,7-tetrahydro-2H-indazol-5-yl)-pyrrolidin-2-one

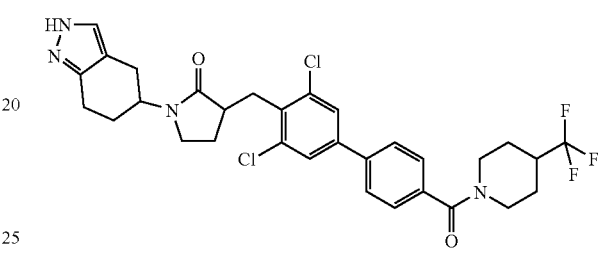

Stir a solution of 5-[3-(4'-Carboxy-3,5-dichloro-biphenyl-4-ylmethyl)-2-oxo-pyrrolidin-1-yl]-4,5,6,7-tetrahydro-indazole-2-carboxylic acid tert-butyl ester (Preparation 74), (0.074 g, 0.13 mmol) in $CH_2Cl_2$ (5 mL), Carbonyldiimidazole (0.033 g, 0.2 mmol), DIPEA (0.11 mL, 0.63 mmol), and 4-Trifluoromethyl-piperidine hydydrochloride (0.06 g, 0.32 mmol) at room temperature for 24 hr. Dilute with $CH_2Cl_2$ and wash with 1N HCl and water. Dry the organic layer ($Na_2SO_4$), remove the solvent under reduced pressure to afford the crude product as the Boc protected titled product. Dissolve in $CH_2Cl_2$ (5.0 mL), treat with TFA and stir for 1 hr at room temperature. Evaporation yields 0.041 g of the titled product as the TFA salt. MS (m/z): 619 (M+).

EXAMPLE 82

(3R)-3-(3,5-Dichloro-4'-fluoro-biphenyl-4-ylmethyl)-1-(4,5,6,7-tetrahydro-1H-indazol-7-yl)-pyrrolidin-2-one

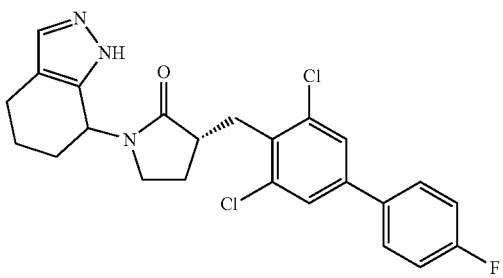

Purge a solution of trifluoro-methanesulfonic acid 3,5-dichloro-4-[(R)-2-oxo-1-(1-trifluoromethanesulfonyl-4,5,6,7-tetrahydro-1H-indazol-7-yl)-pyrrolidin-3-ylmethyl]-phenyl ester and trifluoro-methanesulfonic acid 3,5-dichloro-4-[(R)-2-oxo-1-(2-trifluoromethanesulfonyl-4,5,6,7-tetrahydro-2H-indazol-7-yl)-pyrrolidin-3-ylmethyl]-phenyl ester (Preparation 79) (1.64 g, 2.54 mmol), 4-fluorophenylboronic acid (0.427 g, 3.05 mmol), and 2M sodium carbonate (3.8 mL) in THF (63 mL) with nitrogen. Treat the reaction with tetrakis(triphenylphosphine)palladium(0) (0.147 g, 0.127 mmol) and heat the reaction to 80° C. and stir for 1 hr. Cool to room temperature and treat the reaction with 2N LiOH (12.7 mL) and stir for 1 hr. Dilute the reaction with water and extract with ethyl acetate. The organic layer is dried ($Na_2SO_4$) and the solvent is removed to afford crude product that is purified first with 0 to 10% methanol in $CH_2Cl_2$ and then with a Varian 10 g SCX column with 9/1 $CH_2Cl_2$/MeOH and then 2:1 $CH_2Cl_2$/2M $NH_3$ in MeOH to afford 0.735 g (63%) of the titled product. MS (m/z): 458 (M+1).

EXAMPLES 83 AND 84

(R)-3-(3,5-Dichloro-4'-fluoro-biphenyl-4-ylmethyl)-1-(4,5,6,7-tetrahydro-1H-indazol-7-yl)-pyrrolidin-2-one (Isomers 1 and 2)

The two component mixture (Example 82) can be separated into individual enantiomers via chiral chromatography (Chiralpak AD-H, 4.6×150 mm, 60/40 IPA/heptane/0.2% DMEA, flow=0.6 ml/min, 250 nm).
The following enantiomers are isolated by the procedure above.

| Example | Retention Time (min) | % ee | Isomer Number | $[\alpha]^{23}D$ (c 1.0, DMSO) |
|---|---|---|---|---|
| 83 | 7.2 | >99 | Isomer 1 | −61.5 |
| 84 | 14.2 | >99 | Isomer 2 | −1.00 |

EXAMPLE 85

(3R)-3-(3,5-Dichloro-4'-fluoro-biphenyl-4-ylmethyl)-1-(4,5,6,7-tetrahydro-1H-indazol-6-yl)-pyrrolidin-2-one

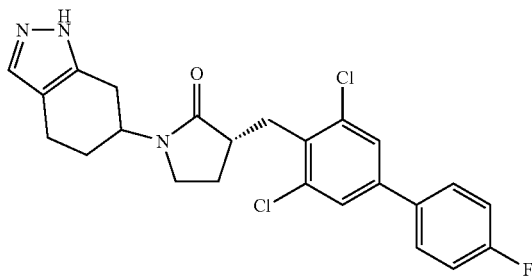

Purge a solution of trifluoro-methanesulfonic acid 3,5-dichloro-4-[(R)-2-oxo-1-(1-trifluoromethanesulfonyl-4,5,6,7-tetrahydro-1H-indazol-6-yl)-pyrrolidin-3-ylmethyl]-phenyl ester and trifluoro-methanesulfonic acid 3,5-dichloro-4-[(R)-2-oxo-1-(2-trifluoromethanesulfonyl-4,5,6,7-tetrahydro-2H-indazol-6-yl)-pyrrolidin-3-ylmethyl]-phenyl ester (Preparation 83) (0.573 g, 0.89 mmol), 4-fluorophenyl-boronic acid (0.149 g, 1.06 mmol), and 2M sodium carbonate (1.3 mL) in THF (22 mL) with nitrogen. Treat the reaction with tetrakis(triphenylphosphine)palladium(0) (0.051 g, 0.044 mmol) and heat the reaction to 80° C. and stir for 1 hr. Cool to room temperature and treat the reaction with 2N LiOH (4.5 mL) and stir for 1 hr. Dilute the reaction with water and extract with ethyl acetate. The organic layer is dried ($Na_2SO_4$) and the solvent is removed to afford crude product that is purified first with 0 to 10% methanol in $CH_2Cl_2$ and then with a Varian 10 g SCX column with 9/1 $CH_2Cl_2$/MeOH and then 2:1 $CH_2Cl_2$/2M $NH_3$ in MeOH to afford 0.233 g (57%) of the titled product. MS (m/z): 458 (M+1).

EXAMPLES 86 AND 87

(R)-3-(3,5-Dichloro-4'-fluoro-biphenyl-4-ylmethyl)-1-(4,5,6,7-tetrahydro-1H-indazol-6-yl)-pyrrolidin-2-one (Isomers 1 and 2)

The two component mixture (Example 85) can be separated into individual enantiomers via chiral chromatography (Chiralpak AD-H, 4.6×150 mm, 60/40 IPA/heptane/0.2% DMEA, flow=0.6 ml/min, 250 nm).
The following enantiomers are isolated by the procedure above.

| Example | Retention Time (min) | % ee | Isomer Number | $[\alpha]^{23}D$ (c 1.0, DMSO) |
|---|---|---|---|---|
| 86 | 6.9 | 95.4 | Isomer 1 | −22.5 |
| 87 | 9.4 | 98.2 | Isomer 2 | +18.8 |

EXAMPLE 88

(3R-5S)-(−)-3-(3,5-Dichloro-4'-fluoro-biphenyl-4-ylmethyl)-1-(4,5,6,7-tetrahydro-2H-indazol-5-yl)-pyrrolidin-2-one This compound is synonomous with and identifiable as (3R)-3-[3,5-Dichloro-4'-fluoro[1,1'-biphenyl]-4-yl)methyl]-1-[(5S)-4,5,6,7-tetrahydro-1H-indazol-5-yl]-2-pyrrolidinone

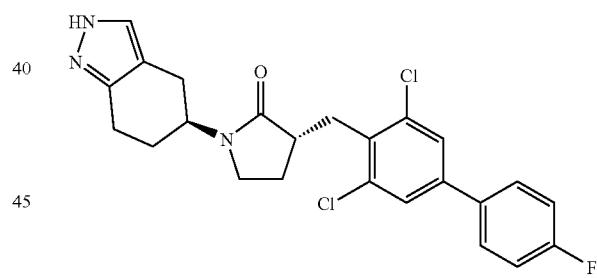

Heat a slurry of 463 g (700 mmoles) of resolved salt (S)-(4,5,6,7-Tetrahydro-1H-indazol-5-yl)amine.½ DTTA (Preparation 86), 436 g (3.151 mmoles) of potassium carbonate, 9 L of acetonitrile and 180 mL of water at 70° C. for 12 h. Allow the mixture to cool to room temperature, filter, and rinse the cake with ACN (2×1.8 L). Distill the filtrate to 5 L of solution, and then add ACN in 1 L portions, distilling off 1 L each time (3 times). Allow the resulting amine solution to cool to 53° C. and then add (R)-3-(3,5-Dichloro-4'-fluoro-biphenyl-4-ylmethyl)-5-hydroxy-dihydro-furan-2-one (Preparation 90) (420 g, 1.181 mmoles). Heat the mixture at 50° C. for 1 h and allow to cool to room temperature. Add Sodium triacetoxyborohydride (413 g, 1.949 mmoles) and stir the mixture for 1.5 h. Heat the mixture at 70° C. for 1.25 h and slowly add water (5 L) to the hot mixture. After heating an additional 1.25 h post water addition, allow the slurry to cool to room temperature and stir overnight. Collect the solid by filtration, rinse with 1:1 ACN/water (2×820 mL), and dry under vacuum to afford 522 g of solid. Dissolve a portion (425 g) of the resulting solid in 4.25 L of 10% aqueous THF at 37° C. Add Darco (carbon, 44 g) and filter the mixture. Rinse the cake with THF (2×425 mL). The filtrate is solvent exchanged into 3A EtOH (95% EtOH, 5% MeOH) and seeded with (3R-5S)-(−)-3-(3,5-Dichloro-4'-fluoro-biphenyl-4-ylmethyl)-1-(4,5,6,7-tetrahydro-2H-indazol-5-yl)-pyrrolidin-2-one to afford a slurry. Cool the slurry to room temperature and collect the solid by filtration. Wash the filter cake with 3A EtOH (2×425 mL) and dry under vacuum to afford 351 g (80% yield) of the title compound. MS (m/z): 458 (M+1, $^{35}$Cl), 460 (M+1, $^{37}$Cl).

EXAMPLE 89

Cyclization of Preparation 94

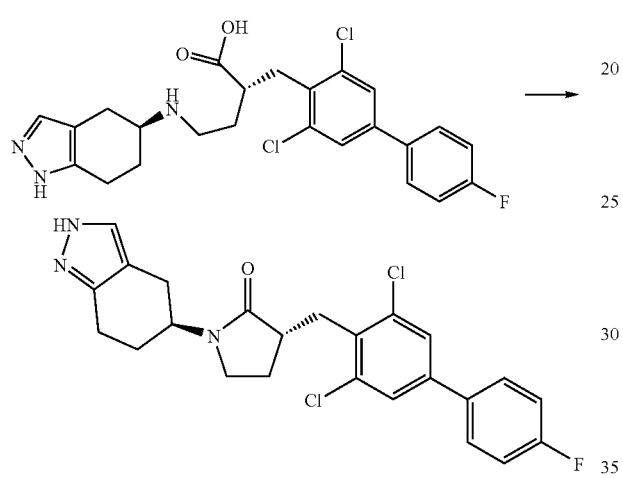

To 1.0 g (2.1 mmoles) of Preparation 91, add 10 mL of toluene and heat the mixture at reflux for 2.75 h. Allow the solution to cool to 40° C. and seed with (R)-3-(3,5-Dichloro-4'-fluoro-biphenyl-4-ylmethyl)-1-(S)-4,5,6,7-tetrahydro-2H-indazol-5-yl-pyrrolidin-2-one. Allow the slurry to stir at room temperature for 2 h and collect the solids by filtration. Rinse the solid with toluene (2×1 mL) and dry under vacuum to afford 492 mg (51%) of the title compound as a white solid.

Alternate procedure: To 0.36 g (0.76 mmoles) of Preparation 94, add 3.6 mL of acetic acid and heat the solution at 100° C. for 2 h. Add 4.5 mL of water at 95° C. and seed with (R)-3-(3,5-Dichloro-4'-fluoro-biphenyl-4-ylmethyl)-1-(S)-4,5,6,7-tetrahydro-2H-indazol-5-yl-pyrrolidin-2-one. Allow to cool to room temperature, collect the solid and rinse with acetonitrile (1×3 mL). Dry the solid under vacuum to afford 250 mg (72%) of the title compound as a solid.

EXAMPLE 90

(3R-5S)-(−)-3-(3,5-Dichloro-4'-fluoro-biphenyl-4-ylmethyl)-1-(4,5,6,7-tetrahydro-2H-indazol-5-yl)-pyrrolidin-2-one Add (R)-4-((R)-4-Benzyl-2-oxo-oxazolidin-3-yl)-3-(3,5-dichloro-4'-fluoro-biphenyl-4-ylmethyl)-4-oxo-butyraldehyde (Preparation 94) (1.13 mmoles; 580.00 mg) (dissolved in 5 ml dichloromethane) to (S)-(4,5,6,7-tetrahydro-1H-indazol-5-yl)amine 1.13 mmoles; 154.69 mg) dissolved in 5 ml Acetonitrile (5 mL). Cool the mixture in an ice water bath and add sodium triacetoxyborohydride (3.38 mmoles; 716.94 mg) portion wise. Remove the cooling bath and warm the mixture to ambient. Cool the mixture in an ice water bath and quench with 10 ml saturated sodium bicarbonate. Add 15 ml of ethyl acetate followed by 10 ml of brine. Charge the solution to a separatory funnel and separate the organic layer, dry over magnesium sulfate, filter, and concentrate to ⅓ volume. Add a seed crystal of (R)-3-(3,5-Dichloro-4'-fluoro-biphenyl-4-ylmethyl)-1-(S)-4,5,6,7-tetrahydro-2H-indazol-5-yl-pyrrolidin-2-one. Stir the solution at ambient temperature for 16 hours. Crystallization occurs and cool the mixture in an ice-water bath. Filter the cold mixture, collect the solid, and dry to give 284 mg of a white solid-crop A. LCMS=100% (M+1) at 458 amu. To the filtrate (now dry after evaporation), add 10 ml of MTBE to crystallize the rest of the product to obtain 89 mg white solid-crop B. LCMS=100% (M+1) at 458 amu 0.373/0.52=71.7%.

EXAMPLE 91

(3R)-3-(3,5-Dichloro-4'-isopropxy-biphenyl-4-ylmethyl)-1-(4,5,6,7-tetrahydro-1H-indazol-4-yl)-pyrrolidin-2-one

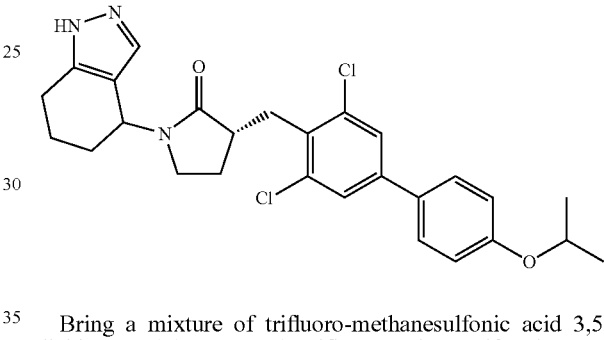

Bring a mixture of trifluoro-methanesulfonic acid 3,5-dichloro-4-[(R)-2-oxo-1-(1-trifluoromethanesulfonyl-4,5,6,7-tetrahydro-1H-indazol-4-yl)-pyrrolidin-3-ylmethyl]-phenyl ester and trifluoro-methanesulfonic acid 3,5-dichloro-4-[(R)-2-oxo-1-(2-trifluoromethanesulfonyl-4,5,6,7-tetrahydro-2H-indazol-4-yl)-pyrrolidin-3-ylmethyl]-phenyl ester (0.43 g, 0.76 mmol), 4-isopropxyphenylboronic acid (0.14 g, 0.8 mmol), sodium carbonate (0.21 g, 2.0 mmol) in THF (15 mL) and water (5 mL) is brought to 60° C. To the mixture (at 60° C.), add Pd(PPh$_3$)$_4$ (0.04 g, 0.03 mmol). Raise the reaction temperature to 80° C. and stir the reaction for 1 hour. Cool the reaction, dilute with ethyl acetate, and wash with water and brine. Dry the organic layer (Na$_2$SO$_4$) and remove the solvent in vacuo to afford crude product (0.40 g). Dissolve the crude in THF (5 mL) and then stir in LiOH (2 N, 3 mL) at room temperature for 1.5 hour. Quench the reaction with HCl (1N, 8 mL), dilute with ethyl acetate and wash with water. Dry the organic layer (Na$_2$SO$_4$) and remove the solvent in vacuo to afford crude product. Purify on silica gel column with 50% ethyl acetate in hexanes to 100% ethyl acetate to afford 0.28 g of the title product. MS (m/z): 499 (M+).

EXAMPLES 92 AND 93

(R)-3-(3,5-Dichloro-4'-isopropxy-biphenyl-4-ylmethyl)-1-(4,5,6,7-tetrahydro-1H-indazol-4-(R)-yl)-pyrrolidin-2-one and (R)-3-(3,5-Dichloro-4'-isopropxy-biphenyl-4-ylmethyl)-1-(4,5,6,7-tetrahydro-1H-indazol-4-(S)-yl)-pyrrolidin-2-one Purify (R)-3-(3,5-Dichloro-4'-isopropxy-biphenyl-4-ylmethyl)-1-(4,5,6,7-tetrahydro-1H-indazol-4-yl)-pyrrolidin-2-one (0.25 g) by chiral separation using a Chiralpak AD-H 4.6×150 mm column with 50/50 Heptane/IPA to elute the pure isomers. The chromatography affords 0.12 g (48%) of isomer 1 and 0.12 g (48%) of isomer 2.

| Example | Retention Time (min) | % ee | Isomer |
|---|---|---|---|
| 92 | 7.9 | >99 | Isomer 1 |
| 93 | 11.7 | >99 | Isomer 2 |

EXAMPLE 94

(3R)-3-(3,5-Dichloro-4'-trifluoromethyl-biphenyl-4-ylmethyl)-1-(4,5,6,7-tetrahydro-1H-indazol-4-yl)-pyrrolidin-2-one

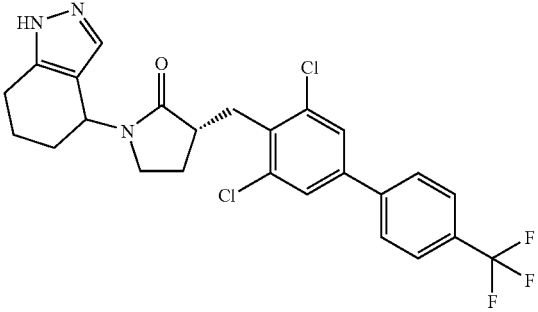

Bring a mixture of trifluoro-methanesulfonic acid 3,5-dichloro-4-[(R)-2-oxo-1-(1-trifluoromethanesulfonyl-4,5,6,7-tetrahydro-1H-indazol-4-yl)-pyrrolidin-3-ylmethyl]phenyl ester and trifluoro-methanesulfonic acid 3,5-dichloro-4-[(R)-2-oxo-1-(2-trifluoromethanesulfonyl-4,5,6,7-tetrahydro-2H-indazol-4-yl)-pyrrolidin-3-ylmethyl]-phenyl ester (0.5 g, 0.78 mmol), 4-trifluoromethylphenylboronic acid (0.18 g, 0.93 mmol), sodium carbonate (0.25 g, 2.3 mmol) in THF (15 mL) and water (5 mL) to 60° C. To the mixture at 60° C., add Pd(PPh$_3$)$_4$ (0.04 g, 0.03 mmol). Raise the reaction temperature to 80° C. and stir the reaction for 1 hour. Cool the reaction, dilute with ethyl acetate, and wash with water and brine. Dry the organic layer (Na$_2$SO$_4$) and remove the solvent in vacuo to afford crude product (0.48 g). Dissolve in THF (5 mL) and stir in LiOH (2 N, 3 mL) at room temperature for 1.5 hour. Quench the reaction with HCl (1N, 8 mL), dilute with ethyl acetate, and wash with water. Dry the organic layer (Na$_2$SO$_4$), remove the solvent in vacuo to afford crude product, and then purify on silica gel column with 100% dichloromethane to 10% methanol in dichloromethane to afford 0.35 g of the title product. MS (m/z): 508 (M+).

EXAMPLES 95 AND 96

(3R)-3-(3,5-Dichloro-4'-trifluoromethyl-biphenyl-4-ylmethyl)-1-(4,5,6,7-tetrahydro-1H-indazol-4-(R)-yl)-pyrrolidin-2-one and (R)-3-(3,5-Dichloro-4'-trifluoromethyl-biphenyl-4-ylmethyl)-1-(4,5,6,7-tetrahydro-1H-indazol-4-(S)-yl)-pyrrolidin-2-one Purify (R)-3-(3,5-Dichloro-4'-trifluoromethyl-biphenyl-4-ylmethyl)-1-(4,5,6,7-tetrahydro-1H-indazol-4-yl)-pyrrolidin-2-one (0.32 g) by chiral separation using a Chiralpak AD-H 4.6×150 mm column with 50/50 Heptane/IPA to elute the pure isomers. Chromatography affords 0.13 g (41%) of isomer 1 and 0.13 g (41%) of isomer 2.

| Example | Retention Time (min) | % ee | Isomer |
|---|---|---|---|
| 95 | 6.4 | >98.5 | Isomer 1 |
| 96 | 10.5 | >95 | Isomer 2 |

EXAMPLE 97

(R)-3-[3,5-Dichloro-4'-(4-trifluoromethyl-piperidine-1-carbonyl)-biphenyl-4-ylmethyl]-1-(4,5,6,7-tetrahydro-1H-indazol-4-yl)-pyrrolidin-2-one

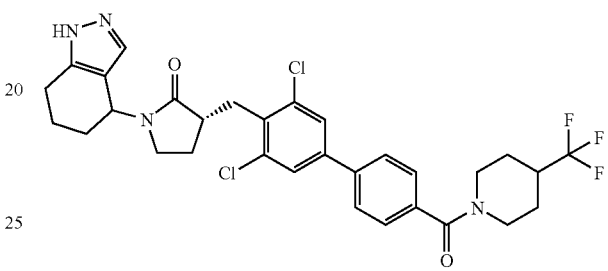

Treat a solution of Preparation 97 (0.36 g, 0.48 mmol) in THF (10 mL) with LiOH (2 M, 5 mL) at 25° C. for 3 hours. Quench the reaction with HCl (1N, 10 mL), dilute with ethyl acetate, and wash with water. Dry the organic layer (Na$_2$SO$_4$), remove the solvent in vacuo to afford crude product, and then purify on silica gel column with 100% dichloromethane to 10% methanol in dichloromethane to afford 0.27 g of the title product. MS (m/z): 619 (M+).

EXAMPLE 98

(3R)-3-(3,5-Dichloro-4'-fluoro-biphenyl-4-ylmethyl)-1-(4,5,6,7-tetrahydro-1H-indazol-4-yl)-pyrrolidin-2-one

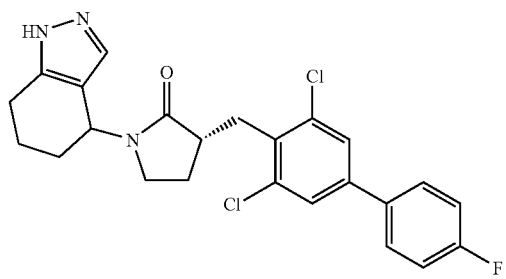

To a solution of (R)-4-[3-(2,6-dichloro-4-trifluoromethanesulfonyloxy-benzyl)-2-oxo-pyrrolidin-1-yl]-4,5,6,7-tetrahydro-indazole-1-carboxylic acid tert-butyl ester and (R)-4-[3-(2,6-dichloro-4-trifluoromethanesulfonyloxy-benzyl)-2-oxo-pyrrolidin-1-yl]-4,5,6,7-tetrahydro-indazole-2-carboxylic acid tert-butyl ester (Preparation 105) (0.90 g, 1.39 mmol) in THF (35 mL), add 2M sodium carbonate (2.1 mL, 2.78 mmol) and 4-fluorophenylboronic acid (0.23 g, 1.64 mmol). Degas the mixture using a nitrogen gas dispenser for 5 minutes. Add Tetrakis(triphenylphosphine)palladium (0.081 g, 0.070 mmol), bring the reaction mixture to 80° C., and stir under nitrogen for 1 hour. Cool the reaction to room temperature and then treat with 2M aqueous LiOH (14 mL) and stir at room temperature for 1 hour. Partition the mixture between ethyl acetate and water; separate the organic, dry over sodium sulfate, filter and concentrate to afford crude product, and then purify by flash chromatography (gradient, 0 to 10% methanol in dichloromethane) to afford 0.57 g (89%) of the desired product as a mixture of regioisomers. LCMS: 458 (M+H).

EXAMPLES 99 AND 100

Separate the two component mixture of Example 98 into individual enantiomers via preparative chiral chromatography (Chiralpak AD, 8×32 cm, 60/40 IPA/heptane/0.2% DMEA, flow=350 mL/min, 260 nm). The analytical conditions are as follows: Chiralpak AD-H, 4.6×150 mm, 60/40 IPA/heptane/0.2% DMEA, flow=0.6 mL/min, 270 nm.

| Example | Retention Time (min) | % ee | Isomer | $[\alpha]^{23}D$ (c 1.0, DMSO) |
|---|---|---|---|---|
| 99 | 6.4 | >99 | Isomer 1 | −33.80 |
| 100 | 10.5 | >99 | Isomer 2 | |

The following procedure and example further illustrates synthesis of the crystalline material of the present invention. All starting materials and reagents are well known and appreciated in the art and readily available or prepared by methods described herein.

EXAMPLE 101

Crystalline (3R-5S)-(−)-3-(3,5-Dichloro-4'-fluoro-biphenyl-4-ylmethyl)-1-(4,5,6,7-tetrahydro-2H-indazol-5-yl)-pyrrolidin-2-one Dissolve (3R-5S)-(−)-3-(3,5-Dichloro-4'-fluoro-biphenyl-4-ylmethyl)-1-(4,5,6,7-tetrahydro-2H-indazol-5-yl)-pyrrolidin-2-one (100 mg) (Example 88) at 70° C. in nPrOH (3 mL). Add water (11 mL) to the solution while maintaining the temperature near 70° C. Persistent clouding and subsequent precipitation of a white solid occurs upon addition of approximately 4 mL of water. Allow the slurry to cool to RT. Isolate the solid product by vacuum filtration and air dry to give the title compound (84 mg).
X-Ray Powder Diffraction X-ray powder diffraction analysis is performed with a D4 Endeaver diffractometer, equipped with a CuKα source (λ=1.54056 Å) operating at 40 kV and 50 mA. The sample is scanned from 3° to 40° in 2θ, with a step size of 0.009° in 2θ and a scan rate of >3 sec per step. Sample displacement errors may be corrected using the NIST standard SRM675 (standard peak at 8.8° in 2θ). It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.1 in 2-theta will take into account these potential variations without hindering the unequivocal identification of the indicated crystal form.

Confirmation of a crystal form may be made based on any unique combination of distinguishing peaks (in units of ° 2θ), typically the more prominent peaks. Crystalline (3R-5S)-(−)-3-(3,5-Dichloro-4'-fluoro-biphenyl-4-ylmethyl)-1-(4,5,6,7-tetrahydro-2H-indazol-5-yl)-pyrrolidin-2-one is characterized by an X-ray powder diffraction pattern having distinguishing peaks at 2θ values of 6.0°, 12.0° and 18.1°. Crystalline (3R-5S)-(−)-3-(3,5-Dichloro-4'-fluoro-biphenyl-4-ylmethyl)-1-(4,5,6,7-tetrahydro-2H-indazol-5-yl)-pyrrolidin-2-one can be further characterized by an X-ray powder diffraction pattern having distinguishing peaks at a 2θ values of 14.5° and 30.4°. All diffraction angles are expressed with a tolerance of ±0.1 degrees.

TABLE X

X-ray powder diffraction (CuKα radiation source, λ = 1.54056 Å) peaks of crystalline (3R-5S)-(−)-3-(3,5-Dichloro-4'-fluoro-biphenyl-4-ylmethyl)-1-(4,5,6,7-tetrahydro-2H-indazol-5-yl)-pyrrolidin-2-one.

| 2-Theta Angle (±0.1°) | Intensity (%) |
|---|---|
| 6.0 | 38.4 |
| 12.0 | 58.4 |
| 14.5 | 60.9 |
| 15.9 | 26.6 |
| 18.1 | 63.9 |
| 20.2 | 73.9 |
| 22.6 | 47.8 |
| 22.7 | 35.0 |
| 24.0 | 100.0 |
| 24.2 | 51.2 |
| 25.6 | 41.3 |
| 26.4 | 22.3 |
| 28.6 | 21.0 |
| 30.4 | 77.3 |

In the following section enzyme and functional assays are described which are useful for evaluating the compounds of the invention.
11β-HSD Type 1 Enzyme Assay Human 11β-HSD type 1 activity is measured by assaying NADPH production by fluorescence assay. Solid compounds are dissolved in DMSO to a concentration of 10 mM. Twenty microliters of each are then transferred to a column of a 96-well polypropylene Nunc plate where they are further diluted 50-fold followed by subsequent two-fold titration, ten times across the plate with additional DMSO using a Tecan Genesis 200 automated system. Plates are then transferred to a Tecan Freedom 200 system with an attached Tecan Temo 96-well head and an Ultra 384 plate reader. Reagents are supplied in 96-well polypropylene Nunc plates and are dispensed individually into black 96-well Molecular Devices High Efficiency assay plates (40 μL/well capacity) in the following fashion: 9 μL/well of substrate (2.22 mM NADP, 55.5 μM Cortisol, 10 mM Tris, 0.25% Prionex, 0.1% Triton X100), 3 μL/well of water to compound wells or 3 μL to control and standard wells, 6 µL/well recombinant human 11β-HSD type 1 enzyme, 2 µL/well of compound dilutions. For ultimate calculation of percent inhibition, a series of wells are added that represent assay minimum and maximum: one set containing substrate with 667 µM carbenoxolone (background), and another set containing substrate and enzyme without compound (maximum signal). Final DMSO concentration is 0.5% for all compounds, controls and standards. Plates are then placed on a shaker by the robotic arm of the Tecan for 15 seconds before being covered and stacked for a three hour incubation period at room temperature. Upon completion of this incubation, the Tecan robotic arm removes each plate individually from the stacker and places them in position for addition of 5 µL/well of a 250 µM carbenoxolone solution to stop the enzymatic reaction. Plates are then shaken once more for 15 seconds then placed into an Ultra 384 microplate reader (355EX/460EM) for detection of NADPH fluorescence.

Data for example compounds in the 11-βHSD1 assay are shown below:

| Example | Structure | Human 11-βHSD1 IC$_{50}$ (nM) |
|---------|-----------|-------------------------------|
| 1 | 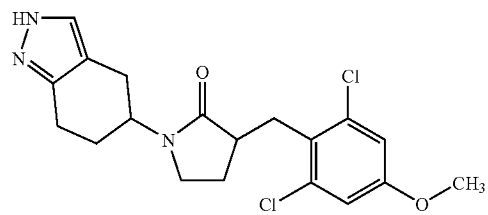 | 100 |
| 7 | 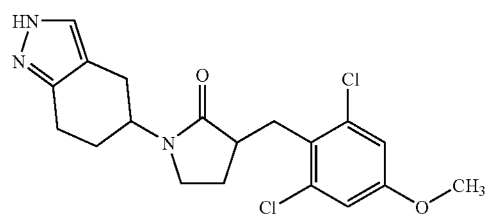 | 37 |
| 35 | 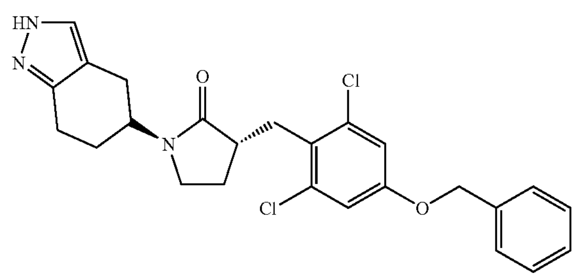 | 243 |
| 36 | 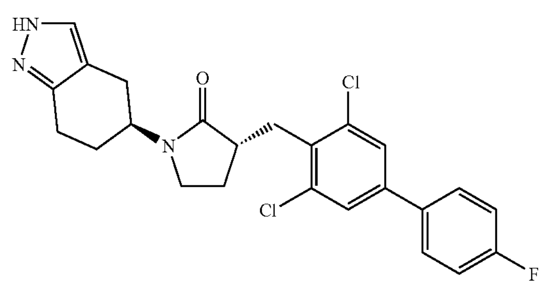 | 276 |

| Example | Structure | Human 11-βHSD1 IC$_{50}$ (nM) |
|---|---|---|
| 57 | 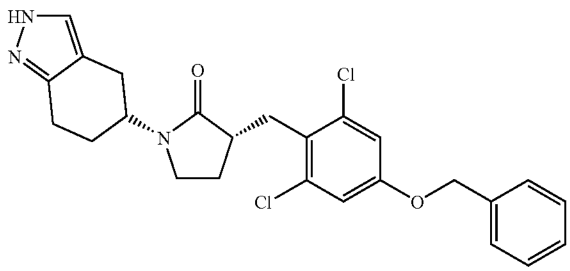 | 1010 |
| 72 | 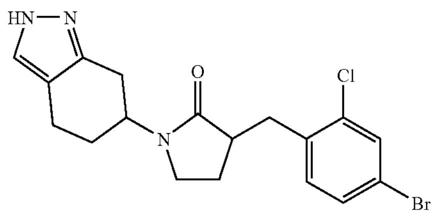 | 416 |

Compounds of the invention can also tested for selectivity against 11-βHSD2 in an assay similar to that described for 11-βHSD1, but using the 11-βHSD2 enzyme. The assay using the 11-βHSD2 enzyme can be carried out by the methods described herein and supplemented by methods known in the art. When tested for selectivity against the 11-βHSD2 enzyme, Example 36 is observed to have 535 fold greater inhibition of 11-βHSD1 enzyme as compared to the inhibition of 11-βHSD2.

Human Aortic Smooth Muscle Cell Assay

Primary human aortic smooth muscle cells (AoSMC) are cultured in 5% FBS growth medium to a passage number of 6, then pelleted by centrifugation and resuspended at a density of $9 \times 10^4$ cells/mL in 0.5% FBS assay medium containing 12 ng/mL hTNFα to induce expression of 11β-HSD1. Cells are seeded into 96-well tissue culture assay plates at 100 μL/well ($9 \times 10^3$ cells/well) and incubated for 48 hours at 37° C., 5% $CO_2$. Following induction, cells are incubated for 4 hours at 37° C., 5% $CO_2$ in assay medium containing test compounds then treated with 10 μL/well of 10 μM cortisone solubilized in assay medium, and incubated for 16 hours at 37° C., 5% $CO_2$. Medium from each well is transferred to a plate for subsequent analysis of cortisol using a competitive fluorescence resonance time resolved immunoassay. In solution, an allo-phycocyanin (APC)-cortisol conjugate and free cortisol analyte compete for binding to a mouse anti-cortisol antibody/Europium (Eu)-anti mouse IgG complex. Higher levels of free cortisol result in diminishing energy transfer from the Europium-IgG to the APC-cortisol complex resulting in less APC fluorescence. Fluorescent intensities for Europium and APC are measured using a LJL Analyst AD. Europium and APC excitation is measured using 360 nm excitation and 615 nm and 650 nm emission filters respectively. Time resolved parameters for Europuium were 1000 μs integration time with a 200 μs delay. APC parameters are set at 150 μs integration time with a 50 μs delay. Fluorescent intensities measured for APC are modified by dividing by the Eu fluorescence (APC/Eu). This ratio is then used to determine the unknown cortisol concentration by interpolation using a cortisol standard curve fitted with a 4-parameter logistic equation. These concentrations are then used to determine compound activity by plotting concentration versus % inhibition, fitting with a 4-parameter curve and reporting the IC$_{50}$.

All of the examples disclosed herein demonstrate activity in the human aortic smooth muscle cell assay with IC$_{50}$ of less than 500 nM. Preferred examples demonstrate activity in the human aortic smooth muscle cell assay with IC$_{50}$ of less than 300 nM. Data for example compounds in the human aortic smooth muscle cell assay are shown below:

| Example | Structure | IC$_{50}$ (nM) |
|---|---|---|
| 11 | 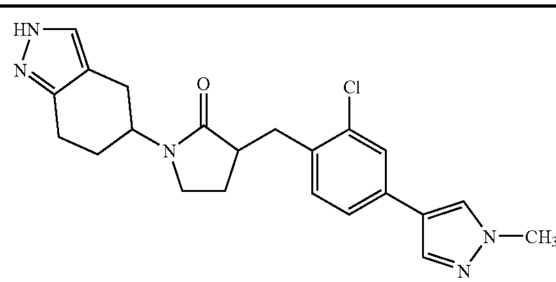 | 24 |

-continued

| Example | Structure | IC₅₀ (nM) |
|---|---|---|
| 20 | 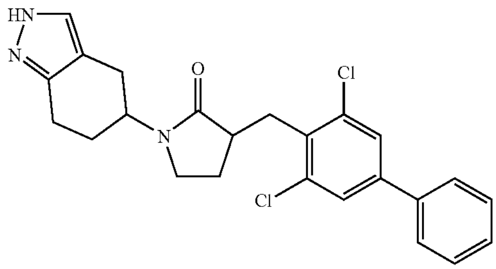 | 2 |
| 36 | 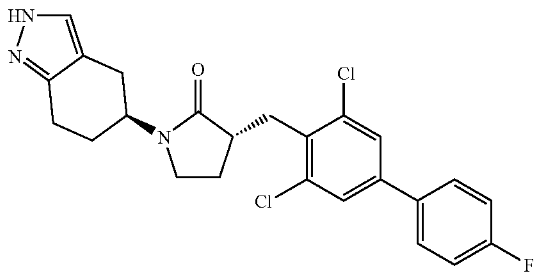 | 0.4 |
| 60 | 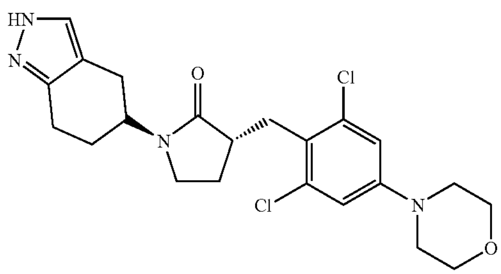 | 1 |
| 70 | 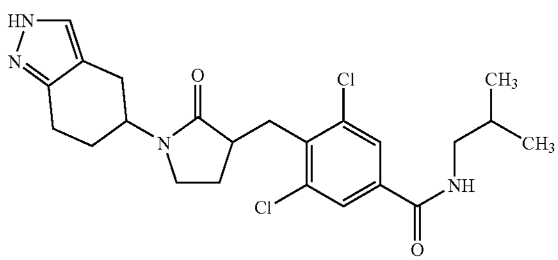 | 16 |
| 71 | 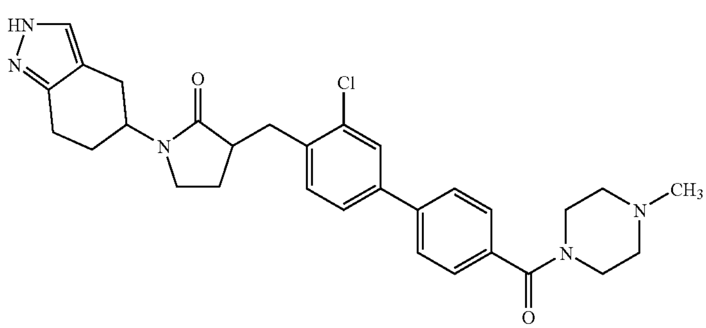 | 6 |

Acute In Vivo Cortisone Conversion Assay

In general, compounds are dosed orally into mice, the mice are challenged with a subcutaneous injection of cortisone at a set timepoint after compound injection, and the blood of each animal is collected some time later. Separated serum is then isolated and analyzed for levels of cortisone and cortisol by LC-MS/MS, followed by calculation of mean cortisol and percent inhibition of each dosing group. Specifically, male C57BL/6 mice are obtained from Harlan Sprague Dawley at average weight of 25 grams. Exact weights are taken upon arrival and the mice randomized into groups of similar weights. Compounds are prepared in 1% w-w HEC, 0.25% w-w polysorbate 80, 0.05% w-w Dow Corning antifoam #1510-US at various doses based on assumed average weight of 25 grams. Compounds are dosed orally, 200 μl per animal, followed by a subcutaneous dose, 200 μl per animal, of 30 mg/kg cortisone at 1 to 24 hours post compound dose. At 10 minutes post cortisone challenge, each animal is euthanized for 1 minute in a $CO_2$ chamber, followed by blood collection via cardiac puncture into serum separator tubes. Once fully clotted, tubes are spun at 2500×g, 4° C. for 15 minutes, the serum transferred to wells of 96-well plates (Corning Inc, Costar #4410, cluster tubes, 1.2 ml, polypropylene), and the plates are frozen at −20° C. until analysis by LC-MS/MS. For analysis, serum samples are thawed and the proteins are precipitated by the addition of acetonitrile containing d4-cortisol internal standard. Samples are vortex mixed and centrifuged. The supernatant is removed and dried under a stream of warm nitrogen. Extracts are reconstituted in methanol/water (1:1) and injected onto the LC-MS/MS system. The levels of cortisone and cortisol are assayed by selective reaction monitoring mode following positive ACPI ionization on a triple quadrupole mass spectrophotometer.

Data for example compounds in the acute in vivo cortisone conversion assay are shown below:

| Example | Structure | % Inhibition after 16 hours (dose of 10 (mg/kg)) |
|---------|-----------|--------------------------------------------------|
| 36 | 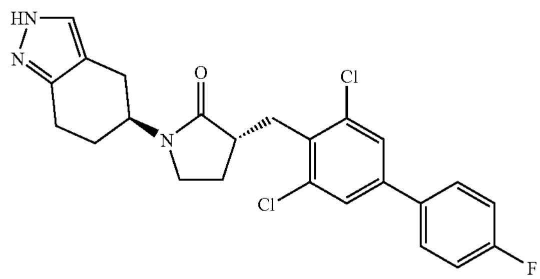 | 95 |
| 41 | 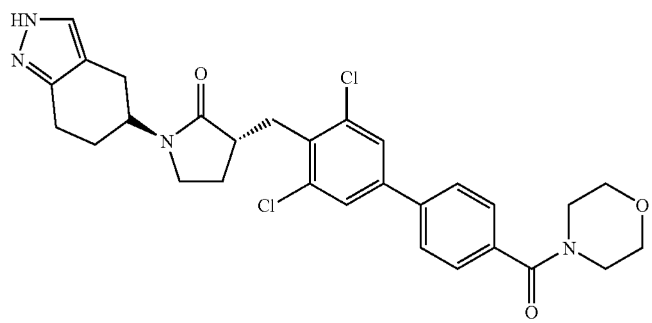 | 84 |
| 44 | 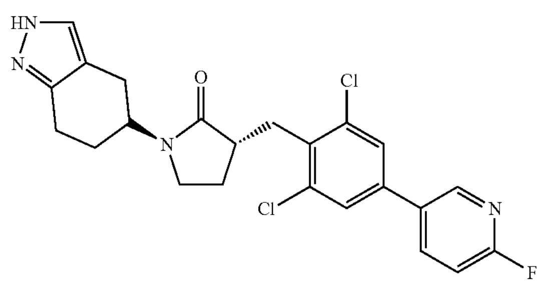 | 92 |

Pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977. The compounds of the present invention are preferably formulated as pharmaceutical compositions administered by a variety of routes. Most preferably, such compositions are for oral administration. Such pharmaceutical compositions and processes for preparing same are well known in the art. See, e.g. REMINGTON: THE SCIENCE AND PRACTICE OF PHARMACY (A. Gennaro, et al., eds., 19th ed., Mack Publishing Co., 1995).

The particular dosage of a compound of formula (I) or a pharmaceutically acceptable salt thereof required to constitute an effective amount according to this invention will depend upon the particular circumstances of the conditions to be treated. Considerations such as dosage, route of administration, and frequency of dosing are best decided by the attending physician. Generally, accepted and effective dose ranges for oral or parenteral administration will be from about 0.1 mg/kg/day to about 10 mg/kg/day which translates into about 6 mg to 600 mg, and more typically between 30 mg and 200 mg for human patients. Such dosages will be administered to a patient in need of treatment from one to three times each day or as often as needed to effectively treat a disease selected from those described herein.

One skilled in the art of preparing formulations can readily select the proper form and mode of administration depending upon the particular characteristics of the compound selected, the disorder or condition to be treated, the stage of the disorder or condition, and other relevant circumstances. (Remington's Pharmaceutical Sciences, 18th Edition, Mack Publishing Co. (1990)). The compounds claimed herein can be administered by a variety of routes. In effecting treatment of a patient afflicted with or at risk of developing the disorders described herein, a compound of formula (I) or a pharmaceutically acceptable salt thereof can be administered in any form or mode that makes the compound bioavailable in an effective amount, including oral and parenteral routes. For example, the active compounds can be administered rectally, orally, by inhalation, or by the subcutaneous, intramuscular, intravenous, transdermal, intranasal, rectal, occular, topical, sublingual, buccal, or other routes. Oral administration may be preferred for treatment of the disorders described herein. In those instances where oral administration is impossible or not preferred, the composition may be made available in a form suitable for parenteral administration, e.g., intravenous, intraperitoneal or intramuscular.

We claim:
1. A compound structurally represented by the formula:

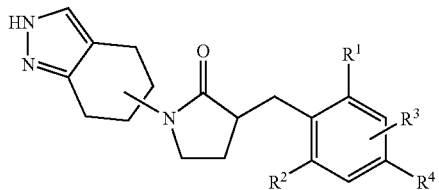

wherein:
R$^1$ is —H, -halogen, —O—CH$_3$ (optionally substituted with one to three halogens), or —CH$_3$ (optionally substituted with one to three halogens);
R$^2$ is —H, -halogen, —O—CH$_3$ (optionally substituted with one to three halogens), or —CH$_3$ (optionally substituted with one to three halogens);
R$^3$ is —H or -halogen;
R$^4$ is
—OH, -halogen, -cyano, —(C$_1$-C$_4$)alkyl(optionally substituted with one to three halogens), —(C$_1$-C$_6$)alkoxy(optionally substituted with one to three halogens), —SCF$_3$, —C(O)O(C$_1$-C$_4$)alkyl, —O—CH$_2$—C(O)NH$_2$, —(C$_3$-C$_8$)cycloalkyl, —O—phenyl-C(O)O—(C$_1$-C$_4$)alkyl, —CH$_2$-phenyl, —NHSO$_2$—(C$_1$-C$_4$)alkyl, —NHSO$_2$-phenyl(R$^{21}$)(R$^{21}$), —(C$_1$-C$_4$)alkyl-C(O)N(R$^{10}$)(R$^{11}$), —C(O)N(R$^{10}$)(R$^{11}$),

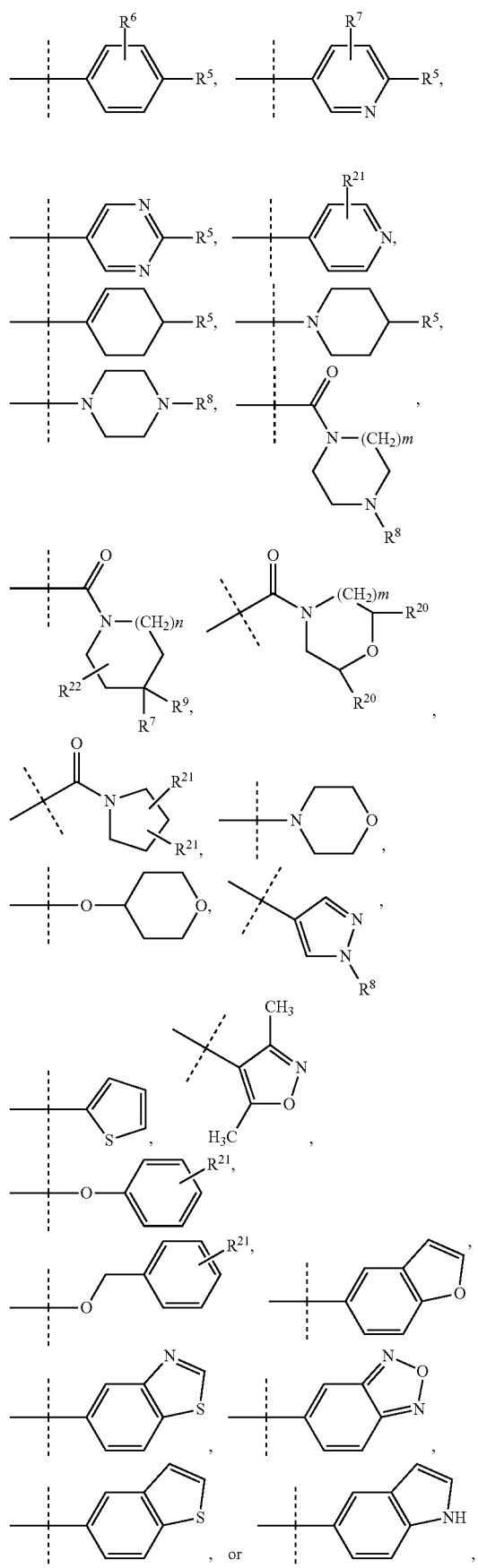

wherein the dashed line represents the point of attachment to the $R^4$ position in formula I;

wherein m is 1, 2, or 3; wherein n is 0, 1, or 2, and wherein when n is 0, then "$(CH_2)_n$" is a bond;

$R^5$ is

—H, -halogen, —OH, —CN, —($C_1$-$C_4$)alkyl(optionally substituted with 1 to 3 halogens), —C(O)OH, —C(O)O—($C_1$-$C_4$)alkyl, —C(O)—($C_1$-$C_4$)alkyl, —O—($C_1$-$C_4$)alkyl(optionally substituted with 1 to 3 halogens), —$SO_2$—($C_1$-$C_4$)alkyl, —N($R^8$)($R^8$), -phenyl($R^{21}$)($R^{21}$), —C(O)—NH—($C_3$-$C_6$)cycloalkyl,

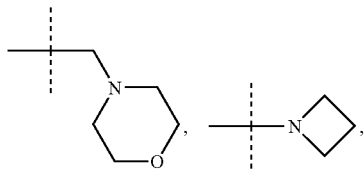

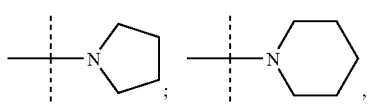

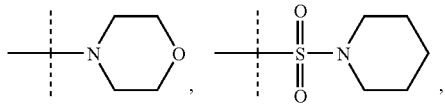

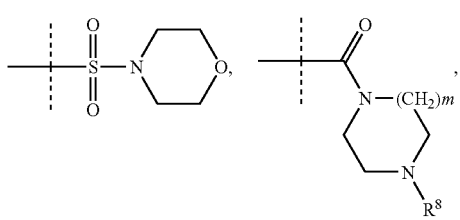

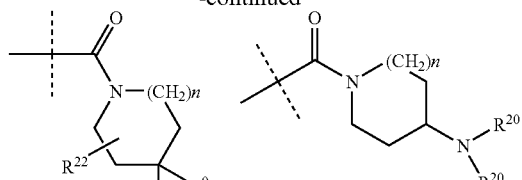

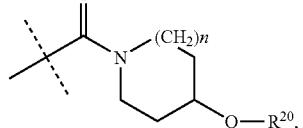

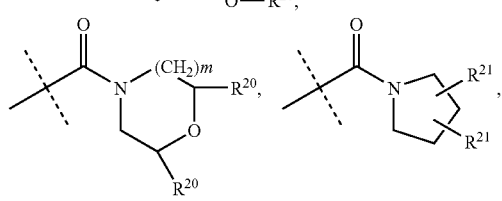

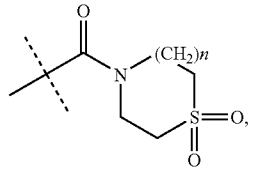

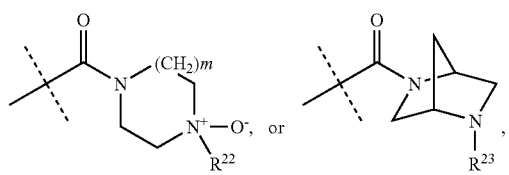

wherein the dashed line represents the point of attachment to the position indicated by $R^5$;

wherein m is 1, 2, or 3; wherein n is 0, 1, or 2, and wherein when n is 0, then "$(CH_2)_n$" is a bond;

$R^6$ is

—H, -halogen, —CN, —($C_1$-$C_4$)alkyl(optionally substituted with 1 to 3 halogens), —O—($C_1$-$C_4$)alkyl (optionally substituted with 1 to 3 halogens), or

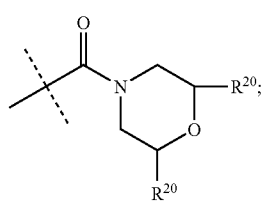

$R^7$ is

—H, -halogen, or —($C_1$-$C_4$)alkyl(optionally substituted with 1 to 3 halogens);

$R^8$ is independently at each occurrence

—H, —($C_1$-$C_6$)alkyl(optionally substituted with 1 to 3 halogens), —C(O)($C_1$-C6)alkyl(optionally substituted with 1 to 3 halogens), —C(O)—($C_3$-$C_8$)cycloalkyl, —S(O₂)—(C₃-C₈)cycloalkyl or —S(O₂)—(C₁-C₃)alkyl(optionally substituted with 1 to 3 halogens);

R⁹ is —H or -halogen;

R¹⁰ and R¹¹ are each independently
—H or —(C₁-C₄)alkyl, or R¹⁰ and R¹¹ taken together with the nitrogen to which they are attached form piperidinyl, piperazinyl, or pyrrolidinyl;

R²⁰ is independently at each occurrence —H, or —(C₁-C₃) alkyl(optionally substituted with 1 to 3 halogens);

R²¹ is independently at each occurrence —H, -halogen, or —(C₁-C₃)alkyl(optionally substituted with 1 to 3 halogens);

R²² is independently at each occurrence —H or —(C₁-C₆) alkyl(optionally substituted with 1 to 3 halogens); and R²³ is independently at each occurrence —H, —(C₁-C₄) alkyl, or —C(O)O—(C₁-C₄)alkyl; or a stereoisomer thereof; or a pharmaceutically acceptable salt thereof.

2. A compound of claim 1 structurally represented by the formula:

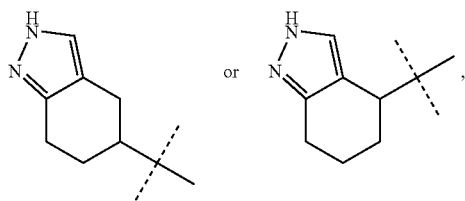

wherein R⁰ is

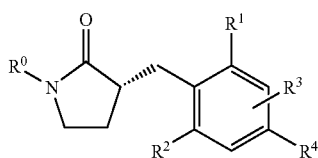

or a stereoisomer thereof; or a pharmaceutically acceptable salt thereof.

3. A compound of claim 2 wherein R¹ and R² are chlorine, or a stereoisomer thereof, or a pharmaceutically acceptable salt thereof.

4. A compound of claim 3 wherein R³ is hydrogen, or a stereoisomer thereof, or a pharmaceutically acceptable salt thereof.

5. A compound of claim 4 wherein R⁰ is

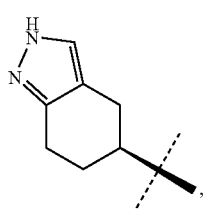

or a pharmaceutically acceptable salt thereof.

6. A compound of claim 4 wherein R⁰ is

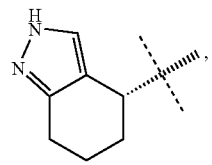

or a pharmaceutically acceptable salt thereof.

7. A compound of claim 4 wherein R⁴ is,

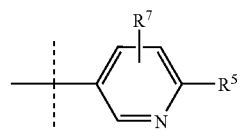

and R⁷ is hydrogen, or a stereoisomer thereof, or a pharmaceutically acceptable salt thereof.

8. A compound of claim 4 wherein R⁴ is,

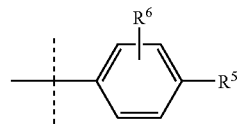

and R⁶ is hydrogen, or a stereoisomer thereof, or a pharmaceutically acceptable salt thereof.

9. A compound of claim 8 wherein R⁵ is

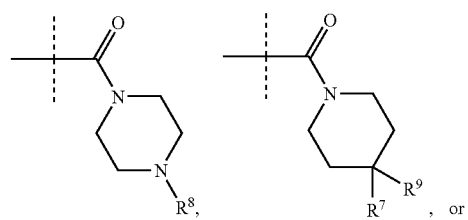

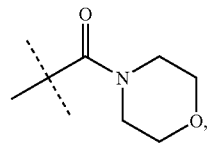

or a stereoisomer thereof; or a pharmaceutically acceptable salt thereof.

10. A compound of claim 8 wherein $R^5$ is chlorine or fluorine, or a stereoisomer thereof, or a pharmaceutically acceptable salt thereof.

11. A compound of claim 8 wherein $R^5$ is fluorine, or a stereoisomer thereof, or a pharmaceutically acceptable salt thereof.

12. A compound that is (3R)-3-[3,5-Dichloro-4'-fluoro[1,1'-biphenyl]-4-yl)methyl]-1-[(5S)-4,5,6,7-tetrahydro-1H-indazol-5-yl]-2- pyrrolidinone or a pharmaceutically acceptable salt thereof.

13. A compound that is (3R)-3-(3,5-Dichloro-4'-fluoro-biphenyl-4-ylmethyl)-1-(4,5,6,7-tetrahydro-1H-indazol-4-yl) - pyrrolidin-2-one or a pharmaceutically acceptable salt thereof.

14. A pharmaceutical composition which comprises a compound of claim 1, or a stereoisomer thereof, or a pharmaceutically acceptable salt thereof, and a pharmaceutically acceptable carrier.

15. A method for treating metabolic syndrome in a patient in need thereof which comprises administering to said patient an effective amount of a compound of claim 1, or a stereoisomer thereof, or a pharmaceutically acceptable salt thereof.

16. A method for treating type 2 diabetes in a patient in need thereof which comprises administering to said patient an effective amount of a compound of claim 1, or a stereoisomer thereof, or a pharmaceutically acceptable salt thereof.

17. A method for treating atherosclerosis in a patient in need thereof which comprises administering to said patient an effective amount of a compound of claim 1, or a stereoisomer thereof, or a pharmaceutically acceptable salt thereof.

18. An intermediate for preparing a compound of claim 12 wherein the intermediate is

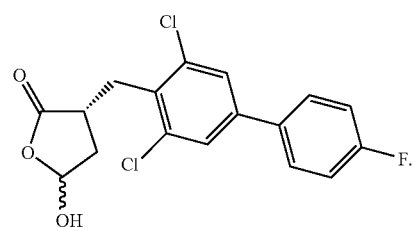

19. An intermediate for preparing a compound of claim 12 wherein the intermediate is

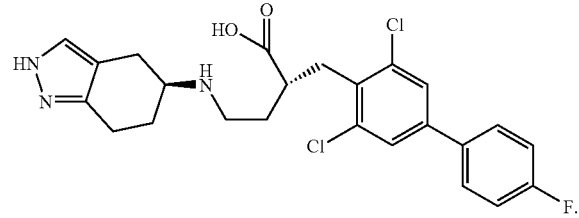

20. A compound of claim 6 wherein $R^4$ is

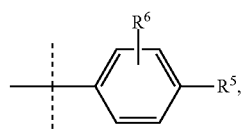

and $R^6$ is hydrogen, or a stereoisomer thereof, or a pharmaceutically acceptable salt thereof.

* * * * *